US011584755B2

(12) United States Patent
Beck et al.

(10) Patent No.: US 11,584,755 B2
(45) Date of Patent: Feb. 21, 2023

(54) DIHYDROTHIENO[3,2-B]PYRIDINE COMPOUNDS

(71) Applicant: IDEAYA BIOSCIENCES, INC., South San Francisco, CA (US)

(72) Inventors: Hilary Plake Beck, South San Francisco, CA (US); Leah Brigit Cleary, South San Francisco, CA (US); Michael Patrick Dillon, South San Francisco, CA (US); Marcos Gonzalez-Lopez, South San Francisco, CA (US); Luis Ruben P. Martinez, South San Francisco, CA (US); James Clifford Sutton, Jr., South San Francisco, CA (US)

(73) Assignee: IDEAYA BIOSCIENCES, INC., South San Francisco, CA (US)

( * ) Notice: Subject to any disclaimer, the term of this patent is extended or adjusted under 35 U.S.C. 154(b) by 84 days.

(21) Appl. No.: 16/648,865

(22) PCT Filed: Sep. 25, 2018

(86) PCT No.: PCT/US2018/052640
§ 371 (c)(1),
(2) Date: Mar. 19, 2020

(87) PCT Pub. No.: WO2019/067442
PCT Pub. Date: Apr. 4, 2019

(65) Prior Publication Data
US 2022/0227780 A1     Jul. 21, 2022

Related U.S. Application Data

(60) Provisional application No. 62/563,404, filed on Sep. 26, 2017.

(51) Int. Cl.
| C07D 495/04 | (2006.01) |
| A61P 35/00 | (2006.01) |
| A61K 31/4365 | (2006.01) |
| A61K 31/437 | (2006.01) |
| A61K 31/5025 | (2006.01) |
| A61K 31/519 | (2006.01) |
| C07D 519/00 | (2006.01) |

(52) U.S. Cl.
CPC .......... *C07D 495/04* (2013.01); *A61K 31/437* (2013.01); *A61K 31/4365* (2013.01); *A61K 31/5025* (2013.01); *A61K 31/519* (2013.01); *A61P 35/00* (2018.01); *C07D 519/00* (2013.01)

(58) Field of Classification Search
CPC .................................................. C07D 495/04
See application file for complete search history.

(56) References Cited

U.S. PATENT DOCUMENTS

| 5,219,864 A | 6/1993 | Suzuki et al. |
| 2009/0156633 A1 | 6/2009 | Allen et al. |
| 2011/0060001 A1 | 3/2011 | Cravo et al. |

OTHER PUBLICATIONS

Golub et al., Science, vol. 286, Oct. 15, 1999, pp. 531-537. (Year: 1999).*
International Search Report for PCT/US2018/052640, dated Jan. 18, 2019, 2 pages.
Written Opinion for PCT/US2018/052640, dated Jan. 18, 2019, 4 pages.
Kelley et al., Targeting DNA repair pathways for cancer treatment: what's new?, Future Oncol. Author Manuscript, May 2014, vol. 10, No. 7, 11 1215-1237.
Ward et al., Small molecule inhibitors uncover synthetic genetic interactions of human flap endonuclease 1 (FEN!) with DNA damage response genes, PLOS One, Jun. 19, 2017, https://doi.org/10.1371/journal.pone.0179278, 25 pages.
Van Pel et al., An Evolutionary Conserved Synthetic Lethal Interaction Network Identifies FEN1 as a Broad-Spectrum Target for Anticancer Therapeutic Development, PLOS Genetics, Jan. 2013, vol. 9, No. 1, e1003254, 11 pages.

* cited by examiner

*Primary Examiner* — Laura L Stockton
(74) *Attorney, Agent, or Firm* — Mintz, Levin, Cohn, Ferris, Glovsky and Popeo, P.C.

(57) ABSTRACT

Compounds are provided having Formula (I):

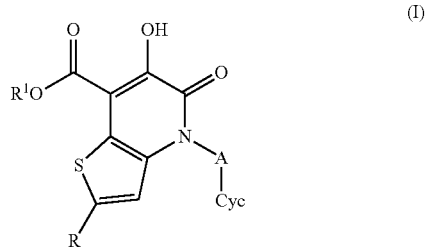

wherein R, R¹, Cyc and A have the meanings provided herein. The compounds have utility in the treatment of diseases, either alone or in combination with other agents.

18 Claims, No Drawings
Specification includes a Sequence Listing.

DIHYDROTHIENO[3,2-B]PYRIDINE COMPOUNDS

CROSS-REFERENCES TO RELATED APPLICATIONS

This application is the U.S. National Stage Entry under § 371 of International Application No. PCT/US2018/052640, filed Sep. 25, 2018, which claims the benefit priority to U.S. Provisional Application No. 62/563,404, filed Sep. 26, 2017, each of which are herein incorporated by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

The Sequence Listing written in file 052326-501N01US_Sequence_Listing_ST25.txt, created Apr. 22, 2021, 1,252 bytes, machine format IBM-PC, MS Windows operating system, is hereby incorporated by reference.

BACKGROUND OF THE INVENTION

Cancer is a leading cause of death throughout the world. A limitation of prevailing therapeutic approaches, e.g. chemotherapy is that their cytotoxic effects are not restricted to cancer cells and adverse side effects can occur within normal tissues. Consequently, novel strategies are urgently needed to better target cancer cells.

Synthetic lethality arises when a combination of deficiencies in the expression of two or more genes leads to cell death, whereas a deficiency in only one of these genes does not. The concept of synthetic lethality originates from studies in *Drosophila* model systems in which a combination of mutations in two or more separate genes leads to cell death (in contrast to viability, which occurs when only one of the genes is mutated or deleted). More recently, a multitude of studies have explored maladaptive genetic changes in cancer cells that render them vulnerable to synthetic-lethality approaches. These tumor-specific genetic defects lead to the use of targeted agents that induce the death of tumor cells while sparing normal cells.

Disruptions in DNA repair pathways predispose cells to accumulating DNA damage. Various types of tumors are known to accumulate progressively more mutations in DNA repair proteins as cancers progress. Therefore, pathways involved DNA repair mechanisms can be targeted by cytotoxic treatments based on synthetic lethality, turning dysregulated repair processes against themselves to induce tumor death.

DNA repair pathways are dependent on a variety of enzymes which include, among others, nucleases that cleave the phosphodiester backbones of DNA and RNA. Nucleases have evolved diverse mechanisms for recognizing and cleaving nucleic acids of specific sequence (e.g., restriction endonucleases), length (e.g., Dicer cleavage of RNA), or structure (e.g., Mre11 nuclease processing of DNA double-strand breaks). The structure-specific nucleases include a conserved superfamily of endo and exonucleases whose eukaryotic members comprise FEN1, EXO1, GEN1, and XPG; also referred to herein as the FEN1 Superfamily.

Flap endonuclease 1 or FEN1 protein removes 5' overhanging "flaps" (or short sections of single stranded DNA that hang off because their nucleotide bases are inhibited from binding to their complementary base pair) in DNA repair and processes the 5' ends of Okazaki fragments in lagging strand DNA synthesis. Direct physical interaction between FEN1 and AP endonuclease 1 during long-patch base excision repair provides coordinated loading of the proteins onto the substrate, thus passing the substrate from one enzyme to another.

FEN1 protein has important functions as revealed by the fact that mutations in its gene resulted in cellular stress and genome instability. In addition, studies of genetic interactions from yeast and human cells, which evaluated a synthetic lethal interaction network comprised of chromosome instability (CIN) genes that are frequently mutated in colorectal cancer, found that FEN1 inhibition is synthetically lethal with several CIN genes (McManus et al, 2009; van Pel et al, PLOs Genetics, 2013; Ward et al, PLOS One, 2017. Given the necessary roles in the critical process of DNA repair as well as its broad and evolutionarily conserved genetic interaction to other CIN genes, FEN1 can be an effective target for anticancer therapeutic development especially that is based on synthetic lethality approaches.

EXO1 is required for a type of DNA damage repair known as mismatch repair (MMR) (Goellner et al, 2015 DNA Repair doi:10.1016/j.dnarep.2015.04.010). Defects in MMR are a cause of micro-satellite instability, prevalent in certain cancers, such as, but not limited to, colorectal cancer. Cancers with defects in MMR are more responsive to immune checkpoint inhibitors, such as PD-1 (D. T. Le et al., Science 10.1126/science.aan6733 (2017)). As such, inhibition of EXO1 may enhance the activity of checkpoint inhibitors. In addition, EXO1 may exhibit synthetic lethality with other DNA damage repair defects common in cancer such as homologous recombination or base excision repair. Finally, EXO1 is required for the repair of DNA that has been damaged by DNA methylating chemotherapeutic agents such as temozolamide or cyclophosphamide (Izumchenko et al, 2012 DNA Repair, doi:10.1016/j.dnarep.2012.09.004), and therefore may enhance the activity in combination with any or all of these agents. These observations indicate that inhibition of EXO1 may be an effective strategy for cancer therapy in a synthetic lethal approach, and as a combination with chemotherapy and immune-oncology agents such as checkpoint inhibitors.

XPG is encoded by the ERCC5 gene. In humans, mutations in ERCC5 can result in xeroderma pigmentosum or Cockayne syndrome. XPG is required for nucleotide excision repair (NER), a pathway that repairs bulky, helix-distorting lesions caused by UV irradiation and chemical mutagens that crosslink adjacent purine bases and form intrastrand adducts. Inhibition of this pathway has been shown to sensitize cells to radiation and the platin family of chemotherapy agents carboplatin, cisplatin, oxaliplatin (Kelley et al, Future Oncology, 2014 doi:10.2217/fon.14.60). These studies suggest that inhibition of XPG could be an effective strategy for treating cancer in a synthetic lethal setting in cancers with defects in other DNA damage repair pathways and in combination with radiation and/or chemotherapy.

BRIEF SUMMARY OF THE INVENTION

Provided herein are compounds having Formula (I)

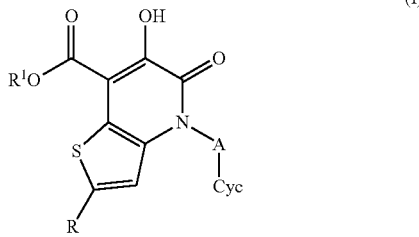

or a pharmaceutically acceptable salt, hydrate, or solvate thereof, wherein the groups shown as R, R¹, A and Cyc have the meanings provided below.

Also provided are pharmaceutical compositions comprising the compounds of Formula (I), as well as methods of using the compounds for the treatment of a variety of cancers.

BRIEF DESCRIPTION OF THE DRAWINGS

NOT APPLICABLE

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Inhibition of FEN1 Superfamily members is defined as encompassing selective and individual inhibition of members of the FEN1 Superfamily, and further encompasses inhibition of members of the FEN1 Superfamily in any combination.

Provided herein, for example, are compounds and compositions for inhibition of FEN1 Superfamily members, and pharmaceutical compositions comprising the same. Also provided herein are, for example, methods of treating or preventing a disease, disorder or condition, or a symptom thereof, mediated by inhibition of one or more FEN1 Superfamily members.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "deuteroalkyl", by itself or as part of another substituent, refers to an alkyl group wherein from one to five hydrogen atoms have been replaced by deuterium. An example of a "deuteroalkyl" group is —$CD_3$.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "heterocycloalkyl" refers to a ring having from four to eight carbon ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

As used herein, a wavy line, "〜", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—$CH_2CH_2$—" is meant to include both —O—$CH_2CH_2$— and —$CH_2CH_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of FEN1, EXO1 and/or XPG, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of FEN1, EXO1 and/or XPG or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering a FEN1, EXO1, XPG and/or GEN1 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of FEN1, EXO1 GEN1 and/or XPG, either directly or indirectly. A modulator may act alone, or it may use a cofactor, e.g., a protein, metal ion, or small molecule. Examples of modulators include small molecule compounds and other bioorganic molecules.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

FEN1 Antagonists—Identification of Compounds Possessing Desirable Characteristics The present invention is drawn, in part, to the identification of FEN1, EXO1, and XPG antagonists with at least one property or characteristic that is of therapeutic relevance.

Candidate antagonists can be identified by using, for example, an art-accepted assay or model, examples of which are will be apparent to the skilled artisan. The assay used to determine the FEN1, EXO1 and XPG antagonist activity of the compounds described herein is set forth in the Experimental section.

After identification, candidate antagonists can be further evaluated by using techniques that provide data regarding characteristics of the antagonsits (e.g., pharmacokinetic parameters). Comparisons of the candidate antagonists to a reference standard (which may the "best-of-class" of current antagonists) are indicative of the potential viability of such candidates.

FEN1, EXO1 and XPG antagonists that can serve as reference or benchmark compounds include 5-chloro-3-hydroxy-1,3-dihydroquinazoline-2,4-dione; (S)-1-[(2,3-dihydrobenzo[b][1,4]dioxin-2-yl)methyl]-3-hydroxythieno[3,2-d]pyrimidine-2,4(1H,3H)-dione; and (R)-1-[(2,3-dihydrobenzo[b][1,4]dioxin-2-yl)methyl)-3-hydroxythieno[3,2-d]pyrimidine-2,4(1H,3H)-dione. Other reference compounds subsequently identified by the skilled artisan can also be used to assess the viability of candidate FEN1, EXO1 and XPG antagonists.

Embodiments

Compounds
Provided herein are compounds having Formula (I)

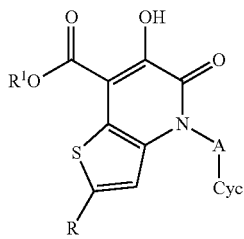

(I)

or a pharmaceutically acceptable salt, hydrate, or solvate thereof, wherein,
R is a member selected from the group consisting of H, halogen, $C_{1-6}$ alkyl, $C_{1-6}$ haloalkyl, $C_{3-6}$ cycloalkyl and benzyl;
$R^1$ is a member selected from the group consisting of H and $C_{1-8}$ alkyl, wherein the $C_{1-8}$ alkyl is optionally substituted with 1 to 4 $R^{1a}$;
A is $C_{1-3}$ alkylene, wherein one or two H atoms are optionally and independently replaced with F or Cl;
Cyc is selected from:
  (i) 5- or 6-membered heteroaryl;
  (ii) phenyl;
  (iii) 9- or 10-membered fused bicyclic heteroaryl;
  (iv) 5- or 6-membered heterocyclic ring, optionally substituted with oxo, and optionally fused to a phenyl; and
  (v) $C_{5-10}$ cycloalkyl;
and each of (i), (ii), (iii), (iv) and (v) is optionally further substituted with
  (i') 1 to 4 members independently selected from $R^2$, $C_{1-3}$ alkylene-$R^2$ and —O—$C_{1-3}$alkylene-$R^2$;
  (ii') phenyl, phenoxy, pyridyl, or pyridyloxy each of which is optionally substituted with from 1 to 4 $R^{2a}$;
  (iii') a $C_{1-3}$alkylene-Y, wherein Y is selected from the group consisting of phenyl, 4- to 7-membered heterocycloalkyl, 5- or 6-membered heteroaryl, and 9- or 10-membered fused bicyclic heteroaryl, each of which is optionally substituted with from 1 to $R^{2a}$ and wherein the $C_{1-3}$ alkylene portion is optionally substituted with oxo;
  (iv') a 9- or 10-membered fused bicyclic heteroaryl, which is optionally substituted with from 1 to 4 $R^{2a}$; and
  (v') a $C_{3-10}$ cycloalkyl, which is optionally substituted with from 1 to 4 $R^{2a}$;
each $R^{1a}$ is a member selected from the group consisting of halogen, —CN, —$CO_2R^a$, —$CONR^aR^b$, —$C(O)R^a$, —$OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$ and —$NR^aS(O)_2R^b$;
each $R^2$ and $R^{2a}$ is a member independently selected from the group consisting of halogen, —CN, —$NO_2$, —$CO_2R^a$, —$CONR^aR^b$, —$C(O)R^a$, —$OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$, —$S(O)_2R^b$, —$S(O)(NR^c)R^b$ and $R^c$,
wherein each $R^a$ and $R^b$ is independently selected from hydrogen, $C_{1-4}$ alkyl, $C_{1-4}$ hydroxyalkyl, $C_{1-4}$ haloalkyl and phenyl; and optionally $R^a$ and $R^b$ when attached to a nitrogen atom are combined for form a 5- or 6-membered ring having from 0 or 1 additional O, S or N atoms as a ring member, wherein the ring is optionally further substituted with —OH, —$NH_2$, oxo, or —$CO_2H$, and each $R^c$ is selected from $C_{1-4}$ alkyl, $C_{1-4}$ hydroxyalkyl and $C_{1-4}$ haloalkyl.

In one group of embodiments, compounds of Formula (I) are provided wherein Cyc is a 5- or 6-membered heteroaryl, and is optionally substituted as provided in groups (i'), (ii'), (iii'), (iv') and (v'), above. In some selected embodiments, Cyc is a 5-membered heteroaryl selected from the group consisting of imidazolyl, isoxazolyl, pyrazolyl, 1,2,3-triazolyl, 1,2,4-triazolyl, thiazolyl, 1,2,4-oxadiazolyl, 1,3,4-oxadiazolyl, and 1,3,4-thiadiazolyl, each of which is optionally substituted as provided in groups (i'), (ii'), (iii'), (iv') and (v'), above. In other selected embodiments, Cyc is a 6-membered heteroaryl selected from the group consisting of pyridyl, pyrazinyl, pyridazinyl, and pyrimidinyl, each of which is optionally substituted as provided in groups (i'), (ii'), (iii'), (iv') and (v'), above.

In another group of embodiments, compounds of Formula (I) are provided wherein Cyc is phenyl, and is optionally substituted as provided in groups (i'), (ii'), (iii'), (iv') and (v'), above. In some selected embodiments, Cyc is phenyl, optionally substituted with 1 to 4 $R^2$.

In still another group of embodiments, compounds of Formula (I) are provided wherein Cyc is a 9- or 10-membered fused bicyclic heteroaryl, and is optionally substituted as provided in groups (i'), (ii'), (iii'), (iv') and (v'), above. In some selected embodiments, Cyc is a 9-10-membered fused bicyclic heteroaryl, selected from the group consisting of

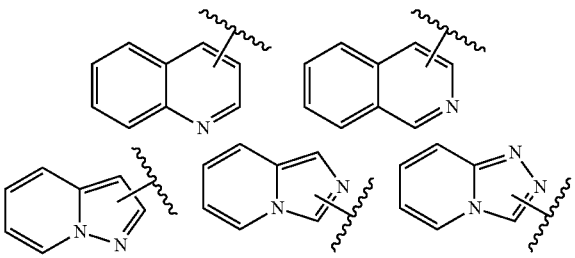

each of which is optionally substituted with:
(i') 1 to 4 $R^2$; and
(ii') a phenyl or a pyridyl, each of which is optionally substituted with from 1 to 4 $R^{2a}$.

In yet another group of embodiments, compounds of Formula (I) are provided wherein Cyc is a 5- or 6-membered heterocyclic ring, which is optionally fused to a phenyl, and is optionally substituted as provided in groups (i'), (ii'), (iii'), (iv') and (v'), above.

In another group of embodiments, compounds of any of the above embodiments are provided wherein $R^1$ is H. In still other embodiments, compounds of any of the above embodiments are provided wherein $R^1$ is $C_{1-4}$ alkyl.

In still other embodiments, compounds of Formula (I), or any of the more specifically recited embodiments are provided wherein A is methylene (—$CH_2$—).

In yet other embodiments, compounds of Formula (I) are provided and are represented by the formulae below:

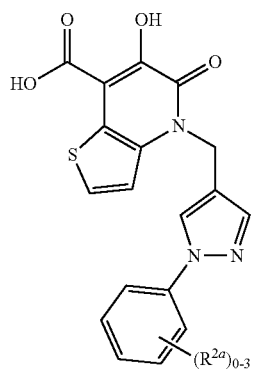
(Ia)

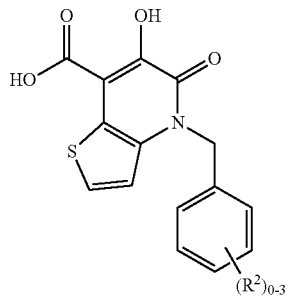
(Ib)

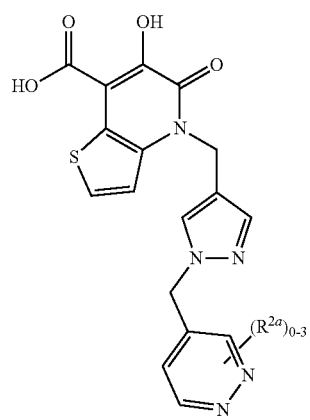
(Ic)

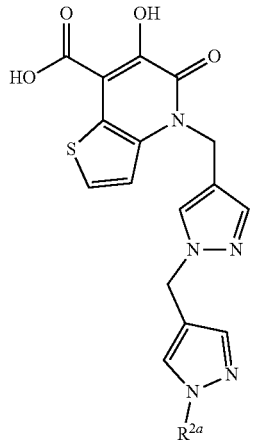
(Id)

In still other embodiments, compounds of Formula (I) are provided and are represented by the formulae below:

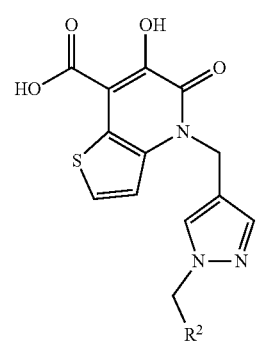
(Ie)

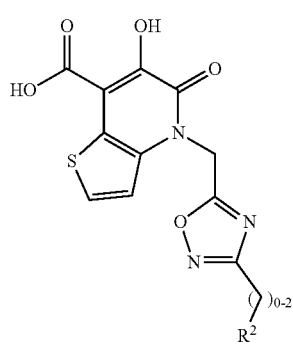
(If)

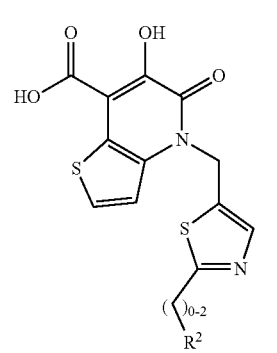
(Ig)

In certain selected embodiments, compounds are provided as described in the Examples and Table 1. In further selected embodiments, compounds are provided as described in the Examples and Table 1, and having * or  activity against FEN1. In still other selected embodiments, compounds are provided as described in the Examples and Table 1, and having , * or  activity against FEN1 and  or * activity against EXO1. In still other selected embodiments, compounds are provided as described in the Examples and Table 1, and having  or * activity against EXO1. In yet other selected embodiments, compounds are provided as described in the Examples and Table 1, and having , * or ** activity against XPG.

Preparation of Compounds—General Synthetic Approaches

The compounds of the present invention may be prepared by a variety of methods, generally using standard chemical techniques. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I), both possible stereoisomers are with the scope of the present invention—that is, not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be accomplished by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Scheme 1

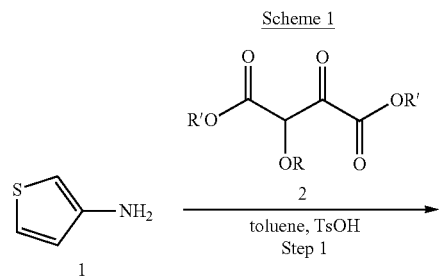

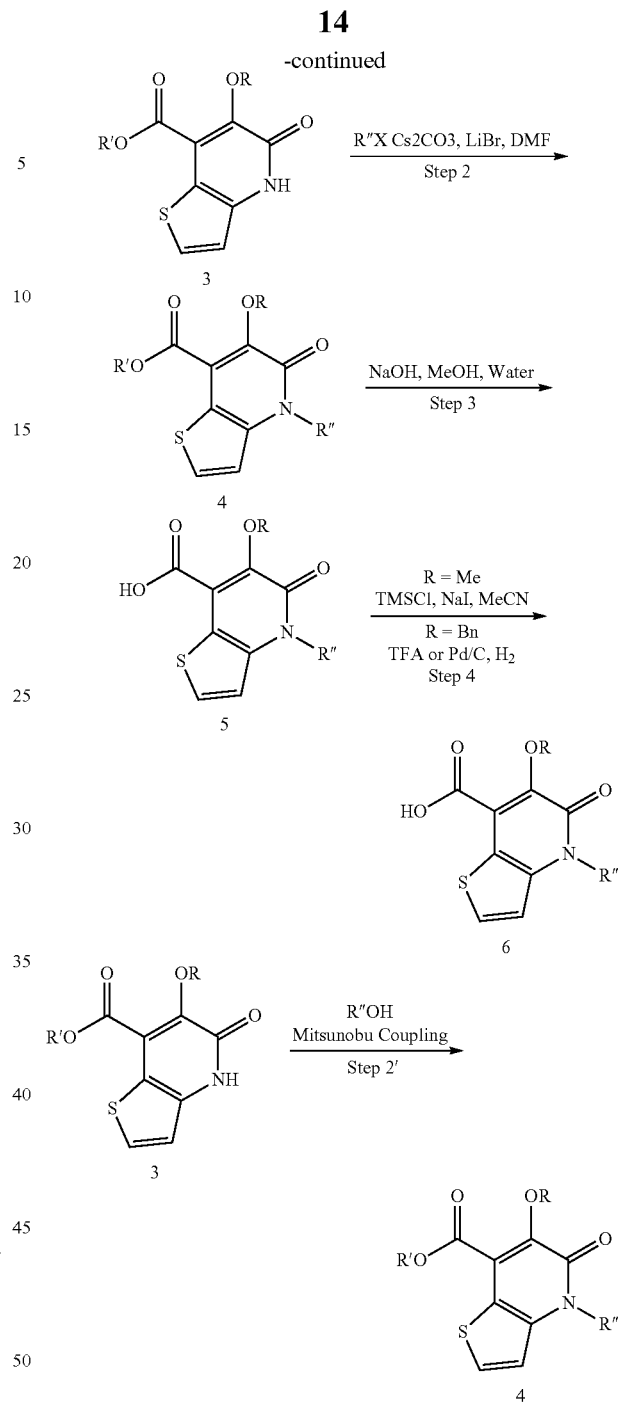

Treatment of thiophen-3-amine with diethyl 2-methoxy-3-oxo-butanedioate, or diethyl 2-benzyloxy-3-oxo-butanedioate, in toluene with catalytic p-toluenesulfonic acid at temperatures approximately between 80 to 120° C. provides intermediate 3. N-alkylation of intermediate 3 with an alkyl halide in the presence of a base such as cesium carbonate, potassium carbonate or sodium hydride in the presence or absence of lithium bromide in a solvent such as dimethylformamide at temperatures approximately between room temperature to 120° C. provides a mixture of N and O alkylated products, which provides the N-alkylated intermediate 4 after purification. Alternately, intermediate 4 can be obtained through a Mitsunobu coupling of intermediate 3 to alcohol R″OH. Removal of the ester to provide intermediate 5 can be done by treatment of intermediate 4 with sodium or lithium hydroxide in a mixture of alcohol, typically methanol, and water at temperatures approximately between 0 to 100° C. Removal of the R=Methyl group to provide compounds of the invention 6 can be done by treatment of intermediate 5 with trimethylsilylchloride and sodium iodide in a solvent such as acetonitrile. Removal of the R=Benzyl group to provide final product 6 can be accomplished by with trifluoroacetic acid neat or diluted in dichloromethane. Alternately, the benzyl group can be removed with hydrogen in the presence of Pd/C typically in an alcohol solvent.

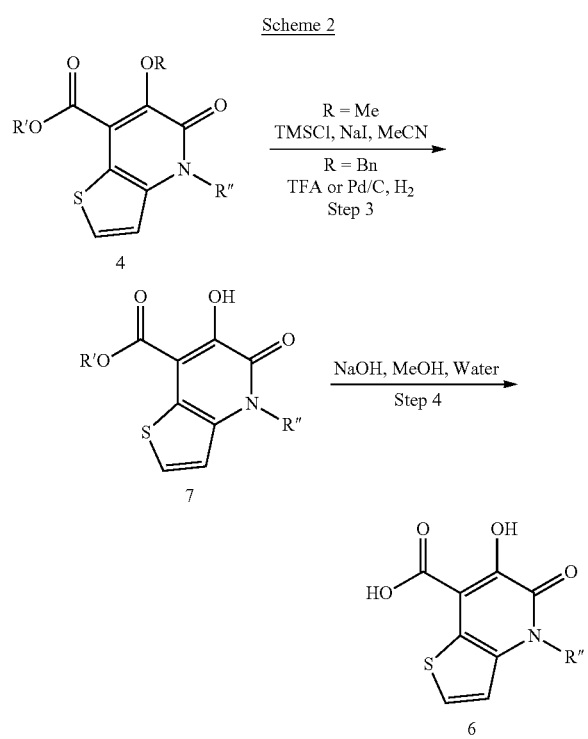

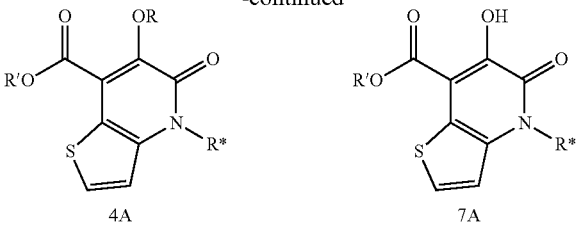

Alternately, the order of deprotection of intermediate 4 can be reversed to provide compounds of the invention 7 which can then be hydrolyzed further to provide compounds of the invention 6.

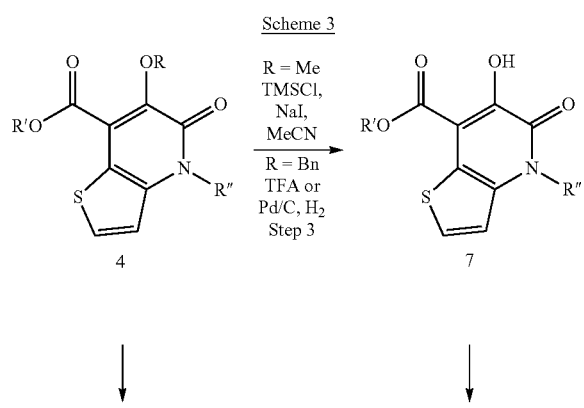

Alternately, the R" group can be amenable to further modifications such as deprotection, hydrolysis, reduction, alkylation, acylation, sulfonylation, organometallic mediated couplings, amide bond couplings and various combinations of these methods. Subsequent deprotection as described in Scheme 1 and Scheme 2 provides compounds of the invention.

Therapeutic and Prophylactic Uses

The present invention contemplates the use of the FEN1, EXO1 or XPG modulators described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present invention, FEN1, EXO1 or XPG antagonist can be used to treat or prevent a proliferative condition or disorder, including a cancer, for example, cancer of the uterus, cervix, breast, prostate, testes, ovary, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia).

In some embodiments, the present invention provides methods for treating a proliferative condition, cancer, tumor, or precancerous condition with a FEN1, EXO1, GEN1 or XPG antagonist and at least one additional therapeutic or diagnostic agent, examples of which are set forth elsewhere herein.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the FEN1, EXO1 or XPG modulators described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The FEN1, EXO1 or XPG modulators provided herein can be used to increase or enhance an immune response; to improve immunization, including increasing vaccine efficacy; and to increase inflammation. The FEN1, EXO1 or XPG modulators can also be used to stimulate the immune system of patients suffering from iatrogenically-induced immune suppression, including those who have undergone bone marrow transplants, chemotherapy, or radiotherapy.

Microbial-related Disorders. By inhibiting the immunosuppressive and anti-inflammatory activity of FEN1, EXO1 or XPG, the present disclosure contemplates the use of the FEN1, EXO1 or XPG modulators described herein in the treatment and/or prevention of any viral, bacterial, fungal, parasitic or other infective disease, disorder or condition for which treatment with a FEN1, EXO1 or XPG modulator may be beneficial. Examples of such diseases and disorders include HIV and AIDS, staphylococcal and streptococcal infections (e.g., *Staphylococcus aureus* and *Streptococcus sanguinis*, respectively), *Leishmania, Toxoplasma, Trichomonas, Giardia, Candida albicans, Bacillus anthracis*, and *Pseudomonas aeruginosa*. Compounds of the invention can be used to treat sepsis, decrease or inhibit bacterial growth, and reduce or inhibit inflammatory cytokines.

CNS-related and Neurological Disorders. Inhibition of FEN1, EXO1 or XPG may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments provided herein also contemplate the administration of the FEN1, EXO1 or XPG modulators described herein to a subject for the treatment or prevention of any other disorder that may benefit from at least some level of FEN1, EXO1 or XPG modulation. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, the FEN1, EXO1 or XPG modulators provided herein may be used to inhibit statin-induced adenosine production, or reduce or decrease increases in blood glucose caused by a statin in a subject taking a statin (e.g., lovastatin and pravastatin)

Pharmaceutical Compositions

The FEN1, EXO1 or XPG modulators provided herein may be in the form of compositions suitable for administration to a subject. In general, such compositions are "pharmaceutical compositions" comprising a FEN1, EXO1 or XPG modulator(s) and one or more pharmaceutically acceptable or physiologically acceptable diluents, carriers or excipients. In certain embodiments, the FEN1, EXO1 or XPG modulator is present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., a modulator of FEN1, EXO1 or XPG function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a FEN1, EXO1 or XPG modulator as provided herein and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver a FEN1, EXO1 or XPG modulator, including implants (e.g., implantable pumps) and catheter systems, slow injection pumps and devices, all of which are well known to the skilled artisan.

Depot injections, which are generally administered subcutaneously or intramuscularly, may also be utilized to release the FEN1, EXO1 or XPG modulators disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the FEN1, EXO1 or XPG modulators in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The FEN1, EXO1 or XPG modulators contemplated by the present invention may be in the form of any other suitable pharmaceutical composition (e.g., sprays for nasal or inhalation use) currently known or developed in the future.

Routes of Administration

The present invention contemplates the administration of one or more FEN1, EXO1 or XPG modulators as provided herein, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the FEN1, EXO1 or XPG modulators disclosed herein over a defined period of time.

Particular embodiments of the present invention contemplate oral administration.

Combination Therapy

The present invention contemplates the use of FEN1, EXO1 or XPG modulators in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the FEN1, EXO1 or XPG modulators are administered or applied sequentially, e.g., where one agent is administered prior to one or more other agents. In other embodiments, the FEN1, EXO1 or XPG modulators are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The FEN1, EXO1 or XPG modulators of the present invention may be used in combination with at least one other (active) agent in any manner appropriate under the circumstances. In one embodiment, treatment with the at least one active agent and at least one FEN1, EXO1 or XPG modulator of the present invention is maintained over a period of time. In another embodiment, treatment with the at least one active agent is reduced or discontinued (e.g., when the subject is stable), while treatment with a FEN1, EXO1 or XPG modulator of the present invention is maintained at a constant dosing regimen. In a further embodiment, treatment with the at least one active agent is reduced or discontinued (e.g., when the subject is stable), while treatment with a FEN1, EXO1 or XPG modulator of the present invention is reduced (e.g., lower dose, less frequent dosing or shorter treatment regimen). In yet another embodiment, treatment with the at least one active agent is reduced or discontinued (e.g., when the subject is stable), and treatment with the FEN1, EXO1 or XPG modulator of the present invention is increased (e.g., higher dose, more frequent dosing or longer treatment regimen). In yet another embodiment, treatment with the at least one active agent is maintained and treatment with the FEN1, EXO1 or XPG modulator of the present invention is reduced or discontinued (e.g., lower dose, less frequent dosing or shorter treatment regimen). In yet another embodiment, treatment with the at least one active agent and treatment with the FEN1, EXO1 or XPG modulator of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with a FEN1, EXO1 or XPG modulator and at least one additional therapeutic or diagnostic agent.

In certain embodiments, the present invention provides methods for administration of a FEN1, EXO1 or XPG modulator described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); (vi) phosphatidyl inositol kinase inhibitors; and (vii) BTK inhibitors. Agents involved in immunomodulation can also be used in combination with one or more FEN1, EXO1 or XPG modulators described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; PARP inhibitors; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with a FEN1, EXO1 or XPG modulator include radiotherapy, a monoclonal antibody against a tumor antigen, a complex of a monoclonal antibody and toxin, a T-cell adjuvant, bone marrow transplant, or antigen presenting cells (e.g., dendritic cell therapy).

Immune Checkpoint Inhibitors. The present invention contemplates the use of the modulators of FEN1, EXO1 or XPG function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints checkpoints include but are not limited to CTLA-4, PD-1/L1, BTLA, TIM3, LAG3, OX40, 41BB, VISTA, CD96, TGFβ, CD73, CD39, A2AR, A2BR, IDO1, IDO2, TDO, Arginase, Glutaminase, B7-H3, B7-H4. Cell-based modulators of anti-cancer immunity are also contemplated. Examples of such modulators include but are not limited to chimeric antigen receptor T-cells, tumor infiltrating T-cells and dendritic-cells.

The present invention contemplates the use of the FEN1, EXO1 or XPG modulators described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with a FEN1, EXO1 or XPG modulator and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the FEN1, EXO1 or XPG modulators described herein include various supplements and herbs (e.g., garlic, policosanol, and guggul).

The present invention encompasses pharmaceutically acceptable salts, acids or derivatives of any of the above.

Immune-related Disorders and Disorders Having an Inflammatory Component. The present invention provides methods for treating and/or preventing immune-related diseases, disorders and conditions; and diseases, disorders and conditions having an inflammatory component; with a FEN1, EXO1 or XPG modulator and at least one additional therapeutic or diagnostic agent.

Examples of therapeutic agents useful in combination therapy are specific to the underlying disease, disorder or condition, and are known to the skilled artisan.

Microbial Diseases. The present invention provides methods for treating and/or preventing viral, bacterial, fungal and parasitic diseases, disorders and conditions, as well as disorders associated therewith, with a FEN1, EXO1 or XPG modulator and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following:

inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with a FEN1, EXO1 or XPG modulator include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the FEN1, EXO1 or XPG modulators described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the FEN1, EXO1 or XPG modulators described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Embodiments of the present invention contemplate the use of the FEN1, EXO1 or XPG modulators described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The FEN1, EXO1, GEN1 or XPG modulators provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of a FEN1, EXO1 or XPG modulator, as provided herein, may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the FEN1, EXO1 or XPG modulators contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired FEN1, EXO1 or XPG modulator is contained in a "unit dosage form". The phrase "unit dosage form" refers to physically discrete units, each unit containing a predetermined amount of the FEN1, EXO1 or XPG modulator, either alone or in combination with one or more additional agents, sufficient to produce the desired effect. It will be appreciated that the parameters of a unit dosage form will depend on the particular agent and the effect to be achieved.

Kits

The present invention also contemplates kits comprising a FEN1, EXO1 or XPG modulator, and pharmaceutical compositions thereof. The kits are generally in the form of a physical structure housing various components, as described below, and may be utilized, for example, in practicing the methods described above.

A kit can include one or more of the FEN1, EXO1 or XPG modulators disclosed herein (provided in, e.g., a sterile container), which may be in the form of a pharmaceutical composition suitable for administration to a subject. The FEN1, EXO1 or XPG modulators can be provided in a form that is ready for use (e.g., a tablet or capsule) or in a form requiring, for example, reconstitution or dilution (e.g., a powder) prior to administration. When the FEN1, EXO1 or XPG modulators are in a form that needs to be reconstituted or diluted by a user, the kit may also include diluents (e.g., sterile water), buffers, pharmaceutically acceptable excipients, and the like, packaged with or separately from the FEN1, EXO1 or XPG modulators. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXAMPLES

The following abbreviations are used herein: ACN, acetonitrile; $Ac_2O$, acetic anhydride; AcCl, acetylchloride; AIBN, 2,2'-Azobis(2-methylpropionitrile); BINAP, 2,2'-bis (diphenylphosphino)-1,1'-binaphthyl; $Boc_2O$ or $(Boc)_2O$, di-tert-butyl dicarbonate; BSA, bovine serum albumin; C, Celsius; d, doublet; dd, doublet of doublets; DEAD, diethyl azodicarboxylate; DIBAL, diisobutylaluminium hydride DIEA, N,N-diisopropylethylamine; DIPEA, N,N-diisopropylethylamine; DMA, dimethylacetamide; DMAP, dimethylaminopyridine; DMF, N,N-dimethylformamide; DME, 1,2-dimethoxyethane; DMSO, dimethylsulfoxide; dppf, 1,1'-Bis(diphenylphosphino)ferrocene; DTT, dithiothreitol; ES, electrospray; EtOAc, ethyl acetate; EtOH, ethanol; g, gram; h, hour(s); hr, hour(s); HATU, 2-(1H-7-azabenzotriazol-1-yl)-1,1,3,3-tetramethyluronium hexafluorophosphate; HEPES, 4-(2-hydroxyethyl)-1-piperazineethylanesulfonic acid; HOAc, acetic acid; HPLC, high pressure liquid chromatography; IPA, isopropyl alcohol; kg, kilogram; L, liter; LC, liquid chromatography; LCMS, liquid chromatography and mass spectrometry; MeCN, acetonitrile; MeOH, methanol; $MeSO_2Cl$, methanesulfonylchloride; MS, mass spectrometry; MsCl, methanesulfonylchloride; m, multiplet; min, minutes; ml, milliliter(s); μM, micromolar; m/z, mass to charge ratio; nm, nanometer; nM, nanomolar; N, normal; NADPH, nicotinamide adenine dinucleotide phosphate; NBS, N-bromosuccinamide; NMP, N-methylpyrrolidone; NMR, nuclear magnetic resonance; Pd/C, palladium on carbon; $Pd_2(dba)_3$, Tris(debenzylideneactone) dipalladium; $Pd(dppf)Cl_2$, 1,1'-bis(diphenylphosphino)ferrocene-palladium(II)dichloride; rac, racemic; Rt, retention time; s, singlet; sat., saturated; t, triplet; TBAB, tetra-n-butylammonium bromide; TEA, triethylamine; TFA, trifluoroacetic acid; THF, tetrahydrofuran; TLC, thin layer chromatography; TMSCl, trimethylsilylchloride; and TsOH, p-toluenesulfonic acid;

Instrumentation

All masses reported are those of the protonated parent ions (M+Hr unless recorded otherwise.

LCMS Method 1: LCMS data were recorded using a SHIMADZU LCMS-2020 System (LabSolutions; Column: Chromolith@Flash RP-18E 25-2 MM; gradient: 5-95% acetonitrile with 0.01875 TFA in water with 0.0375 TFA over a 1.5 min period; flow rate 1.5 mL/min; molecular weight range 50-1500; Qarray DC Voltage 20 V; column temperature 50° C.).

LCMS Method 2: LCMS data were recorded using a SHIMADZU LCMS-2020 System (LabSolutions; Column: Kinetex EVO C18 2.1×30 mm, 5 um; gradient: 5-95% acetonitrile in water with 0.025% NH3·H2O over a 1.5 min period; flow rate 1.5 mL/min; molecular weight range 50-1500; Qarray DC Voltage 20 V; column temperature 40° C.).

LCMS Method 3: LCMS data were recorded using a Agilent 1100\G1956A System (Agilent ChemStation; Column: Chromolith Flash RP-18e 25*2.0 mm; gradient: 5-95% acetonitrile with 0.01875% TFA in water with 0.0375% TFA over a 1.5 min period; flow rate 1.5 mL/min; molecular weight range 50-1500; Capillary Voltage 3500 V; column temperature 50° C.

LCMS Method 4: LCMS data were recorded using a Agilent 1290, 6150 Quadrapole System, AJS-ES (Agilent ChemStation; Column: XSelect CSH C18 2.5 um, 2.1*50 mm; gradient: 2-98% acetonitrile with 0.1% formic acid in water with 0.1% formic acid over a 1.2 min period; flow rate 1.2 mL/min; molecular weight range 130-850; Capillary Voltage 3500 V; Nozzle Voltage 500 V; column temperature 55° C.).

Intermediates

Intermediate A: ethyl 6-methoxy-5-oxo-4,5-dihydrothieno[3,2-b]pyridine-7-carboxylate

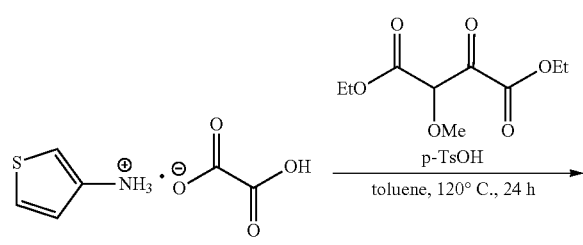

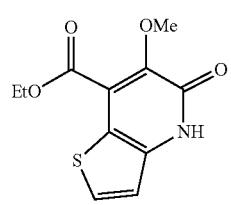

A solution of thiophen-3-amine oxalate salt (8.0 g, 42 mmol), p-toluenesulfonic acid (0.73 g, 4.2 mmol) and diethyl 2-methoxy-3-oxo-butanedioate (9.2 g, 42 mmol) in toluene (240 mL) was stirred at 120° C. for 24 hours. On completion, the solution was concentrated to dryness in vacuo. The residue was purified by column chromatography [petroleum ether/ethyl acetate=5:1-2:1] to give Intermediate A (6.0 g, 56% yield) as a pale gray solid. $^{1}$H-NMR (CDCl$_{3}$, 400 MHz): δ 8.08 (s, 1H), 7.22-7.17 (d, J=5.6 Hz, 1H), 6.64-6.61 (d, J=5.2 Hz 1H), 4.23-4.18 (m, 1H), 4.11-4.07 (m, 1H), 3.69 (s, 3H), 1.11 (t, J=7.2 Hz, 3H).

Intermediate B: ethyl 4-(3-bromobenzyl)-6-methoxy-5-oxo-4,5-dihydrothieno[3,2-b]pyridine-7-carboxylate

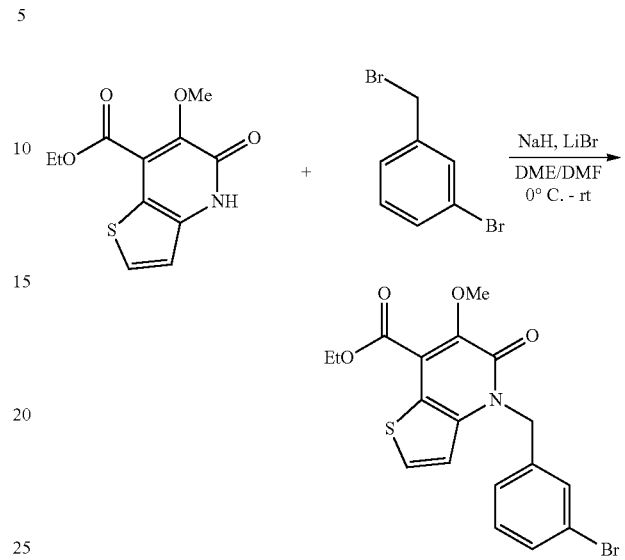

A solution of Intermediate A (0.8 g, 3.2 mmol) in dimethoxyethane (8.0 mL) and N,N-dimethylformamide (0.8 mL) was treated with sodium hydride (0.19 g, 4.7 mmol) slowly at 0° C. The solution was stirred at 0° C. for 10 min, then LiBr (0.82 g, 9.5 mmol) was added. The solution was stirred at 25° C. for 20 min. Finally, 1-bromo-3-(bromomethyl)benzene (1.2 g, 4.7 mmol) was added and the solution was stirred at 25° C. for 15.5 hours. On completion, the solution was poured into ice water (10 mL) and extracted with ethyl acetate (2×50 mL). The organic layer was concentrated to dryness in vacuo. The residue was purified by column chromatography [petroleum ether:ethyl acetate=2:1] to give Intermediate B (0.6 g, 45% yield) as a yellow solid. $^{1}$H NMR (CD$_{3}$OD, 400 MHz): δ 7.77 (d, J=6 Hz, 1H), 7.49 (s, 1H), 7.47 (m, 1H), 7.26-7.21 (m, 3H), 5.56 (s, 2H), 4.53-4.48 (q, J=7.2 Hz, 2H), 4.00 (s, 3H), 1.47 (t, J=7.2 Hz, 3H).

Intermediate C: ethyl 6-(benzyloxy)-5-oxo-4,5-dihydrothieno[3,2-b]pyridine-7-carboxylate

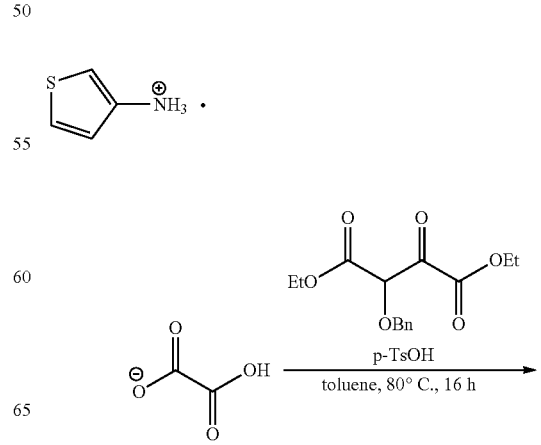

-continued

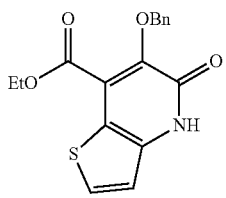

A solution of thiophen-3-amine (10 g, 53 mmol), p-toluenesulfonic acid (1.01 g, 5.29 mmol) and diethyl 2-benzyloxy-3-oxo-butanedioate (19 g, 64 mmol) in toluene (300 mL) was stirred at 80° C. for 16 hours. On completion, the solution was concentrated to dryness in vacuo. The residue was purified by column chromatography [petroleum ether: ethyl acetate=5:1~2:1] to give Intermediate C (11 g, 70% purity, 44% yield) as a gray solid. $^1$H NMR (CDCL$_3$, 400 MHz): δ 7.60 (d, J=7.2 Hz, 2H), 7.55 (d, J=5.6 Hz, 1H), 7.3-7.4 (m, 3H), 7.15 (d, J=6.0 Hz, 1H), 5.39 (s, 2H) 4.44 (q, J=7.2 Hz, 2H), 1.39 (t, J=7.2 Hz, 3H).

Intermediate D: ethyl 6-benzyloxy-5-oxo-4-(1H-pyrazol-4-ylmethyl)thieno[3,2-b]pyridine-7-carboxylate

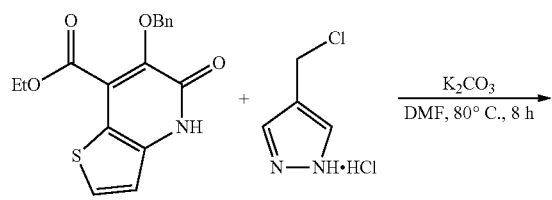

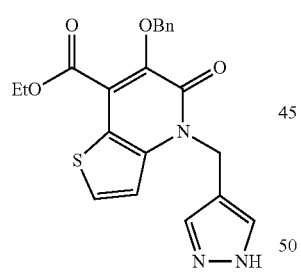

To a solution of ethyl 6-benzyloxy-5-oxo-4H-thieno[3,2-b]pyridine-7-carboxylate (4.5 g, 13.66 mmol) in N,N-dimethylformamide (45 mL) was added potassium carbonate (5.66 g, 40.99 mmol) and Intermediate C (2.93 g, 19.13 mmol, 1.4 eq, HCl). The solution was stirred at 80° C. for 8 hours. The solution was poured into water (100 mL) and extracted with ethyl acetate (200 mL×3). The organic layer was concentrated to dryness in vacuo and purified by column chromotography (petroleum ether:ethyl acetate=2:1-1:2), Intermediate D (1.2 g, 21% yield) was obtained as a yellow solid. $^1$H NMR (DMSO-d6, 400 MHz): δ 7.93 (d, J=5.6 Hz, 1H), 7.77 (s, 2H), 7.58 (d, J=5.6 Hz, 1H), 7.49 (d, J=6.8 Hz, 2H), 7.35-7.40 (m, 3H), 5.34 (s, 2H), 5.24 (s, 2H), 4.32 (q, J=7.2 Hz, 2H), 1.25 (t, J=7.2 Hz, 3H).

Intermediate E: 3-bromo-4-(chloromethyl)-1-(4-methoxyphenyl)-1H-pyrazole

Step E1: (3-bromo-1-(4-methoxyphenyl)-1H-pyrazol-4-yl)methanol

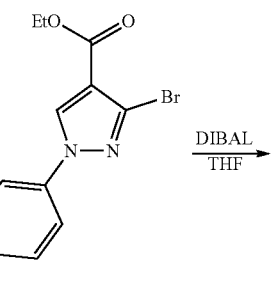

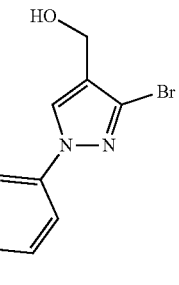

A flask was charged with ethyl 3-bromo-1-(4-methoxyphenyl)-1H-pyrazole-4-carboxylate (200 mg, 0.615) in THF (1.3 mL). The solution was cooled to −78° C., and a 1 M solution of DIBAL in dichloromethane (1.7 mL, 2.8 equiv) was added dropwise over 5 min. The reaction was warmed to 0° C. The mixture was cooled back to −78° C., and EtOAc (3 mL) was slowly added followed by 1 N HCl (6 mL). The biphasic mixture was partitioned, and the aqueous layer was extracted with EtOAc (3×3 mL). The combined organics were washed with brine, dried over sodium sulfate, filtered, and concentrated in vacuo to give (3-bromo-1-(4-methoxyphenyl)-1H-pyrazol-4-yl)methanol as a white solid (175 mg, 82% yield). LCMS: (ES$^+$) m/z (M+H)$^+$=383, 385.

Step E2: 3-bromo-4-(chloromethyl)-1-(4-methoxyphenyl)-1H-pyrazole

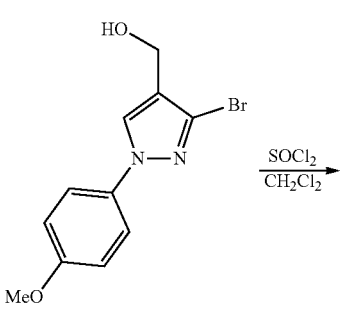

Chloroform-d₃) δ 9.37 (d, J=6.9 Hz, 1H), 8.40 (s, 1H), 7.75 (dd, J=7.5, 1.1 Hz, 1H), 7.01 (t, J=7.2 Hz, 1H), 4.46 (q, J=7.1 Hz, 2H), 1.46 (t, J=7.1 Hz, 3H). LCMS: (ES⁺) m/z (M+H)⁺= 269, 271.

Step F2: (8-bromoimidazo[1,2-a]pyridin-3-yl)methanol

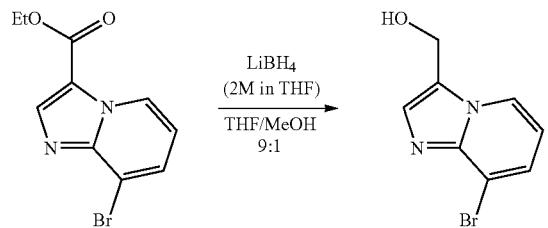

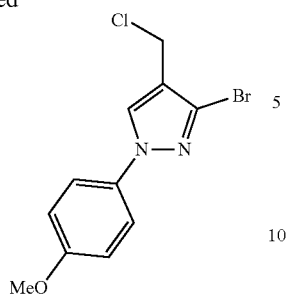

To a solution of (3-bromo-1-(4-methoxyphenyl)-1H-pyrazol-4-yl)methanol (175 mg, 0.618 mmol) in methylene chloride (1.2 mL) at room temperature was added thionyl chloride (0.1 mL, 2.2 equiv.). The heterogenous mixture was stirred at rt for 5 h. The mixture was concentrated to dryness under reduced pressure to give 3-bromo-4-(chloromethyl)-1-(4-methoxyphenyl)-1H-pyrazole (192 mg, 92% yield) as an off white solid. The mixture was dried overnight under high vacuum and then used directly in next reaction. LCMS: (ES⁺) m/z (M+CH₄O)⁺=297, 299.

Intermediate F: 8-bromo-3-(chloromethyl)imidazo[1,2-a]pyridine

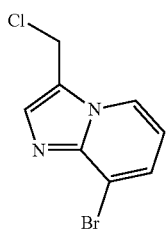 [SMILES: ClCc1cnc2c(Br)cccn12]

To a solution of ethyl 8-bromoimidazo[1,2-a]pyridine-3-carboxylate (900 mg, 3.34 mmol) in THF (14 mL) at 0° C. was added a 2 M lithium borohydride solution in THF (8.4 mL, 16.7 mmol, 5 equiv). Methanol (1.6 mL) was then added dropwise to minimize effervescence. The reaction was warmed to room temperature and stirred for 16 h. Excess methanol (10 mL) was added to quench the remaining lithium borohydride. Ethyl acetate (60 mL) was added and the heterogenous mixture was filtered to remove lithium salts. The filtrate was concentrated to dryness in vacuo and purified via column chromatography (50-100% hex/EtOAc) to provide the desired (8-bromoimidazo[1,2-a]pyridin-3-yl)methanol (670 mg, 72% yield). ¹H NMR (400 MHz, CDCl₃) δ 8.31 (dd, J=6.8, 1.0 Hz, 1H), 7.48 (dd, J=7.3, 1.0 Hz, 1H), 7.37 (s, 1H), 6.75 (t, J=7.1 Hz, 1H), 4.93 (s, 2H).

Step F1: ethyl 8-bromoimidazo[1,2-a]pyridine-3-carboxylate

Step F3: 8-bromo-3-(chloromethyl)imidazo[1,2-a]pyridine

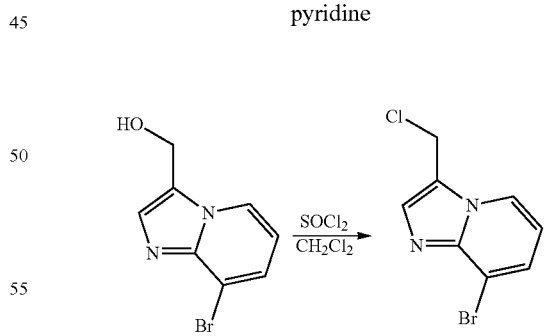

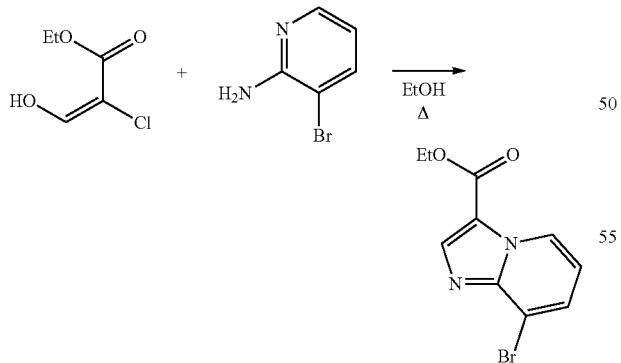

Ethyl (E)-2-chloro-3-hydroxyacrylate (5.0 g, 33.2 mmol, 1.5 equiv) and 3-bromopyridin-2-amine (3.8 g, 22.1 mmol) were dissolved in ethanol and heated to 85° C. for 16 h. The reaction was concentrated to dryness to provide the desired ethyl 8-bromoimidazo[1,2-a]pyridine-3-carboxylate as an off-white solid (2.1 g, 35% yield). ¹H NMR (400 MHz, To a solution of (8-bromoimidazo[1,2-a]pyridin-3-yl)methanol (670 mg, 2.95 mmol) in methylene chloride (14 mL) at room temperature was added thionyl chloride (0.86 mL, 10 equiv.). The heterogeneous mixture was stirred at rt for 5 h. The mixture was concentrated to dryness under reduced pressure to give 8-bromo-3-(chloromethyl)imidazo[1,2-a]pyridine (790 mg, 95% yield) as an off white solid. The mixture dried overnight under high vacuum and then used directly in next reaction.

Intermediate G: ethyl 6-(benzyloxy)-2-bromo-4-(4-methoxybenzyl)-5-oxo-4,5-dihydrothieno[3,2-b]pyridine-7-carboxylate

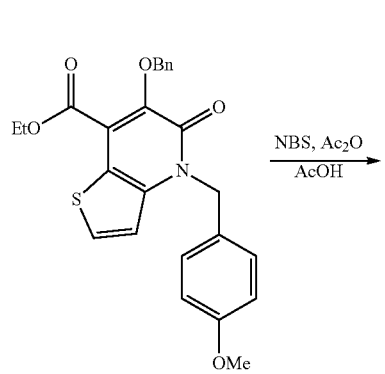

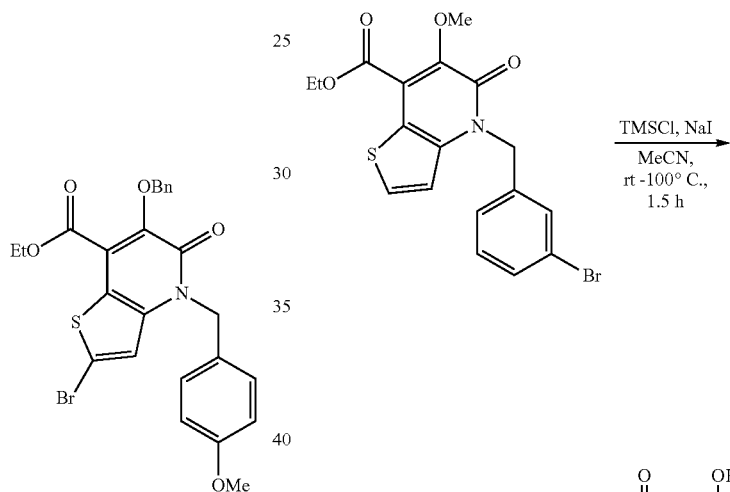

Ethyl 6-(benzyloxy)-4-(4-methoxybenzyl)-5-oxo-4,5-dihydrothieno[3,2-b]pyridine-7-carboxylate (500 mg, 1.11 mmol) was dissolved in acetic acid (11 mL), then acetic anhydride (45 μL, 1.11 mmol) and N-bromosuccinamide (218 mg, 1.22 mmol) were added. The reaction was stirred for 30 min until conversion to the desired product was observed by LCMS. The reaction was diluted with EtOAc (20 mL) and quenched with a saturated solution of aqueous sodium thiosulfate (10 mL) and extracted with additional EtOAc (3×10 mL). The combined organic layers were dried over sodium sulfate, filtered and concentrated in vacuo to provide ethyl 6-(benzyloxy)-2-bromo-4-(4-methoxybenzyl)-5-oxo-4,5-dihydrothieno[3,2-b]pyridine-7-carboxylate as a tan solid (588 mg, 92% yield) after purification via column chromatography (0-50% hex/EtOAc). $^1$H NMR (400 MHz, CDCL$_3$)$^1$H NMR (400 MHz, CDCl$_3$) δ 7.60-7.53 (d, J=7.6 Hz, 2H), 7.43-7.32 (m, 3H), 7.21 (d, J=8.6 Hz, 2H), 7.02 (s, 1H), 6.88 (d, J=8.8 Hz, 2H), 5.39 (s, 4H), 4.41 (q, J=7.1 Hz, 2H), 3.81 (s, 3H), 1.36 (t, J=7.1 Hz, 3H). LCMS: (ES$^+$) m/z (M+H)$^+$=422, 424.

Example 1: 4-(3-bromobenzyl)-6-hydroxy-5-oxo-4,5-dihydrothieno[3,2-b]pyridine-7-carboxylic acid

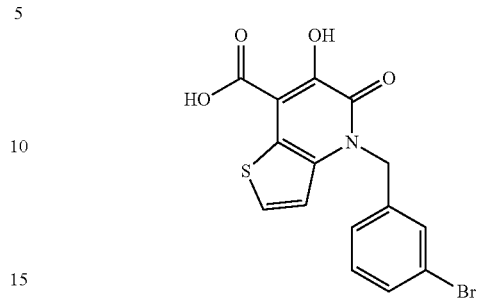

Step 1: ethyl 4-(3-bromobenzyl)-6-hydroxy-5-oxo-4,5-dihydrothieno[3,2-b]pyridine-7-carboxylate To a solution of sodium iodide (1.60 g, 10.7 mmol) in acetonitrile (45 mL) was added trimethylchlorosilane (1.16 g, 10.7 mmol) and the mixture solution was stirred at 25° C. for 0.2 hour, followed by adding Intermediate B (0.35 g, 0.78 mmol). After stirring for 0.3 hour, the mixture was heated at 100° C. for 1 hour The solution was cooled to room temperature then poured into ice water (50 mL) and extracted with ethyl acetate (3×50 mL). The organic layer was concentrated to dryness in vacuo and the residue was purified by column chromotography [dichloromethane:methanol=100:1-50:1] give ethyl 4-(3-bromobenzyl)-6-hydroxy-5-oxo-4,5-dihydrothieno[3,2-b]pyridine-7-carboxylate (400 mg, 92% yield) as brown solid. LCMS: (ES+) m/z (M+H)$^+$=407.9.

Step 2: 4-(3-bromobenzyl)-6-hydroxy-5-oxo-4,5-dihydrothieno[3,2-b]pyridine-7-carboxylic acid

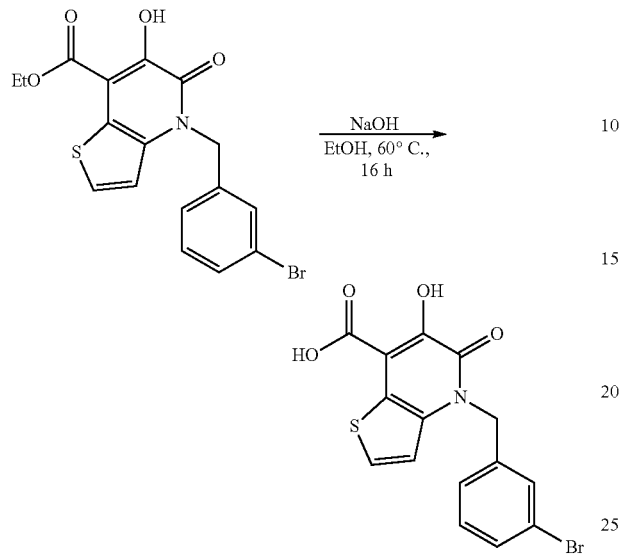

To a solution of intermediate Example 1, Step 1 (0.3 g, 0.73 mmol) in ethanol (20 mL) was added sodium hydroxide (88 mg, 2.2 mmol) and stirred at 60° C. for 16 hours. On completion, the solution was concentrated to dryness in vacuo, and the residue was diluted with water (30 mL). The solution was adjusted the pH to 3-4 with 2 M hydrochloric acid and then extracted with ethyl acetate (50 mL×2). The organic layer was concentrated to dryness in vacuo and the residue was purified by preparative HPLC [Instrument: GX-B; Phenomenex Synergi C18 150×25 mm, particle size: 10 μm; Mobile phase: 20-50% acetonitrile in $H_2O$ (add 0.1% TFA, v/v)]. Each set of collected fractions was concentrated to dryness at room temperature and lyophilized to give the title compound, Example 1 (90 mg, 32% yield) as a gray solid. $^1$H NMR (DMSO-$d_6$, 400 MHz): δ 7.63 (d, J=5.6 Hz, 1H), 7.54 (s, 1H), 7.47 (d, J=7.6 Hz, 1H), 7.31-7.24 (m, 3H), 5.50 (s, 2H); LCMS: (ES+) m/z (M+H)$^+$=379.9.

Example 2: 4-((3'-acetamido-[1,1'-biphenyl]-3-yl)methyl)-6-hydroxy-5-oxo-4,5-dihydrothieno[3,2-b]pyridine-7-carboxylic acid

Step 1: ethyl-4-((3'-acetamido-[1,1'-biphenyl]-3-yl)methyl)-6-methoxy-5-oxo-4,5-dihydrothieno[3,2-b]pyridine-7-carboxylate

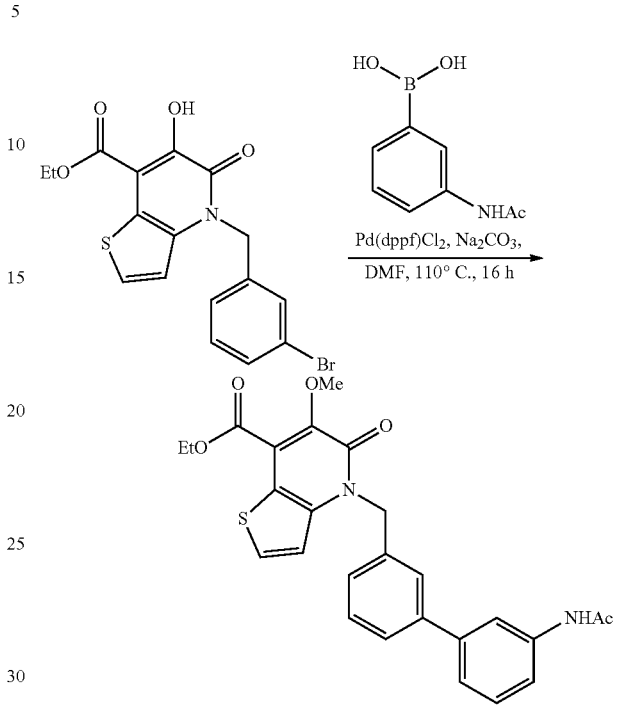

A solution of ethyl Intermediate B (0.50 g, 1.2 mmol), (3-acetamidophenyl)boronic acid (0.42 g, 2.4 mmol), Pd(dppf)Cl$_2$ (96 mg, 0.12 mmol) and sodium carbonate (81 mg, 0.76 mmol) in N, N-dimethylformamide (12 mL) was stirred at 110° C. for 16 hours. Upon completion, the solution was cooled to room temperature and then diluted with water (30 mL) and extracted with ethyl acetate (50 mL×2). The organic layer was concentrated to dryness. The residue was purified by column chromatography [dichloromethane:methanol=50:1-20:1] to give ethyl-4-((3'-acetamido-[1,1'-biphenyl]-3-yl)methyl)-6-methoxy-5-oxo-4,5-dihydrothieno[3,2-b]pyridine-7-carboxylate (0.25 g, 44% yield) as pale yellow solid. LCMS: (ES+) m/z (M+H)$^+$= 477.0.

Step 2: ethyl-4-[(3'-acetamido-[1,1'-biphenyl]-3-yl)methyl]-6-hydroxy-5-oxo-4,5-dihydrothieno[3,2-b]pyridine-7-carboxylate

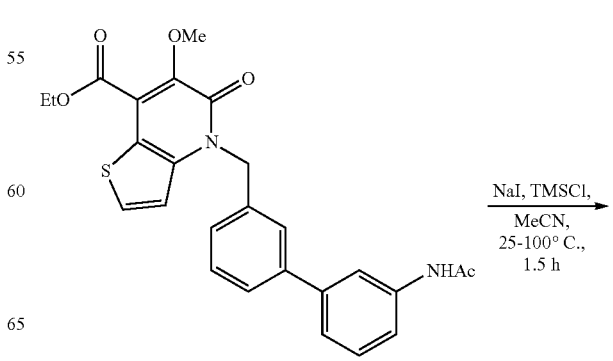

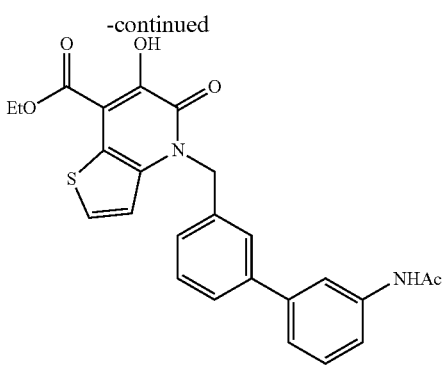

To a solution of sodium iodide (0.72 g, 4.8 mmol) in acetonitrile (23 mL) was added trimethylchlorosilane (0.52 g, 4.8 mmol) and the mixture solution was stirred at 25° C. for 12 min, followed by adding ethyl 4-((3'-acetamido-[1,1'-biphenyl]-3-yl)methyl)-6-methoxy-5-oxo-4,5-dihydrothieno[3,2-b]pyridine-7-carboxylate (0.15 g, 0.30 mmol). After stirring for 15 min, the mixture was heated at 100° C. for 1 hour. The reaction mixture was cooled to room temperature and then poured into ice water (50 mL) and extracted with ethyl acetate (2×80 mL). The combined organic were concentrated in vacuo. The residue was purified by column chromatography [dichloromethane:methanol=100:1-20:1] to give ethyl-4-[(3'-acetamido-[1,1'-biphenyl]-3-yl)methyl]-6-hydroxy-5-oxo-4,5-dihydrothieno[3,2-b]pyridine-7-carboxylate (0.25 g, crude) as yellow solid. LCMS: (ES+) m/z (M+H)$^+$=463.0.

Step 3: 4-[(3'-acetamido-[1,1'-biphenyl]-3-yl)methyl]-6-hydroxy-5-oxo-4,5-dihydrothieno[3,2-b]pyridine-7-carboxylic acid

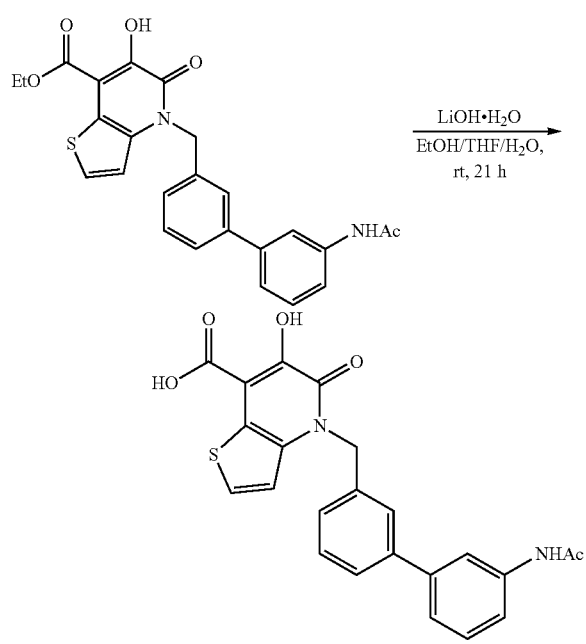

To a solution of ethyl-4-[(3'-acetamido-[1,1'-biphenyl]-3-yl)methyl]-6-hydroxy-5-oxo-4,5-dihydrothieno[3,2-b]pyridine-7-carboxylate (0.22 g, 0.48 mmol) in ethanol (5 mL), tetrahydrofuran (5 mL) and water (5 mL) was added lithium hydroxide monohydrate (0.10 g, 2.4 mmol). The solution was stirred at 25° C. for 21 hours. Upon competition, the reaction mixture was concentrated to dryness in vacuo. The residue was diluted with water (10 mL), the pH adjusted to 3-4 with 2 M hydrochloric acid and then extracted with ethyl acetate (50 mL×2). The organic layer was separated and concentrated. The residue was purified by preparative-HPLC [Instrument: GX-B; Phenomenex Synergi C18 150× 25 mm, particle size: 10 μm; Mobile phase: 20-50% acetonitrile in H$_2$O (add 0.1% TFA, v/v)]. Each set of collected fractions was concentrated to dryness at room temperature and lyophilized, and the desired fractions combined to give the title compound, Example 2, (40 mg, 19% yield) as a gray solid. LCMS: (ES+) m/z (M+H)$^+$=435.0; $^1$H NMR (DMSO-d$_6$, 400 MHz): δ 10.04 (s, 1H), 7.81 (s, 1H), 7.63-7.57 (m, 3H), 7.47 (d, J=8 Hz, 1H), 7.42-7.36 (m, 2H), 7.28-7.20 (m, 3H), 5.57 (s, 2H), 2.07 (s, 3H).

Example 3: 4-benzyl-6-hydroxy-5-oxo-4,5-dihydrothieno[3,2-b]pyridine-7-carboxylic acid

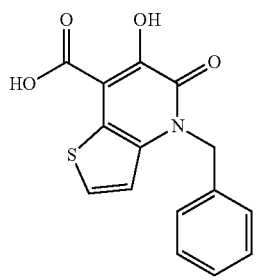

Step 1: ethyl 4-benzyl-6-methoxy-5-oxo-4,5-dihydrothieno[3,2-b]pyridine-7-carboxylate

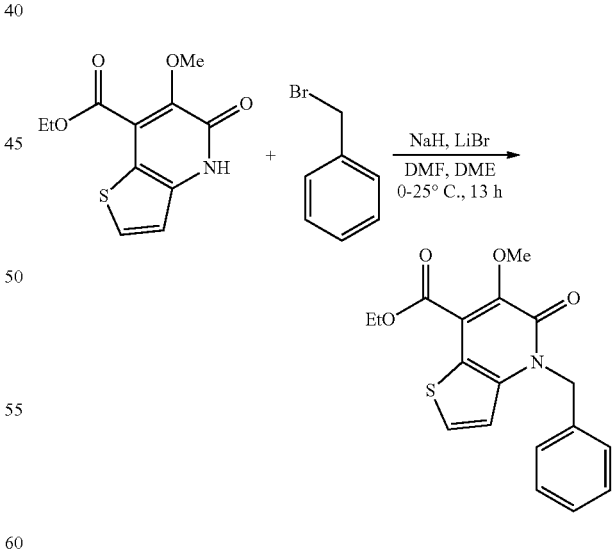

To a solution of Intermediate A (500 mg, 1.97 mmol) in dimethoxyethane (5.0 mL) and dimethyl formamide (100 μL) was added sodium hydride (118 mg, 2.96 mmol) at 0° C. for 10 mins. Then lithium bromide (513 mg, 5.91 mmol, 3.0 eq) was added into the reaction mixture and warmed to 25° C. for 20 mins, then (51 mg, 296 uμmol) was added into the mixture. The reaction was stirred at 25° C. for 12 hours.

The reaction mixture was poured into 30 mL of water and extracted with (30 mL×2) of dichloromethane. The organic layer was dried with sodium sulfate and concentrated under vacuum. The residue was purified by column chromatography (petroleum ether/ethyl acetate=7:1 to 5:1) to give compound ethyl 4-benzyl-6-methoxy-5-oxo-4,5-dihydrothieno[3,2-b]pyridine-7-carboxylate (240 mg, 36% yield). LCMS: (ES+) m/z (M+H)⁺=344.0

Step 2: 4-benzyl-6-methoxy-5-oxo-4,5-dihydrothieno[3,2-b]pyridine-7-carboxylic acid

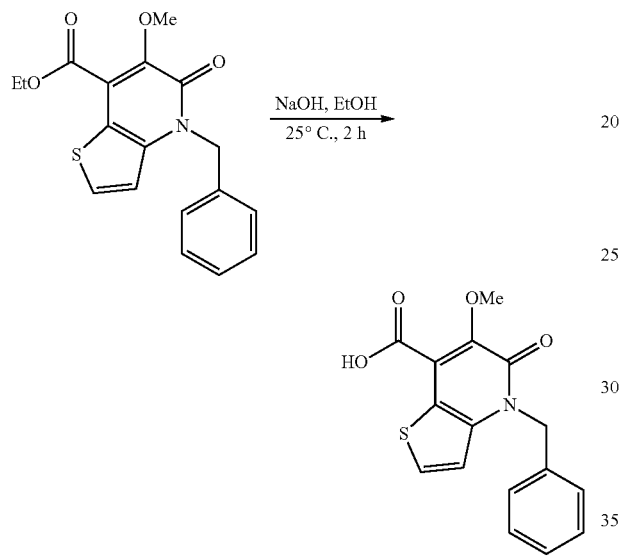

To a solution of ethyl 4-benzyl-6-methoxy-5-oxo-4,5-dihydrothieno[3,2-b]pyridine-7-carboxylate (240 mg, 699 μμmol) in ethanol (10 mL) was added sodium hydroxide (111.8 mg, 2.8 mmol). The mixture was stirred at 25° C. for 2 hours. Upon completion, the reaction mixture was concentrated to dryness under vacuum. To the residue was added 20 mL of 2N hydrochloric acid. The solid was filtered to give compound 4-benzyl-6-methoxy-5-oxo-4,5-dihydrothieno[3,2-b]pyridine-7-carboxylic acid (210 mg, 95% yield). LCMS: (ES+) m/z (M+H)⁺=316.1.

Step 3: 4-benzyl-6-hydroxy-5-oxo-4,5-dihydrothieno[3,2-b]pyridine-7-carboxylic acid

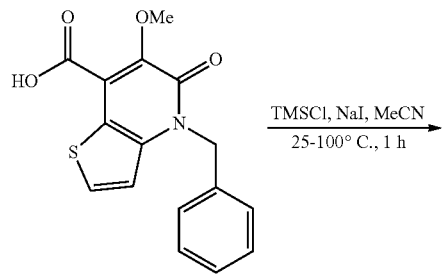

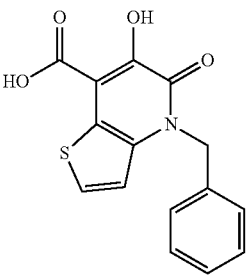 [SMILES: O=C(O)c1c(O)c(=O)n(Cc2ccccc2)c2ccsc12]

To a solution of sodium iodide (998 mg, 6.66 mmol) in acetonitrile (20 mL) was added trimethylchlorosilane (724 mg, 6.66 mmol). The mixture was stirred at 25° C. for 10 mins followed by addition of 4-benzyl-6-methoxy-7-oxo-thieno[3,2-b]pyridine-5-carboxylic acid (210 mg, 666 μμmol). After stirring for 20 mins at 25° C., the reaction mixture was heated to 100° C. for 1 hour. Upon completion the reaction was cooled to room temperature and was concentrated to dryness under vacuum. The residue was purified by preperative-HPLC (preperative-HPLC column: Phenomenex Synergi C18 150×25×10 um; mobile phase: [water (0.1% TFA)-ACN]; B %: 25%-55%, 11 min) and lyophilized to give the title compound, Example 3, (4.0 mg, 2% yield). LC-MS: (ES+) m/z (M+H)⁺=302.1; ¹H NMR (DMSO-d₆, 400 MHz): δ 7.55 (d, J=2.4 Hz, 1H), δ 7.34-7.18 (m, 5H), δ 5.50 (S, 1H).

Example 4: 6-hydroxy-5-oxo-4-(2-phenylethyl)-6,7-dihydrothieno[3,2-b]pyridine-7-carboxylic acid

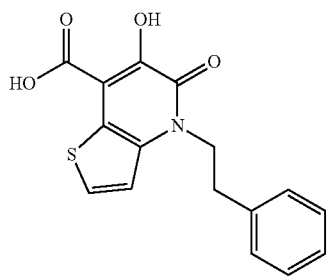 [SMILES: O=C(O)c1c(O)c(=O)n(CCc2ccccc2)c2ccsc12]

Step 1: ethyl-6-methoxy-5-oxo-4-(2-phenylethyl)thieno[3,2-b]pyridine-7-carboxylate

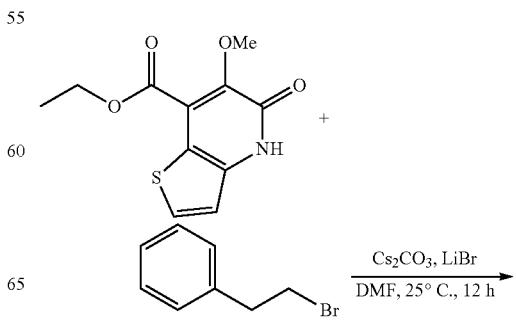

Step 3: 6-hydroxy-5-oxo-4-(2-phenylethyl)-6,7-dihydrothieno[3,2-b]pyridine-7-carboxylic acid

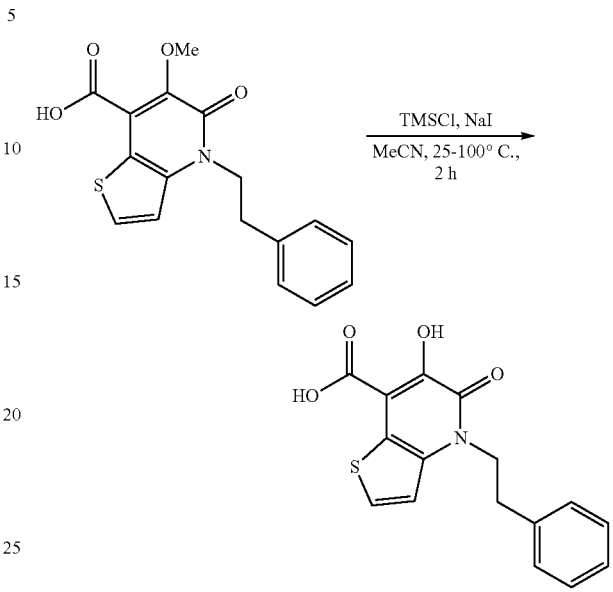

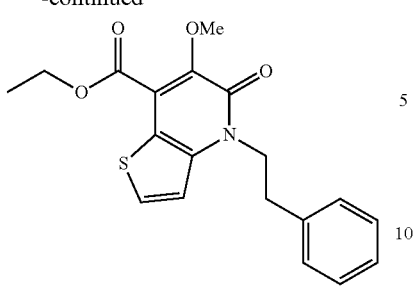

To a solution of Intermediate A (300 mg, 1.18 mmol) in N,N-dimethylformamide (10 mL) was added cesium carbonate (772 mg, 2.37 mmol) and lithium bromide (309 mg, 3.55 mmol). The solution was stirred at 25° C. for 30 min. Then 2-bromoethylbenzene (329 mg, 1.78 mmol) was added into the above solution. The resulting mixture was stirred 12 hours at 25° C. Upon completion the mixture was evaporated in vacuo. The crude residue was purified by flash chromatographic column (petroleum ether/ethyl acetate=3:1) to give ethyl-6-methoxy-5-oxo-4-(2-phenylethyl)thieno[3,2-b]pyridine-7-carboxylate (70 mg, μmol 17% yield) as a white solid. LCMS: (ES+) m/z (M+H)$^+$=385.2.

Step 2: 6-methoxy-5-oxo-4-(2-phenylethyl)thieno[3,2-b]pyridine-7-carboxylic acid

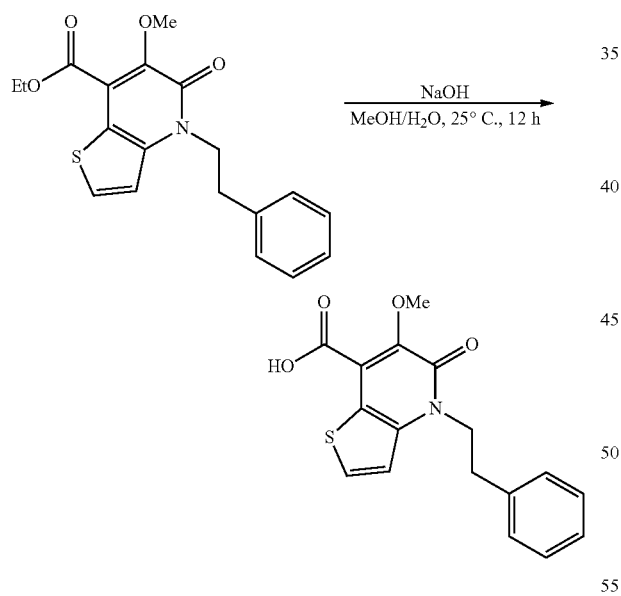

To a solution of ethyl-6-methoxy-5-oxo-4-(2-phenylethyl)thieno[3,2-b]pyridine-7-carboxylate (70 mg, 196 μμmol) in water (3 mL) and methanol (3 mL) was added sodium hydroxide (12 mg, 294 μμmol) at 25° C. and the reaction mixture was stirred for 12 h. The methanol was evaporated and 10 ml of 1M hydrochloric acid was added to the residue. The solution was extracted with dichloromethane (20 mL×3). The organic phase was evaporated to give 6-methoxy-5-oxo-4-(2-phenylethyl)thieno[3,2-b]pyridine-7-carboxylic acid (50 mg, 152 μmol, 78% yield) as white solid. LCMS: (ES+) m/z (M+H)$^+$=330.0

To a solution of sodium iodide (273 mg, 1.82 mmol) in acetonitrile (3 mL) was added trimethylchlorosilane (198 mg, 1.82 mmol) at room temperature under nitrogen. The mixture was stirred at 25° C. for 1 hour. Then 6-methoxy-5-oxo-4-(2-phenylethyl)thieno[3,2-b]pyridine-7-carboxylic acid (60 mg, 182 μμmol) was added to the above solution. The reaction mixture was heated to 100° C. and stirred 1 hour. Upon completion the reaction was cooled to room temperature and concentrated in vacuo. The crude residue was purified by preperative-HPLC (column: Phenomenex Synergi C18 150×25×10 μm; mobile phase: [water (0.1% TFA)-ACN]; B-%: 24%-54%, 13 min) to give the title compound, Example 4, (16.7 mg, 52.6 μμmol, 29% yield) as a green solid. $^1$H NMR (CD$_3$OD, 400 MHz) δ 7.59 (d, J=6 Hz, 1H), 7.21-7.28 (m, 5H), 7.17 (d, J=6 Hz, 1H), 4.54 (t, J=7.6 Hz, 2H), 3.08 (t, J=7.6 Hz 2H).

Example 5: 4-(4-bromobenzyl)-6-hydroxy-5-oxo-4,5-dihydrothieno[3,2-b]pyridine-7-carboxylic acid

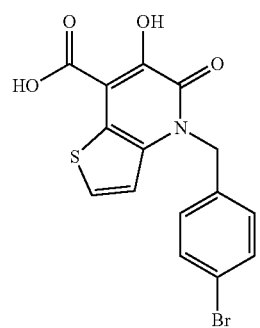

Step 1: ethyl 4-(4-bromobenzyl)-6-methoxy-5-oxo-4,5-dihydrothieno[3,2-b]pyridine-7-carboxylate

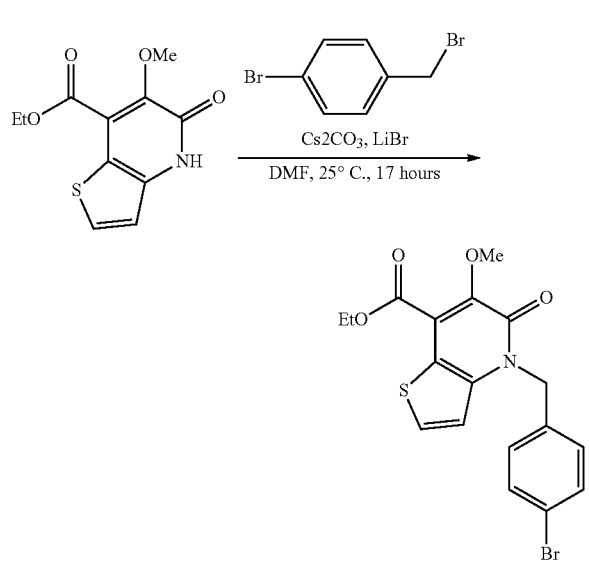

A solution of Intermediate A (500 mg, 1.97 mmol) in DMF (10 mL) was added Cs$_2$CO$_3$ (1.28 g, 3.94 mmol) and LiBr (513 mg, 5.91 mmol) and then the solution was stirred at 25° C. for 30 min. 1-Bromo-4-(bromomethyl)benzene (739 mg, 2.96 mmol) was added to the above solution. The reaction mixture was stirred at 25° C. for 17 hours. On completion, the solution was poured into saturated aqueous NH$_4$Cl solution (50 mL) and washed by water (50 mL). Then the solution was extracted with ethyl acetate (2×50 mL). The organic layer was concentrated to dryness in vacuo. The residue was purified by column chromatography [dichloromethane/methanol=20:1 to 10:1] to give ethyl 4-(4-bromobenzyl)-6-methoxy-5-oxo-4,5-dihydrothieno[3,2-b]pyridine-7-carboxylate (550 mg, 1.30 mmol, 66% yield) as yellow solid. $^1$H NMR (DMSO-d$_6$, 400 MHz): δ 7.9 (d, J=5.33 Hz, 1H), 7.52 (m, 2H), 7.31 (d, J=5.65 Hz, 1H), 7.24 (d, J=8.41 Hz, 2H), 5.46 (s, 2H), 4.42 (q, J=5.25 Hz, 2H), 3.91 (s, 3H), 1.37 (t, J=14.18 Hz, 3H). LCMS: (ES+) m/z (M+H)$^+$=423.0.

Step 2: ethyl-4-(4-bromobenzyl)-6-hydroxy-5-oxo-4,5-dihydrothieno[3,2-b]pyridine-7-carboxylate

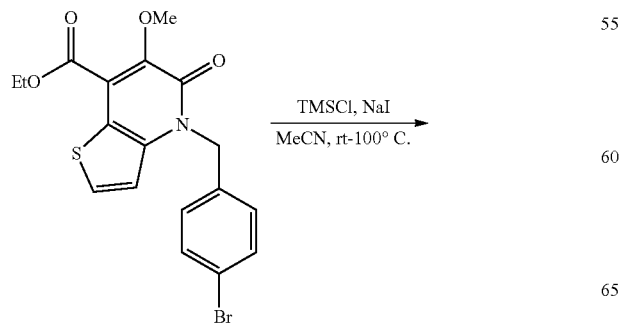

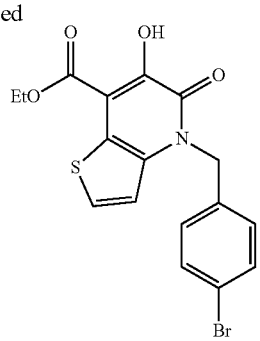

To a solution of TMSCl (363 mg, 3.34 mmol) in CH$_3$CN (3 mL) was added NaI (501 mg, 3.34 mmol) under nitrogen. The reaction mixture was stirred at 25° C. for 1 h and then ethyl 4-(4-bromobenzyl)-6-methoxy-5-oxo-4,5-dihydrothieno[3,2-b]pyridine-7-carboxylate (141 mg, 334 μμmol) was added. The mixture was heated to 100° C. and stirred for 1 h. On completion, the solution was evaporated under reduced pressure, then washed by water (50 mL) and extracted with dichloromethane (20 mL×3) and the mixture was evaporated in vacuo. The residue was purified by column chromatography (dichloromethane/methanol=20:1) to give compound ethyl-4-(4-bromobenzyl)-6-hydroxy-5-oxo-4,5-dihydrothieno[3,2-b]pyridine-7-carboxylate (74 mg, 54% yield) as yellow solid. LCMS: (ES+) m/z (M+H)$^+$=410.0.

Step 3: 4-(4-bromobenzyl)-6-hydroxy-5-oxo-4,5-dihydrothieno[3,2-b]pyridine-7-carboxylic acid

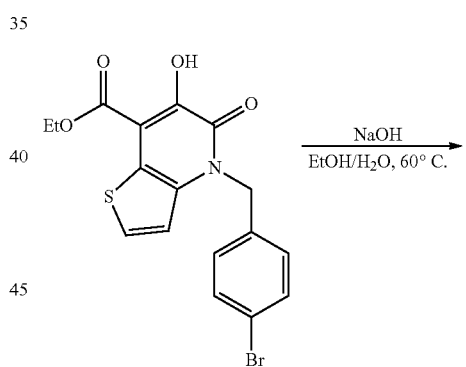

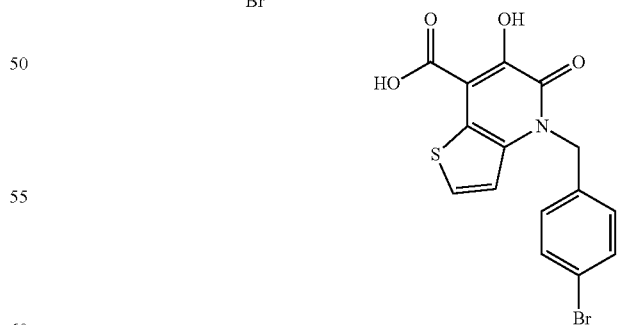

To a mixture of ethyl-4-(4-bromobenzyl)-6-hydroxy-5-oxo-4,5-dihydrothieno[3,2-b]pyridine-7-carboxylate (74 mg, 181 μμmol) and ethanol (5 mL) in water (2 mL) was added sodium hydroxide (22 mg, 544 μmol). Then the mixture was stirred at 60° C. for 16 h. On completion, the solution was evaporated to remove ethanol and diluted with water (20 ml). The solution was adjusted pH to 3-4 with 1N hydrochloric acid, extracted with ethyl acetate (30 mL×3) and the organic layer was concentrated to dryness in vacuo. The residue was purified by preperative-HPLC (column: Phenomenex Synergi C18 150×25×10 um; mobile phase: [water (0.1% TFA)-ACN]; B %: 29%-59%, 13 min) to give the title compound, Example 5, (15 mg, 22% yield) as white solid. LCMS: (ES+) m/z (M+H)$^+$=381.0; 1H NMR (DMSO-d$_6$, 400 MHz) δ 7.55 (d, J=5.6 Hz, 1H), 7.45 (d, J=7.6 2H), 7.19 (m, 3H), 5.56 (s, 2H).

Example 6: 6-hydroxy-4-[(3-nitrophenyl)methyl]-5-oxo-thieno[3,2-b]pyridine-7-carboxylic acid

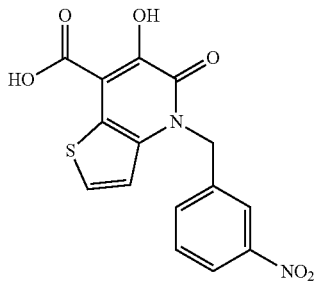 [SMILES: O=C(O)c1c(O)c(=O)n(Cc2cccc([N+](=O)[O-])c2)c2ccsc12]

Step 1: ethyl-6-methoxy-4-[(3-nitrophenyl)methyl]-5-oxo-6,7-dihydrothieno[3,2-b]pyridine-7-carboxylate

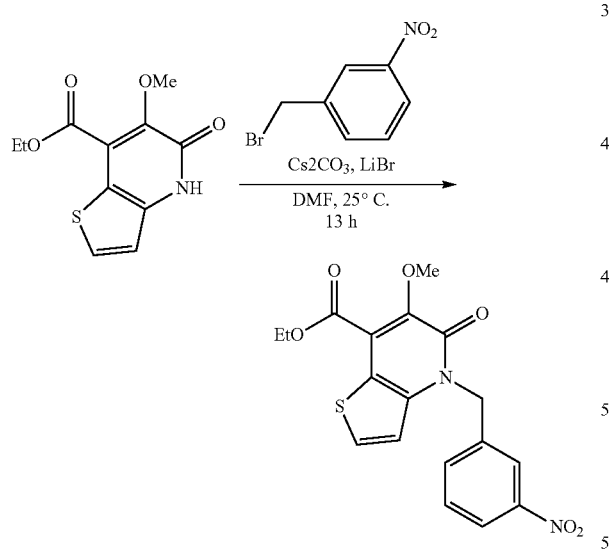

To a solution of ethyl 6-methoxy-5-oxo-4H-thieno[3,2-b]pyridine-7-carboxylate (500 mg, 1.97 mmol) in N,N-dimethylformamide (10 mL) was added cesium carbonate (1.28 g, 3.94 mmol) and lithium bromide (513 mg, 5.91 mmol) under nitrogen. The mixture was stirred at 25° C. for 30 min and then 1-(bromomethyl)-3-nitro-benzene (638 mg, 2.96 mmol) was added to the reaction mixture. The resulting solution was stirred at 25° C. for 12.5 hours. To the mixture was added water (10 mL) and extracted with ethyl acetate (10 mL×3). The organic phase was evaporated under vacuum. The crude product was purified by flash chromatographic column (petroleum ether/ethyl acetate=5:1 to give ethyl-6-methoxy-4-[(3-nitrophenyl)methyl]-5-oxo-6,7-dihydrothieno[3,2-b]pyridine-7-carboxylate (450 mg, 1.15 mmol, 59% yield) as a yellow solid. LCMS: (ES+) m/z (M+H)$^+$=389.1.

Step 2: ethyl-6-hydroxy-4-[(3-nitrophenyl)methyl]-5-oxo-6,7-dihydrothieno[3,2-b]pyridine-7-carboxylate

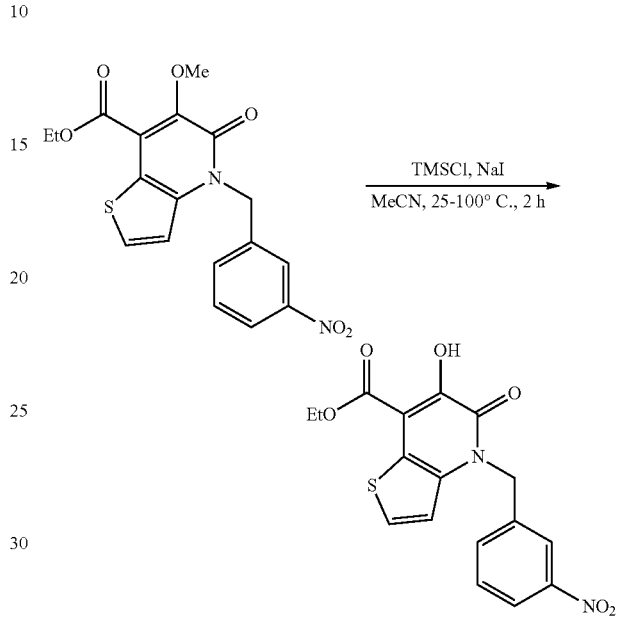

To a solution of sodium iodide (960 mg, 6.40 mmol) in acetonitrile (3.0 mL) was added trimethylchlorosilane (6968 mg, 6.40 mmol) under nitrogen. The reaction was stirred at 25° C. for 1 hour. Then ethyl-6-methoxy-4-[(3-nitrophenyl)methyl]-5-oxo-6,7-dihydrothieno[3,2-b]pyridine-7-carboxylate (250 mg, 640 μmol) was added to the above solution. The mixture was heated to 100° C. and stirred 1 h. Upon completion the mixture was cooled to room temperature and the residue was added into saturated aqueous sodium thiosulfate solution (30 mL). The aqueous was extracted with ethyl acetate (30 mL×3). The organic phase was concentrated to dryness under reduced pressure to give ethyl-6-hydroxy-4-[(3-nitrophenyl)methyl]-5-oxo-6,7-dihydrothieno[3,2-b]pyridine-7-carboxylate (200 mg, 531 μmol, 83% yield) as a yellow solid. LCMS: (ES+) m/z (M+H)$^+$= 375.0.

Step 3: 6-hydroxy-4-[(3-nitrophenyl)methyl]-5-oxo-thieno[3,2-b]pyridine-7-carboxylic acid

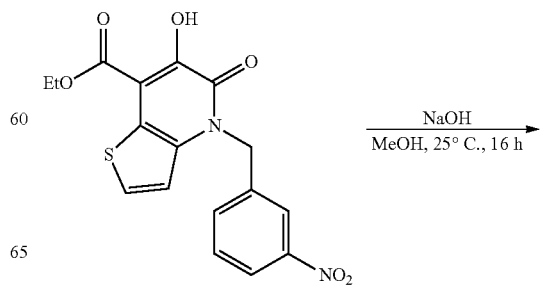

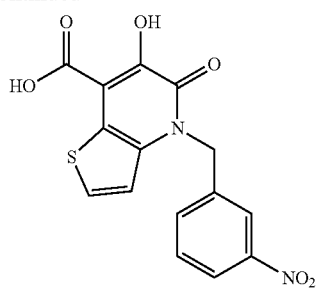

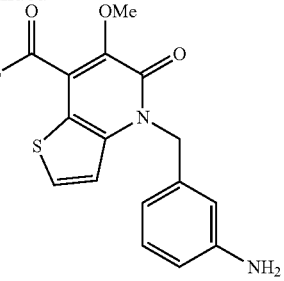

To a solution of ethyl-6-hydroxy-4-[(3-nitrophenyl)methyl]-5-oxo-6,7-dihydrothieno[3,2-b]pyridine-7-carboxylate (50 mg, 134 μmol) in the methanol (10 mL) was added sodium hydroxide (16 mg, 401 μmol). The reaction mixture was stirred at 25° C. for 16 h. Upon completion, the mixture was cooled to room temperature and to the residue was added into 1M hydrochloric acid (50 mL) and filtered to get the filter cake. The crude product was purified by preperative-HPLC column: Phenomenex Synergi C18 150× 25×10 um; mobile phase: [water (0.1% TFA) ACN]; B %: 20%-50%, 11 min) to give the title compound, Example 6 (40 mg, 87% yield). LCMS: (ES+) m/z (M+H)$^+$=346.9; $^1$H NMR (DMSO-d$_6$, 400 MHz) δ 9.72 (br s, 1H), 8.22 (s, 2H), 8.14 (d, J=8H, 1H), 7.71 (d, J=8 Hz, 1H), 7.61-7.65 (m, 2H), 7.30 (d, J=5.6 Hz, 1H), 5.64 (s, 2H).

To a solution of ethyl 6-methoxy-4-[(3-nitrophenyl)methyl]-5-oxo-thieno[3,2-b]pyridine-7-carboxylate (170 mg, 438 μmol) in acetic acid (1 mL) was added iron (245 mg, 4.4 mmol) and the reaction mixture was stirred at 25° C. for 12 h. Upon completion the reaction mixture was evaporated under vacuum. Water (10 mL) was added to the residue and the aqueous layer then extracted by dichloromethane (3×10 mL). The organic phase was washed with 1M sodium hydroxide (20 mL) and the organic layer was separated and concentrated in vacuo. The crude mixture was purified by column chromatography (petroleum ether/ethyl acetate=3:1) to give ethyl-4-[(3-aminophenyl)methyl]-6-methoxy-5-oxo-thieno[3,2-b]pyridine-7-carboxylate (120 mg, 76% yield) as a red solid. LCMS: (ES+) m/z (M+H)$^+$=359.0

Step 2: ethyl-4-[(3-acetamidophenyl)methyl]-6-methoxy-5-oxo-thieno[3,2-b]pyridine-7-carboxylate Example 7: 4-[(3-acetamidophenyl)methyl]-6-hydroxy-5-oxo-thieno[3,2-b]pyridine-7-carboxylic acid

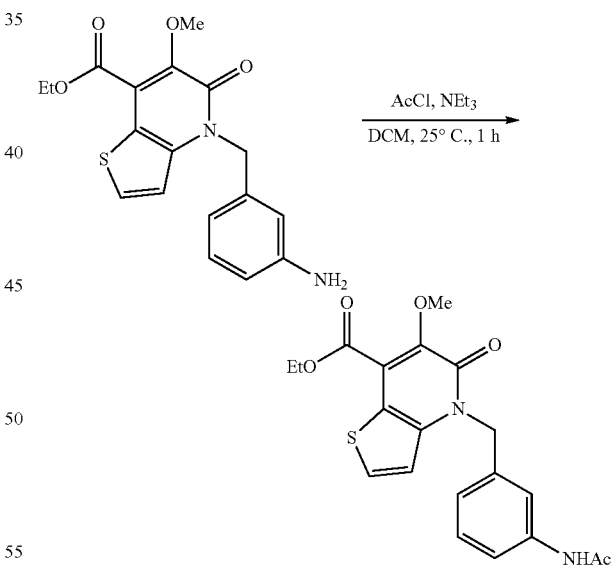

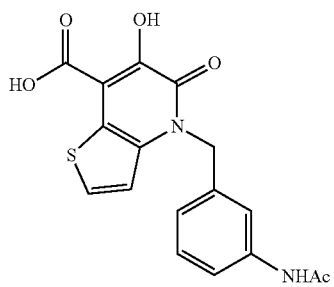 [SMILES: CC(=O)Nc1cccc(Cn2c(=O)c(O)c(C(=O)O)c3sccc32)c1]

Step 1: ethyl-4-[(3-aminophenyl)methyl]-6-methoxy-5-oxo-thieno[3,2-b]pyridine-7-carboxylate

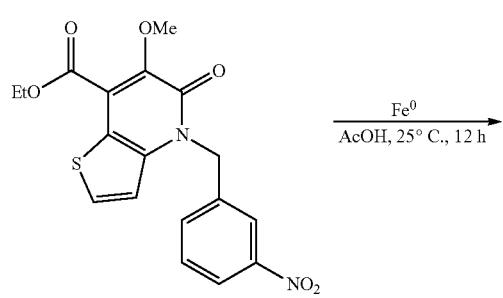

To a solution of ethyl-4-[(3-aminophenyl)methyl]-6-methoxy-5-oxo-thieno[3,2-b]pyridine-7-carboxylate (120 mg, 335 μmol) in dichloromethane (10 mL) was added triethylamine (68 mg, 670 μmol, 93 μL) and acetylchloride (50 mg, 670 μmol). The resulting solution was stirred at 25° C. for 1 h. The mixture was concentrated to dryness under vacuum to give ethyl-4-[(3-acetamidophenyl)methyl]-6-methoxy-5-oxo-thieno[3,2-b]pyridine-7-carboxylate (120 mg, 300 μmol, 90% yield) as a brown solid. LCMS: (ES+) m/z (M+H)$^+$=401.2.

Step 3: ethyl-4-[(3-acetamidophenyl)methyl]-6-hydroxy-5-oxo-thieno[3,2-b]pyridine-7-carboxylate

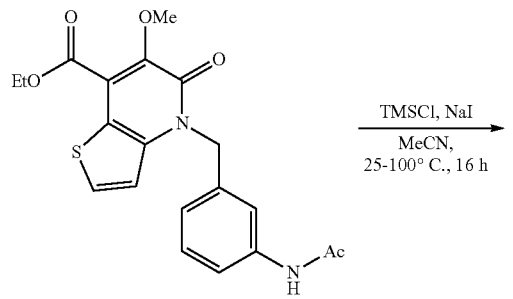

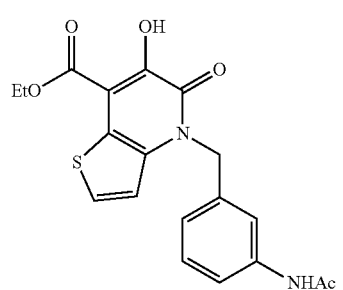

To a solution of sodium iodide (412 mg, 2.8 mmol) in acetonitrile (1.0 mL) was added trimethylchlorosilane (298 mg, 2.8 mmol, 347 uL). The resulting solution was stirred at 25° C. for 1 h. Then ethyl-4-[(3-acetamidophenyl)methyl]-6-methoxy-5-oxo-thieno[3,2-b]pyridine-7-carboxylate (110 mg, 275 μmol) was added and heated to 100° C. for 16 h. Upon completion, the mixture was evaporated, saturated aqueous sodium thiosulfate (30 mL) was added and the aqueous layer was extracted with ethyl acetate (3×30 mL). The organic phase was concentrated to dryness by vacuum to give ethyl-4-[(3-acetamidophenyl)methyl]-6-hydroxy-5-oxo-thieno[3,2-b]pyridine-7-carboxylate (50 mg, 130 μmol, 47% yield) as a yellow solid. LCMS: (ES+) m/z (M+H)+= 387.1.

Step 4: 4-[(3-acetamidophenyl)methyl]-6-hydroxy-5-oxo-thieno[3,2-b]pyridine-7-carboxylic acid

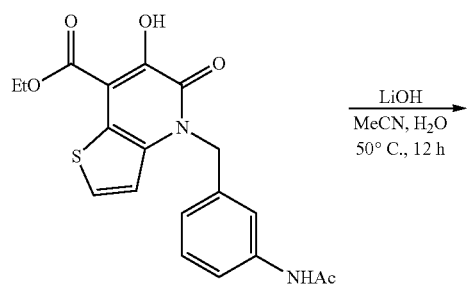

-continued

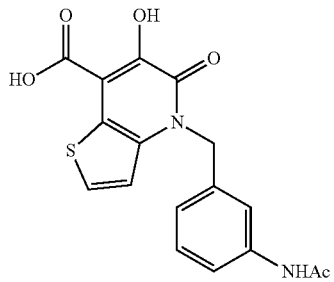

To a solution of ethyl-4-[(3-acetamidophenyl)methyl]-6-hydroxy-5-oxo-thieno[3,2-b]pyridine-7-carboxylate (100 mg, 259 μmol) in methanol (5 mL) and water (5 mL) was added lithium hydroxide (31 mg, 1.3 mmol). The mixture was stirred at 50° C. for 12 hours. The methanol was evaporated. To the residue was added 1M hydrochloric acid (20 mL) and the mixture was extracted with ethyl acetate (3×30 mL). The combined organic extracts were concentrated under reduced pressure. The crude product was purified by preperative-HPLC (column: Phenomenex Synergi C18 150 mm×25 mm×10 um; mobile phase: [water (0.1% TFA)-ACN]; B %: 13%-43%, 13 min) to give the title compound, Example 7, (5.0 mg, 14 μmol, 5% yield) as a green solid. m/z $^1$H NMR (DMSO-$d_6$, 400 MHz): δ 9.91 (s, 1H), 7.59 (t, J=6 Hz, 2H), 7.26 (d, J=12 Hz, 2H), 7.14 (d, J=5.6 Hz, 1H), 6.98 (d, J=7.6 Hz, 1H), 5.47 (s, 2H), 1.98 (s, 3H); LCMS: (ES+) m/z (M+H)+=359.0.

Example 8: 6-hydroxy-5-oxo-4-(tetrahydrofuran-2-ylmethyl)thieno[3,2-b]pyridine-7-carboxylic acid

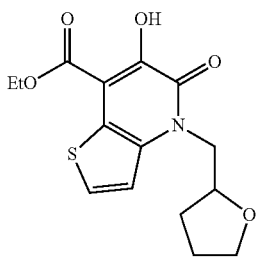 [SMILES: CCOC(=O)c1c(O)c(=O)n(CC2CCCO2)c2ccsc12]

Step 1: ethyl-6-benzyloxy-5-oxo-4-(tetrahydrofuran-2-ylmethyl)thieno[3,2-b]pyridine-7-carboxylate

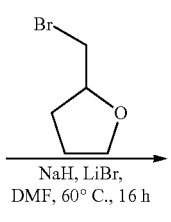

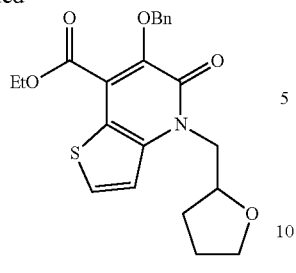

To a solution of Intermediate C (200 mg, 607 μmol) in DMF (5 mL) and LiBr (158 mg, 1.8 mmol, 46 μL) was added NaH (49 mg, 1.2 mmol). The mixture was stirred at 25° C. for 30 min. Then 2-(bromomethyl)tetrahydrofuran (301 mg, 1.8 mmol) was added to the above solution. The mixture was stirred at 60° C. for 16 h. On completion, the solution was quenched with saturated aqueous NH$_4$Cl (20 mL). The solution was extracted with ethyl acetate (20 mL×3) and the extracts were evaporated under reduced pressure. The solution was purified by preperative TLC (petroleum ether/ethyl acetate=3:1) to give compound ethyl-6-benzyloxy-5-oxo-4-(tetrahydrofuran-2-ylmethyl)thieno[3,2-b]pyridine-7-carboxylate (20 mg, 48 μmol, 8% yield) as a pale yellow solid. LCMS: (ES$^+$) m/z (M+H)$^+$=414.0

Step 2: ethyl-6-hydroxy-5-oxo-4-(tetrahydrofuran-2-ylmethyl)thieno[3,2-b]pyridine-7-carboxylate

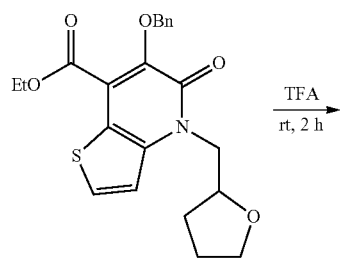

To a solution of ethyl 6-benzyloxy-5-oxo-4-(tetrahydrofuran-2-ylmethyl)thieno[3,2-b]pyridine-7-carboxylate (20 mg, 48 μmol) in TFA (3 mL) was stirred at 25° C. for 2 h. On completion, the solution was evaporated under reduced pressure to provide ethyl-6-hydroxy-5-oxo-4-(tetrahydrofuran-2-ylmethyl)thieno[3,2-b]pyridine-7-carboxylate. The crude was used in the next step without further purification. LCMS: (ES$^+$) m/z (M+H)$^+$=324.0

Step 3: 6-hydroxy-5-oxo-4-(tetrahydrofuran-2-ylmethyl)thieno[3,2-b]pyridine-7-carboxylic acid

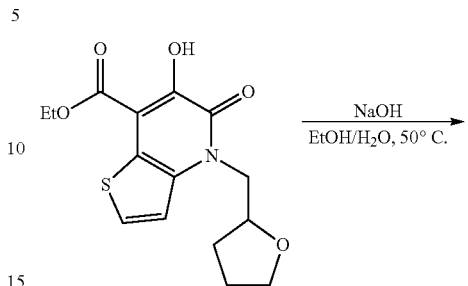

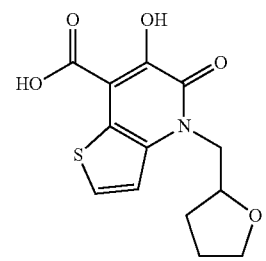

To a solution of ethyl 6-hydroxy-5-oxo-4-(tetrahydrofuran-2-ylmethyl)thieno[3,2-b]pyridine-7-carboxylate (20 mg, 62 μmol) in H$_2$O (1 mL) and EtOH (1 mL) was added NaOH (7.4 mg, 186 μmol). The mixture was stirred at 50° C. for 16 hours. On completion, the solution was evaporated under reduced pressure. The residue was adjusted pH 5 with 1M hydrochloric acid solution, extracted with ethyl acetate (3×20 mL) and the combined organic extracts were evaporated. The residue was purified by preperative-HPLC (column: Phenomenex Synergi C18 150*25*10 μm; mobile phase: [water (0.1% TFA)-ACN]; B %: 12%-42%, 13 min) to give the title compound, Example 8, (15 mg, 82% yield) as a white solid. $^1$H NMR (CD$_3$OD, 400 MHz): δ 7.59 (d, J=5.6, 1H), 7.33 (d, J=5.6 Hz, 1H), 4.43 (t, J=8, 3H), 3.89 (q, J=7.6, 1H), 3.73 (s, 1H), 2.11 (d, J=6, 1H), 1.97 (t, J=7.6, 2H), 1.82 (s, 1H); LCMS: (ES$^+$) m/z (M+H)$^+$=296.0.

Example 9: 4-[(1-acetyl-4-piperidyl)methyl]-6-hydroxy-5-oxo-thieno[3,2-b]pyridine-7-carboxylic acid

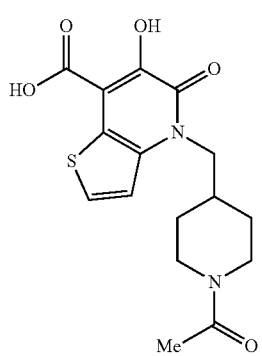 [SMILES: CC(=O)N1CCC(Cn2c(=O)c(O)c(C(=O)O)c3sccc32)CC1]

Step 1: ethyl-6-benzyloxy-4-[(1-tert-butoxycarbonyl-4-piperidyl)methyl]-5-oxo-thieno[3,2-b]pyridine-7-carboxylate

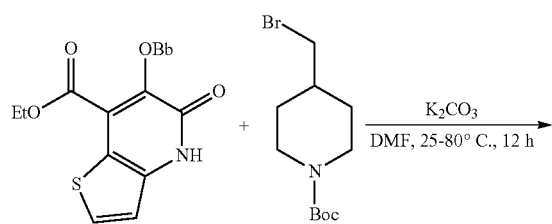

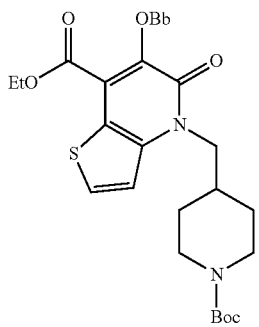

To a solution of Intermediate C (550 mg, 1.67 mmol) in N,N-dimethylformamide (15 mL) was added potassium carbonate (692 mg, 5.01 mmol) and stirred 30 min at 25° C., then tert-butyl 4-(bromomethyl)piperidine-1-carboxylate (697 mg, 2.50 mmol) was added and stirred at 80° C. for 12 hours. To the mixture was added water (30 mL) and the aqueous phase was extracted with ethyl acetate (3×20 mL). The combined organic extracts were concentrated, and the crude product was purified by column chromatography (Petroleum ether/Ethyl acetate=7:1 to 3:1) to give ethyl-6-benzyl oxy-4-[(1-tert-butoxycarbonyl-4-piperidyl)methyl]-5-oxo-thieno[3,2-b]pyridine-7-carboxylate (600 mg, 68% yield) as a yellow solid. LCMS: (ES+) m/z (M+H)$^+$=471.1

Step 2: ethyl-6-benzyloxy-5-oxo-4-(4-piperidylmethyl)thieno[3,2-b]pyridine-7-carboxylate

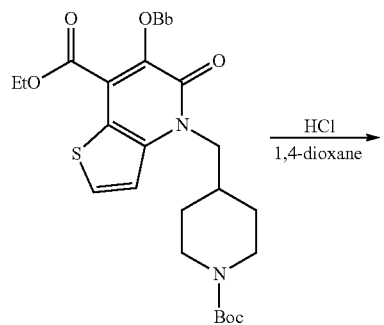

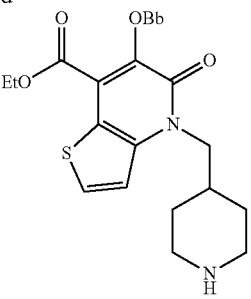

A solution of ethyl-6-benzyloxy-4-[(1-tert-butoxycarbonyl-4-piperidyl)methyl]-5-oxo-thieno[3,2-b]pyridine-7-carboxylate (200 mg, 379.77 µmol) in 4 M hydrochloric acid/dioxane (20 mL, 80 mmol) and stirred at 25° C. for 1 h. The mixture was then concentrated under vacuum to provide ethyl-6-benzyloxy-5-oxo-4-(4-piperidylmethyl)thieno[3,2-b]pyridine-7-carboxylate (150 mg, 93% yield) as a yellow solid. The material was used in the next reaction without further purification.

Step 3: ethyl-4-[(1-acetyl-4-piperidyl)methyl]-6-benzyloxy-5-oxo-thieno[3,2-b]pyridine-7-carboxylate

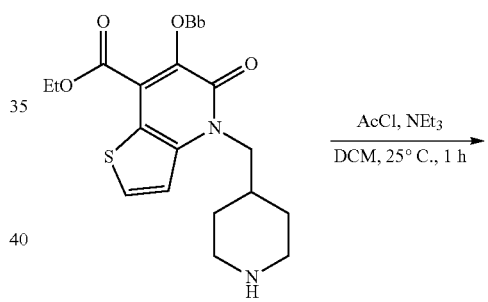

A solution of ethyl-6-benzyloxy-5-oxo-4-(4-piperidylmethyl)thieno[3,2-b]pyridine-7-carboxylate (150 mg, 352 µmol, 1.0 eq) in dichloromethane (10 mL) was added triethylamine (142 mg, 1.41 mmol, 195.00 uL), acetyl chloride (33 mg, 422 µmol) and stirred at 25° C. for 1 h. The mixture was concentrated to dryness to give ethyl-4-[(1-acetyl-4-piperidyl)methyl]-6-benzyloxy-5-oxo-thieno[3,2-b]pyridine-7-carboxylate (150 mg, 91% yield) as a green solid. The material was used in the next reaction without further purification.

Step 4: 4-[(1-acetyl-4-piperidyl)methyl]-6-benzy-loxy-5-oxo-thieno[3,2-b]pyridine-7-carboxylic acid

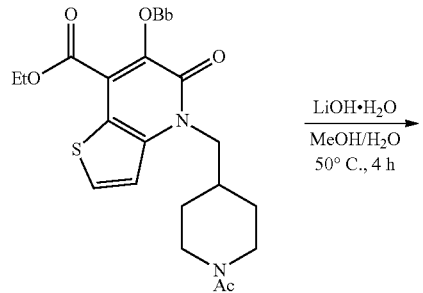

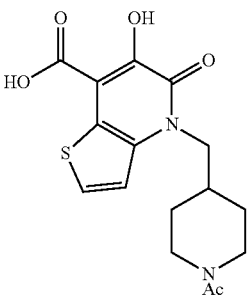

To a solution of ethyl-4-[(1-acetyl-4-piperidyl)methyl]-6-benzyloxy-5-oxo-thieno[3,2-b]pyridine-7-carboxylate (100 mg, 213 µmol) in water (5 mL) and methyl alcohol (5 mL) was added lithium hydroxide monohydrate (15 mg, 640 µmol) and stirred at 50° C. at 4 h. The solvent was evaporated and 1M hydrochloric acid (10 mL) was added and the aqueous mixture was extracted with ethyl acetate (3×20 mL) and the organic phase was concentrated to dryness to give 4-[(1-acetyl-4-piperidyl)methyl]-6-benzyloxy-5-oxo-thieno[3,2-b]pyridine-7-carboxylic acid (80 mg, 85% yield) as a brown oil. LCMS: (ES+) m/z (M+H)⁺=441.1.

A solution of 4-[(1-acetyl-4-piperidyl)methyl]-6-benzyloxy-5-oxo-thieno[3,2-b]pyridine-7-carboxylic acid (80 mg, 182 µmol) in trifluoroacetic acid (1 mL) and stirred at 25° C. for 48 min. The mixture was concentrated to dryness in vacuo. The crude product was purified by preperative-HPLC (column: Phenomenex Synergi C18 150×25×10 µm; mobile phase: [water (0.1% TFA)-ACN]; B %: 5%-35%, 11 min) to give the title compound, Example 9, (16 mg, 46 µmol, 25% yield). $^1$H NMR (400 MHz, CD$_3$OD) δ 7.63 (d, J=5.6 Hz, 1H), 7.32 (d, J=5.6 Hz, 1H), 4.52 (d, J=14.4 Hz, 1H), 4.31 (d, J=8.4 Hz, 1H), 3.93 (d, J=14.0 Hz, 1H), 3.05 (d, J=12.0 Hz, 1H), 2.59 (d, J=10.8 Hz, 1H), 2.25 (d, J=7.6 Hz, 1H), 2.10 (s, 3H), 1.69 (s, 2H), 1.32-1.45 (m, 2H); LCMS: (ES+) m/z (M+H)⁺=351.

Example 10: 6-hydroxy-5-oxo-4-(4-piperidylmethyl)thieno[3,2-b]pyridine-7-carboxylic acid Step 5: 4-[(1-acetyl-4-piperidyl)methyl]-6-hydroxy-5-oxo-thieno[3,2-b]pyridine-7-carboxylic acid

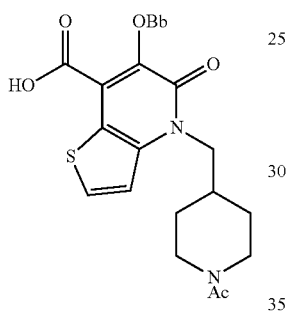

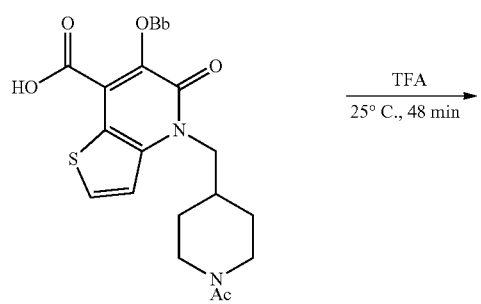

Step 1: ethyl-6-benzyloxy-4-[(1-tert-butoxycarbonyl-4-piperidyl)methyl]-5-oxo-thieno[3,2-b]pyridine-7-carboxylate

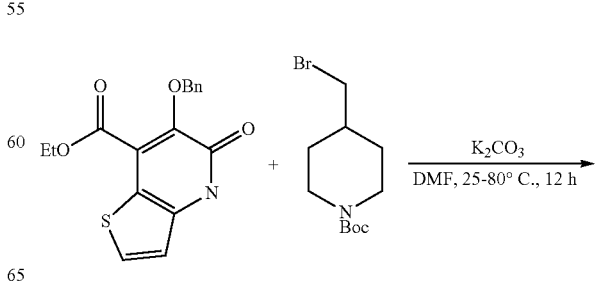

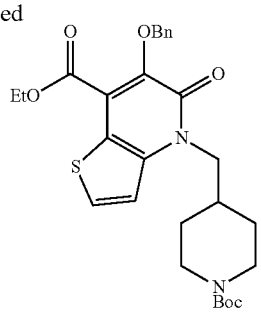

To a solution of ethyl 6-benzyloxy-5-oxo-4H-thieno[3,2-b]pyridine-7-carboxylate (230 mg, 698 μmol) in N,N-dimethylformamide (15 mL) was added potassium carbonate (290 mg, 2.09 mmol). The mixture was stirred 30 min at 25° C., then the tert-butyl 4-(bromomethyl) piperidine-1-carboxylate (291 mg, 1.05 mmol) was added and stirred at 80° C. for 12 hours. The mixture was added water 30 mL and extracted with ethyl acetate (3×20 mL). and the organic phase was concentrated. The crude product was purified by column chromatography (petroleum ether/ethyl acetate=7:1-3:1) to give ethyl-6-benzyloxy-4-[(1-tert-butoxycarbonyl-4-piperidyl)methyl]-5-oxo-thieno[3,2-b]pyridine-7-carboxylate (300 mg, 82% yield) as a yellow solid.

Step 2: ethyl-4-[(1-tert-butoxycarbonyl-4-piperidyl)methyl]-6-hydroxy-5-oxo-thieno[3,2-b]pyridine-7-carboxylate

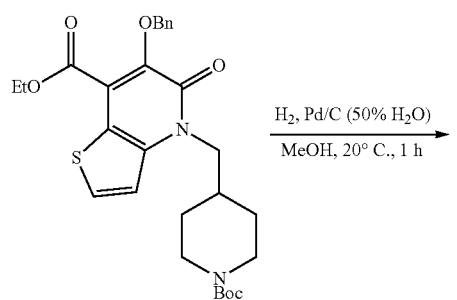

To a solution of ethyl-6-benzyloxy-4-[(1-tert-butoxycarbonyl-4-piperidyl)methyl]-5-oxo-thieno[3,2-b]pyridine-7-carboxylate (100 mg, 190 μmol) in methanol (5 mL) was added palladium on carbon (50 mg, 190 μmol, 10% purity) and stirred at 20° C. for 1 h under an atmosphere of hydrogen. The mixture was filtered and the organic phase was concentrated to dryness to give ethyl-4-[(1-tert-butoxycarbonyl-4-piperidyl)methyl]-6-hydroxy-5-oxo-thieno[3,2-b]pyridine-7-carboxylate (80 mg, 97% yield) as a yellow solid.

Step 3: 4-[(1-tert-butoxycarbonyl-4-piperidyl)methyl]-6-hydroxy-5-oxo-thieno[3,2-b]pyridine-7-carboxylic acid

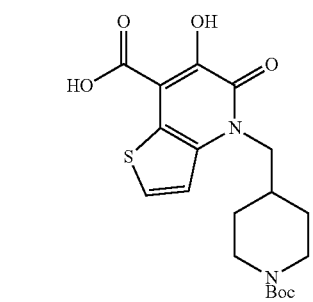 [SMILES: O=C(O)c1c(O)c(=O)n(CC2CCNCC2)c2ccsc12]

To a solution of ethyl-4-[(1-tert-butoxycarbonyl-4-piperidyl)methyl]-6-hydroxy-5-oxo-thieno[3,2-b]pyridine-7-carboxylate (80 mg, 183 μmol) in methanol (5 mL) and water (5 mL) was added sodium hydroxide (22 mg, 550 μmol) and the reaction was stirred at 50° C. for 10 h. The solvent was evaporated under reduced pressure and added 1M hydrochloric acid (10 mL). The aqueous phase was extracted with ethyl acetate (3×20 mL) and the combined organic extracts was concentrated to dryness in vacuo. The crude product was purified by preparative-HPLC (column: Phenomenex Synergi C18 150×25×10 μm; mobile phase: [water (0.1% TFA)-ACN]; B %: 33%-63%, 13 min) to give 4-[(1-tert-butoxycarbonyl-4-piperidyl)methyl]-6-hydroxy-5-oxo-thieno[3,2-b]pyridine-7-carboxylic acid (20 mg, 27% yield). LCMS: (ES+) m/z (M+H)$^+$=353.0.

Step 4: 6-hydroxy-5-oxo-4-(4-piperidylmethyl)thieno[3,2-b]pyridine-7-carboxylic acid

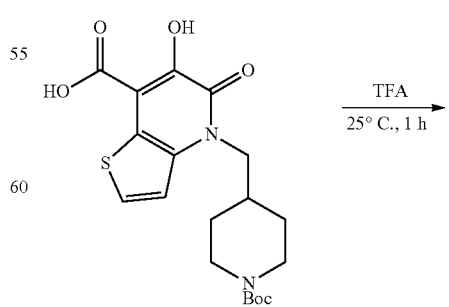

-continued

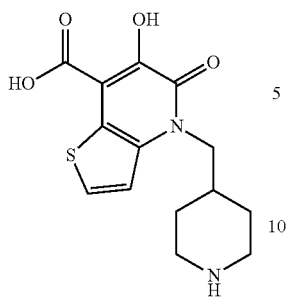

To a solution of 4-[(1-tert-butoxycarbonyl-4-piperidyl)methyl]-6-hydroxy-5-oxo-thieno[3,2-b]pyridine-7-carboxylic acid (10 mg, 24 μmol, 1.0 eq) in hydrochloric acid/ethyl acetate (1 mL) was stirred at 25° C. for 1 hour. The mixture was concentrated to dryness to give the title compound, Example 10, (5 mg, 16 μmol, 66% yield). LCMS: (ES+) m/z (M+H)$^+$=309.0; $^1$H NMR (400 MHz, DMSO-d$_6$) δ 8.79 (s, 1H), 8.53 (s, 1H), 7.60 (d, J=5.6 Hz, 1H), 7.31 (d, J=5.2 Hz, 1H), 4.2 (d, J=7.6 Hz, 2H), 3.2 (d, J=12.4 Hz, 2H), 2.8 (t, J=12.0 Hz, 2H). 2.12 (s, 1H), 1.73 (d, J=12.8 Hz, 2H), 1.50 (d, J=11.6 Hz, 2H).

Example 11: 4-(3-fluorobenzyl)-6-hydroxy-5-oxo-4,5-dihydrothieno[3,2-b]pyridine-7-carboxylic acid

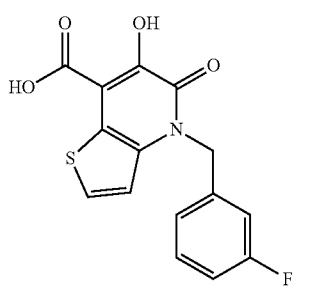 [SMILES: O=C(O)c1c(O)c(=O)n(Cc2cccc(F)c2)c2ccsc12]

Step 1: ethyl-6-(benzyloxy)-4-(3-fluorobenzyl)-5-oxo-4,5-dihydrothieno[3,2-b]pyridine-7-carboxylate

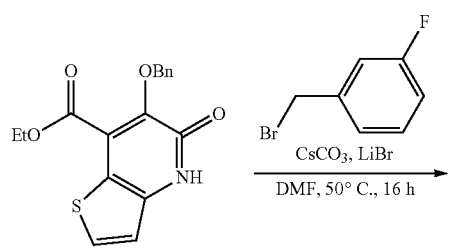

-continued

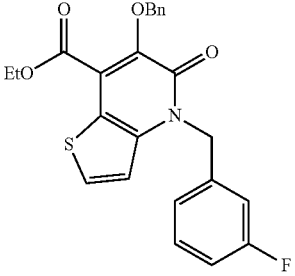

To a solution of Intermediate C (250 mg, 759 μmol) in DMF (5 mL) was added cesium carbonate (495 mg, 1.52 mmol), LiBr (198 mg, 2.28 mmol). The reaction mixture was stirred at 25° C. for 0.5 hours, then 1-(bromomethyl)-3-fluoro-benzene (215 mg, 1.14 mmol) was added to the mixture and stirred at 50° C. for 16 hours. The reaction mixture was diluted with water (50 mL) and then extracted with ethyl acetate (3×20 mL). The combine organic layer was evaporated and the residue was purified by preperative-TLC (petroleum ether/ethyl acetate=1:1). to give ethyl-6-(benzyloxy)-4-(3-fluorobenzyl)-5-oxo-4,5-dihydrothieno[3,2-b]pyridine-7-carboxylate (150 mg, 45% yield). LCMS: (ES$^+$) m/z (M+H)$^+$=438.0.

Step 2: 6-(benzyloxy)-4-(3-fluorobenzyl)-5-oxo-4,5-dihydrothieno[3,2-b]pyridine-7-carboxylic acid

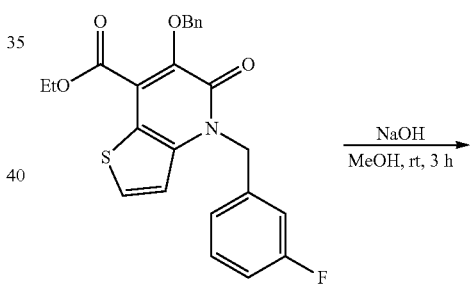

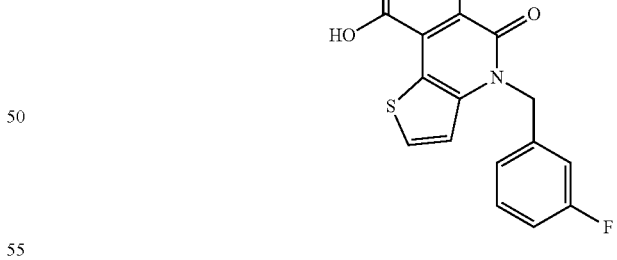

To a solution of ethyl-6-(benzyloxy)-4-(3-fluorobenzyl)-5-oxo-4,5-dihydrothieno[3,2-b]pyridine-7-carboxylate (140 mg, 320 μmol) in Methanol (1 mL) and water (1 mL) was added 2M sodium hydroxide (480 uL). The reaction mixture was stirred at 25° C. for 3 h. The solution was then evaporated under reduced pressure to remove solvent and acidified with 1M hydrochloric acid (5 mL) to pH=5. The solid was filtered and washed with water (2 mL) to give crude 6-(benzyloxy)-4-(3-fluorobenzyl)-5-oxo-4,5-dihydrothieno[3,2-b]pyridine-7-carboxylic acid (100 mg, crude). LCMS: (ES$^+$) m/z (M+H)$^+$=410.0.

Step 3: 4-(3-fluorobenzyl)-6-hydroxy-5-oxo-4,5-dihydrothieno[3,2-b]pyridine-7-carboxylic acid Step 1: ethyl-6-benzyloxy-4-[(4-methoxyphenyl)methyl]-5-oxo-thieno[3,2-b]pyridine-7-carboxylate

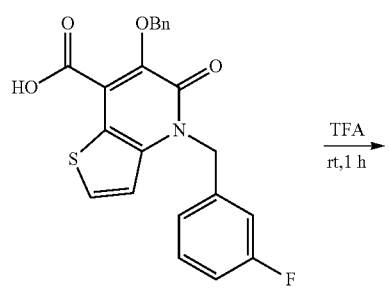

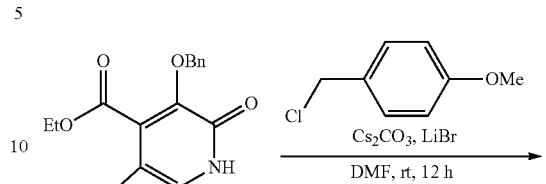

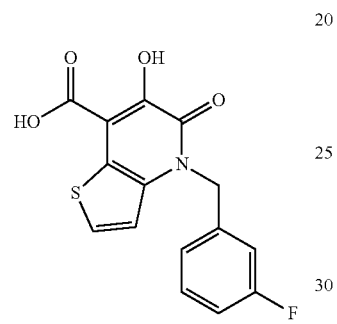

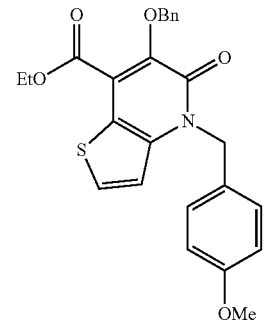

To a solution of 6-(benzyloxy)-4-(3-fluorobenzyl)-5-oxo-4,5-dihydrothieno[3,2-b]pyridine-7-carboxylic acid (90 mg, 220 μmol) in Trifluoroacetic acid (5 mL) was stirred at 25° C. for 2 h. On completion, the solution was evaporated under reduced pressure and the residue was purified by preperative-HPLC (column: Phenomenex Synergi C18 150×25×10 μm; mobile phase: [water (0.1% TFA)-ACN]; B %: 23%-53%, 13 min) to give the title compound, Example 11, (14 mg, 20% yield); $^1$H NMR (MeOD-$d_4$, 400 MHz): δ 7.52 (d, J=5.6, 1H), 7.30-7.38 (m, 1H), 7.16 (d, J=5.6-1H), 6.90-7.30 (m, 3H), 5.60 (s, 2H); LCMS: (ES$^+$) m/z (M+H)$^+$=320.0H NMR J=J=

To a solution of Intermediate C (200 mg, 607 μmol) in N,N-dimethylformamide (10 mL) was added cesium carbonate (396 mg, 1.21 mmol) and LiBr (158 mg, 1.82 mmol). The reaction mixture was stirred for 30 min at 25° C. and then 1-(chloromethyl)-4-methoxy-benzene (143 mg, 911 μmol) was added. The reaction mixture was stirred for 12 hours at 25° C. The mixture was added to water (20 mL) and extracted with ethyl acetate (3×20 mL). The combined organic phase was then concentrated. The crude product was purified by column chromatography (petroleum ether/ethyl acetate=10:1) to give ethyl-6-benzyloxy-4-[(4-methoxyphenyl)methyl]-5-oxo-thieno[3,2-b]pyridine-7-carboxylate (200 mg, 73% yield).

Example 12: 6-hydroxy-4-[(4-methoxyphenyl)methyl]-5-oxo-thieno[3,2-b]pyridine-7-carboxylic acid Step 2: 6-benzyloxy-4-[(4-methoxyphenyl)methyl]-5-oxo-thieno[3,2-b]pyridine-7-carboxylic acid

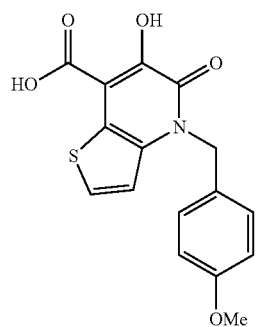

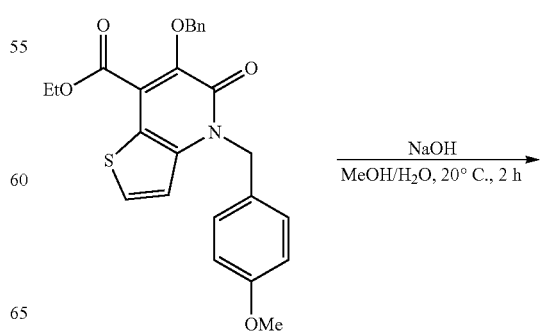

Step 3: 6-hydroxy-4-[(4-methoxyphenyl)methyl]-5-oxo-thieno[3,2-b]pyridine-7-carboxylic acid

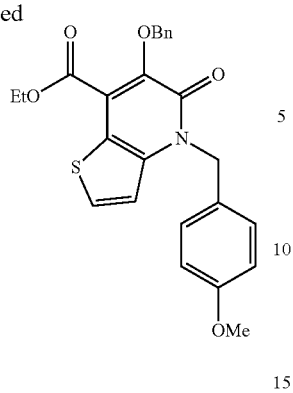

To a solution of ethyl-6-benzyloxy-4-[(4-methoxyphenyl)methyl]-5-oxo-thieno[3,2-b]pyridine-7-carboxylate (160 mg, 356 μmol) in methanol (5 mL) and water (5 mL) was added sodium hydroxide (43 mg, 1.07 mmol). The reaction mixture was stirred at 20° C. for 2 hours. The mixture was concentrated to dryness. 1M Hydrochloric acid (10 mL) was added to the residue which was then extracted with ethyl acetate (3×20 mL). The combined organic phase was concentrated to dryness to give 6-benzyloxy-4-[(4-methoxyphenyl)methyl]-5-oxo-thieno[3,2-b]pyridine-7-carboxylic acid (120 mg, 68% yield). LCMS: (ES+) m/z (M+H)$^+$=422.0.

Step 3: 6-hydroxy-4-[(4-methoxyphenyl)methyl]-5-oxo-thieno[3,2-b]pyridine-7-carboxylic acid

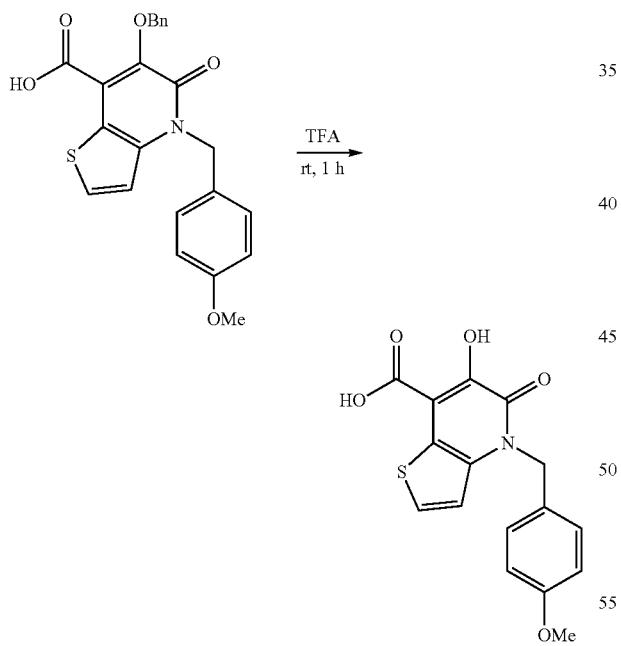

A solution of 6-benzyloxy-4-[(4-methoxyphenyl)methyl]-5-oxo-thieno[3,2-b]pyridine-7-carboxylic acid (100 mg, 237 μmol) in trifluoroacetic acid (5 mL) was stirred at 25° C. for 1 h. The mixture was concentrated in vacuo. The crude product was purified by preperative-HPLC to give the title compound, Example 12, (40 mg, 51% yield). $^1$H NMR (400 MHz, DMSO-d$_6$) δ 7.59 (d, J=5.6 Hz, 1H), 7.25 (m, 3H), 6.86 (d, J=8.8 Hz, 2H), 5.24 (s, 2H), 3.7 (s, 3H); LCMS: (ES+) m/z (M+H)$^+$=332.0.

Example 13: 4-(2,3-dihydro-1,4-benzodioxin-3-ylmethyl)-6-hydroxy-5-oxo-thieno[3,2-b]pyridine-7-carboxylic acid

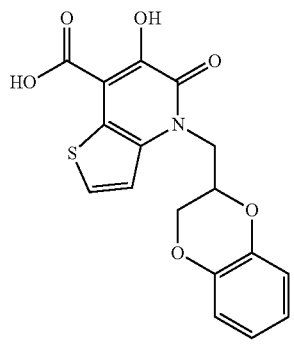 [SMILES: O=C(O)c1c(O)c(=O)n(CC2COc3ccccc3O2)c2ccsc12]

Step 1: ethyl-6-benzyloxy-4-(2,3-dihydro-1,4-benzodioxin-3-ylmethyl)-5-oxo-thieno[3,2-b]pyridine-7-carboxylate

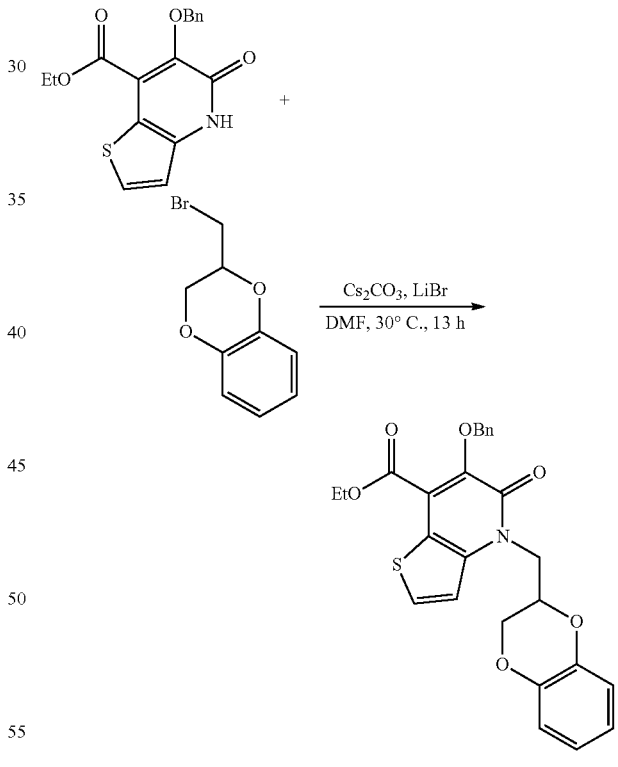

To a solution of Intermediate C (180 mg, 492 μmol) in N,N-dimethylformamide (4 mL) was added cesium carbonate (481 mg, 1.48 mmol), LiBr (128 mg, 1.48 mmol, 37 uL). The reaction mixture was stirred for 30 min at 30° C. and then 3-(bromomethyl)-2,3-dihydro-1,4-benzodioxine (169 mg, 738 μmol) was added. The reaction mixture was stirred at 30° C. for 12 h. The reaction mixture was poured into 50 mL of water and extracted with (3×30 mL) of ethyl acetate. The organic layer was dried over sodium sulfate and concentrated under vacuum. The residue was purified by column chromatography (petroleum ether/ethyl acetate=10:1-5:1) to give ethyl-6-benzyloxy-4-(2,3-dihydro-1,4-benzodioxin-3-ylmethyl)-5-oxo-thieno[3,2-b]pyridine-7-carboxylate (120 mg, 51% yield) as a white solid.

Step 2: 6-benzyloxy-4-(2,3-dihydro-1,4-benzodioxin-3-ylmethyl)-5-oxo-thieno[3,2-b]pyridine-7-carboxylic acid

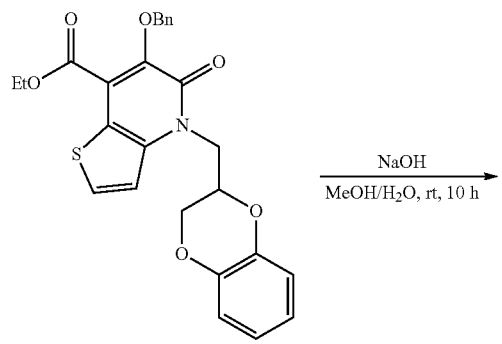

A solution of ethyl-6-benzyloxy-4-(2,3-dihydro-1,4-benzodioxin-3-ylmethyl)-5-oxo-thieno[3,2-b]pyridine-7-carboxylate (120 mg, 251 µmol) in water (5 mL) and methanol (5 mL) was added sodium hydroxide (30 mg, 753.87 µmol). The reaction mixture was stirred at 25° C. for 10 h. Upon reaction completion the solvent was evaporated and 1M hydrochloric acid (10 mL) was added. The mixture was extracted with ethyl acetate (3×20 mL) and the combined organic extracts were concentrated to give 6-benzyloxy-4-(2,3-dihydro-1,4-benzodioxin-3-ylmethyl)-5-oxo-thieno[3,2-b]pyridine-7-carboxylic acid (110 mg, 97% yield). LCMS: (ES+) m/z (M+H)$^+$=450.0.

Step 3: 4-(2,3-dihydro-1,4-benzodioxin-3-ylmethyl)-6-hydroxy-5-oxo-thieno[3,2-b]pyridine-7-carboxylic acid

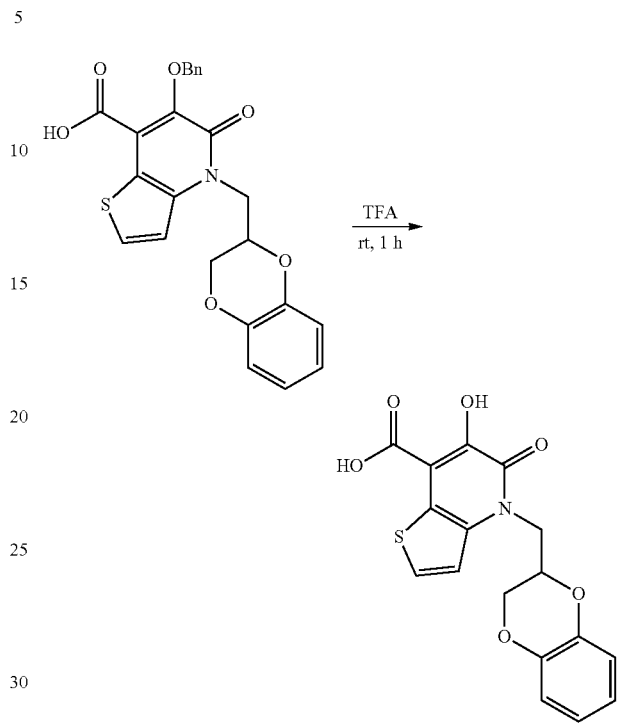

A solution of 6-benzyloxy-4-(2,3-dihydro-1,4-benzodioxin-3-ylmethyl)-5-oxo-thieno[3,2-b]pyridine-7-carboxylic acid (90 mg, 200 µmol) in trifluoroacetic acid (5 mL) was stirred at 25° C. for 1 h. The mixture was concentrated in vacuo and the crude product was purified by preperative-HPLC (column: Phenomenex Synergi C18 150×25×10 µm; mobile phase: [water (0.1% TFA)-ACN]; B %: 29%-59%, 13 min) to give the title compound, Example 13, (40 mg, 56% yield). $^1$H NMR (400 MHz, DMSO-d$_6$) δ 7.51 (d, J=6.0 Hz, 1H), 7.17 (s, 1H), 6.8-6.87 (m, 3H), 6.7 (s, 1H), 4.62-4.69 (m, 3H), 4.35 (d, J=11.6 Hz, 1H), 4.1-4.14 (m, 1H); LCMS: (ES+) m/z (M+H)$^+$=360.

Example 14: 4-(4-acetamido-3-chlorobenzyl)-6-hydroxy-5-oxo-4,5-dihydrothieno[3,2-b]pyridine-7-carboxylic acid

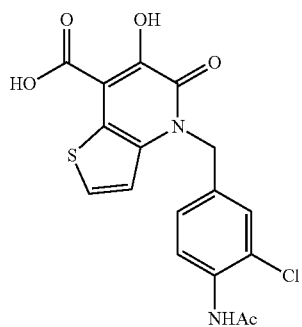 [SMILES: CC(=O)Nc1ccc(Cn2c(=O)c(O)c(C(=O)O)c3sccc32)cc1Cl]

Step 1: 4-(N-acetylacetamido)-3-chlorobenzyl acetate

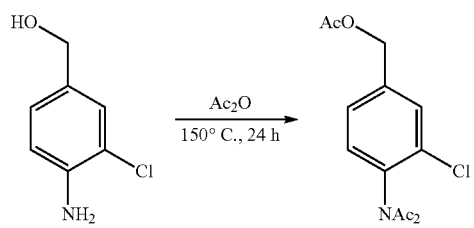

A solution of (4-amino-3-chlorophenyl)methanol (1.20 g, 7.6 mmol) in acetic anhydride (3.3 g, 32 mmol, 3.0 mL) was stirred at 150° C. for 24 hours. On completion, the reaction was quenched with 20 mL aqueous saturated sodium bicarbonate, and extracted with ethyl acetate (3×20 mL). The combined organic phase was dried over anhydrous sodium sulfate, concentrated in vacuo. The residue was purified by column chromatography (petroleum ether/ethyl acetate=5:1) to give 4-(N-acetylacetamido)-3-chlorobenzyl acetate (1.0 g, 39% yield) as a white solid. m/z $^1$H NMR (400 MHz, CDCl$_3$): δ 7.59 (s, 1H), 7.40 (dd, J=8.0, 2.0 Hz, 1H), 7.30 (d, J=8.8 Hz, 1H), 7.83 (s, 1H), 5.17 (s, 2H), 2.35 (s, 6H), 2.20 (s, 3H); LCMS: (ES$^+$) m/z (M+H)$^+$=284.1.

Step 2: N-(2-chloro-4-(hydroxymethyl)phenyl)acetamide

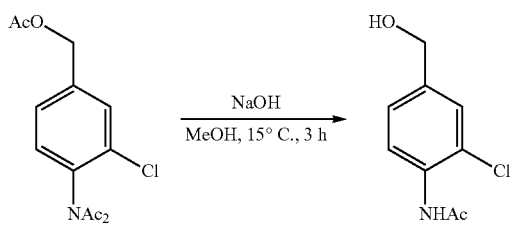

To a solution of 4-(N-acetylacetamido)-3-chlorobenzyl acetate (800 mg, 2.8 mmol) in methanol (10 mL) was added 2 M sodium hydroxide (5.7 mL) and the mixture was stirred at 15° C. for 3 h. The reaction was concentrated to remove methanol, the pH adjusted to 7 with 1 M hydrochloric acid, and the product extracted with ethyl acetate (3×50 mL). The combined organic phase was concentrated to dryness in vacuo to give N-(2-chloro-4-(hydroxymethyl)phenyl)acetamide (300 mg, 53% yield) as a white solid. $^1$H NMR (400 MHz, CDCl3): δ 8.34 (d, J=8.4 Hz, 1H), 7.62 (br. s, 1H), 7.42 (d, J=1.2 Hz, 1H), 7.50 (d, J=8.4 Hz, 1H), 4.62 (s, 2H), 2.25 (s, 3H).

Step 3: N-(2-chloro-4-(chloromethyl)phenyl)acetamide

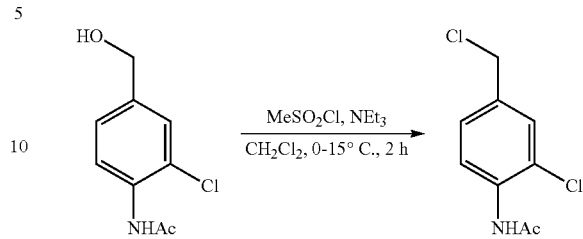

To a mixture of N-(2-chloro-4-(hydroxymethyl)phenyl)acetamide (400 mg, 2.0 mmol) and triethylamine (405 mg, 4.00 mmol) in dichloromethane (10 mL) was added methanesulfonyl chloride (840 mg, 7.3 mmol) at 0° C. The reaction mixture was then then stirred at 15° C. for 2 h. The mixture was diluted with ethyl acetate (20 mL), quenched with methanol (2 mL) and water (50 mL). The aqueous phase was then extracted with ethyl acetate (3×20 mL) and the combined organic extracts were dried over anhydrous sodium sulfate, filtered and concentrated in vacuo. The residue was triturated with ethyl acetate to give N-(2-chloro-4-(chloromethyl)phenyl)acetamide (220 mg, 50% yield) as a white solid. $^1$H NMR (400 MHz, CDCl$_3$): δ 7.78 (d, J=8.4 Hz, 1H), 7.51 (d, J=2.0 Hz, 1H), 7.34 (d, J=8.4 Hz, 1H), 4.62 (s, 2H), 2.19 (s, 3H).

Step 4: ethyl 4-(4-acetamido-3-chlorobenzyl)-6-(benzyloxy)-5-oxo-4,5-dihydrothieno[3,2-b]pyridine-7-carboxylate

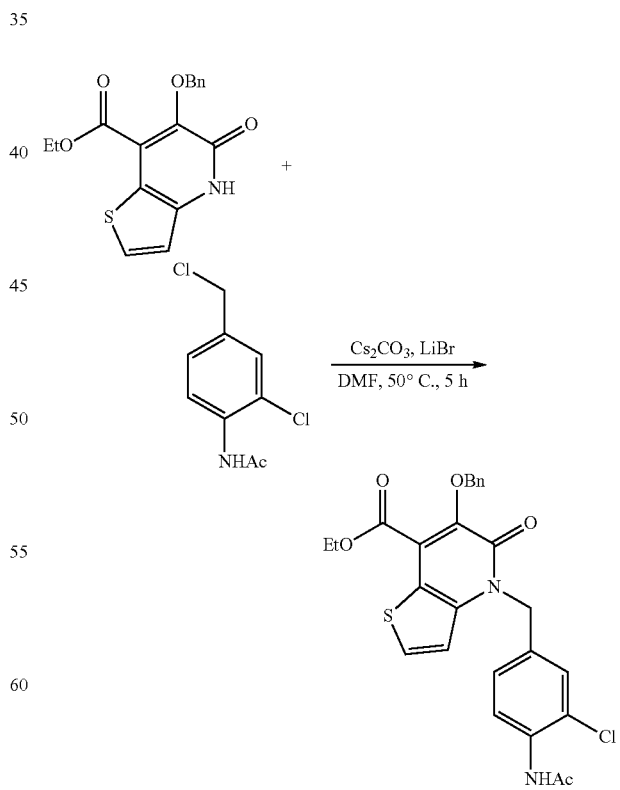

To a mixture of Intermediate C (302 mg, 917 μmol), cesium carbonate (598 mg, 1.8 mmol) and lithium bromide (239 mg, 2.8 mmol) in N,N dimethylformamide (3 mL) was added N-(2-chloro-4-(chloromethyl)phenyl)acetamide (200 mg, 917 μmol). The reaction mixture was then stirred at 50° C. for 5 h. The reaction mixture was diluted with water (50 mL) and extracted with ethyl acetate (3×20 mL). The combined organic phase was dried over anhydrous sodium sulfate, filtered, and then concentrated in vacuo. The residue was purified by column chromatography (petroleum ether/ethyl acetate=3:1) to give ethyl 4-(4-acetamido-3-chlorobenzyl)-6-(benzyloxy)-5-oxo-4,5-dihydrothieno[3,2-b]pyridine-7-carboxylate (180 mg, 38% yield) as a white solid. $^1$H NMR (400 MHz, CDCl$_3$): δ 8.32 (d, J=8.0 Hz, 1H), 7.59-7.50 (m, 3H), 7.38-7.36 (m, 3H), 7.28 (s, 1H), 7.19 (d, J=8.4 Hz, 1H), 6.95 (d, J=5.6 Hz, 1H), 5.45 (s, 2H), 5.37 (s, 2H), 4.42 (q, J=7.2 Hz, 2H), 2.23 (s, 3H), 1.37 (t, J=7.2 Hz, 3H).

Step 5: 4-(4-acetamido-3-chlorobenzyl)-6-(benzyloxy)-5-oxo-4,5-dihydrothieno[3,2-b]pyridine-7-carboxylic acid

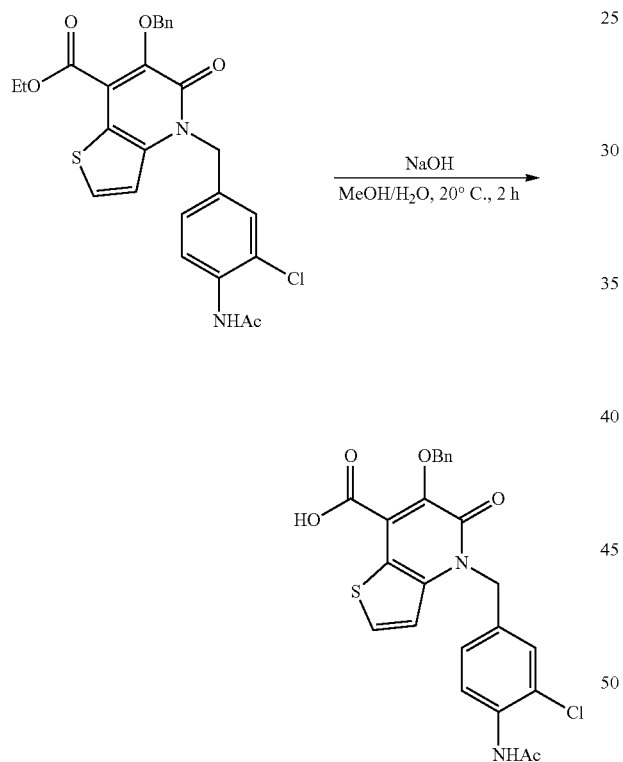

Following procedures described above, the ethyl ester of ethyl-4-(4-acetamido-3-chlorobenzyl)-6-(benzyloxy)-5-oxo-4,5-dihydrothieno[3,2-b]pyridine-7-carboxylate (180 mg, 352 μmol) was hydrolyzed with sodium hydroxide in methanol and water to provide 4-(4-acetamido-3-chlorobenzyl)-6-(benzyloxy)-5-oxo-4,5-dihydrothieno[3,2-b]pyridine-7-carboxylic acid (150 mg, 86% yield) as a white solid. m/z $^1$H NMR (400 MHz, DMSO-d6): δ 9.53 (s, 1H), 7.88 (d, J=5.6 Hz, 1H), 7.68 (s, 1H), 7.50 (d, J=6.8 Hz, 2H), 7.43 (d, J=8.4 Hz, 1H), 7.40-7.29 (m, 4H), 7.09-7.06 (m, 1H), 5.49 (s, 2H), 5.21 (s, 2H), 2.06 (s, 3H). LCMS: (ES$^+$) m/z (M+H)$^+$=483.0.

Step 6: 4-(4-acetamido-3-chlorobenzyl)-6-hydroxy-5-oxo-4,5-dihydrothieno[3,2-b]pyridine-7-carboxylic acid

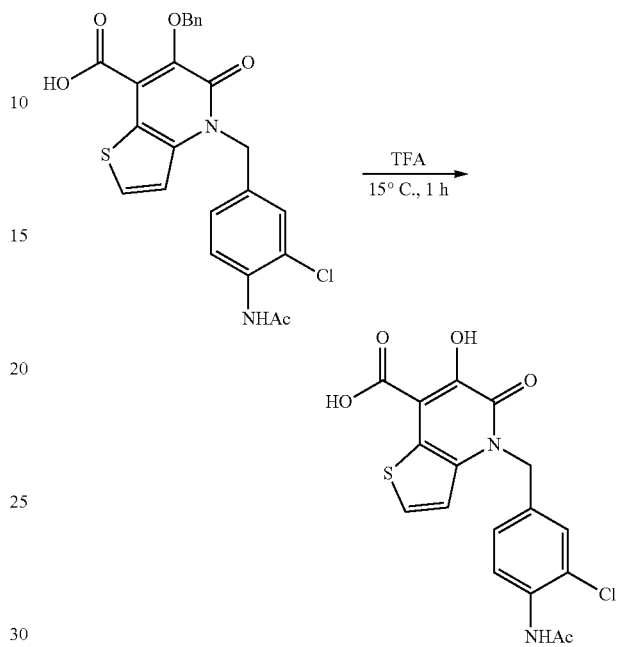

Following procedures described above, 4-(4-acetamido-3-chlorobenzyl)-6-(benzyloxy)-5-oxo-4,5-dihydrothieno[3,2-b]pyridine-7-carboxylic acid (150 mg, 310 μmol) was treated with TFA. Upon completion of the reaction, solvent was removed under reduced pressure to provide Example 14 (20 mg, 16% yield) as a light green solid. LCMS: (ES$^+$) m/z (M+H)$^+$=393.0; $^1$H NMR (DMSO-d6, 400 MHz): δ 9.51 (s, 1H), 7.61 (s, 1H), 7.57 (d, J=5.6 Hz, 1H), 7.42 (d, J=8.0 Hz, 1H), 7.18 (d, J=6.0 Hz, 1H), 7.06 (d, J=8.4 Hz, 1H), 5.47 (s, 2H), 2.04 (s, 3H).

Example 15: ethyl 6-(benzyloxy)-4-(4-((tert-butoxycarbonyl)amino)benzyl)-5-oxo-4,5-dihydrothieno[3,2-b]pyridine-7-carboxylate Step 1: Ethyl 4-(4-aminobenzyl)-6-(benzyloxy)-5-oxo-4,5-dihydrothieno[3,2-b]pyridine-7-carboxylate

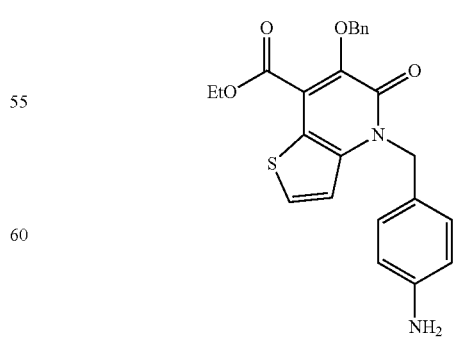

Ethyl 4-(4-aminobenzyl)-6-(benzyloxy)-5-oxo-4,5-dihydrothieno[3,2-b]pyridine-7-carboxylate was prepared from Intermediate C and 1-(chloromethyl)-4-nitrobenzene following the methods described in Example 6 and Example 7.

Step 2: ethyl 6-(benzyloxy)-4-(4-((tert-butoxycarbonyl)amino)benzyl)-5-oxo-4,5-dihydrothieno[3,2-b]pyridine-7-carboxylate

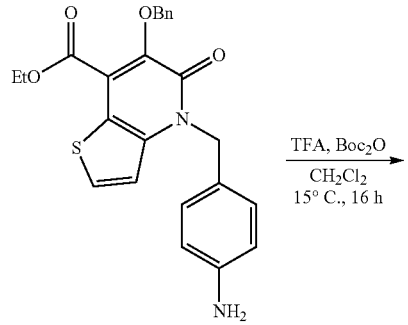

A solution of ethyl 4-(4-aminobenzyl)-6-(benzyloxy)-5-oxo-4,5-dihydrothieno[3,2-b]pyridine-7-carboxylate (0.25 g, 0.58 mmol) in dichloromethane (5 mL) was treated with triethylamine (120 mg, 1.15 mmol) and di-tert-butyl dicarbonate (190 mg, 0.86 mmol). The mixture solution was stirred at 15° C. for 16 h. On completion, the solution was diluted with dichloromethane (30 mL) and washed with brine (10 mL). The organic layer was concentrated in vacuo and purified by column chromatography [petroleum ether/ethyl acetate=10:1-3:1] to give ethyl 6-(benzyloxy)-4-(4-((tert-butoxycarbonyl)amino)benzyl)-5-oxo-4,5-dihydrothieno[3,2-b]pyridine-7-carboxylate (230 mg, 67% yield) as yellow solid. $^1$H NMR (CDCl$_3$, 400 MHz): δ 7.59-7.57 (m, 2H), 7.49 (d, J=5.6 Hz, 1H), 7.41-7.31 (m, 5H), 7.22 (d, J=8.8 Hz, 1H), 7.00 (d, J=5.6 Hz, 1H), 6.47 (s, 2H), 5.48 (s, 2H), 5.38 (s, 2H), 4.43 (q, J=7.2 Hz, 2H), 1.52 (s, 9H), 1.36 (t, J=7.2 Hz, 3H).

Step 3: 6-(benzyloxy)-4-(4-((tert-butoxycarbonyl)amino)benzyl)-5-oxo-4,5-dihydrothieno[3,2-b]pyridine-7-carboxylic acid

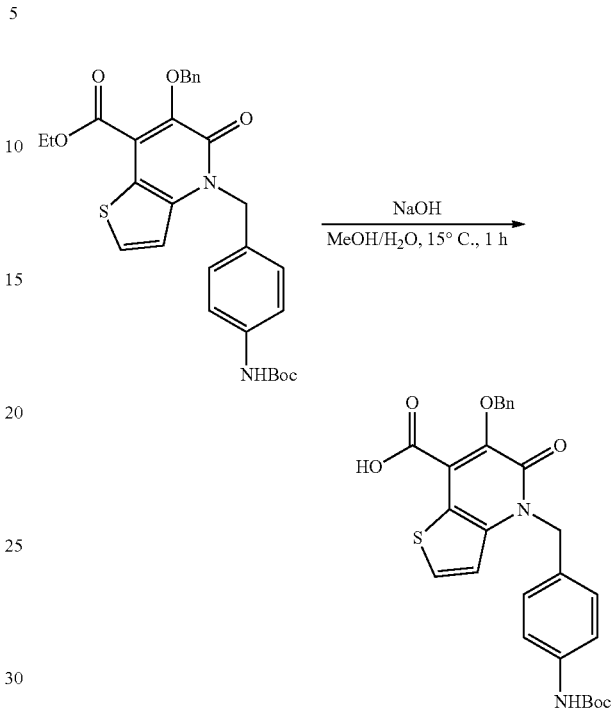

To a solution of ethyl 6-(benzyloxy)-4-(4-((tert-butoxycarbonyl)amino)benzyl)-5-oxo-4,5-dihydrothieno[3,2-b]pyridine-7-carboxylate (200 mg, 0.37 mmol) in methanol (7 mL) and water (7 mL) was added sodium hydroxide (45 mg, 1.12 mmol) and the mixture ws stirred at 15° C. for 1 h. On completion, the solution was concentrated in vacuo to remove the solvent and the residue was adjusted the pH to 6-7 with 1 M hydrochloric acid. The solution was concentrated to dryness in vacuo to provide 6-(benzyloxy)-4-(4-((tert-butoxycarbonyl)amino)benzyl)-5-oxo-4,5-dihydrothieno[3,2-b]pyridine-7-carboxylic acid (180 mg, crude) as a yellow solid.

Step 4: 4-(4-((tert-butoxycarbonyl)amino)benzyl)-6-hydroxy-5-oxo-4,5-dihydrothieno[3,2-b]pyridine-7-carboxylic acid

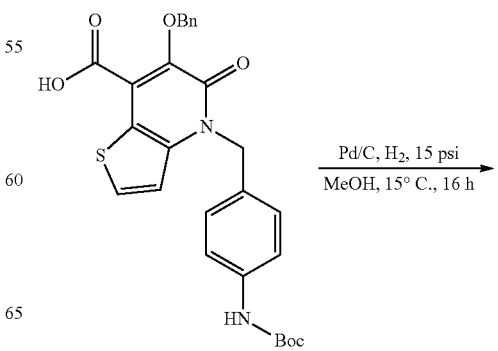

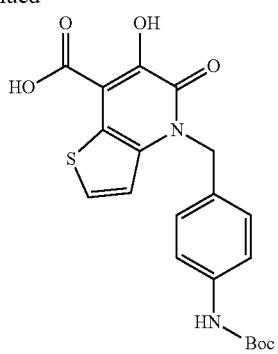

A solution of 6-(benzyloxy)-4-(4-((tert-butoxycarbonyl)amino)benzyl)-5-oxo-4,5-dihydrothieno[3,2-b]pyridine-7-carboxylic acid (150 mg, 0.30 mmol) in methanol (1 mL) was treated with Pd/C (15 mg) and stirred at 15° C. for 16 h under an atmosphere of hydrogen. On completion, the solution was filtered and the resulting filtrate was concentrated to dryness. The residue was purified by preperative-HPLC [Instrument: GX-B; Phenomenex Synergi C18 150× 25 mm, particle size: 10 μm; Mobile phase: 30-60% acetonitrile in H$_2$O (add 0.1% TFA, v/v)]. Each set of collected fractions was concentrated to dryness at room temperature and lyophilized to give the title compound, Example 15, (50 mg, 41% yield) as a solid. LCMS: (ES+) m/z (M+H)$^+$=417.0; $^1$H NMR (DMSO-d$_6$, 400 MHz): δ 9.32 (s, 1H), 7.58 (d, J=6.0 Hz, 1H), 7.37 (d, J=8.4 Hz, 2H), 7.22-7.18 (m, 3H), 5.41 (s, 2H), 1.45 (s, 9H).

Example 16: 6-hydroxy-4-[[4-(methanesulfonamido)phenyl]methyl]-5-oxo-thieno[3,2-b]pyridine-7-carboxylic acid

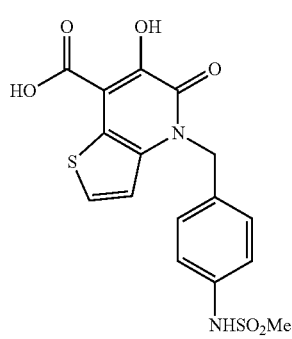

Step 1: ethyl 6-benzyloxy-4-[[4-(methanesulfonamido)phenyl]methyl]-5-oxo-thieno[3,2-b]pyridine-7-carboxylate

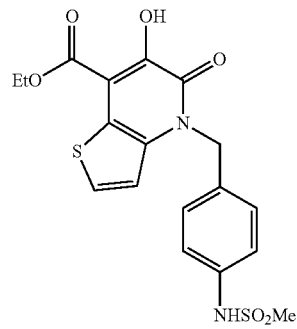

To a solution of ethyl 4-[(4-aminophenyl)methyl]-6-benzyloxy-5-oxo-thieno[3,2-b]pyridine-7-carbox-ylate (200 mg, 460 μmol) in dichloromethane (1 mL) was added methylsufonyl chloride (58 mg, 506 μmol) and triethylamine (61 mg, 598 μmol) and the reaction was stirred at 0° C. for 30 min. The mixture was added water (10 mL), and extracted with ethyl acetate (3×20 mL). The combined organic phase was concentrated in vacuo providing ethyl 6-benzyloxy-4-[[4-(methanesulfonamido)phenyl]methyl]-5-oxo-thieno[3,2-b]pyridine-7-carboxylate (200 mg, 85% yield) as a brown oil. LCMS: (ES+) m/z (M+H)$^+$=513.0.

Step 2: 6-benzyloxy-4-[[4-(methanesulfonamido)phenyl]methyl]-5-oxo-thieno[3,2-b]pyridine-7-carboxylic acid -continued

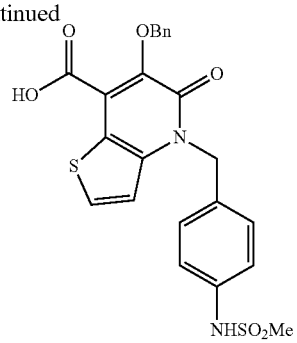

To solution of ethyl 6-benzyloxy-4-[[4-(methanesulfonamido)phenyl]methyl]-5-oxo-thieno[3,2-b]pyridine-7-carboxylate (0.1 g, 195 μmol) in water (1 mL) and methanol (1 mL) was added sodium hydroxide (31 mg, 780 μmol) and the reaction was stirred at 20° C. for 30 min. To the mixture was added 1M hydrochloric acid (10 mL) and the aqueous phase was extracted with ethyl acetate (3×20 mL). The combined organic phase was concentrated to dryness to give crude 6-benzyloxy-4-[[4-(methanesulfonamido)phenyl]methyl]-5-oxo-thieno[3,2-b]pyridine-7-carboxylic acid (80 mg, 85% yield) as a brown oil.

Step 3: 6-hydroxy-4-[[4-(methanesulfonamido)phenyl]methyl]-5-oxo-thieno[3,2-b]pyridine-7-carboxylic acid

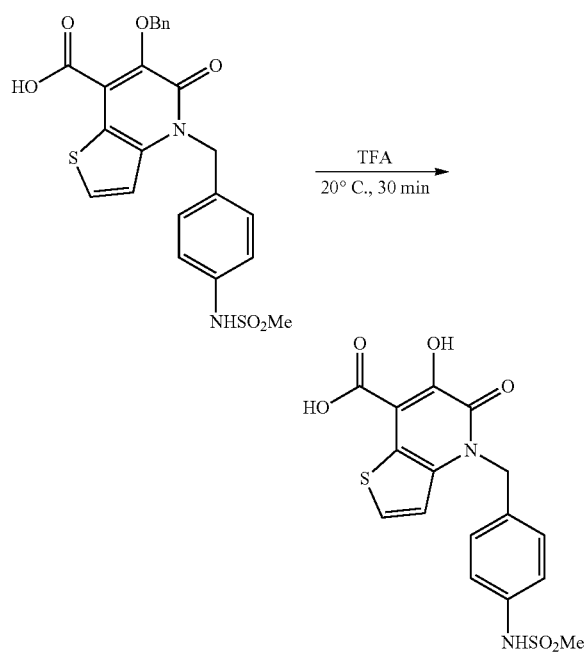

A solution of 6-benzyloxy-4-[[4-(methanesulfonamido)phenyl]methyl]-5-oxo-thieno[3,2-b]pyridine-7-carboxylic acid (80 mg, 165 μmol) in trifluoroacetic acid (5 mL) was stirred at 20° C. for 30 min. The mixture was concentrated to dryness in vacuo. The crude product was purified by preperative-HPLC (column: Boston pH-lex150×2510 μm; mobile phase: [water (0.1% TFA)-ACN]; B %: 18%-48%, 10 min), to give the title compound, Example 16, (30 mg, 45% yield). m/z $^1$H NMR (400 MHz, DMSO-d$_6$) δ 9.74 (s, 1H), 7.61 (d, J=5.2 Hz, 1H), 7.24-7.28 (m, 3H), 7.14 (d, J=8.4 Hz, 2H), 5.45 (s, 2H), 3.95 (s, 3H); LCMS: (ES+) m/z (M+H)$^+$=394.9.

Example 17: 6-hydroxy-5-oxo-4-[(2-oxo-1H-quinolin-6-yl)methyl]thieno[3,2-b]pyridine-7-carboxylic acid

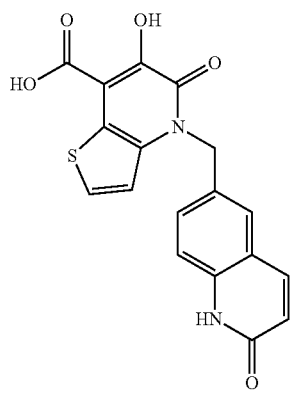 [SMILES: O=C(O)c1c(O)c(=O)n(Cc2ccc3[nH]c(=O)ccc3c2)c2ccsc12]

Step 1: tert-butyl 6-methyl-2-oxo-quinoline-1-carboxylate and tert-butyl (6-methyl-2-quinolyl) carbonate

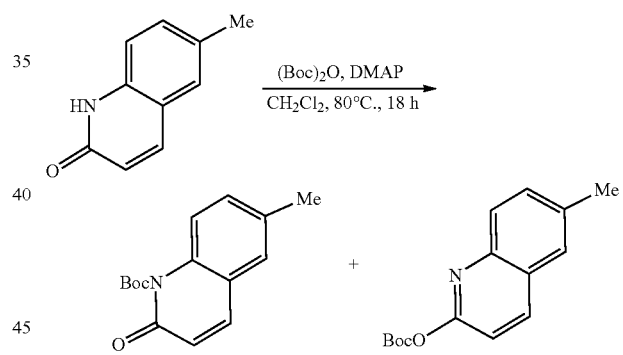

To a solution of 6-methyl-1H-quinolin-2-one (500 mg, 3 mmol) in dichloromethane (4 mL) was added 4-dimethyaminopyridine (460 mg, 3.8 mmol) and di-tert-butyl pyrocarbonate (1 g, 4.7 mmol). The mixture was stirred at 80° C. for 18 h. The reaction mixture was diluted with water (20 mL) and extracted with ethyl acetate (3×20 mL). The combined organic layers were washed with brine (15 mL), dried over anhydrous sodium sulfate, filtered, and concentrated under reduced pressure to give a crude residue. The residue was purified by column chromatography (petroleum ether/ethyl acetate=20:1-10:1) to give tert-butyl (6-methylquinolin-2-yl) carbonate and 6-methylquinolin-2(1H)-one (120 mg, 15% yield) and tert-butyl (6-methylquinolin-2-yl) carbonate (120 mg, 15% yield). $^1$H NMR (DMSO-d$_6$, 400 MHz): δ 8.16 (d, J=8.8 Hz, 1H), 7.92 (d, J=8.4 Hz, 1H), 7.62 (s, 1H), 7.75 (d, J=8.8 Hz, 1H), 7.22 (d, J=8.8 Hz, 1H), 2.55 (s, 3H), 1.60 (s, 9H). $^1$H NMR (DMSO-d$_6$, 400 MHz): δ 7.57 (d, J=8.8 Hz, 1H), 7.28-7.26 (m, 1H), 7.19 (d, J=1.6 Hz, 1H), 6.97 (d, J=8.4 Hz, 1H), 6.52 (d, J=9.6 Hz, 1H), 2.34 (s, 3H), 1.62 (s, 9H).

Step 2: [6-(bromomethyl)-2-quinolyl]tert-butyl carbonate

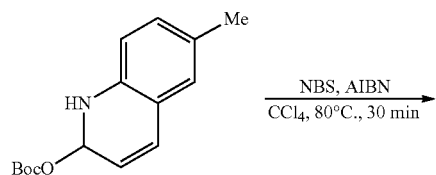

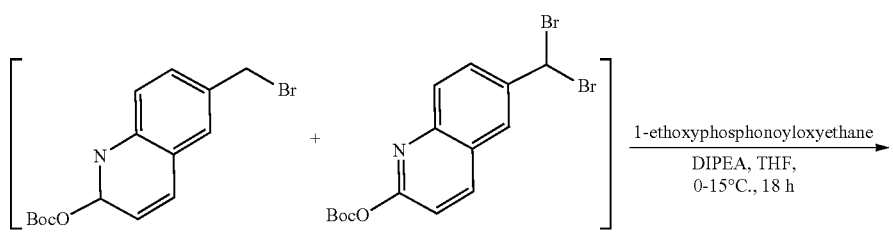

To a solution of tert-butyl (6-methyl-2-quinolyl) carbonate (250 mg, 964 µmol) in tetrachloromethane (1 mL) was added N-Bromosuccinimide (172 mg, 964 µmol) and AIBN (2 mg, 9.6 µmol). The mixture was stirred at 80° C. for 30 min. The reaction mixture was diluted with water (10 mL) and extracted with ethyl acetate (3×15 mL). The combined organic layers were washed with brine 30 mL (3×10 mL), dried over anhydrous sodium sulfate, filtered and concentrated under reduced pressure to give a crude residue. The residue was purified by column chromatography (petroleum ether/ethyl acetate=15:1-10:1) to give a mixture of the mono- and di-bromo intermediate (300 mg, 75% yield).

To a solution of the mono-brom and di-bromo intermediates above (300 mg, 719 µmol) in tetrahydrofuran (1 mL) was added 1-ethoxyphosphonoyloxyethane (99 mg, 719 µmol) and N,N-diisopropylethylamine (93 mg, 719 µmol) at 0° C. The mixture was stirred at 15° C. for 18 h. The reaction mixture was diluted with water (10 mL) and aqueous layer was extracted with ethyl acetate (3×20 mL). The combined organic layers were washed with saturated sodium bicarbonate solution (3×10 mL), dried over anhydrous sodium sulfate, filtered and concentrated under reduced pressure to give a crude residue. The crude residue was purified by column chromatography (SiO$_2$, Petroleum ether/Ethyl acetate=8:1-4:1) to give compound [6-(bromomethyl)-2-quinolyl] tert-butyl carbonate (200 mg, 82% yield).

Step 3: ethyl-6-benzyloxy-4-[(2-tert-butoxycarbonyloxy-6-quinolyl)methyl]-5-oxo-thieno[3,2-b]pyridine-7-carboxylate

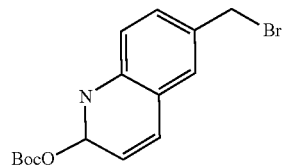

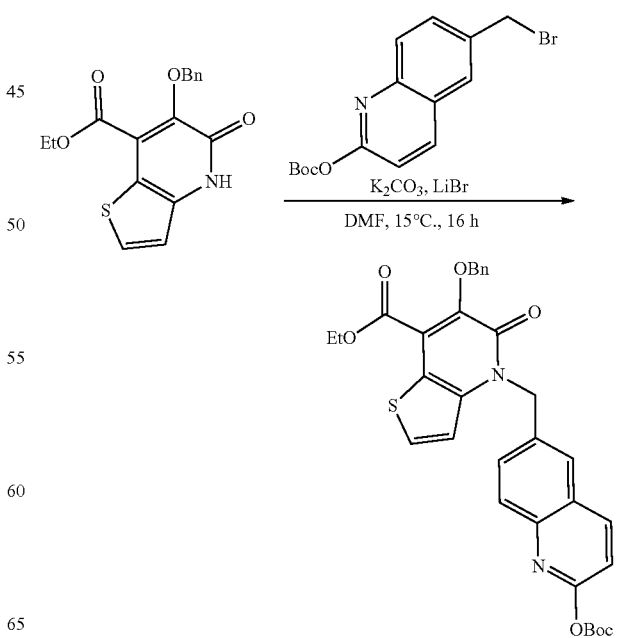

To a solution of Intermediate C (180 mg, 503 μmol) in N,N-dimethylformamide (3 mL) was added potassium carbonate (327 mg, 1.0 mmol, 2.0 eq) and lithium bromide (131 mg, 1.5 mmol, 3 eq) at 15° C. for 1 h. Then [6-(bromomethyl)-2-quinolyl] tert-butyl carbonate (170 mg, 503 μmol) was added, the mixture was stirred at 15° C. for 15 h. The reaction mixture was diluted with water (10 mL) and extracted with ethyl acetate (3×20 mL). The combined organic layers were washed with brine (3×10 mL), dried over anhydrous sodium sulfate, filtered and concentrated under reduced pressure to give a crude residue. The crude residue was purified by column chromatography (petroleum ether/ethyl acetate=15:1-8:1) to give ethyl-6-benzyloxy-4-[(2-tert-butoxycarbonyloxy-6-quinolyl)methyl]-5-oxo-thieno[3,2-b]pyridine-7-carboxylate (100 mg, 34% yield). LCMS: (ES$^+$) m/z (M-C$_5$H$_8$O$_2$)$^+$=487.2.

Step 5: 6-benzyloxy-4-[(2-tert-butoxycarbonyloxy-6-quinolyl)methyl]-5-oxo-thieno[3,2-b]pyridine-7-carboxylic acid

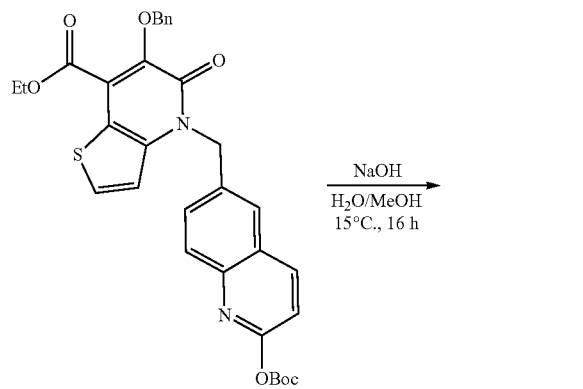

To a solution of ethyl-6-benzyloxy-4-[(2-tert-butoxycarbonyloxy-6-quinolyl)methyl]-5-oxo-thieno[3,2-b]pyridine-7-carboxylate (100 mg, 170 μmol, 1.0 eq) in ethanol (1 mL) and water (1 mL) was added sodium hydroxide (34 mg, 852 μmol, 5.0 eq). The mixture was stirred at 15° C. for 16 hours. The reaction mixture was concentrated under reduced pressure to remove ethanol. The residue was adjust pH=5 with 1 mol/L hydrochloric acid (5 mL), and extracted with ethyl acetate (3×5 mL). The combined organic layers were washed with water (3×5 mL) and concentrated under reduced pressure to give crude 6-benzyloxy-4-[(2-tert-butoxycarbonyloxy-6-quinolyl)methyl]-5-oxo-thieno[3,2-b]pyridine-7-carboxylic acid (80 mg, 84% yield). LCMS: (ES$^+$) m/z (M-C$_5$H$_8$O$_2$)$^+$=459.0.

Step 6: 6-hydroxy-5-oxo-4-[(2-oxo-1H-quinolin-6-yl)methyl]thieno[3,2-b]pyridine-7-carboxylic acid

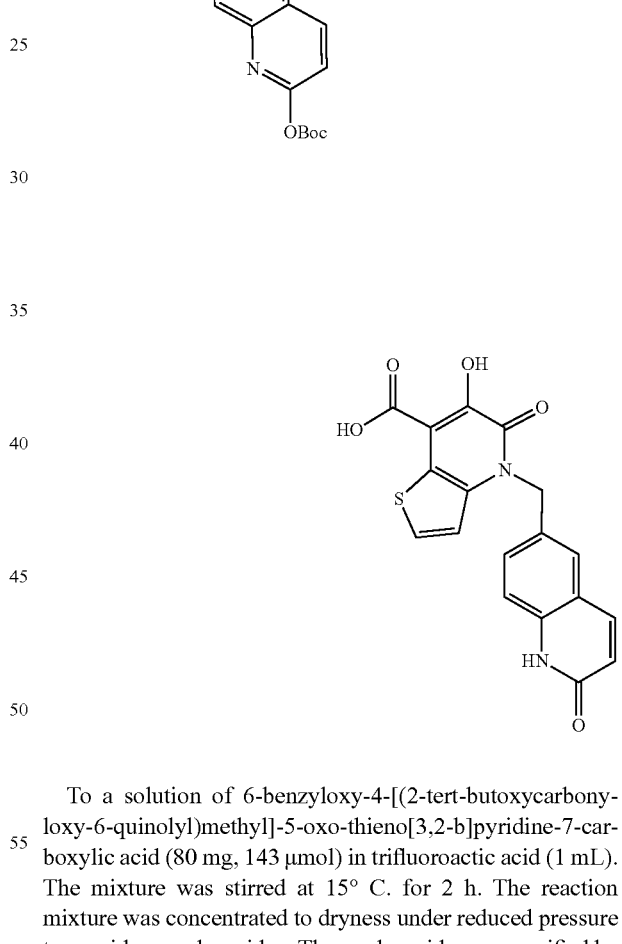

To a solution of 6-benzyloxy-4-[(2-tert-butoxycarbonyloxy-6-quinolyl)methyl]-5-oxo-thieno[3,2-b]pyridine-7-carboxylic acid (80 mg, 143 μmol) in trifluoroactic acid (1 mL). The mixture was stirred at 15° C. for 2 h. The reaction mixture was concentrated to dryness under reduced pressure to provide a crude residue. The crude residue was purified by preperative-HPLC (column: Phenomenex Synergi C18 150× 25×10 μm; mobile phase: [water (0.1% TFA)-ACN]; B %: 14%-41%, 12 min) to give the title compound, Example 17, (18 mg, 33% yield). $^1$H NMR (DMSO d$_6$, 400 MHz): δ 11.73 (s, 1H), 7.85 (d, J=9.2 Hz, 1H), 7.58-7.56 (m, 2H), 7.46 (d, J=8.4 Hz, 1H), 7.24 (t, J=8.4 Hz, 2H), 6.46 (d, J=9.2 Hz, 1H), 5.52 (s, 2H); LCMS: (ES$^+$) m/z (M+H)$^+$=368.9.

Example 18: 6-hydroxy-5-oxo-4-((1-phenyl-1H-1,2,3-triazol-4-yl)methyl)-4,5-dihydrothieno[3,2-b]pyridine-7-carboxylic acid

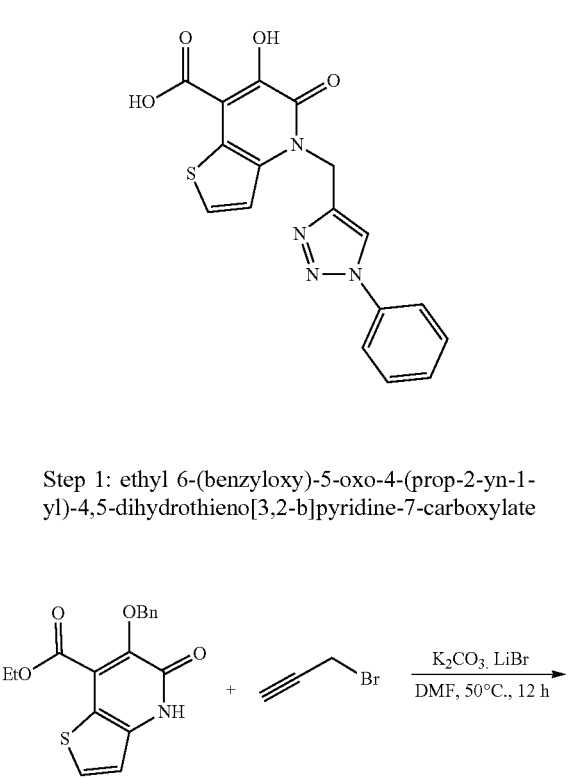

Step 1: ethyl 6-(benzyloxy)-5-oxo-4-(prop-2-yn-1-yl)-4,5-dihydrothieno[3,2-b]pyridine-7-carboxylate A solution of Intermediate C (300 mg, 911 μmol), 3-bromoprop-1-yne (130 mg, 1.09 mmol) and cesium carbonate (594 mg, 1.82 mmol) in N,N-dimethylformamide (5 mL) was stirred at 50° C. for 12 h. On completion, the reaction was diluted with water (20 mL), extracted with ethyl acetate (3×10 mL). The combined organic phase was washed with brine, dried over anhydrous sodium sulfate and concentrated in vacuo. The residue was purified by column chromatography (petroleum ether/ethyl acetate=10:1-5:1) to give ethyl 6-(benzyloxy)-5-oxo-4-(prop-2-yn-1-yl)-4,5-dihydrothieno[3,2-b]pyridine-7-carboxylate (300 mg, 86% yield) as a brown oil. $^1$H NMR (CDCl3, 400 MHz): δ 7.61 (d, J=5.6 Hz, 1H), 7.58-7.55 (m, 2H), 7.42-7.30 (m, 3H), 7.21 (d, J=5.6 Hz, 1H), 5.33 (s, 2H), 5.10 (d, J=2.8 Hz, 1H), 4.40 (q, J=7.2 Hz, 2H), 2.30 (t, J=2.4 Hz, 1H), 1.35 (t, J=7.2 Hz, 3H); LCMS: (ES$^+$) m/z (M+H)$^+$=368.0.

Step 2: ethyl 6-(benzyloxy)-5-oxo-4-[(1-phenyl-1H-1,2,3-triazol-4-yl)methyl]-4,5-dihydrothieno[3,2-b]pyridine-7-carboxylate

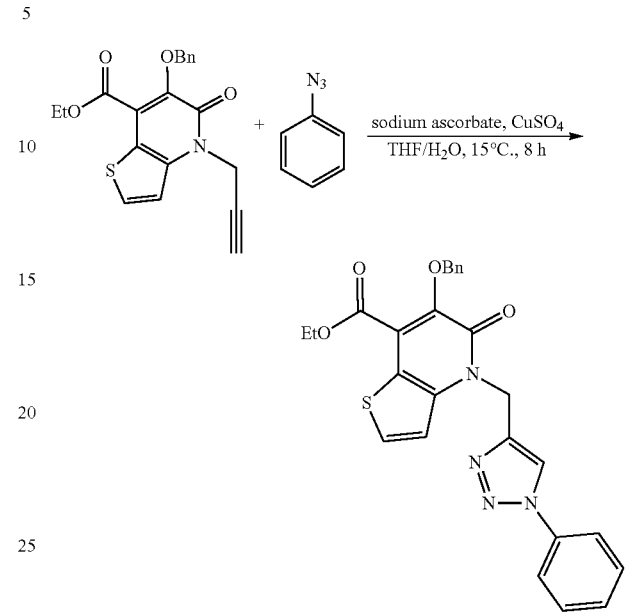

A mixture of ethyl 6-(benzyloxy)-5-oxo-4-(prop-2-yn-1-yl)-4,5-dihydrothieno[3,2-b]pyridine-7-carboxylate (300 mg, 786 μmol), azidobenzene (94 mg, 786 μmol), sodium ascorbate (62 mg, 315 μmol) and copper sulfate (13 mg, 79 μmol) in tetrahydrofuran (2 mL) and water (1 mL) was stirred at 15° C. for 8 h. On completion, the mixture was diluted with water (20 mL), and extracted with ethyl acetate (3×10 mL). The combined organic phase was washed with brine, dried over anhydrous sodium sulfate and concentrated in vacuo. The residue was purified by column chromatography (silica gel, petroleum ether:ethyl acetate=3:1 to 2:1) to give ethyl 6-(benzyloxy)-5-oxo-4-[(1-phenyl-1H-1,2,3-triazol-4-yl)methyl]-4,5-dihydrothieno[3,2-b]pyridine-7-carboxylate (220 mg, 58% yield) as a white solid. $^1$H NMR (DMSO-d6, 400 MHz): δ 8.77 (s, 1H), 7.97-7.81 (m, 3H), 7.61-7.42 (m, 6H), 7.40-7.25 (m, 3H), 5.64 (s, 2H), 5.23 (s, 2H), 4.33 (q, J=7.2 Hz, 2H), 1.26 (t, J=7.2 Hz, 3H).

Step 3: 6-(benzyloxy)-5-oxo-4-[(1-phenyl-1H-1,2,3-triazol-4-yl)methyl]-4,5-dihydrothieno[3,2-b]pyridine-7-carboxylic acid

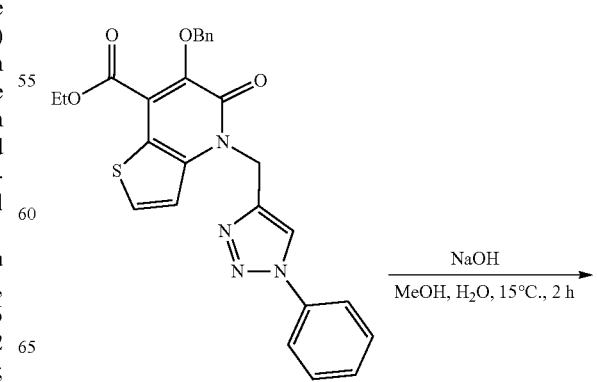

-continued

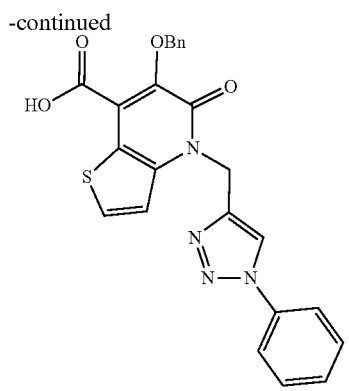

A mixture of ethyl 6-(benzyloxy)-5-oxo-4-[(1-phenyl-1H-1,2,3-triazol-4-yl)methyl]-4,5-dihydrothieno[3,2-b]pyridine-7-carboxylate (200 mg, 411 μmol) and sodium hydroxide (49 mg, 1.23 mmol) in methanol (3 mL) and water (1 mL) was stirred at 15° C. for 2 hours. On completion, the reaction was concentrated to dryness in vacuo. The residue was adjusted pH to 4 with 1 M hydrochloric acid solution and a white solid was isolated after precipitation. The solid was washed with water (3 mL), dried in vacuo to give 6-(benzyloxy)-5-oxo-4-[(1-phenyl-1H-1,2,3-triazol-4-yl)methyl]-4,5-dihydrothieno[3,2-b]pyridine-7-carboxylic acid (160 mg, 85% yield) as a white solid. $^1$H NMR (DMSO-d6, 400 MHz): δ 8.77 (s, 1H), 7.92-7.85 (m, 3H), 7.57 (d, J=8.0 Hz, 2H), 7.53-7.45 (m, 4H), 7.38-7.28 (m, 3H), 5.62 (s, 2H), 5.19 (s, 2H).

Step 4: 6-hydroxy-5-oxo-4-[(1-phenyl-1H-1,2,3-triazol-4-yl)methyl]-4,5-dihydrothieno[3,2-b]pyridine-7-carboxylic acid

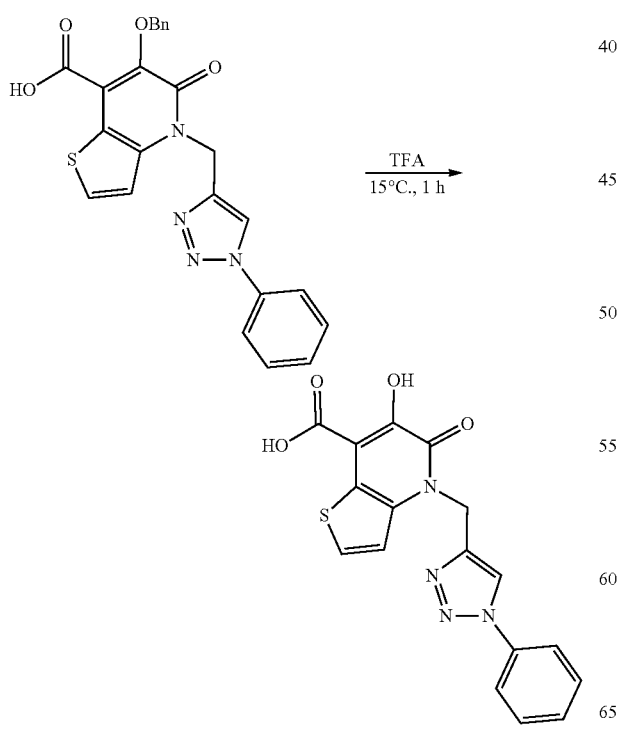

A mixture of 6-(benzyloxy)-5-oxo-4-((1-phenyl-1H-1,2,3-triazol-4-yl)methyl)-4,5-dihydrothieno[3,2-b]pyridine-7-carboxylic acid (160 mg, 349 μmol) and trifluoroacetic acid (3 mL) was stirred at 15° C. for 1 h. On completion, the reaction was concentrated to dryness in vacuo. The residue was purified by preperative-HPLC (column: Phenomenex Synergi C18 150×25×10 μm; mobile phase: [water (0.1% TFA)-ACN]; B %: 24%-54%, 13 min) to give the title compound, Example 18, (10 mg, 8% yield) as a white solid. $^1$H NMR (DMSO-d6, 400 MHz): δ 8.71 (s, 1H), 7.86 (d, J=7.6 Hz, 2H), 7.61 (d, J=5.6 Hz, 2H), 7.56 (t, J=8.0 Hz, 2H), 7.46 (t, J=7.2 Hz, 1H), 7.39 (d, J=5.6 Hz, 1H), 5.60 (s, 2H). LCMS: (ES$^+$) m/z (M+H)$^+$=369.0.

Example 19: 4-{[1-(3-chlorophenyl)pyrazol-4-yl]methyl}-6-hydroxy-5-oxo-thieno[3,2-b]pyridine-7-carboxylic acid

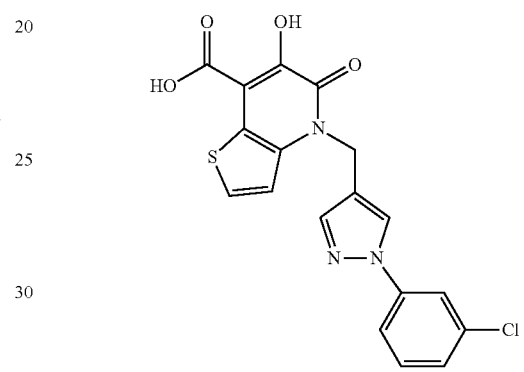

Step 1: ethyl 6-benzyloxy-4-{[1-(3-chlorophenyl)pyrazol-4-yl]methyl}-5-oxo-thieno[3,2-b]pyridine-7-carboxylate

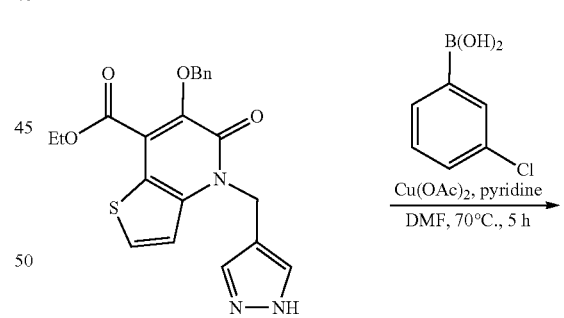

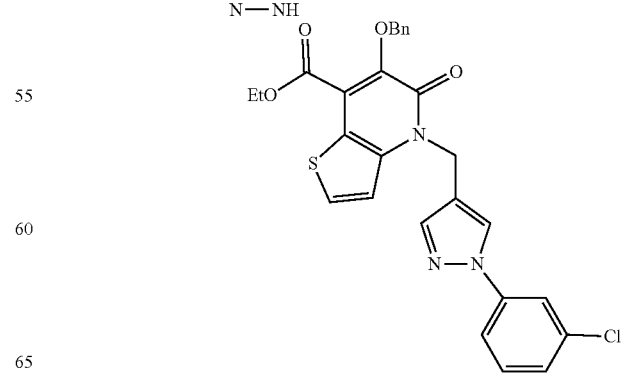

A mixture of Intermediate D (200 mg g, 488 µmol), (3-chlorophenyl)boronic acid (153 mg, 977 µmol), copper acetate (67 mg, 366 µmol) and pyridine (77 mg, 977 µmol) in N,N-dimethylformamide (4 mL) was stirred at 70° C. under atmosphere for 5 h. The mixture was diluted with water (10 mL), and the aqueous phase was extracted with ethyl acetate (3×30 mL). The residue was purified by column chromatography (petroleum ether/ethyl acetate=3:1), ethyl 6-benzyloxy-4-{[1-(3-chlorophenyl)pyrazol-4-yl]methyl}-5-oxo-thieno[3,2-b]pyridine-7-carboxylate (150 mg, 59% yield) was obtained as a yellow oil.

Step 2: 6-benzyloxy-4-{[1-(3-chlorophenyl)pyrazol-4-yl]methyl}-5-oxo-thieno[3,2-b]pyridine-7-carboxylic acid

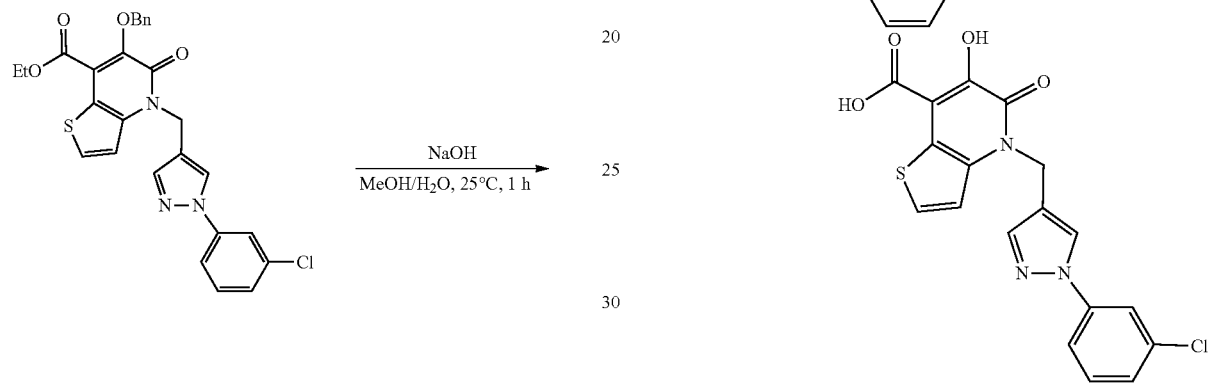

To a solution of ethyl 6-benzyloxy-4-{[1-(3-chlorophenyl)pyrazol-4-yl]methyl}-5-oxo-thieno[3,2-b]pyridine-7-carboxylate (70 mg, 135 µmol) in methanol (2 mL) and water (2 mL) was added sodium hydroxide (22 mg, 538 µmol) and stirred at 25° C. for 1 h. The mixture was added 1M hydrochloric acid (30 mL), and the aqueous phase was extracted with ethyl acetate (3×30 mL), and the combined organic phase was concentrated to dryness in vacuo, 6-benzyloxy-4-{[1-(3-chlorophenyl)pyrazol-4-yl]methyl}-5-oxo-thieno[3,2-b]pyridine-7-carboxylic acid (60 mg) was obtained as a yellow oil and was used crude in the next reaction without further purification.

Step 3: 4-{[1-(3-chlorophenyl)pyrazol-4-yl]methyl}-6-hydroxy-5-oxo-thieno[3,2-b]pyridine-7-carboxylic acid

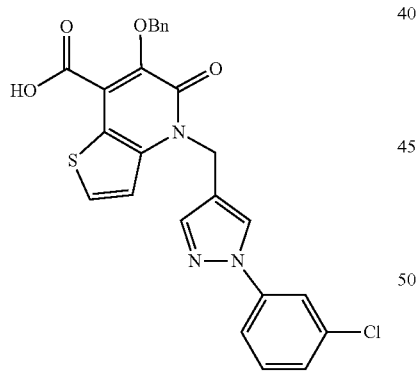

A solution of 6-benzyloxy-4-{[1-(3-chlorophenyl)pyrazol-4-yl]methyl}-5-oxo-thieno[3,2-b]pyridine-7-carboxylic acid (50 mg, 102 µmol) in trifluoroacetic acid (5 mL) was stirred at 20° C. for 1 h. The mixture was concentrated to dryness in vacuo. The crude product was purified by preperative-HPLC (column: Phenomenex Synergi C18 150× 25×10 µm; mobile phase: [water (0.1% TFA)-ACN]; B %: 30%-60%, 12 min) to give the title compound, Example 19, (30 mg, 69% yield). LCMS: (ES+) m/z (M+H)$^+$=401; $^1$H NMR (400 MHz, DMSO-d$_6$) δ 8.60 (s, 1H), 7.88 (s, 1H), 7.77 (d, J=8.4 Hz, 2H), 7.62 (d, J=5.6 Hz, 1H), 7.48 (d, J=8 Hz, 1H), 7.44 (d, J=5.6 Hz, 1H), 7.36 (s, 1H), 5.36 (s, 2H).

Example 20: 6-hydroxy-5-oxo-4-[(1-phenyl-1H-1,2,4-triazol-3-yl)methyl]-4,5-dihydrothieno[3,2-b]pyridine-7-carboxylic acid

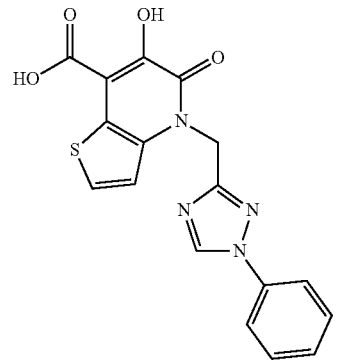 [SMILES: O=C(O)c1c(O)c(=O)n(Cc2ncn(-c3ccccc3)n2)c2ccsc12]

Step 1: 3-(bromomethyl)-1-phenyl-1H-1,2,4-triazole

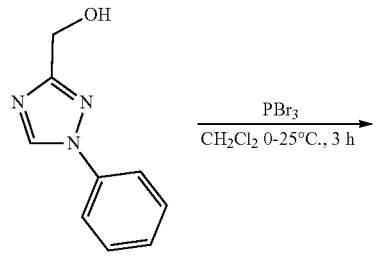

To a solution of the above alcohol (190 mg, 1.08 mmol) in Dichloromethane (5 mL) was added phosphorus tribromide (1.47 g, 5.42 mmol) at 0° C. The mixture was stirred at 25° C. for 3 h. The mixture was quenched with water (10 mL) and extracted with Ethyl acetate (3×10 mL). The combine organic layer was evaporated and the residue was purified by column chromatography (petroleum ether/ethyl acetate=10:1-1:1) to give 3-(bromomethyl)-1-phenyl-1H-1,2,4-triazole (160 mg, 62% yield) as a brown oil. LCMS: (ES$^+$) m/z (M+H)$^+$=238.0.

Step 2: ethyl 6-(benzyloxy)-5-oxo-4-[(1-phenyl-1H-1,2,4-triazol-3-yl)methyl]-4,5-dihydrothieno[3,2-b]pyridine-7-carboxylate

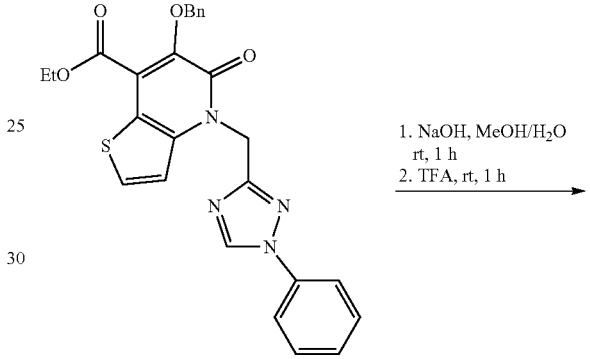

To a solution of Intermediate C (138 mg, 420 μmol) in N,N-dimethylformamide (5 mL) was added cesium carbonate (274 mg, 840 μmol) and lithium bromide (109 mg, 1.26 mmol). The mixture was stirred at 25° C. for 30 min, then 3-(bromomethyl)-1-phenyl-1H-1,2,4-triazole (0.12 g, 504 μmol) was added into the mixture and stirred at 50° C. for 16 h. The mixture was diluted with water (10 mL) and extracted with ethyl acetate (3×10 mL). The combine organic layers were concentrated in vacuo and the crude residue was purified by column chromatography (petroleum ether/ethyl acetate=7:1-:1) to give ethyl 6-(benzyloxy)-5-oxo-4-[(1-phenyl-1H-1,2,4-triazol-3-yl)methyl]-4,5-dihydrothieno[3,2-b]pyridine-7-carboxylate (200 mg, 98% yield) as a yellow solid. LCMS: (ES$^+$) m/z (M+H)$^+$=487.1

Step 3 & 4: 6-hydroxy-5-oxo-4-[(1-phenyl-1H-1,2,4-triazol-3-yl)methyl]-4,5-dihydrothieno[3,2-b]pyridine-7-carboxylic acid

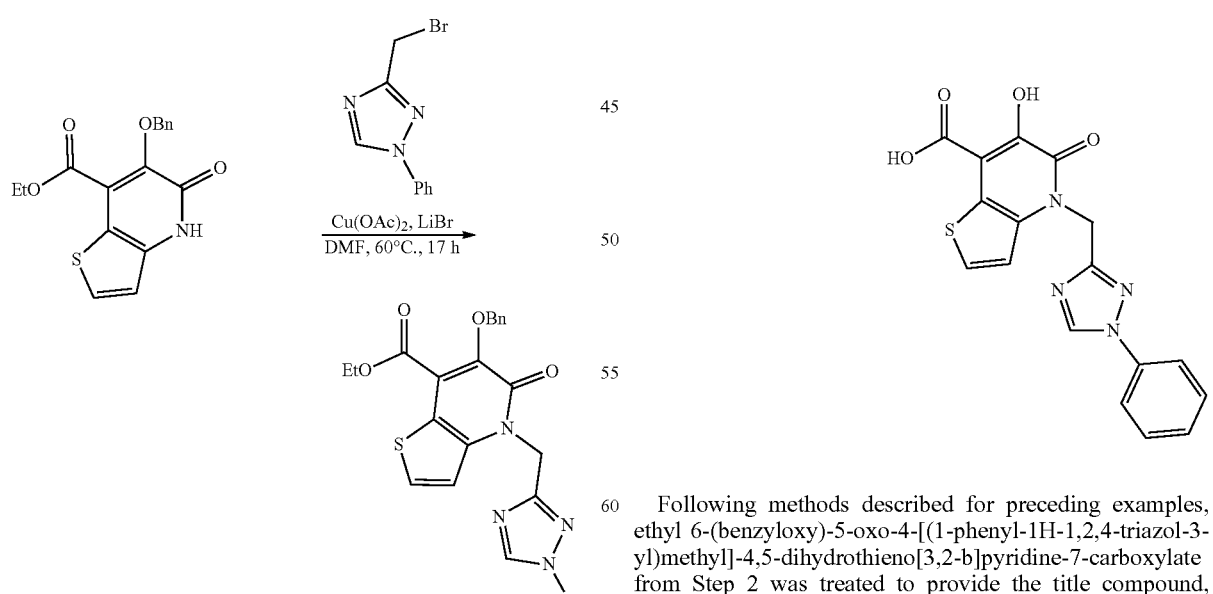

Following methods described for preceding examples, ethyl 6-(benzyloxy)-5-oxo-4-[(1-phenyl-1H-1,2,4-triazol-3-yl)methyl]-4,5-dihydrothieno[3,2-b]pyridine-7-carboxylate from Step 2 was treated to provide the title compound, Example 20 (3 mg). LCMS: (ES$^+$) m/z (M+H)$^+$=368.9; $^1$H NMR (DMSO-d$_6$, 400 MHz): δ 9.19 (s, 1H), 7.70 (d, J=7.6 Hz, 2H), 7.51-7.55 (m, 3H), 7.41 (d, J=7.6 Hz, 1H), 7.24-7.25 (m, 1H), 5.61 (s, 2H).

Example 21: 6-hydroxy-4-{[1-(4-nitrophenyl)-1H-pyrazol-4-yl]methyl}-5-oxo-4,5-dihydrothieno[3,2-b]pyridine-7-carboxylic acid

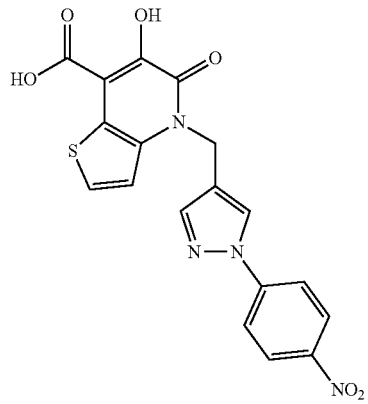 [SMILES: O=C(O)c1c(O)c(=O)n(Cc2cnn(-c3ccc([N+](=O)[O-])cc3)c2)c2ccsc12]

Step 1: ethyl 6-(benzyloxy)-4-{[1-(4-nitrophenyl)-1H-pyrazol-4-yl]methyl}-5-oxo-4,5-dihydrothieno[3,2-b]pyridine-7-carboxylate

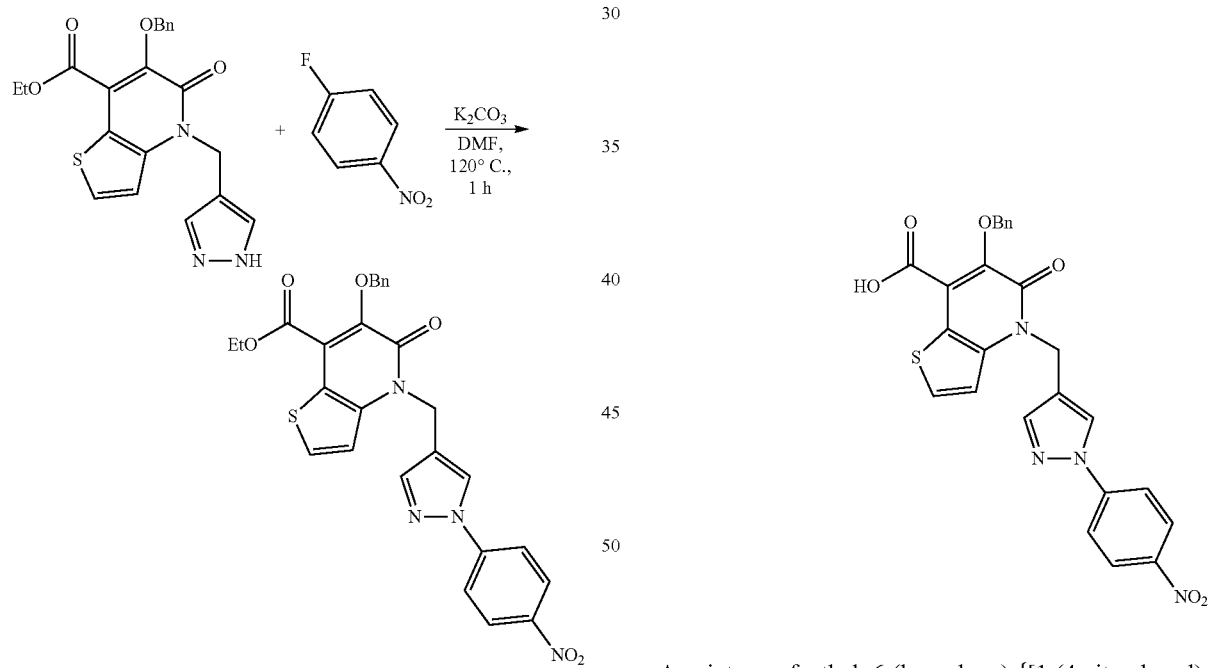

A mixture of ethyl Intermediate D (1.0 g, 2.44 mmol), 1-fluoro-4-nitro-benzene (413 mg, 2.93 mmol), potassium carbonate (675 mg, 4.88 mmol) in N,N-dimethylformamide (10 mL) was stirred at 120° C. for 1 h. On completion, the reaction was diluted with water (40 mL), extracted with ethyl acetate (3×20 mL). The combined organic phase was washed with brine, dried over anhydrous sodium sulfate and concentrated. The residue was purified by column chromatography (petroleum ether/ethyl acetate=3:1-2:1) to give ethyl 6-(benzyloxy)-4-{[1-(4-nitrophenyl)-1H-pyrazol-4-yl] methyl}-5-oxo-4,5-dihydrothieno[3,2-b]pyridine-7-carboxylate (700 mg, 54% yield) as a white solid. $^1$H NMR (400 MHz, CDCl$_3$) δ 8.24 (d, J=9.2 Hz, 2H), 8.04 (s, 1H), 7.78-7.72 (m, 3H), 7.54 (d, J=5.2 Hz, 1H), 7.48 (d, J=6.8 Hz, 2H), 7.31-7.27 (m, 3H), 7.11 (d, J=5.6 Hz, 1H), 5.34 (s, 2H), 5.27 (s, 2H), 4.33 (q, J=7.2 Hz, 2H), 1.27 (t, J=7.2 Hz, 1H).

Step 2: 6-(benzyloxy)-4-{[1-(4-nitrophenyl)-1H-pyrazol-4-yl]methyl}-5-oxo-4,5-dihydrothieno[3,2-b]pyridine-7-carboxylic acid

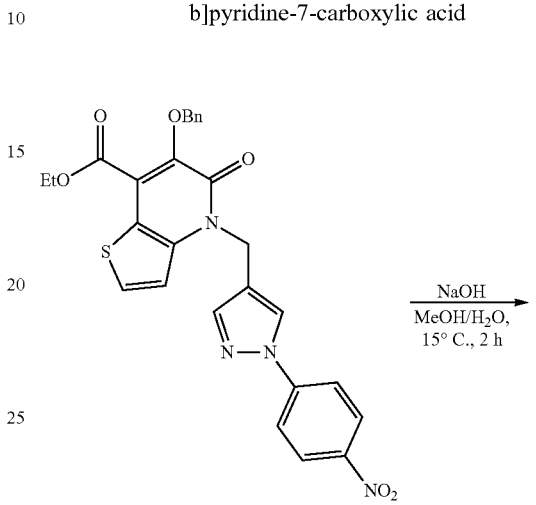

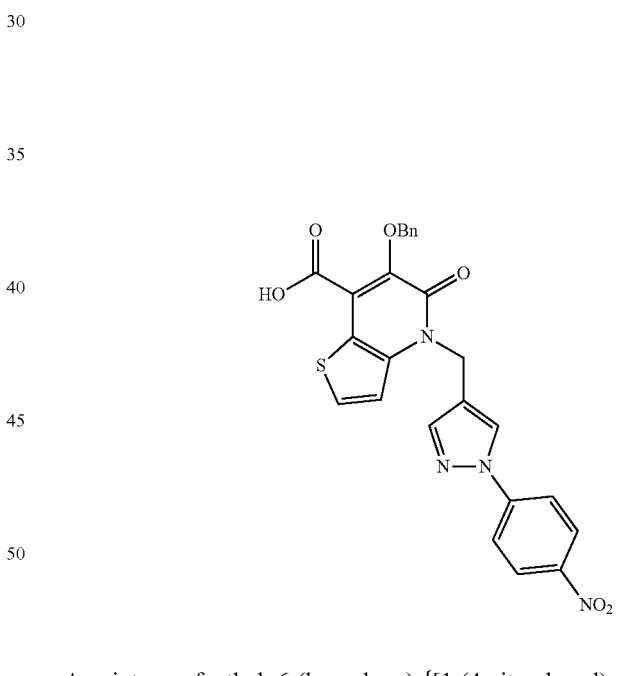

A mixture of ethyl 6-(benzyloxy)-{[1-(4-nitrophenyl)-1H-pyrazol-4-yl]methyl}-5-oxo-4,5-dihydrothieno[3,2-b] pyridine-7-carboxylate (100 mg, 188 μmol) and sodium hydroxide (23 mg, 565 μmol) in methanol (1.5 mL) and water (0.5 mL) was stirred at 15° C. for 2 h. On completion, the reaction was concentrated in vacuo to remove the methanol. The residue was adjusted pH to 3 with 1 M hydrochloric acid and a white solid precipitate was isolated. The solid was collected and dried under vacuum to give 6-(benzyloxy)-4-{[1-(4-nitrophenyl)-1H-pyrazol-4-yl] methyl}-5-oxo-4,5-dihydrothieno[3,2-b]pyridine-7-carboxylic acid (70 mg, crude) as a white solid. LCMS: (ES$^+$) m/z (M+H)$^+$=503.1.

Step 3: 6-hydroxy-4-{[1-(4-nitrophenyl)-1H-pyrazol-4-yl]methyl}-5-oxo-4,5-dihydrothieno[3,2-b]pyridine-7-carboxylic acid

Example 22: 4-{[1-(4-acetamidophenyl)-1H-pyrazol-4-yl]methyl}-6-hydroxy-5-oxo-4,5-dihydrothieno[3,2-b]pyridine-7-carboxylic acid

Step 1: ethyl 4-((1-(4-aminophenyl)-1H-pyrazol-4-yl)methyl)-6-(benzyloxy)-5-oxo-4,5-dihydrothieno[3,2-b]pyridine-7-carboxylate

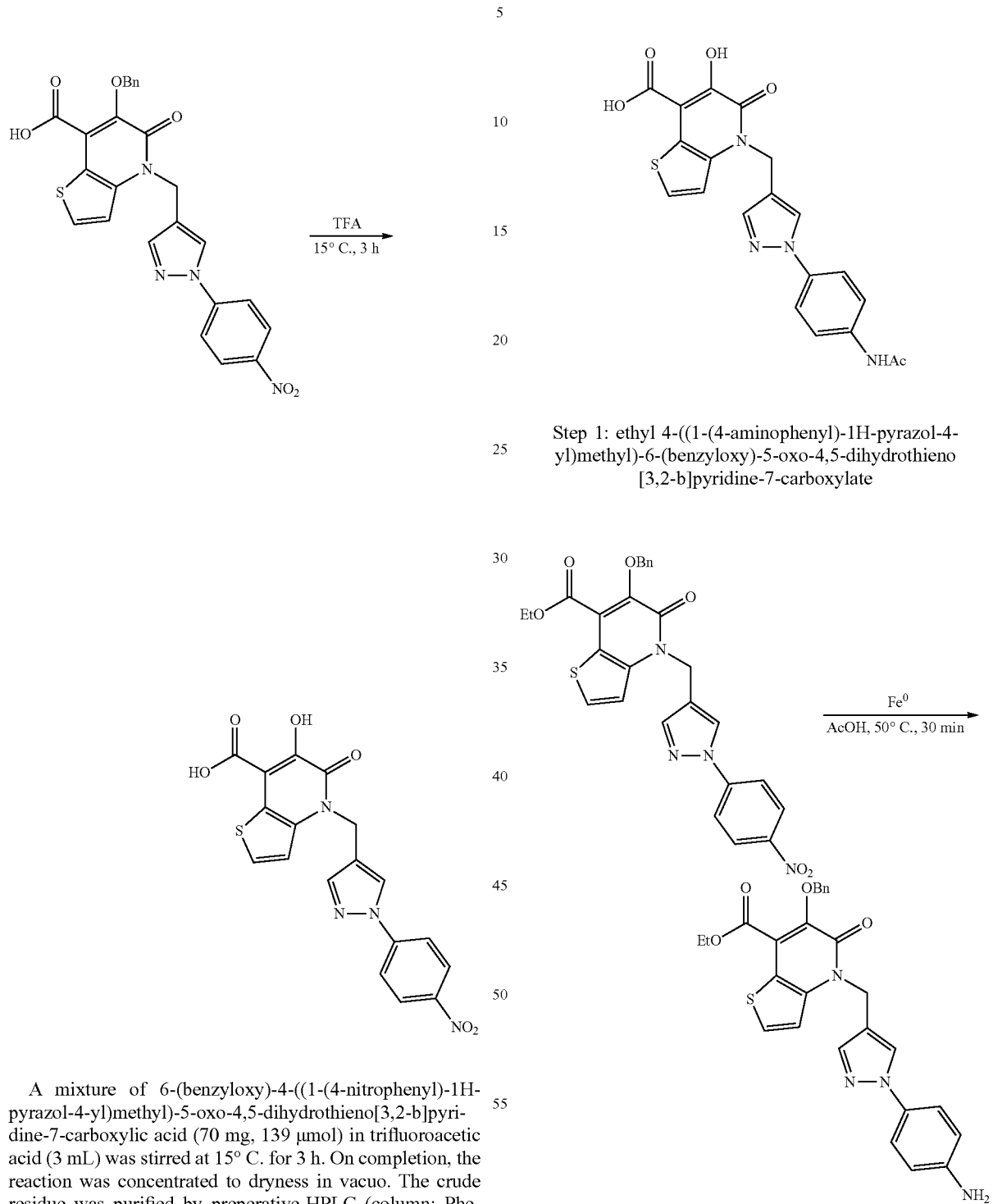

A mixture of 6-(benzyloxy)-4-((1-(4-nitrophenyl)-1H-pyrazol-4-yl)methyl)-5-oxo-4,5-dihydrothieno[3,2-b]pyridine-7-carboxylic acid (70 mg, 139 μmol) in trifluoroacetic acid (3 mL) was stirred at 15° C. for 3 h. On completion, the reaction was concentrated to dryness in vacuo. The crude residue was purified by preperative-HPLC (column: Phenomenex Synergi C18 150×25×10 uμm; mobile phase: [water (0.1% TFA)-ACN]; B %: 30%-60%, 10 min) to give the title compound, Example 21, (5.1 mg, 9% yield) as a white solid. $^1$H NMR (400 MHz, DMSO-d$_6$) δ 8.72 (s, 1H), 8.32 (d, J=9.6 Hz, 2H), 8.04 (d, J=8.4 Hz, 2H), 7.90 (s, 1H), 7.60 (d, J=5.6 Hz, 1H), 7.45 (d, J=4.8 Hz, 1H), 5.38 (s, 2H). LCMS: (ES$^+$) m/z (M+H)$^+$=413.0.

To a solution of ethyl 6-benzyloxy-4-{[1-(4-nitrophenyl)pyrazol-4-yl]methyl}-5-oxo-thieno[3,2-b]pyridine-7-carboxylate (600 mg, 1.13 mmol) in acetic acid (5 mL) was added iron powders (316 mg, 5.65 mmol) portion-wise and at the reaction was heated to 50° C. and stirred for 30 min. On completion, the mixture was filtered and the filtrate was adjusted pH to 9 with 1 M sodium hydroxide and extracted with ethyl acetate (3×50 mL). The combined organic phase was washed with brine, dried over anhydrous sodium sulfate to give ethyl 4-{[1-(4-aminophenyl)-1H-pyrazol-4-yl]methyl}-6-(benzyloxy)-5-oxo-4,5-dihydrothieno[3,2-b]pyridine-7-carboxylate (300 mg) as a yellow solid. ¹H NMR (400 MHz, CDCl₃) δ 7.88 (s, 1H), 7.71 (s, 1H), 7.64-7.52 (m, 3H), 7.30-7.47 (m, 6H), 7.22 (d, J=5.6 Hz, 1H), 6.72 (d, J=8.0 Hz, 1H), 5.41 (s, 2H), 5.36 (s, 2H), 4.41 (q, J=7.2 Hz, 2H), (t, J=7.2 Hz, 2H); LCMS: (ES⁺) m/z (M+H)⁺=501.1.

Step 2: ethyl 4-{[1-(4-acetamidophenyl)-1H-pyrazol-4-yl]methyl}-6-(benzyloxy)-5-oxo-4,5-dihydrothieno[3,2-b]pyridine-7-carboxylate

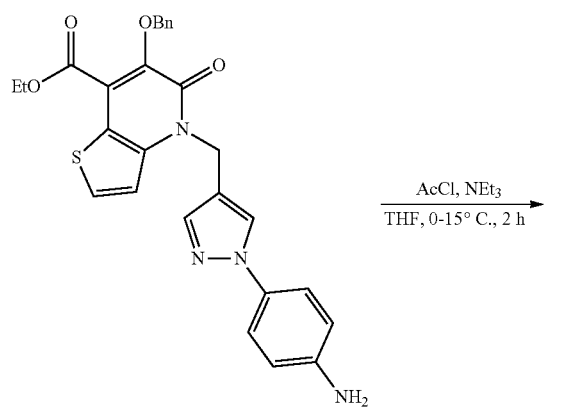

Step 3 & 4: 4-((1-(4-acetamidophenyl)-1H-pyrazol-4-yl)methyl)-6-hydroxy-5-oxo-4,5-dihydrothieno[3,2-b]pyridine-7-carboxylic acid

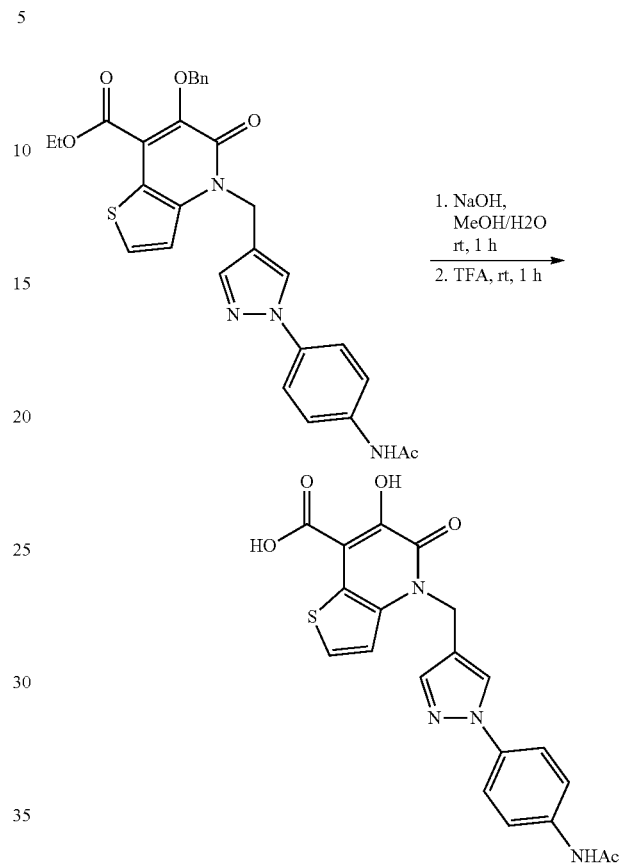

Following the methods described for preceding examples, ethyl 4-{[1-(4-acetamidophenyl)-1H-pyrazol-4-yl]methyl}-6-(benzyloxy)-5-oxo-4,5-dihydrothieno[3,2-b]pyridine-7-carboxylate was treated to provide the title compound, Example 22, (11.6 mg, 28%) as a white solid. ¹H NMR (DMSO-d6, 400 MHz): δ 10.06 (s, 1H), 8.41 (s, 1H), 7.72 (s, 1H), 7.66-7.64 (m, 5H), 7.48 (d, J=5.6 Hz, 1H), 5.38 (s, 2H), 2.04 (s, 3H); LCMS: (ES⁺) m/z (M+H)⁺=425.0.

Example 24: 6-hydroxy-5-oxo-4-(pyrazolo[1,5-a]pyridin-3-ylmethyl)-4,5-dihydrothieno[3,2-b]pyridine-7-carboxylic acid

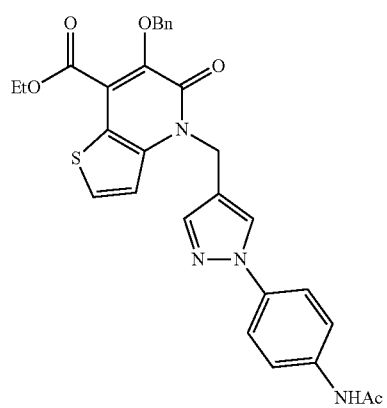 [SMILES: CC(=O)Nc1ccc(-n2cc(Cn3c(=O)c(O)c(C(=O)O)c4sccc43)cn2)cc1]

To a solution of ethyl-4-{[1-(4-aminophenyl)-1H-pyrazol-4-yl]methyl}-6-(benzyloxy)-5-oxo-4,5-dihydrothieno[3,2-b]pyridine-7-carboxylate (80 mg, 160 μmol) and triethylamine (24 mg, 240 μmol) in tetrahydrofuran (3 mL) was added acetyl chloride (14 mg, 176 μmol) at 0° C. The reaction mixture was then t stirred at 15° C. for 2 h. The reaction mixture was concentrated to dryness in vacuo to remove tetrahydrofuran to give ethyl 4-{[1-(4-acetamidophenyl)-1H-pyrazol-4-yl]methyl}-6-(benzyloxy)-5-oxo-4,5-dihydrothieno[3,2-b]pyridine-7-carboxylate (90 mg) as a yellow oil. LCMS: (ES⁺) m/z (M+H)⁺=543.0.

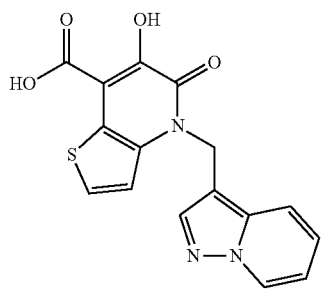 [SMILES: O=C(O)c1c(O)c(=O)n(Cc2cnn3ccccc23)c2ccsc12]

Step 1: ethyl 6-(benzyloxy)-5-oxo-4-(pyrazolo[1,5-a]pyridin-3-ylmethyl)-4,5-dihydrothieno[3,2-b]pyridine-7-carboxylate

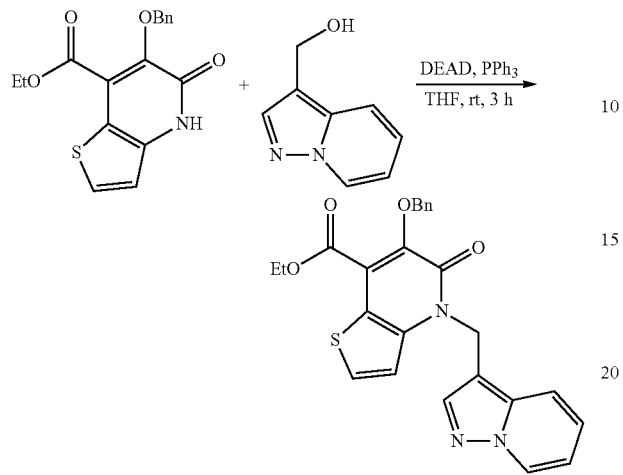

To a solution of ethyl 6-benzyloxy-5-oxo-4H-thieno[3,2-b]pyridine-7-carboxylate (206 mg, 627 μmol) in tetrahydrofuran (5 mL) was added diethyl azodicarboxylate (120 mg, 689.4 μmol) and triphenylphosphine (181 mg, 689.40 μmol). The mixture was stirred at 25° C. for 30 min, then pyrazolo[1,5-a]pyridin-3-ylmethanol (130 mg, 878 μmol) was added and the mixture was stirred at 5° C. for 3 h. The solution was evaporated under reduced pressure and the residue was purified by prep-TLC (petroleum ether/ethyl acetate=1:1) to give ethyl 6-(benzyloxy)-5-oxo-4-(pyrazolo[1,5-a]pyridin-3-ylmethyl)-4,5-dihydrothieno[3,2-b]pyridine-7-carboxylate (0.06 g, 21% yield) as a yellow solid. LCMS: (ES$^+$) m/z (M+H)$^+$=460.0.

Step 2 & 3: 6-hydroxy-5-oxo-4-(pyrazolo[1,5-a]pyridin-3-ylmethyl)-4,5-dihydrothieno[3,2-b]pyridine-7-carboxylic acid

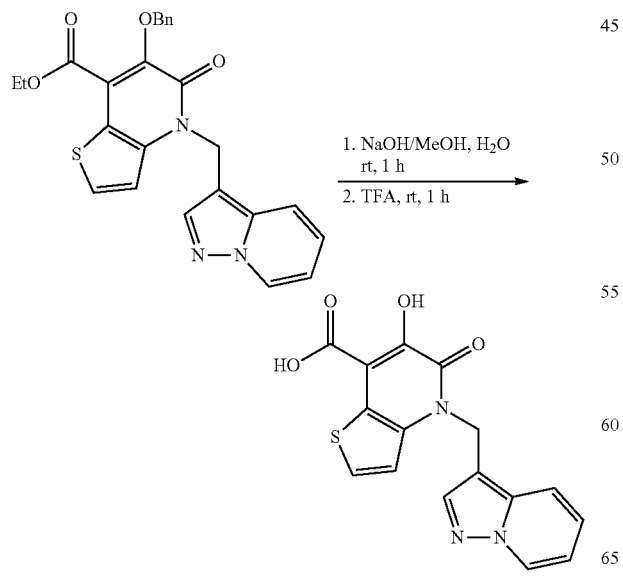

Following the methods described for preceding examples, ethyl 6-(benzyloxy)-5-oxo-4-(pyrazolo[1,5-a]pyridin-3-ylmethyl)-4,5-dihydrothieno[3,2-b]pyridine-7-carboxylate was treated to provide the title compound, Example 24, (1.7 mg, 5% yield) as a white solid. $^1$H NMR (DMSO-d$_6$, 400 MHz): δ 8.60 (d, J=6.8, 1H), 8.17 (s, 1H), 7.95 (s, 1H), 7.54-7.56 (m, 2H), 7.24-7.25 (m, 1H), 6.88 (d, J=6.8 Hz, 1H), 5.61 (s, 2H); LCMS: (ES$^+$) m/z (M+Na)$^+$=363.9.

Example 25: 6-hydroxy-4-{[1-(4-methoxyphenyl)triazol-4-yl]methyl}-5-oxo-thieno[3,2-b]pyridine-7-carboxylic acid

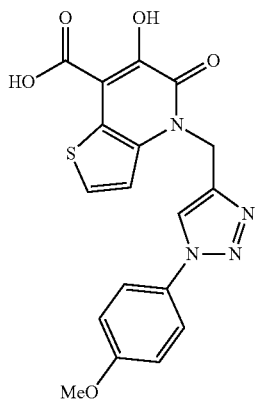 [SMILES: COc1ccc(-n2cc(Cn3c(=O)c(O)c(C(=O)O)c4sccc43)nn2)cc1]

Step 1: ethyl 6-hydroxy-5-oxo-4-prop-2-ynyl-thieno[3,2-b]pyridine-7-carboxylate

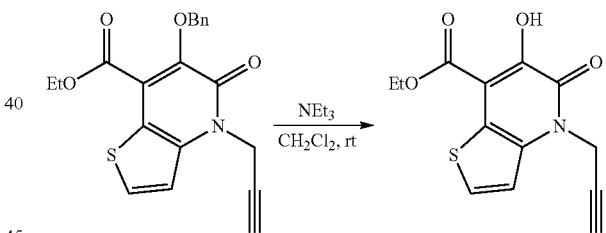

Ethyl 6-hydroxy-5-oxo-4-prop-2-ynyl-thieno[3,2-b]pyridine-7-carboxylate was prepared from ethyl 6-(benzyloxy)-5-oxo-4-(prop-2-yn-1-yl)-4,5-dihydrothieno[3,2-b]pyridine-7-carboxylate by treatment with trifluoroacetic acid in dichloromethane.

Step 2: ethyl 6-benzyloxy-4-{[1-[(2-methylpyrazol-3-yl)methyl]pyrazol-4-yl]methyl}-5-oxo-thieno[3,2-b]pyridine-7-carboxylate

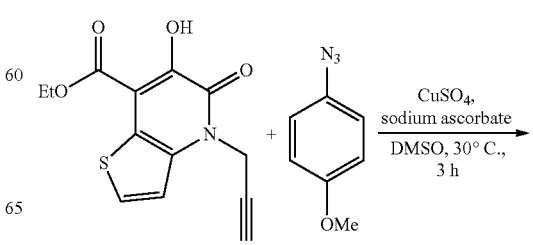

-continued

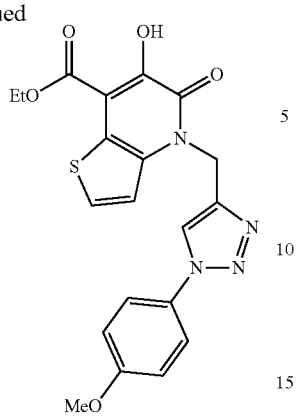

A mixture of ethyl 6-hydroxy-5-oxo-4-prop-2-ynyl-thieno[3,2-b]pyridine-7-carboxylate (100 mg, 361 µmol), 1-azido-4-methoxy-benzene (80 mg, 540 µmol), copper sulfate (12 mg, 72 µmol), sodium ascorbate (29 mg, 144 µmol, 0.4 eq) in dimethylsulfoxide (3 mL). Then the mixture was stirred at 25° C. for 1 h. The mixture was purified by reverse phase column chromatography to give ethyl 6-benzyloxy-4-({1-[(2-methylpyrazol-3-yl)methyl]pyrazol-4-yl}methyl)-5-oxo-thieno[3,2-b]pyridine-7-carboxylate (45 mg, 29% yield) as a yellow solid. 41 NMR (300 MHz, DMSO-d6) δ 8.58 (s, 1H), 7.76 (d, J=9.0 Hz, 2H), 7.55 (s, 1H), 7.38 (s, 1H), 7.18-7.02 (m, 2H), 5.69-5.46 (m, 2H), 4.36 (s, 2H), 3.81 (s, 3H), 1.33 (t, J=7.6 Hz, 3H); LCMS: (ES$^+$) m/z (M–H)$^-$=424.9.

Step 3: 6-hydroxy-4-{[1-(4-methoxyphenyl)triazol-4-yl]methyl}-5-oxo-thieno[3,2-b]pyridine-7-carboxylic acid

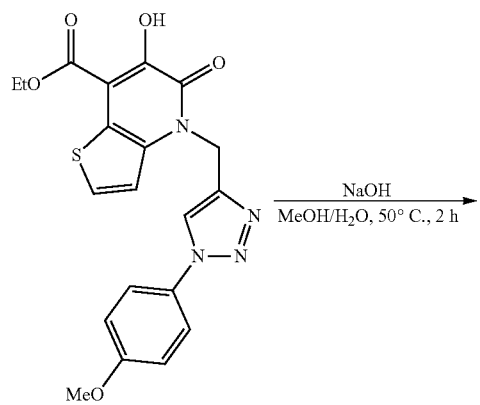

Following methods described for preceding examples, ethyl 6-benzyloxy-4-({1-[(2-methylpyrazol-3-yl)methyl]pyrazol-4-yl}methyl)-5-oxo-thieno[3,2-b]pyridine-7-carboxylate was treated to provide the title compound, Example 25, (4 mg, 5%). $^1$H NMR (400 MHz, DMSO-d6) δ 8.63 (s, 1H), 7.75 (d, J=8.8 Hz, 2H), 7.68 (d, J=6.0 Hz, 1H), 7.43 (d, J=5.6 Hz, 1H), 7.09 (d, J=8.8 Hz, 2H), 5.59 (s, 2H), 3.80 (s, 3H); LCMS: (ES+) m/z (M+H)$^+$=399.0.

Example 26: 4-{[1-(4-cyano-3-methoxybenzyl)-1H-pyrazol-4-yl]methyl}-6-hydroxy-5-oxo-4,5-dihydrothieno[3,2-b]pyridine-7-carboxylic acid

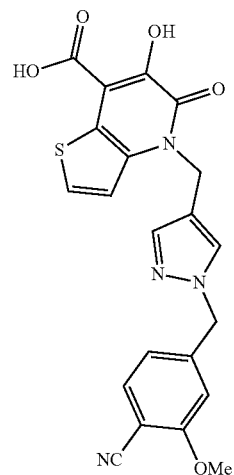 [SMILES: COc1cc(Cn2cc(Cn3c(=O)c(O)c(C(=O)O)c4sccc43)cn2)ccc1C#N]

Step 1: ethyl 6-(benzyloxy)-4-{[1-(4-bromo-3-methoxybenzyl)-1H-pyrazol-4-yl]methyl}-5-oxo-4,5-dihydrothieno[3,2-b]pyridine-7-carboxylate

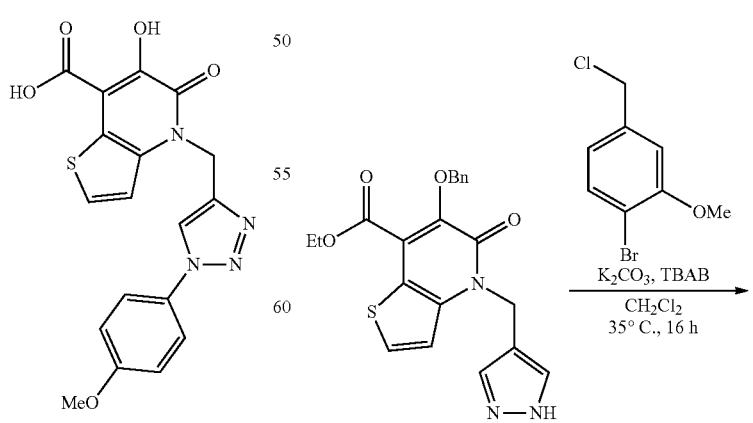

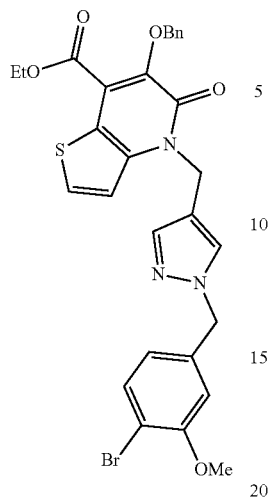

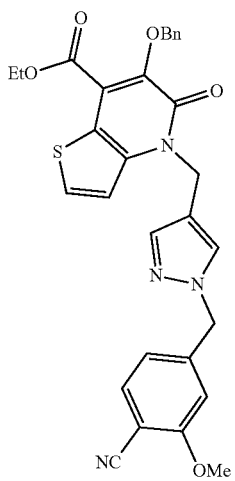

To a solution of Intermediate D (200 mg, 0.49 mmol), tetrabutylammonium bromide (32 mg, 98 μmol), potassium carbonate (270 mg, 2.0 mmol) in dichloromethane (8 mL) was added 1-bromo-4-(chloromethyl)-2-methoxybenzene (230 mg, 0.98 mmol). The mixture was stirred at 35° C. for 16 h. On completion, the solution concentrated in vacuo and purified by column chromatography [petroleum ether/ethyl acetate=5:1-2:1] to give compound ethyl 6-(benzyloxy)-4-{[1-(4-bromo-3-methoxybenzyl)-1H-pyrazol-4-yl]methyl}-5-oxo-4,5-dihydrothieno[3,2-b]pyridine-7-carboxylate (260 mg, 88% yield) as a yellow solid. $^1$H NMR (CDCl$_3$, MHz): δ 7.60-7.55 (m, 6H), 7.39-7.37 (m, 3H), 7.16 (d, J=5.6 Hz, 1H), 6.70-6.67 (m, 2H), 5.33 (s, 4H), 5.19 (s, 2H), 4.41 (q, J=7.2 Hz, 2H), 3.81 (s, 3H), 1.36 (t, J=7.2 Hz, 3H).

A solution of compound ethyl 6-(benzyloxy)-4-{[1-(4-bromo-3-methoxybenzyl)-1H-pyrazol-4-yl]methyl}-5-oxo-4,5-dihydrothieno[3,2-b]pyridine-7-carboxylate (250 mg, 0.41 mmol), tris(debenzylideneactone) dipalladium (11 mg, 12 μmol), zinc cyanide (29 mg, 0.25 mmol) and 1,1'-bis(diphenylphosphino)ferrocene (11 mg, 20 μmol) in dimethylacetamide (8 mL) was heated at 150° C. for 1 h by microwave. The reaction mixture was cooled to room temperature, poured into water (20 mL) and extracted with ethyl acetate (2×50 mL). The organic layer was separate and concentrated directly. The residue was purified by column chromatography [petroleum ether/ethyl acetate=4:1-1:1] to give compound ethyl 6-(benzyloxy)-4-{[1-(4-cyano-3-methoxybenzyl)-1H-pyrazol-4-yl]methyl}-5-oxo-4,5-dihydrothieno[3,2-b]pyridine-7-carboxylate (70 mg, 31% yield) as a yellow solid.

Step 2: ethyl 6-(benzyloxy)-4-{[1-(4-cyano-3-methoxybenzyl)-1H-pyrazol-4-yl]methyl}-5-oxo-4,5-dihydrothieno[3,2-b]pyridine-7-carboxylate Step 3: 6-(benzyloxy)-4-{[1-(4-cyano-3-methoxybenzyl)-1H-pyrazol-4-yl]methyl}-5-oxo-4,5-dihydrothieno[3,2-b]pyridine-7-carboxylic acid

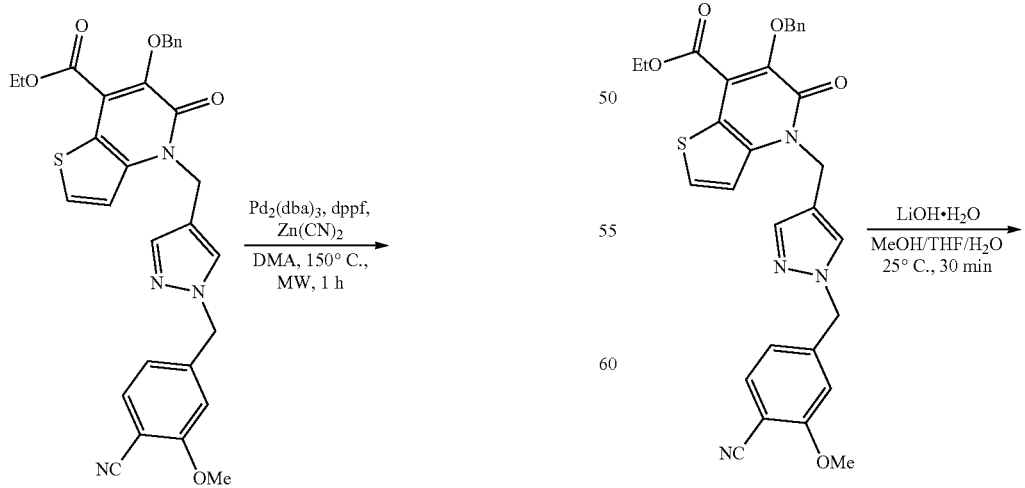

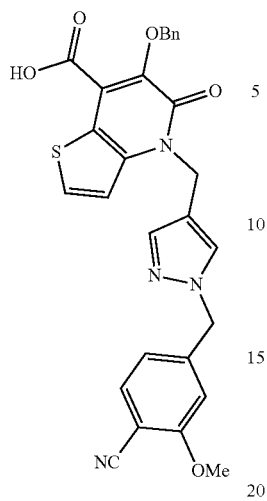

To a solution of compound ethyl 6-(benzyloxy)-4-{[1-(4-cyano-3-methoxybenzyl)-1H-pyrazol-4-yl]methyl}-5-oxo-4,5-dihydrothieno[3,2-b]pyridine-7-carboxylate (50 mg, 90 µmol) in methanol (2 mL), tetrahydrofuran (2 mL), water (1 mL) was added lithium hydroxide monohydrate (11 mg, 0.27 mmol). The mixture was stirred at 25° C. for 30 min. On completion, the solution was concentrated in vacuo to remove the organic solvent. The crude residue was diluted with water (5 mL) and adjusted the pH to 4-5 with 1 M hydrochloric acid solution and then filtered. The cake was collected and dried under vacuum to give compound 6-(benzyloxy)-4-{[1-(4-cyano-3-methoxybenzyl)-1H-pyrazol-4-yl]methyl}-5-oxo-4,5-dihydrothieno[3,2-b]pyridine-7-carboxylic acid (35 mg, 74% yield) as white solid. $^1$H NMR (DMSO-d$_6$, 400 MHz): δ 7.94-7.89 (m, 2H), 7.66 (d, J=8.0 Hz, 1H), 7.58-7.51 (m, 4H), 7.37-7.35 (m, 3H), 7.03 (s, 1H), 6.78 (d, J=8.0 Hz, 1H), 5.35 (s, 2H), 5.31 (s, 2H), 5.19 (s, 2H), 3.80 (s, 3H).

Step 4: 4-{[1-(4-cyano-3-methoxybenzyl)-1H-pyrazol-4-yl]methyl}-6-hydroxy-5-oxo-4,5-dihydrothieno[3,2-b]pyridine-7-carboxylic acid

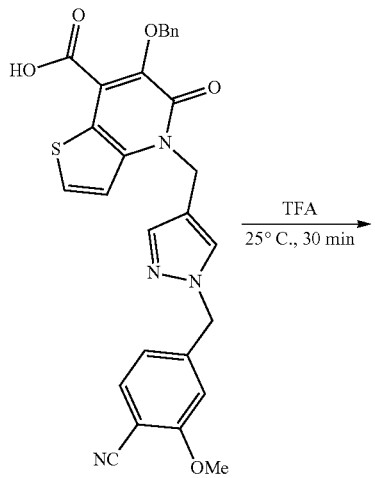

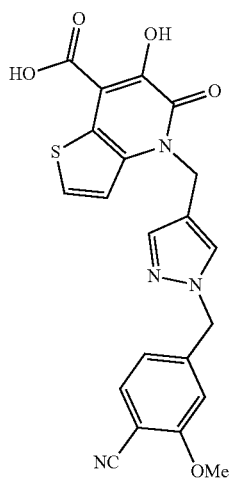

To a solution of 6-(benzyloxy)-4-{[1-(4-cyano-3-methoxybenzyl)-1H-pyrazol-4-yl]methyl}-5-oxo-4,5-dihydrothieno[3,2-b]pyridine-7-carboxylic acid (30 mg, 57 µmol) in trifluoroacetic acid (4 mL) was stirred at 25° C. for 30 min. On completion, the solution was concentrated to dryness in vacuo and the crude residue was purified by preperative-HPLC [Instrument: GX-B; Phenomenex Synergi C18 120×30 mm, particle size: 10 µm; Mobile phase: 18-48% acetonitrile in H$_2$O (add 0.1% TFA, v/v)]. Each set of collected fractions were concentrated at room temperature and lyophilized to give the title compound, Example 26, (12 mg, 34% yield) as a pale green solid. $^1$H NMR (DMSO-d6, 400 MHz): δ 7.89 (s, 1H), 7.66 (d, J=8.0 Hz, 1H), 7.61 (d, J=5.6 Hz, 1H), 7.55 (s, 1H), 7.43 (d, J=6.0 Hz, 1H), 7.03 (s, 1H), 6.77 (d, J=8.4 Hz, 1H), 5.34 (s, 2H), 5.26 (s, 2H), 3.81 (s, 3H); LCMS: (ES+) m/z (M+H)$^+$=437.0.

Example 27: 6-hydroxy-4-[(1-{2-[(3R)-3-hydroxypyrrolidin-1-yl]-2-oxo-ethyl}pyrazol-4-yl)methyl]-5-oxo-thieno[3,2-b]pyridine-7-carboxylic acid

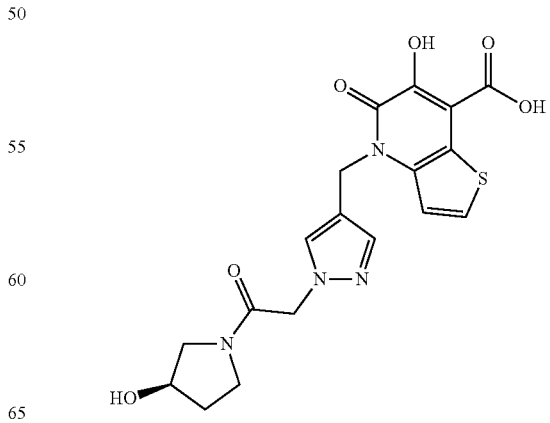

Step 1: ethyl 6-benzyloxy-4-{[1-(2-tert-butoxy-2-oxo-ethyl)pyrazol-4-yl]methyl}-5-oxo-thieno[3,2-b]pyridine-7-carboxylate (1)

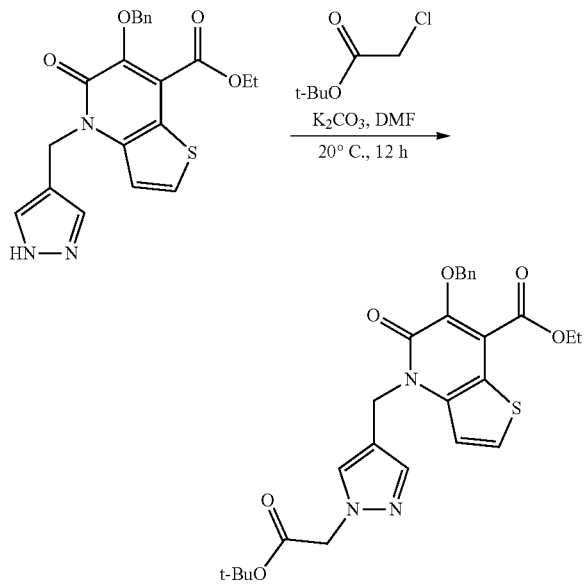

To a solution of ethyl Intermediate D (700 mg, 1.71 mmol in N,N-dimethylformamide (20 mL) was added potassium carbonate (709 mg, 5.13 mmol) and tert-butyl 2-chloroacetate (386 mg, 2.56 mmol, 368 uL). The mixture was stirred at 20° C. for 12 h. The reaction mixture diluted with water (30 mL) and extracted with ethyl acetate (3×30 mL). The combined organic layers were washed with brine (3×20 mL), dried over anhydrous sodium sulfate, filtered and concentrated under reduced pressure to give a crude residue. The crude residue was purified by column chromatography (petroleum ether/ethyl acetate=2:1-1:1) to give ethyl 6-benzyloxy-4-{[1-(2-tert-butoxy-2-oxo-ethyl)pyrazol-4-yl]methyl}-5-oxo-thieno[3,2-b]pyridine-7-carboxylate (720 mg, 80% yield) as a light yellow solid. ¹H NMR (400 MHz, DMSO-d₆) δ 7.97-7.93 (m, 1H), 7.80 (s, 1H), 7.60-7.54 (m, 2H), 7.49 (d, J=6.8 Hz, 2H), 7.42-7.31 (m, 3H), 5.33 (s, 2H), 5.24 (s, 2H), 4.88 (s, 2H), 4.33 (q, J=7.2 Hz, 2H), 1.38 (s, 9H), 1.25 (t, J=7.2 Hz, 3H).

Step 2: 2-(4-{[7-(ethoxycarbonyl)-6-hydroxy-5-oxothieno[3,2-b]pyridin-4(5H)-yl]methyl}-1H-pyrazol-1-yl)acetic acid

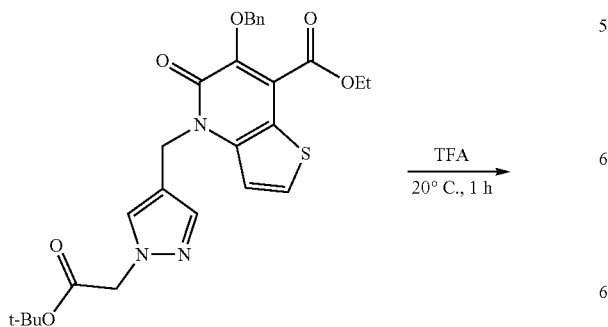

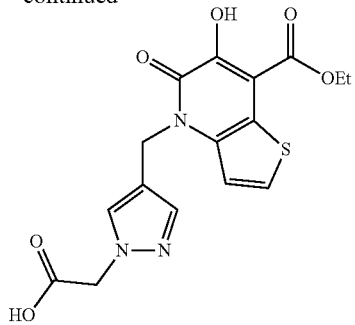

A mixture of ethyl 6-benzyloxy-4-{[1-(2-tert-butoxy-2-oxo-ethyl)pyrazol-4-yl]methyl-5-oxo-thieno[3,2-b]pyridine-7-carboxylate (700 mg, 1.34 mmol) in trifluoroacetic acid (10 mL) was stirred at 20° C. for 1 h. The mixture was concentrated to dryness in vacuo to provide a crude residue. The crude residue was triturated with acetonitrile (10 mL) at 20° C. for 2 h to give 2-(4-{[7-(ethoxycarbonyl)-6-hydroxy-5-oxothieno[3,2-b]pyridin-4(5H)-yl]methyl}-1H-pyrazol-1-yl)acetic acid (450 mg, 89% yield) as a light yellow solid. ¹H NMR (400 MHz, DMSO-d6) δ 7.76-7.71 (m, 2H), 7.54-7.50 (m, 2H), 5.32 (s, 2H), 4.87 (s, 2H), 4.39 (q, J=7.2 Hz, 2H), 1.35 (t, J=7.2 Hz, 3H); LCMS: (ES⁺) m/z (M–H)⁻=375.8.

Step 3: ethyl 6-hydroxy-4-[(1-{2-[(3R)-3-hydroxy-pyrrolidin-1-yl]-2-oxo-ethyl}pyrazol-4-yl)methyl]-5-oxo-thieno[3,2-b]pyridine-7-carboxylate

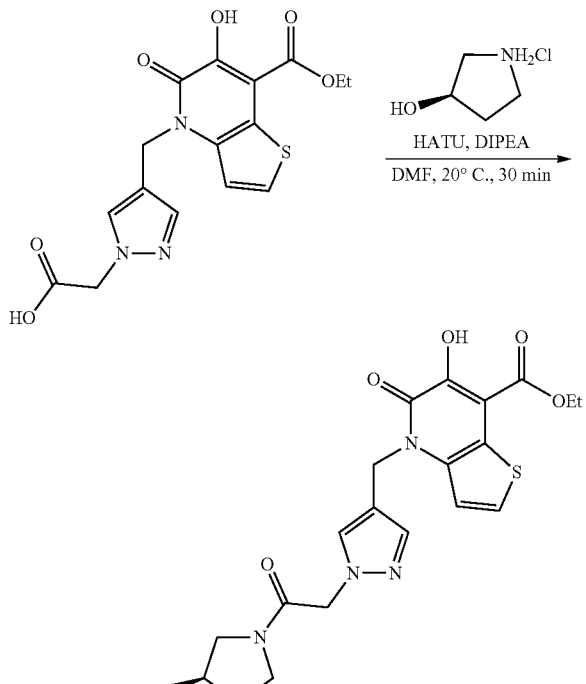

To a solution of 2-(4-{[7-(ethoxycarbonyl)-6-hydroxy-5-oxothieno[3,2-b]pyridin-4(5H)-yl]methyl}-1H-pyrazol-1-yl)acetic acid (100 mg, 265 µmol) in dimethylformamide (5 mL) was added [bis(dimethylamino)methylene]-1H-1,2,3-trizole[4,5-b]pyridinium 3-oxid hexafluorophosphate (202 mg, 530 µmol) and diisopropylethylamine (137 mg, 1.06 mmol). The mixture was stirred at 20° C. for 10 min and then (3R)-pyrrolidin-3-ol hydrochloric acid (49.12 mg, 397.49 µmol, 46.78 uL) was added, the mixture was stirred at 20° C. for 30 min. The mixture was purified by reverse-phase column with no work up to give ethyl 6-hydroxy-4-[(1-{2-[(3R)-3-hydroxypyrrolidin-1-yl]-2-oxo-ethyl}pyrazol-4-yl)methyl]-5-oxo-thieno[3,2-b]pyridine-7-carboxylate (30 mg, 22% yield) as a yellow solid. $^1$H NMR (400 MHz, DMSO-d6) δ 7.73 (d, J=5.6 Hz, 1H), 7.70 (s, 1H), 7.53 (d, J=5.6 Hz, 1H), 7.48 (s, 1H), 5.32 (s, 2H), 4.94 (dd, J=3.2, 20.0 Hz, 2H), 4.39 (q, J=7.2 Hz, 3H), 4.22-4.35 (m, 2H), 3.48-3.58 (m, 2H), 3.23-3.44 (m, 2H), 3.22 (br s, 1H), 3.10 (s, 1H), 1.68-1.99 (m, 2H), 1.35 (t, J 7.2 Hz, 3H)

Step 4: 6-hydroxy-4-[(1-{2-[(3R)-3-hydroxypyrrolidin-1-yl]-2-oxo-ethyl}pyrazol-4-yl]methyl)-5-oxo-thieno[3,2-b]pyridine-7-carboxylic acid

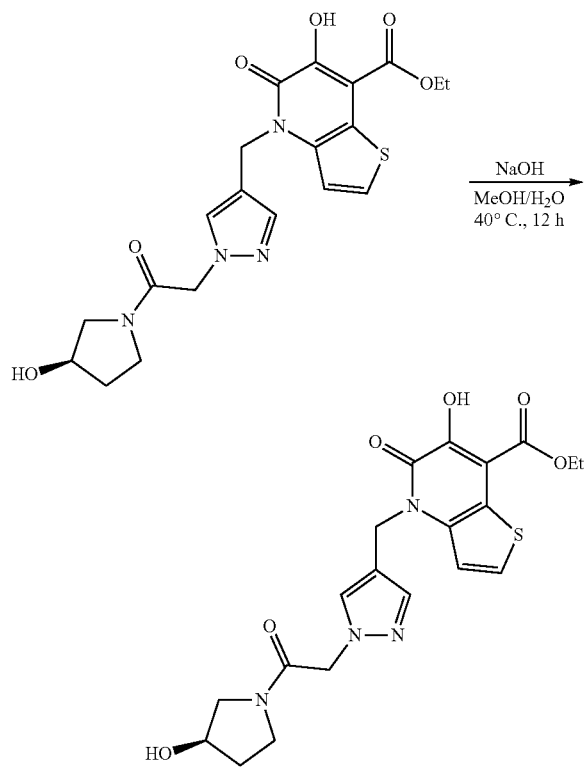

To a solution of ethyl 6-hydroxy-4-[(1-{2-[(3R)-3-hydroxypyrrolidin-1-yl]-2-oxo-ethyl}pyrazol-4-yl)methyl]-5-oxo-thieno[3,2-b]pyridine-7-carboxylate (30 mg, 67 µmol) in methanol (6 mL), tetrahydrofuran (2 mL), and water (2 mL) was added sodium hydroxide (8 mg, 202 µmol). The mixture was stirred at 40° C. for 12 h. The mixture was concentrated to remove the solvent and acidified with 1N hydrochloric acid s to pH=5. The solid was filtered and purified by preperative-HPLC (column: Phenomenex Synergi C18 150×25×10 µm; mobile phase: [water (0.1% TFA)-ACN]; B %: 1%-28%, 11 min) to give to give the title compound, Example 27, (5 mg, 17% yield). $^1$H NMR (400 MHz, DMSO-d$_6$) δ 7.68 (s, 1H), 7.61 (d, J=5.6 Hz, 1H), 7.45-7.47 (m, 2H), 5.27 (s, 2H), 4.93 (br dd, J=3.2, 20.0 Hz, 2H), 4.22-4.35 (m, 2H), 3.44-3.58 (m, 3H), 3.22-3.43 (m, 2H), 1.69-1.96 (m, 2H); LCMS: (ES$^+$) m/z (M–H)$^-$=419.0.

Example 28: 6-hydroxy-5-oxo-4-({1-[2-(4-pyridyl)ethyl]pyrazol-4-yl}methyl)thieno[3,2-b]pyridine-7-carboxylic acid

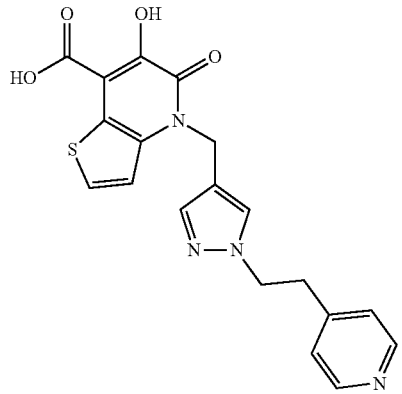 [SMILES: O=C(O)c1c(O)c(=O)n(Cc2cnn(CCc3ccncc3)c2)c2ccsc12]

Step 1: ethyl 6-benzyloxy-5-oxo-4-({1-[2-(4-pyridyl)ethyl]pyrazol-4-yl}methyl)thieno[3,2-b]pyridine-7-carboxylate

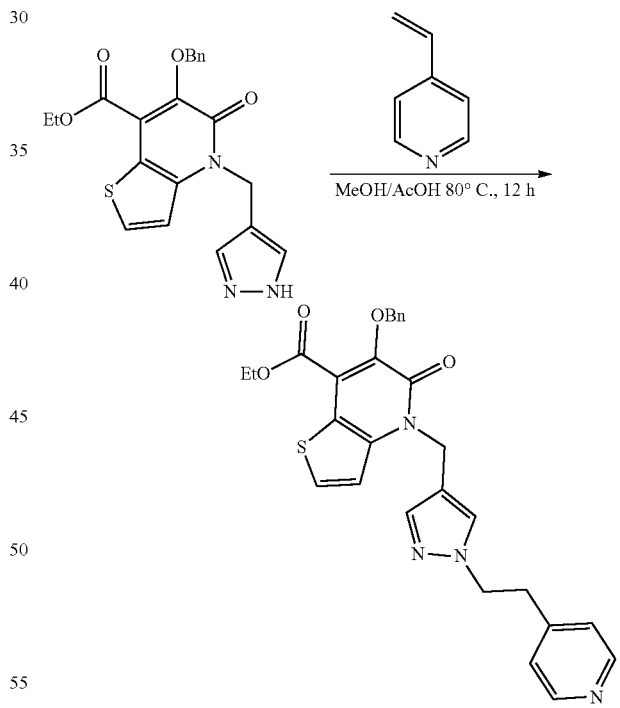

To Intermediate D (0.15 g, 366 µmol), 4-vinylpyridine (77 mg, 733 µmol) and acetic acid (66 mg, 1.10 mmol) in methanol (5 mL). The mixture was degassed and purged with N$_2$ for 3 times and stirred at 80° C. for 12 h under N$_2$ atmosphere. The crude product was purified by preperative-HPLC (column: Phenomenex Synergi C18 150×25×10 um; mobile phase: [water (0.1% TFA)-ACN]; B %: 30%-51%, 10 min) to give ethyl 6-benzyloxy-5-oxo-4-({1-[2-(4-pyridyl)ethyl]pyrazol-4-yl}methyl)thieno[3,2-b]pyridine-7-carboxylate (180 mg, 95% yield) as a white solid. $^1$H NMR (400 MHz, CDCl₃) δ 8.63 (d, J=6.8 Hz, 2H), 7.64 (d, J=5.6 Hz, 1H), 7.55-7.58 (m, 3H), 7.35-7.42 (m, 6H), 7.10 (d, J=6 Hz, 1H), 5.33 (s, 2H), 5.28 (s, 2H), 4.38-4.45 (m, 4H), 3.38 (t, J=6.4 Hz, 2H), 1.36 (t, J=6.8 Hz, 3H)

Steps 2 & 3: 6-hydroxy-5-oxo-4-[[1-[2-(4-pyridyl)ethyl]pyrazol-4-yl]methyl]thieno[3,2-b]pyridine-7-carboxylic acid

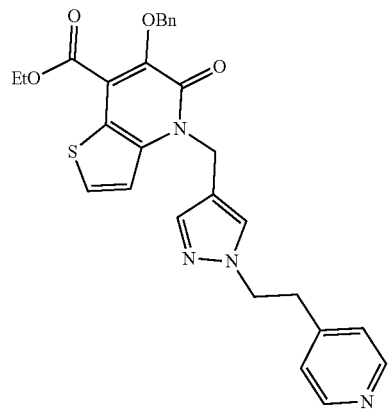

1. NaOH, MeOH/H₂O 30° C., 1 h
2. TFA, rt, 30 min

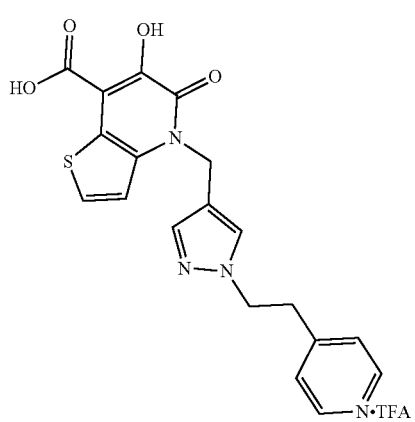

Following methods described for preceding examples, ethyl 6-benzyloxy-5-oxo-4-[[1-[2-(4-pyridyl)ethyl]pyrazol-4-yl]methyl]thieno[3,2-b]pyridine-7-carboxylate was treated to provide the title compound, Example 28, (37 mg, 29% yield) as a green solid. =¹H NMR (400 MHz, DMSO-d₆) δ 8.72 (d, J=6.0 Hz, 2H), 7.81 (d, J=6.0 Hz, 2H), 7.70 (d, J=4.4 Hz, 1H), 7.67 (s, 1H), 7.46 (s, 1H), 7.36 (d, J=5.6 Hz, 1H), 4.44 (t, J=6.8 Hz, 2H), 3.35 (t, J=6.8 Hz, 2H); LCMS: (ES+) m/z (M+H)⁺=397.0.

Example 29: 2-benzyl-6-hydroxy-4-(4-methoxybenzyl)-5-oxo-4,5-dihydrothieno[3,2-b]pyridine-7-carboxylic acid

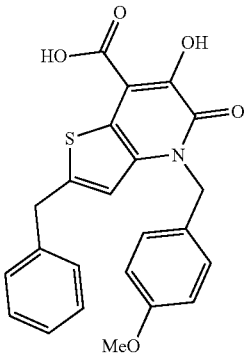 [SMILES: COc1ccc(Cn2c(=O)c(O)c(C(=O)O)c3sc(Cc4ccccc4)cc32)cc1]

Step 1: ethyl 2-benzyl-6-(benzyloxy)-4-(4-methoxybenzyl)-5-oxo-4,5-dihydrothieno[3,2-b]pyridine-7-carboxylate

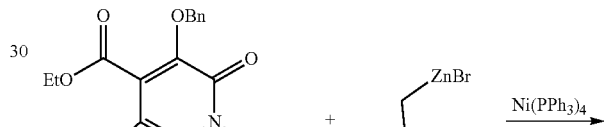

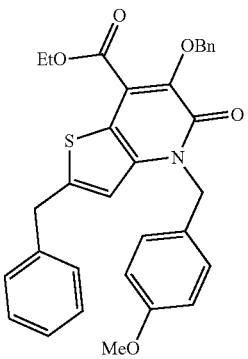

A vial was charged with ethyl 6-(benzyloxy)-2-bromo-4-(4-methoxybenzyl)-5-oxo-4,5-dihydrothieno[3,2-b]pyridine-7-carboxylate (100 mg, 0.24 mmol) and a stir bar and purged with nitrogen. Nickel tetrakistriphenylphosphine (26 mg, 0.024 mmol) was added under a stream of nitrogen and the reaction was sealed with Teflon cap. Tetrahydrofuran (0.5 mL) was added followed by a solution of benzyl zinc bromide (0.5 M solution in THF, 0.94 mL). Reaction was stirred for 2 h at room temperature. The crude mixture was filtered over celite and eluted with ethyl acetate. The filtrate was dissolved on silica and purified via column chromatography (EtOAc/hex=0-50%) to provide ethyl 2-benzyl-6-

(benzyloxy)-4-(4-methoxybenzyl)-5-oxo-4,5-dihydrothieno[3,2-b]pyridine-7-carboxylate (61 mg, 60% yield). 1H NMR (400 MHz, CDCl$_3$) δ 7.59-7.53 (d, J=7.9 Hz, 2H), 7.43-7.32 (m, 6H), 7.25-7.18 (m, 4H), 6.85 (d, J=8.7 Hz, 2H), 6.74 (t, J=1.0 Hz, 1H), 5.39 (s, 2H), 5.35 (s, 2H), 4.38 (q, J=7.2 Hz, 2H), 1.33 (t, J=7.1 Hz, 3H).

Step 2 & 3: 2-benzyl-6-hydroxy-4-(4-methoxybenzyl)-5-oxo-4,5-dihydrothieno[3,2-b]pyridine-7-carboxylic acid

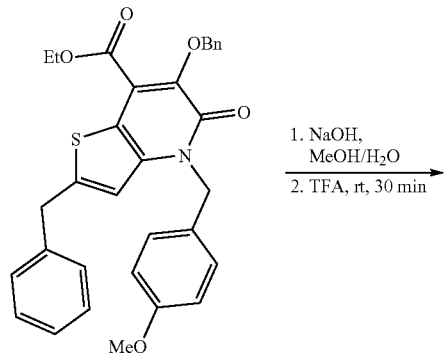

1. NaOH, MeOH/H$_2$O
2. TFA, rt, 30 min

Following methods described for preceding examples, ethyl 2-benzyl-6-(benzyloxy)-4-(4-methoxybenzyl)-5-oxo-4,5-dihydrothieno[3,2-b]pyridine-7-carboxylate was treated to provide the title compound, Example 29, (4.8 mg). $^1$H NMR (400 MHz, Methanol-d$_4$) δ 7.22-7.05 (m, 7H), 6.83 (s, 1H), 6.75 (d, J=8.6 Hz, 2H), 5.34 (s, 2H), 4.03 (s, 2H), 3.66 (s, 3H); LCMS: (ES−) m/z (M−H)$^-$ 420.0.

Example 30: 2-cyclopropyl-6-hydroxy-4-(4-methoxybenzyl)-5-oxo-4,5-dihydrothieno[3,2-b]pyridine-7-carboxylic acid Step 1: ethyl 6-(benzyloxy)-2-cyclopropyl-4-(4-methoxybenzyl)-5-oxo-4,5-dihydrothieno[3,2-b]pyridine-7-carboxylate

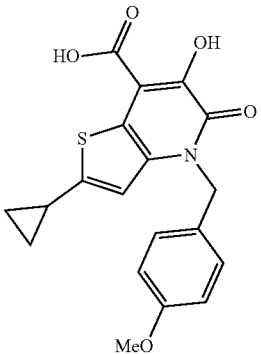 [SMILES: COc1ccc(Cn2c(=O)c(O)c(C(=O)O)c3sc(C4CC4)cc32)cc1]

+ cyclopropyl—B(OH)$_2$ $\xrightarrow{\text{Pd(PPh}_3)_4, \text{Cs}_2\text{CO}_3, \text{PdMe/H}_2\text{O}}$ A vial was charged with ethyl 6-(benzyloxy)-2-bromo-4-(4-methoxybenzyl)-5-oxo-4,5-dihydrothieno[3,2-b]pyridine-7-carboxylate (100 mg, 0.19 mmol), palladium tetrakistriphenylphosphine (22 mg, 0.019 mmol), cesium carbonate (185 mg, 0.57 mmol) and cyclopropyl boronic acid (32.5 mg, 0.378 mmol). Toluene (1.9 mL) and water (0.5 mL) were added. The reaction was heated for 16 h at 85° C. The reaction was cooled to room temp, water (10 mL) was added, and the aqueous layer was extracted with EtOAc (3×10 mL). Purified via column chromatography (EtOAc/hexane=0-75%) to provide ethyl 6-(benzyloxy)-2-cyclopropyl-4-(4-methoxybenzyl)-5-oxo-4,5-dihydrothieno[3,2-b]pyridine-7-carboxylate (32 mg, 31% yield). $^1$H NMR (400 MHz, CDCl$_3$) δ 7.61-7.54 (m, 2H), 7.44-7.29 (m, 3H), 7.27-7.22 (m, 2H), 6.90-6.84 (m, 2H), 6.74 (s, 1H), 5.40 (d, J=2.6 Hz, 2H), 5.36 (s, 2H), 4.46-4.36 (m, 2H), 3.78 (s, 3H), 2.09 (ttd, J=8.3, 5.0, 0.6 Hz, 1H), 1.36 (t, J=7.1 Hz, 3H), 1.11-1.03 (m, 2H), 0.83-0.74 (m, 2H)

Step 2&3: 2-cyclopropyl-6-hydroxy-4-(4-methoxybenzyl)-5-oxo-4,5-dihydrothieno[3,2-b]pyridine-7-carboxylic acid

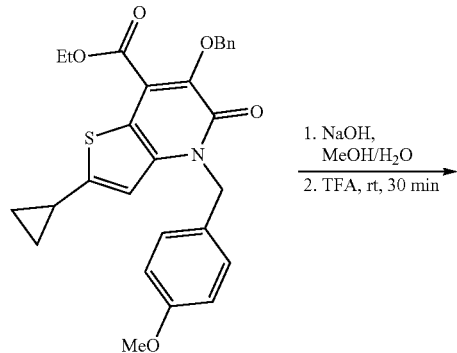

Following methods described for preceding examples, ethyl 6-(benzyloxy)-2-cyclopropyl-4-(4-methoxybenzyl)-5-oxo-4,5-dihydrothieno[3,2-b]pyridine-7-carboxylate was treated to provide the title compound, Example 30, (4.1 mg). $^1$H NMR (400 MHz, Methanol-$d_4$) δ 7.11 (d, J=9.0 Hz, 2H), 6.83-6.72 (m, 3H), 5.34 (s, 2H), 3.65 (s, 3H), 2.01 (m, 1H), 1.01-0.87 (m, 2H), 0.63 (m, 2H); LCMS: (ES−) m/z (M−H)$^-$ 370.0.

Example 31: 6-hydroxy-5-oxo-4-{[8-(pyridin-4-yl)imidazo[1,2-a]pyridin-3-yl]methyl}-4,5-dihydrothieno[3,2-b]pyridine-7-carboxylic acid

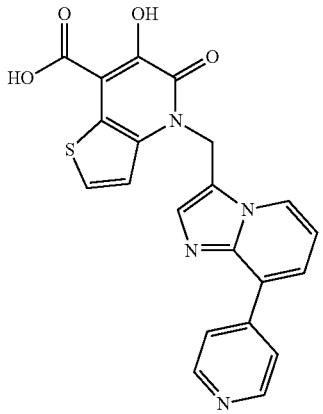 [SMILES: O=C(O)c1c(O)c(=O)n(Cc2cnc3c(-c4ccncc4)cccn23)c2ccsc12]

Step 2: ethyl 6-(benzyloxy)-5-oxo-4-((8-(pyridin-4-yl)imidazo[1,2-a]pyridin-3-yl)methyl)-4,5-dihydrothieno[3,2-b]pyridine-7-carboxylate

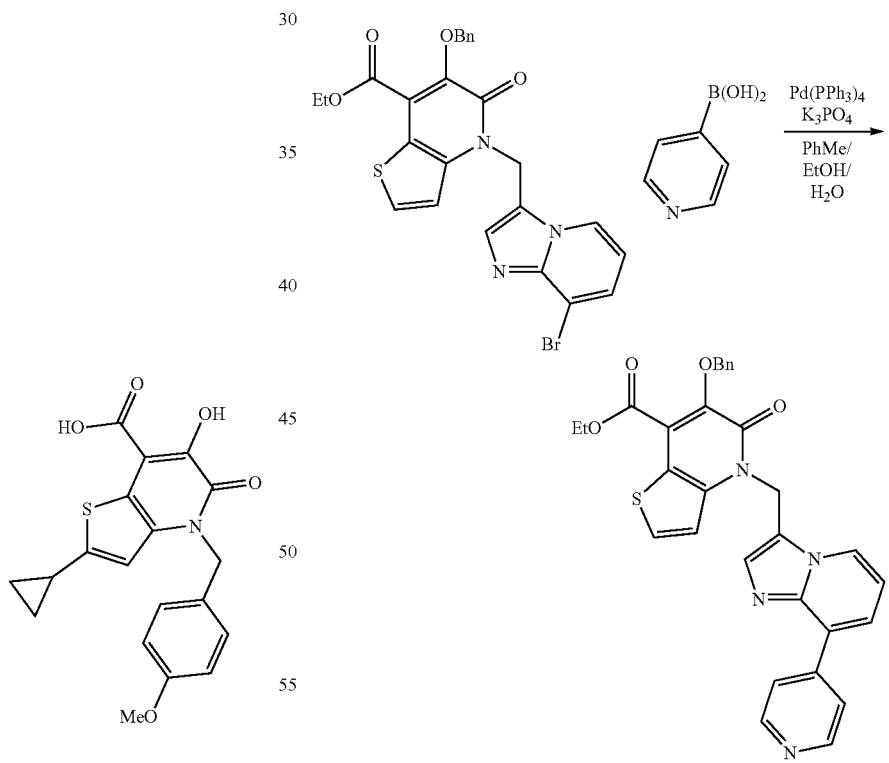

A vial equipped with a stir bar was charged with ethyl 6-(benzyloxy)-4-[(8-bromoimidazo[1,2-a]pyridin-3-yl)methyl]-5-oxo-4,5-dihydrothieno[3,2-b]pyridine-7-carboxylate (100 mg, 0.186 mmol), phenylboronic acid (34.2 mg, 0.279 mmol), palladium tetrakistriphenylphosphine (11 mg, 0.009 mmol) and tribasic potassium phosphate (128 mg, 0.557 mmol). Vial was sparged with nitrogen for 15 min. Degassed toluene (2.5 mL), water (0.25 mL) and ethanol (0.13 mL) were added and the reaction was heated at 80° C. for 14 h. The reaction was cooled, poured into ethyl acetate (20 mL), washed with brine, separated, and concentrated. The residue was purified by column chromatography (hex/EtOAc=25-75%). The product containing fractions were concentrated to provide ethyl 6-(benzyloxy)-5-oxo-4-{[8-(pyridin-4-yl)imidazo[1,2-a]pyridin-3-yl]methyl}-4,5-dihydrothieno[3,2-b]pyridine-7-carboxylate as a white solid (71 mg, 71% yield). LCMS: (ES+) m/z (M+H)+=537.0.

Step 3 & 4: 6-hydroxy-5-oxo-4-((8-(pyridin-4-yl)imidazo[1,2-a]pyridin-3-yl)methyl)-4,5-dihydrothieno[3,2-b]pyridine-7-carboxylic acid

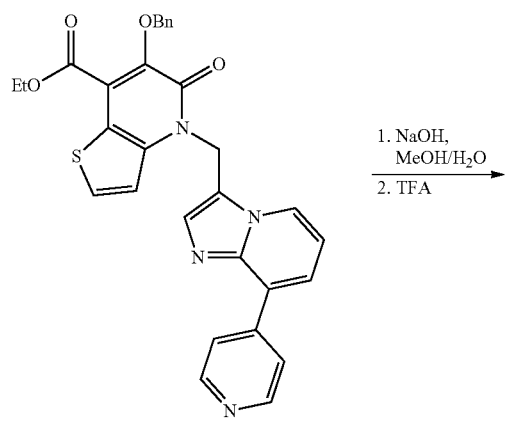

1. NaOH, MeOH/H₂O
2. TFA

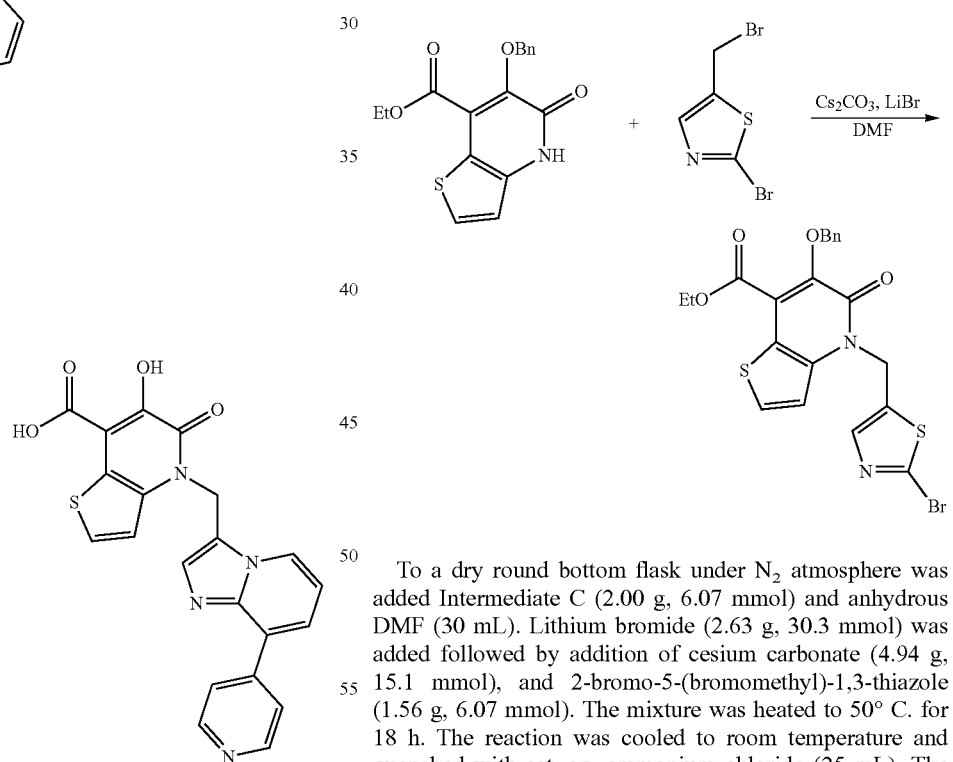

Following methods described for preceding examples, ethyl 6-(benzyloxy)-5-oxo-4-{[8-(pyridin-4-yl)imidazo[1,2-a]pyridin-3-yl]methyl}-4,5-dihydrothieno[3,2-b]pyridine-7-carboxylate was treated to provide the title compound, Example 31, (4.1 mg). ¹H NMR (400 MHz, Methanol-d₄) δ 8.92 (s, 1H), 8.53 (d, J=5.0 Hz, 2H), 8.17 (s, 3H), 7.88-7.85 (m, 2H), 7.72 (s, 1H), 7.46 (m, 2H), 7.05 (s, 1H), 5.91 (s, 2H); LCMS: (ES−) m/z (M−H)⁻=417.0.

Example 32: 6-hydroxy-4-{[2-(4-methoxyphenyl)thiazol-5-yl]methyl}-5-oxo-4,5-dihydrothieno[3,2-b]pyridine-7-carboxylic acid

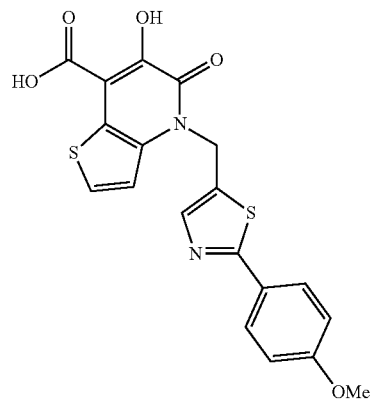 [SMILES: COc1ccc(-c2ncc(Cn3c(=O)c(O)c(C(=O)O)c4sccc43)s2)cc1]

Step 1: ethyl 6-(benzyloxy)-4-[(2-bromothiazol-5-yl)methyl]-5-oxo-4,5-dihydrothieno[3,2-b]pyridine-7-carboxylate To a dry round bottom flask under N₂ atmosphere was added Intermediate C (2.00 g, 6.07 mmol) and anhydrous DMF (30 mL). Lithium bromide (2.63 g, 30.3 mmol) was added followed by addition of cesium carbonate (4.94 g, 15.1 mmol), and 2-bromo-5-(bromomethyl)-1,3-thiazole (1.56 g, 6.07 mmol). The mixture was heated to 50° C. for 18 h. The reaction was cooled to room temperature and quenched with sat. aq. ammonium chloride (25 mL). The aqueous layer was extracted with EtOAc (3×30 mL). The combined organic extracts were washed with a 10% by weight aq. lithium chloride solution (30 mL) and dried over sodium sulfate. The organic extract was then concentrated under vacuum. The residue was purified by column chromatography [hexanes/EtOAc=9:1-1:1] to give ethyl 6-(benzyloxy)-4-[(2-bromothiazol-5-yl)methyl]-5-oxo-4,5-dihydrothieno[3,2-b]pyridine-7-carboxylate (1.5 g, 48% yield) as a yellow oil. ¹H NMR (400 MHz, CDCl₃) δ 7.63 (s, 1H), 7.62 (d, J=5.6 Hz, 1H), 7.57-7.49 (m, 2H), 7.43-7.30 (m, 3H), 7.13 (d, J=5.6 Hz, 1H), 5.51 (s, 2H), 5.35 (s, 3H), 4.39 (q, J=7.1 Hz, 2H), 1.33 (t, J=7.1 Hz, 3H); LCMS (ES+) m/z (M+H)+=506.

Step 2: ethyl 6-(benzyloxy)-4-{[2-(4-methoxyphenyl)thiazol-5-yl]methyl}-5-oxo-4,5-dihydrothieno[3,2-b]pyridine-7-carboxylate

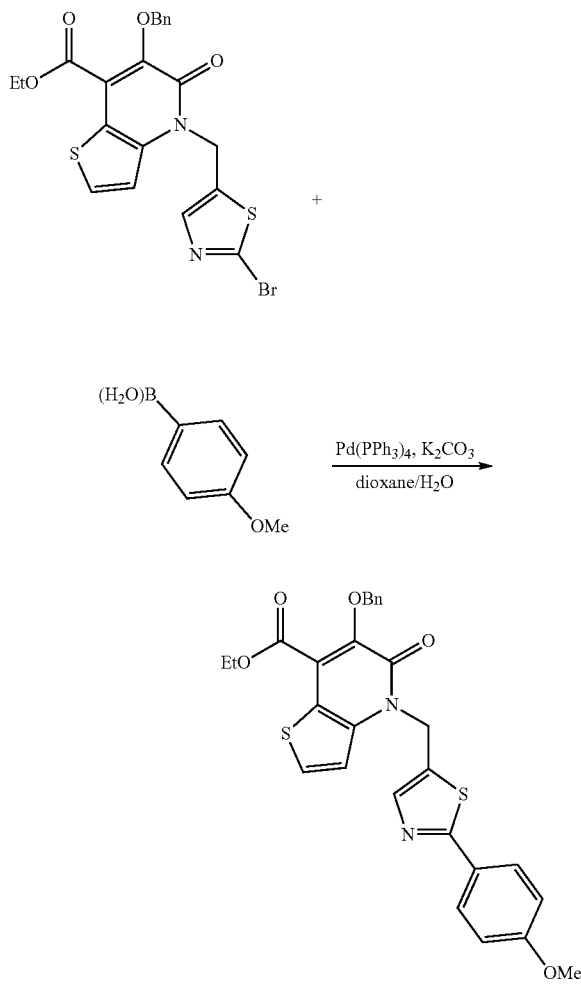

To a round bottom flask under N₂ was added ethyl 6-(benzyloxy)-4-((2-bromothiazol-5-yl)methyl)-5-oxo-4,5-dihydrothieno[3,2-b]pyridine-7-carboxylate (0.20 g, 0.39 mmol) followed by addition of 4-methoxyphenylboronic acid (0.09 g, 0.59 mmol), potassium carbonate (0.13 g, 0.99 mmol), and palladium tetrakistriphenylphosphine (0.06 g, 0.06 mmol). A thoroughly degassed solution of dioxane/H₂O (4:1) (2 mL) was then added and the reaction vessel was sealed under N₂ atmosphere and stirred at 90° C. for 3 hours. The mixture was then cooled to room temperature, diluted with ethyl acetate (3 mL) and filtered through a pad of Celite®. The filtrate was concentrated to dryness to dryness under vacuum. The residue was purified by column chromatography [hexanes/EtOAc=20:1-1:1] to give ethyl 6-(benzyloxy)-4-((2-(4-methoxyphenyl)thiazol-5-yl)methyl)-5-oxo-4,5-dihydrothieno[3,2-b]pyridine-7-carboxylate (0.14 g, 67% yield) as a pale yellow oil. ¹H NMR (400 MHz, DMSO-d₆) δ 8.00 (s, 1H), 7.79 (d, J=8.8 Hz, 2H), 7.43 (d, J=2.0 Hz, 2H), 7.00 (d, J=8.9 Hz, 2H), 5.59 (s, 2H), 3.79 (s, 3H); LCMS (ES+) m/z (M+H)+=533.0.

Step 3 &4: 6-hydroxy-4-(2-(4-methoxyphenyl)thiazol-5-yl)methyl)-5-oxo-4,5-dihydrothieno[3,2-b]pyridine-7-carboxylic acid

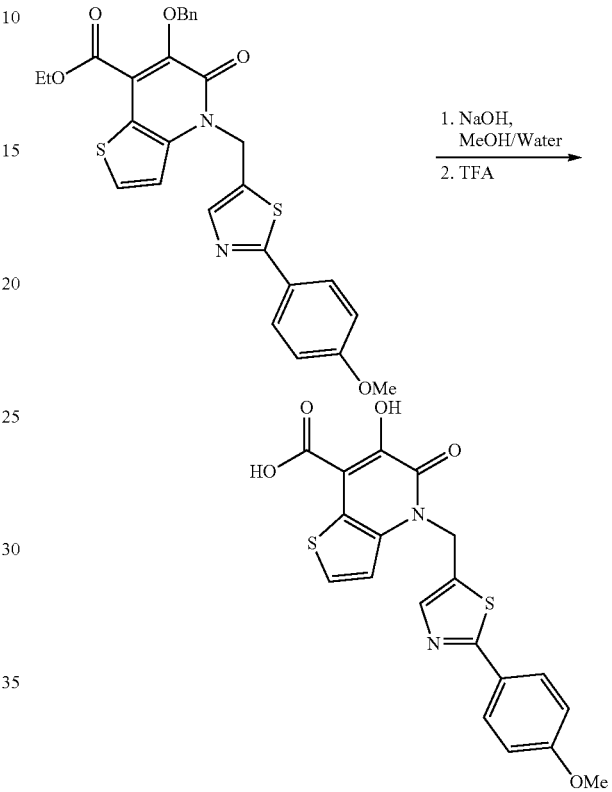

Following methods described for preceding examples, ethyl 6-(benzyloxy)-4-((2-(4-methoxyphenyl)thiazol-5-yl)methyl)-5-oxo-4,5-dihydrothieno[3,2-b]pyridine-7-carboxylate was treated to provide the title compound, Example 32. ¹H NMR (400 MHz, DMSO-d₆) δ 8.00 (s, 1H), 7.79 (d, J=8.8 Hz, 2H), 7.43 (d, J=2.0 Hz, 2H), 7.00 (d, J=8.9 Hz, 2H), 5.59 (s, 2H), 3.79 (s, 3H); LCMS (ES+) m/z (M+H)+= 415.

Table 1: The Examples of the invention in the following table were prepared following methods described in the preceding description of Intermediates and Examples. Relevant methods are referenced in the column entitled Intermediate, Reference Methods, Alkylating Agent & Base and deprotection methods are referenced in the column entitled Deprotection Methods. In the column Deprotection Methods, the nomenclature A. refers to methods for the hydrolysis of the ester functionality, B. refers to methods for the removal of the methyl from the methyl protected intermediates, and C. refers to methods for the removal of the benzyl protecting group. On occasion, where other protecting groups are used within the synthesis (e.g. Boc) it is generally highlighted in the Deprotection Methods column how these are removed. Also, the order in which A., B. and C. appear in the Deprotection Methods column indicates the order in which the methods were applied within the synthesis of the specific Example.

TABLE 1

| Example # | Structure | Intermediate, Reference Methods, Alkylating Agent & Base | Deprotection Methods | Analytics |
|---|---|---|---|---|
| 33 | ethyl 6-hydroxy-4-(4-methoxybenzyl)-5-oxo-4,5-dihydrothieno[3,2-b]pyridine-7-carboxylate | Coupling: Intermediate from Step 1, from Example 12 | C. TFA | $(M + H)^+$ = 360.0 $^1$H NMR (DMSO-d$_6$, 400 MHz): δ 10.50 (s, 1H), 7.67 (d, J = 6.0 Hz, 1H), 7.32 (d, J = 5.6 Hz, 1H), 7.26 (d, J = 8.4 Hz, 2H), 6.88 (d, J = 8.4 Hz, 2H), 5.45 (s, 2H), 4.41 (q, J = 7.2 Hz, 2H), 1.35 (t, J = 7.2 Hz, 3H). |
| 34 | 4-(3-chlorobenzyl)-6-hydroxy-5-oxo-4,5-dihydrothieno[3,2-b]pyridine-7-carboxylic acid | Coupling: Intermediate A; (3-chlorobenzyl bromide); Cs$_2$CO$_3$, LiBr | B. TMSCl, NaI A. NaOH, EtOH, H$_2$O | $(M + H)^+$ = 336.1 $^1$H NMR (DMSO-d$_6$, 400 MHz): δ 7.54 (d, J = 4.8 Hz, 1H), 7.33-7.28 (m, 3H), 7.21-7.16 (m, 2H), 5.59 (s, 2H) |
| 35 | 4-(2-bromobenzyl)-6-hydroxy-5-oxo-4,5-dihydrothieno[3,2-b]pyridine-7-carboxylic acid | Coupling: Intermediate A; (2-bromobenzyl bromide); Cs$_2$CO$_3$, LiBr | B. TMSCl, NaI A. NaOH, EtOH, H$_2$O | $(M + H)^+$ = 381.0 $^1$H NMR (DMSO-d$_6$, 400 MHz): δ 7.72-7.70 (m, 1H), 7.56-7.54 (d, J = 8.0 Hz, 1H), 7.27-7.21 (m, 2H), 6.97 (s, 1H), 6.62-6.59 (m, 1H), 5.46 (s, 2H). |
| 37 | 6-hydroxy-4-(2-nitrobenzyl)-5-oxo-4,5-dihydrothieno[3,2-b]pyridine-7-carboxylic acid | Intermediate A; (2-nitrobenzyl bromide); Cs$_2$CO$_3$, LiBr | B. TMSCl, NaI A. NaOH, EtOH, H$_2$O | $(M + H)^+$ = 347.0 $^1$H NMR (d$_6$-DMSO, 400 MHz): δ 8.21 (d, J = 7.6 Hz, 1H), 7.62-7.55 (m, 2H), 7.53-7.50 (m, 1H), 7.15 (d, J = 5.6, 1H), 6.75 (d, J = 7.2 Hz, 1H), 5.80 (s, 2H). |

TABLE 1-continued

| Example # | Structure | Intermediate, Reference Methods, Alkylating Agent & Base | Deprotection Methods | Analytics |
|---|---|---|---|---|
| 38 | 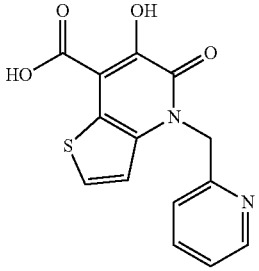 [SMILES: O=C(O)c1c(O)c(=O)n(Cc2ccccn2)c2ccsc12]<br>6-hydroxy-5-oxo-4-(pyridin-2-ylmethyl)-4,5-dihydrothieno[3,2-b]pyridine-7-carboxylic acid | Intermediate A<br>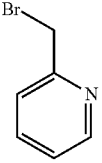<br>NaH, LiBr, DMF | B. TMSCl, NaI<br>A. NaOH, EtOH, H$_2$O | (M + H)$^+$ = 303.0<br>$^1$H NMR (DMSO-d$_6$, 400 MHz): δ 8.50 (d, J = 4.8 Hz, 1H), 7.82 (t, J = 7.2 Hz, 1H), 7.58 (d, J = 5.6 Hz, 1H), 7.34 (t, J = 5.2 Hz, 1H), 7.29 (d, J = 7.6 Hz, 1H), 7.16 (d, J = 6.0 Hz, 1 H), 5.60 (s, 2H) |
| 39 | 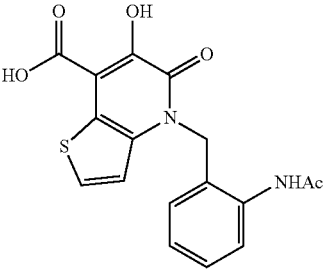 [SMILES: CC(=O)Nc1ccccc1Cn1c(=O)c(O)c(C(=O)O)c2sccc21]<br>4-(2-acetamidobenzyl)-6-hydroxy-5-oxo-4,5-dihydrothieno[3,2-b]pyridine-7-carboxylic acid | Intermediate A<br>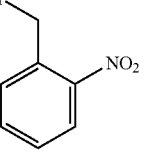<br>Methods: Example 7 | Methods: Example 7 | (M + H)$^+$ = 359.1<br>$^1$H NMR (d$_6$-DMSO, 400 MHz): δ 9.87 (s, 1H), 7.51 (d, J = 5.6, 1H), 7.40 (d, J = 8, 1H), 7.24 (t, J = 7.2 Hz, 1H), 7.06 (t, J = 5.6 Hz, 1H), 6.91 (d, J = 5.6, 1H), 6.69 (d, J = 7.6, 2H), 6.38 (s, 2H), 2.13 (s, 3H). |
| 40 | 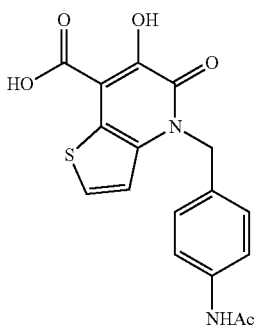 [SMILES: CC(=O)Nc1ccc(Cn2c(=O)c(O)c(C(=O)O)c3sccc32)cc1]<br>4-(4-acetamidobenzyl)-6-hydroxy-5-oxo-4,5-dihydrothieno[3,2-b]pyridine-7-carboxylic acid | Intermediate A<br>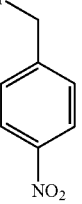<br>Methods: Example 7 | Methods: Example 7 | (M + H)$^+$ = 359.0<br>$^1$H NMR (DMSO-d$_6$, 400 MHz): δ 9.93 (s, 1H), 7.49-7.55 (m, 3H), 7.19-7.23 (m, 1H), 8.18 (d, 3H), 5.43 (s, 2H), 2.01 (s, 3H). |
| 41 | 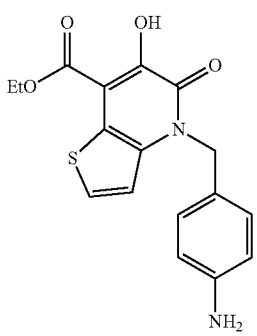 [SMILES: CCOC(=O)c1c(O)c(=O)n(Cc2ccc(N)cc2)c2ccsc12]<br>ethyl 4-(4-aminobenzyl)-6-hydroxy-5-oxo-4,5-dihydrothieno[3,2-b]pyridine-7-carboxylate | Intermediate C<br>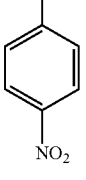<br>Cs$_2$CO$_3$, LiBr | NO$_2$ reduction: Example 7, Step 1<br>C. TFA | (M + Na)$^+$ = 367.0<br>$^1$H NMR (DMSO-d$_6$, 400 MHz): δ 7.67 (d, J = 5.6 Hz, 1H), 7.28 (d, J = 5.6 Hz, 1H), 7.22-7.20 (m, 2H), 6.91 (m, 2H), 5.44 (s, 2H), 4.41 (q, J = 7.2 Hz, 2H), 1.36 (t, J = 7.2 Hz, 3H) |

TABLE 1-continued

| Example # | Structure | Intermediate, Reference Methods, Alkylating Agent & Base | Deprotection Methods | Analytics |
|---|---|---|---|---|
| 42 | 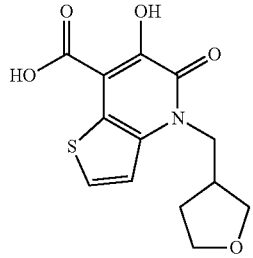 [SMILES: O=C(O)c1c(O)c(=O)n(CC2CCOC2)c2ccsc12]<br>6-hydroxy-5-oxo-4-((tetrahydrofuran-3-yl)methyl)-4,5-dihydrothieno[3,2-b]pyridine-7-carboxylic acid | Intermediate C<br><br>NaH, LiBr, DMF | A. NaOH, EtOH, Water<br>C. TFA | $(M + H)^+$ = 296.0<br>$^1$H NMR (CD$_3$OD, 400 MHz): δ 7.62 (d, J = 5.6 Hz, 1H), 7.32 (d, J = 5.6 Hz, 1H), 4.39-4.49 (m, 2H), 3.77-4.00 (m, 1H), 3.70-3.77 (m, 3H), 2.89 (t, J = 6 Hz, 1H), 2.01-2.08 (m, 1H), 1.80-1.85 (m, 1H) |
| 43 | 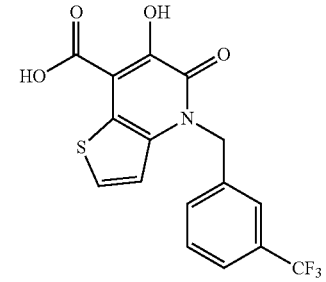 [SMILES: O=C(O)c1c(O)c(=O)n(Cc2cccc(C(F)(F)F)c2)c2ccsc12]<br>6-hydroxy-5-oxo-4-(3-(trifluoromethyl)benzyl)-4,5-dihydrothieno[3,2-b]pyridine-7-carboxylic acid | Intermediate C<br>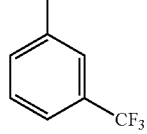<br>Cs$_2$CO$_3$, LiBr | C. TFA<br>A. NaOH, MeOH, Water | $(M + H)^+$ = 369.9<br>$^1$H NMR (DMSO-d$_6$, 400 MHz): δ 7.76 (s, 1H), 7.52-7.66 (m, 4H), 7.28-7.29 (d, J = 5.6 Hz, 1H), 5.59 (s, 2H). |
| 44 | 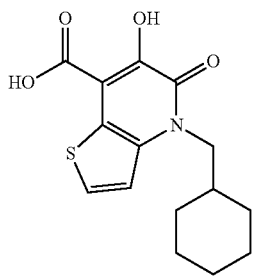 [SMILES: O=C(O)c1c(O)c(=O)n(CC2CCCCC2)c2ccsc12]<br>4-(cyclohexylmethyl)-6-hydroxy-5-oxo-4,5-dihydrothieno[3,2-b]pyridine-7-carboxylic acid | Intermediate C<br>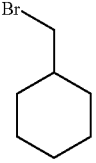<br>K$_2$CO$_3$, DMF | C. TFA<br>A. NaOH, MeOH, Water | $(M + H)^+$ = 308.0<br>$^1$H NMR (DMSO-d$_6$, 400 MHz): δ 7.63 (d, J = 5.6 Hz, 1H), 7.28 1(d, J = 5.6 Hz, 1H), 4.10 (d, J = 7.2 Hz, 2H), 1.81 (s, 1H), 1.65~1.54 (m, 5H), 1.12~1.06 (m, 5H). |
| 45 | 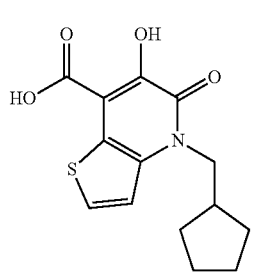 [SMILES: O=C(O)c1c(O)c(=O)n(CC2CCCC2)c2ccsc12]<br>4-(cyclopentylmethyl)-6-hydroxy-5-oxo-4,5-dihydrothieno[3,2-b]pyridine-7-carboxylic acid | Intermediate C<br><br>K$_2$CO$_3$, DMF | C. TFA<br>A. NaOH, MeOH, Water | $(M + H)^+$ = 294.1<br>$^1$H NMR (DMSO-d$_6$, 400 MHz): δ 7.65 (d, J = 5.6 Hz, 1H), 7.33 (d, J = 5.6 Hz, 1H), 4.22 (d, J = 7.6 Hz, 2H), 2.36~2.33 (m, 1H), 1.65~1.56 (m, 4H), 1.50~1.47 (m, 2H), 1.35~1.31 (m, 2H). |

TABLE 1-continued

| Example # | Structure | Intermediate, Reference Methods, Alkylating Agent & Base | Deprotection Methods | Analytics |
|---|---|---|---|---|
| 47 | 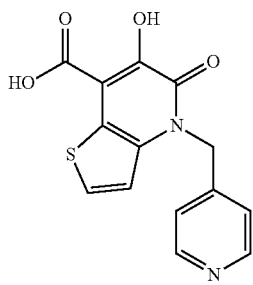 [SMILES: O=C(O)c1c(O)c(=O)n(Cc2ccncc2)c2ccsc12]<br>6-hydroxy-5-oxo-4-(pyridin-4-ylmethyl)-4,5-dihydrothieno[3,2-b]pyridine-7-carboxylic acid | Intermediate C<br>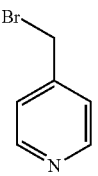<br>NaH, LiBr, DMF | A. NaOH, MeOH, Water<br>C. TFA | $(M + H)^+$ = 303.0<br>1H NMR (DMSO-$d_6$, 400 MHz): δ 8.84 (s, 2H), 7.49 (d, J = 4.0 Hz, 1H), 7.45 (m, 2H), 7.10 (d, J = 5.6 Hz, 1H), 5.61 (s, 2H). |
| 48 | 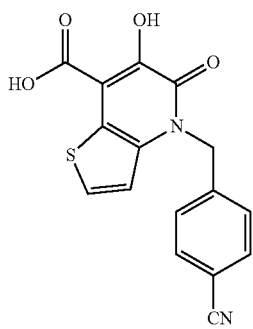 [SMILES: N#Cc1ccc(Cn2c(=O)c(O)c(C(=O)O)c3sccc32)cc1]<br>4-(4-cyanobenzyl)-6-hydroxy-5-oxo-4,5-dihydrothieno[3,2-b]pyridine-7-carboxylic acid | Intermediate C<br>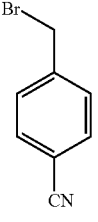<br>$Cs_2CO_3$, LiBr | A. NaOH, MeOH, $H_2O$<br>C. TFA | $(M + H)^+$ = 326.9<br>$^1$H NMR ($CD_3OD$, 400 MHz): δ 7.70 (d, J = 8.4, 2H), 7.57 (d, J = 5.6 Hz, 1H), 7.65 (d, J = 8.4 Hz, 2H), 7.13 (d, J = 5.6 Hz, 1H), 5.68 (s, 2H). |
| 49 | 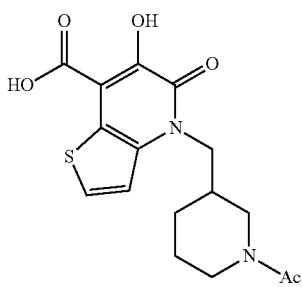 [SMILES: CC(=O)N1CCCC(Cn2c(=O)c(O)c(C(=O)O)c3sccc32)C1]<br>4-((1-acetylpiperidin-3-yl)methyl)-6-hydroxy-5-oxo-4,5-dihydrothieno[3,2-b]pyridine-7-carboxylic acid | Intermediate C<br>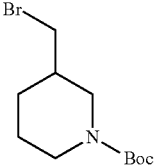<br>Methods: Example 9 | Methods: Example 9 | $(M + H)^+$ = 351.0<br>$^1$H NMR (DMSO-$d_6$, 400 MHz): δ 7.68~7.63 (m, 1H), 7.35~7.29 (m, 1H), 4.41~4.26 (m, 3H), 3.85~3.78 (m, 1H), 3.19~3.10 (m, 1H), 2.82~2.68 (m, 1H), 2.10~2.00 (m, 4H), 1.89~1.76 (m, 2H), 1.53~1.41 (m, 2H). |

TABLE 1-continued

| Example # | Structure | Intermediate, Reference Methods, Alkylating Agent & Base | Deprotection Methods | Analytics |
|---|---|---|---|---|
| 50 | 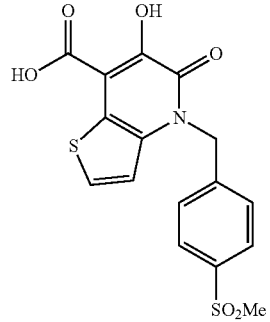 [SMILES: CS(=O)(=O)c1ccc(Cn2c(=O)c(O)c(C(=O)O)c3sccc32)cc1]<br>6-hydroxy-4-(4-(methylsulfonyl)benzyl)-5-oxo-4,5-dihydrothieno[3,2-b]pyridine-7-carboxylic acid | Intermediate C<br>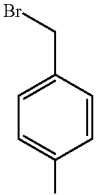<br>Cs$_2$CO$_3$, LiBr | A. NaOH, MeOH, H$_2$O<br>C. TFA | (M + H)$^+$ = 379.9<br>$^1$H NMR (, DMSO-d$_6$, 400 MHz) δ 7.89 (d, J = 8.0 Hz, 2H), 7.51 (d, J = 8.0 Hz, 3H), 7.17 (d, J = 5.2 Hz, 1H), 5.60 (s, 2H), 3.18 (s, 3H). |
| 51 | 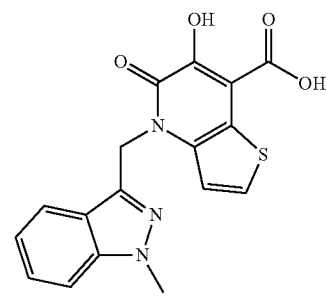 [SMILES: Cn1nc(Cn2c(=O)c(O)c(C(=O)O)c3sccc32)c2ccccc21] | Intermediate C<br>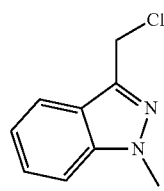<br>K$_2$CO$_3$, DMF | C. TFA<br>A. NaOH, MeOH, H$_2$O | (M + H)$^+$ = 354.1 (M + H$^+$).<br>$^1$H NMR (CD$_3$OD, 400 MHz,): δ 7.79 (d, J = 8.3 Hz, 1H), 7.52-7.25 (m, 4H), 7.07 (t, J = 7.5 Hz, 1H), 5.87 (s, 2H), 4.01 (s, 3H) ppm. |
| 52 | 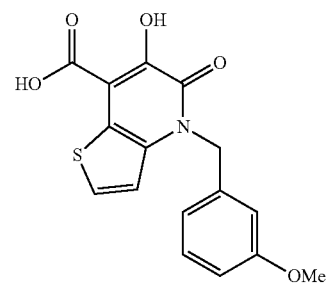 [SMILES: COc1cccc(Cn2c(=O)c(O)c(C(=O)O)c3sccc32)c1]<br>6-hydroxy-4-(3-methoxybenzyl)-5-oxo-4,5-dihydrothieno[3,2-b]pyridine-7-carboxylic acid | Intermediate C<br>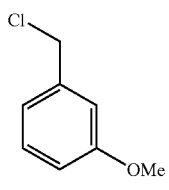<br>Cs$_2$CO$_3$, LiBr | A. NaOH, MeOH, H$_2$O<br>C. TFA | (M + H)$^+$ = 332.0<br>$^1$H NMR (CD$_3$OD, 400 MHz): δ 7.54 (d, J = 5.6, 1H), 7.25 (m, 1H), 7.20 (d, J = 5.6, 1H), 6.81-6.89 (m, 3H), 5.58 (s, 2H), 3.76 (s, 3H). |
| 53 | 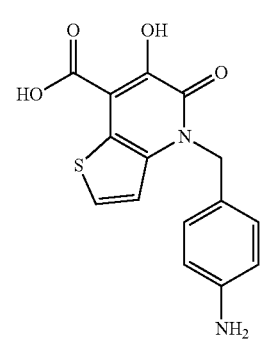 [SMILES: Nc1ccc(Cn2c(=O)c(O)c(C(=O)O)c3sccc32)cc1]<br>4-(4-aminobenzyl)-6-hydroxy-5-oxo-4,5-dihydrothieno[3,2-b]pyridine-7-carboxylic acid | | Prepared from Example 15 Boc removal: TFA | (M + H)$^+$ = 316.9<br>$^1$H NMR (DMSO-d$_6$, 400 MHz): δ 7.53 (d, J = 5.6 Hz, 1H), 7.30 (d, J = 8.4 Hz, 2H), 7.18-7.16 (m, 3H), 5.49 (s, 2H). |

TABLE 1-continued

| Example # | Structure | Intermediate, Reference Methods, Alkylating Agent & Base | Deprotection Methods | Analytics |
|---|---|---|---|---|
| 54 | 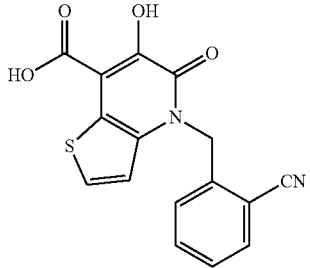 [SMILES: N#Cc1ccccc1Cn1c(=O)c(O)c(C(=O)O)c2sccc21]<br>4-(2-cyanobenzyl)-6-hydroxy-5-oxo-4,5-dihydrothieno[3,2-b]pyridine-7-carboxylic acid | Intermediate C<br><br>Br–⟨⟩–CN<br><br>Cs$_2$CO$_3$, LiBr | A. NaOH, MeOH, H$_2$O<br>C. TFA | $(M + H)^+ = 326.9$<br>$^1$H NMR (400 MHz, DMSO-d$_6$) δ 7.93 (d, J = 7.6 Hz, 1H), 7.57-7.6 (m, 2H), 7.46-7.50 (m, 1H), 7.16 (d, J = 5.6 Hz, 1H), 6.90 (d, J = 8.0 Hz, 1H), 5.65 (s, 2H). |
| 55 | 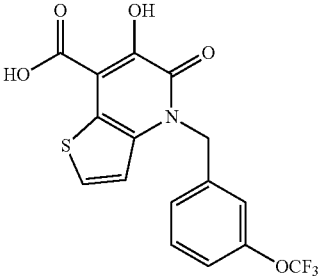 [SMILES: O=C(O)c1c(O)c(=O)n(Cc2cccc(OC(F)(F)F)c2)c2ccsc12]<br>6-hydroxy-5-oxo-4-(3-(trifluoromethoxy)benzyl)-4,5-dihydrothieno[3,2-b]pyridine-7-carboxylic acid | Intermediate C<br><br>Br–⟨⟩–OCF$_3$<br><br>Cs$_2$CO$_3$, LiBr | A. NaOH, MeOH, H$_2$O<br>C. TFA | $(M + H)^+ = 385.9$<br>$^1$H NMR (DMSO-d$_6$, 400 MHz): δ 7.56 (d, J = 5.6, 1H), 7.44-7.51 (m, 1H), 7.35 (s, 1H), 7.20-7.28 (m, 3H), 5.53 (s, 2H); |
| 56 | 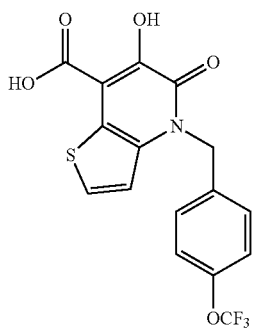 [SMILES: O=C(O)c1c(O)c(=O)n(Cc2ccc(OC(F)(F)F)cc2)c2ccsc12]<br>6-hydroxy-5-oxo-4-(4-(trifluoromethoxy)benzyl)-4,5-dihydrothieno[3,2-b]pyridine-7-carboxylic acid | Intermediate C<br><br>Br–⟨⟩–OCF$_3$<br><br>Cs$_2$CO$_3$, LiBr | A. NaOH, MeOH, H$_2$O<br>C. TFA | $(M + H)^+ = 386.0$<br>$^1$H NMR (DMSO-d$_6$, 400 MHz): δ 7.60 (d, J = 5.6, 1H), 7.4 (d, J = 8.8 Hz, H), 7.30 (d, J = 8.0 Hz, 2H), 7.18-7.22 (m, 1H), 5.52 (s, 2H). |

TABLE 1-continued

| Example # | Structure | Intermediate, Reference Methods, Alkylating Agent & Base | Deprotection Methods | Analytics |
|---|---|---|---|---|
| 57 | 4-(4-(difluoromethoxy)benzyl)-6-hydroxy-5-oxo-4,5-dihydrothieno[3,2-b]pyridine-7-carboxylic acid | Intermediate C<br><br>Br—⟨⟩—OCHF$_2$<br><br>Cs$_2$CO$_3$, LiBr | A. NaOH, MeOH, H$_2$O<br>C. TFA | (M + H)$^+$ = 367.9<br>$^1$H NMR (DMSO-d$_6$, 400 MHz): δ 7.62 (d, J = 5.6 Hz, 1H), 7.36-7.34 (m, 2H), 7.25 (d, J = 5.6 Hz, 1H), 7.19 (t, J = 7.4 Hz, 1H), 7.14-7.12 (m, 2H), 5.49 (s, 2H). |
| 58 | 4-(3-cyanobenzyl)-6-hydroxy-5-oxo-4,5-dihydrothieno[3,2-b]pyridine-7-carboxylic acid | Intermediate C<br><br>Br—⟨⟩—CN<br><br>Cs$_2$CO$_3$, LiBr | A. NaOH, MeOH, H$_2$O<br>C. TFA | (M + H)$^+$ = 326.9<br>$^1$H NMR (DMSO-d$_6$, 400 MHz): δ 7.85 (s, 1H), 7.75 (d, J = 7.2 Hz, 1H), 7.50-7.56 (m, 3H), 7.20 (s, 1H), 5.52 (s, 2H). |
| 59 | 4-(3,4-dichlorobenzyl)-6-hydroxy-5-oxo-4,5-dihydrothieno[3,2-b]pyridine-7-carboxylic acid | Intermediate C<br><br>Br—⟨⟩—Cl,Cl<br><br>Cs$_2$CO$_3$, LiBr | C. TFA<br>A. NaOH, MeOH, H$_2$O | (M + H)$^+$ = 369.9<br>$^1$H NMR (DMSO-d$_6$, 400 MHz): δ 7.63 (s, 1H), 7.59~7.56 (m, 2H), 7.24~7.21 (m, 2H), 5.48 (s, 2H) |
| 60 | 6-hydroxy-5-oxo-4-(pyridin-3-ylmethyl)-4,5-dihydrothieno[3,2-b]pyridine-7-carboxylic acid | Intermediate C<br><br>Br—⟨pyridine⟩<br><br>NaH, LiBr | A. NaOH, MeOH, H$_2$O<br>C. TFA | (M + H)$^+$ = 303.0<br>$^1$H NMR (DMSO-d$_6$, 400 MHz): δ 8.71 (s, 1H), 8.59 (s, 1H), 7.84-7.88 (m, 1H), 7.57 (s, 2H), 7.31 (d, J = 5.2, 1H), 5.56 (s, 2H); |

TABLE 1-continued

| Example # | Structure | Intermediate, Reference Methods, Alkylating Agent & Base | Deprotection Methods | Analytics |
|---|---|---|---|---|
| 61 | 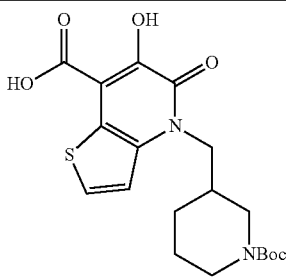<br>4-{[1-(tert-butoxycarbonyl)piperidin-3-yl]methyl}-6-hydroxy-5-oxo-4,5-dihydrothieno[3,2-b]pyridine-7-carboxylic acid | Intermediate C<br>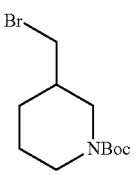<br>Methods: Example 9 | Methods: Example 9 | $(M - C_5H_8O_2)^+ = 309.0$<br>1H NMR (DMSO-$d_6$, 400 MHz): δ 7.64 (d, J = 5.6 Hz, 1H), 7.29 (d, J = 5.6 Hz, 1H), 4.34~4.25 (m, 2H), 3.93 (d, J = 10.8 Hz, 2H), 2.84~2.71 (m, 2H), 2.08 (s, 1H), 1.87 (s, 1H), 1.73 (s, 1H), 1.47~1.28 (m, 11H) |
| 62 | 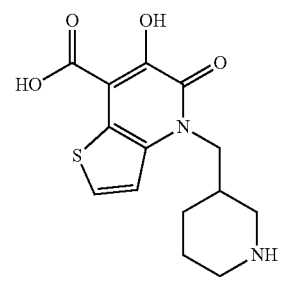 [SMILES: O=C(O)c1c(O)c(=O)n(CC2CCCNC2)c2ccsc12]<br>6-hydroxy-5-oxo-4-(piperidin-3-ylmethyl)-4,5-dihydrothieno[3,2-b]pyridine-7-carboxylic acid | Intermediate C<br>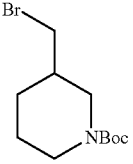<br>Methods: Example 9 & 10 | Boc removal: TFA | $(M + H)^+ = 309.0$<br>$^1$H NMR (DMSO-$d_6$, 400 MHz): δ 7.67 (d, J = 5.6 Hz, 1H), 7.34 (d, J = 5.6 Hz, 1H), 4.48 (dd, $J_1$ = 8.4 Hz, $J_2$ = 4.8 Hz, 1H), 4.28 (dd, $J_1$ = 5.6 Hz, $J_2$ = 5.6 Hz, 1H), 3.26 (s, 1H), 2.99 (q, J = 12.0 Hz, 2H), 2.44 (s, 1H), 2.04~1.96 (m, 2H), 1.79~1.72 (m, 1H), 1.60~1.52 (m, 1H). |
| 63 | 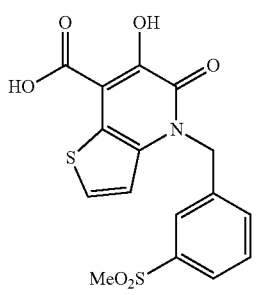 [SMILES: CS(=O)(=O)c1cccc(Cn2c(=O)c(O)c(C(=O)O)c3sccc32)c1]<br>6-hydroxy-4-[3-(methylsulfonyl)benzyl]-5-oxo-4,5-dihydrothieno[3,2-b]pyridine-7-carboxylic acid | Intermediate C<br><br>$Cs_2CO_3$, LiBr | A. NaOH, MeOH, $H_2O$<br>C. TFA | $(M + H)^+ = 379.9$<br>$^1$H NMR (DMSO-$d_6$, 400 MHz): δ 7.93 (s, 1H), 7.85 (d, J = 7.6 Hz, 1H), 7.62-7.54 (m, 3H), 7.27 (d, J = 5.2 Hz, 1H), 5.61 (s, 2H), 3.21 (s, 3H). |
| 64 | 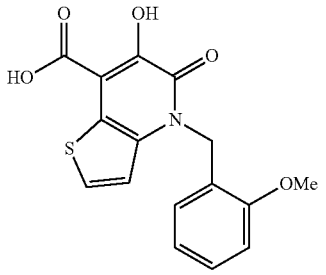 [SMILES: COc1ccccc1Cn1c(=O)c(O)c(C(=O)O)c2sccc21]<br>6-hydroxy-4-(2-methoxybenzyl)-5-oxo-4,5-dihydrothieno[3,2-b]pyridine-7-carboxylic acid | Intermediate C<br>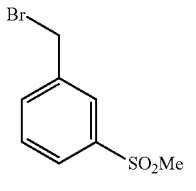 [SMILES: CS(=O)(=O)c1cccc(CBr)c1]<br>$Cs_2CO_3$, LiBr | A. NaOH, MeOH, $H_2O$<br>C. TFA | $(M + H)^+ = 332.0$<br>$^1$H NMR (DMSO-$d_6$, 400 MHz): δ 7.48 (s, 1H), 7.27-7.23 (m, 1H), 7.07 (d, J = 8.4 Hz, 1H), 6.80 (t, J = 7.2 Hz, 1H), 6.62 (d, J = 6.8 Hz, 1H), 5.41 (s, 2H), 3.91 (s, 3H) |

TABLE 1-continued

| Example # | Structure | Intermediate, Reference Methods, Alkylating Agent & Base | Deprotection Methods | Analytics |
|---|---|---|---|---|
| 65 | 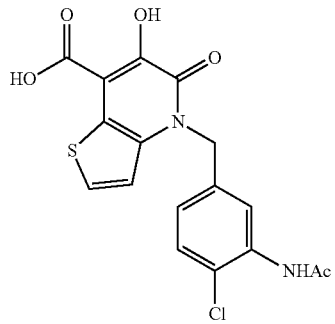 [SMILES: CC(=O)Nc1cc(Cn2c(=O)c(O)c(C(=O)O)c3sccc32)ccc1Cl]<br>4-(3-acetamido-4-chlorobenzyl)-6-hydroxy-5-oxo-4,5-dihydrothieno[3,2-b]pyridine-7-carboxylic acid | Intermediate C<br>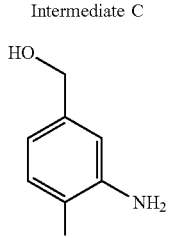<br>Methods: Example 14 | Methods: Example 14 | (M + H)⁺ = 392.9<br>$^1$H NMR (DMSO-$d_6$, 400 MHz): δ 9.52 (s, 1H), 7.64-7.61 (m, 2H), 7.44 (d, J = 1.6 Hz, 1H), 7.28 (d, J = 5.6 Hz, 1H), 7.20 (dd, J = 8.4 Hz, 2.0 Hz, 1H), 5.46 (s, 2H), 2.05 (s, 3H). |
| 66 | 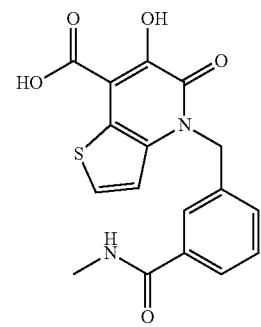 [SMILES: CNC(=O)c1cccc(Cn2c(=O)c(O)c(C(=O)O)c3sccc32)c1]<br>6-hydroxy-4-[3-(methylcarbamoyl)benzyl]-5-oxo-4,5-dihydrothieno[3,2-b]pyridine-7-carboxylic acid | Intermediate C<br>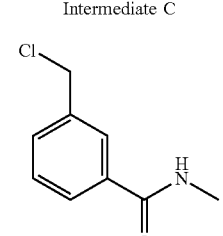<br>Cs$_2$CO$_3$, LiBr | A. NaOH, MeOH, H$_2$O<br>C. TFA | (M + H)⁺ = 359.0<br>$^1$H NMR (DMSO-$d_6$, 400 MHz): δ 8.45-8.44 (m, 1 H), 7.74 (s, 1H), 7.71-7.69 (m, 1H), 7.54 (d, J = 6.0 Hz, 1H), 7.42-7.39 (m, 2H), 7.17 (d, J = 5.2 Hz, 1H), 5.53 (s, 2H), 2.75 (d, J = 4.4 Hz, 3H). |
| 67 | 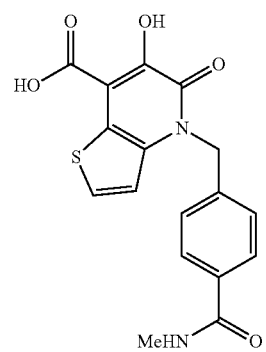 [SMILES: CNC(=O)c1ccc(Cn2c(=O)c(O)c(C(=O)O)c3sccc32)cc1]<br>6-hydroxy-4-(4-(methylcarbamoyl)benzyl)-5-oxo-4,5-dihydrothieno[3,2-b]pyridine-7-carboxylic acid | Intermediate C<br>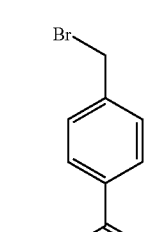<br>Cs$_2$CO$_3$, LiBr | A. NaOH, MeOH, H$_2$O<br>C. TFA | (M + H)⁺ = 359.0<br>$^1$H NMR (DMSO-$d_6$, 400 MHz): δ 8.38 (m, 1 H), 7.76 (d, J = 8.4 Hz, 2H), 7.61 (d, J = 5.6 Hz, 1H), 7.32 (d, J = 8.4 Hz, 2H), 7.19 (d, J = 5.6 Hz, 1H), 5.54 (s, 2H), 2.76 (d, J = 4.8 Hz, 3H). |

TABLE 1-continued

| Example # | Structure | Intermediate, Reference Methods, Alkylating Agent & Base | Deprotection Methods | Analytics |
|---|---|---|---|---|
| 68 | 4-(2-fluorobenzyl)-6-hydroxy-5-oxo-4,5-dihydrothieno[3,2-b]pyridine-7-carboxylic acid | Intermediate C<br><br>2-fluorobenzyl bromide<br><br>$Cs_2CO_3$, LiBr | A. NaOH, MeOH, $H_2O$<br>C. TFA | $(M + H)^+ = 320.0$<br>$^1H$ NMR (DMSO-$d_6$, 400 MHz): δ 7.50 (d, J = 5.2, 1H), 7.30-7.35 (m, 2H), 7.09-7.23 (m, 2H), 6.85-6.93 (m, 1H), 5.50 (s, 2H). |
| 69 | 6-hydroxy-5-oxo-4-[(tetrahydro-2H-pyran-4-yl)methyl]-4,5-dihydrothieno[3,2-b]pyridine-7-carboxylic acid | Intermediate C<br><br>4-(bromomethyl)tetrahydro-2H-pyran<br><br>$Cs_2CO_3$, LiBr | A. NaOH, MeOH, $H_2O$<br>C. TFA | $(M + H)^+ = 310.0$<br>$^1H$ NMR (DMSO-$d_6$, 400 MHz): δ 7.65 (d, J = 6.0, 1H), 7.37 (d, J = 6.0 Hz, 1H), 4.15 (d, J = 7.2 Hz, 2H), 3.81 (d, J = 10.8 Hz, 2H), 7.99 (t, J = 9.6 Hz, 2H), 2.04-2.11 (m, 1H), 1.37-1.47 (m, 4H). |
| 70 | 4-(3-chloro-4-methoxybenzyl)-6-hydroxy-5-oxo-4,5-dihydrothieno[3,2-b]pyridine-7-carboxylic acid | Intermediate C<br><br>3-chloro-4-methoxybenzyl chloride<br><br>$Cs_2CO_3$, LiBr | A. NaOH, MeOH, $H_2O$<br>C. TFA | $(M + H)^+ = 365.9$<br>$^1H$ NMR (DMSO-$d_6$, 400 MHz): δ 7.56 (d, J = 5.6 Hz, 1H), 7.44 (d, J = 2.0 Hz, 1H), 7.29-7.25 (m, 2H), 7.08 (d, J = 8.4 Hz, 1H), 5.42 (s, 2H), 3.80 (s, 3H). |
| 71 | 4-(3,4-dimethoxybenzyl)-6-hydroxy-5-oxo-4,5-dihydrothieno[3,2-b]pyridine-7-carboxylic acid | Intermediate C<br><br>3,4-dimethoxybenzyl bromide<br><br>$Cs_2CO_3$, LiBr | A. NaOH, MeOH, $H_2O$<br>C. TFA | $(M + H)^+ = 362$<br>$^1H$ NMR (DMSO-$d_6$, 400 MHz) δ 7.55 (d, J = 5.6 Hz, 1H), 7.25 (d, J = 5.6 Hz, 1H), 7.06 (s, 1H), 6.85 (d, J = 8.4 Hz, 1H), 6.74 (d, J = 8.4 Hz, 1H), 5.41 (s, 2H), 3.71 (d, J = 8.8 Hz, 6H). |

TABLE 1-continued

| Example # | Structure | Intermediate, Reference Methods, Alkylating Agent & Base | Deprotection Methods | Analytics |
|---|---|---|---|---|
| 72 | 4-(benzo[c][1,2,5]oxadiazol-4-ylmethyl)-6-hydroxy-5-oxo-4,5-dihydrothieno[3,2-b]pyridine-7-carboxylic acid | Intermediate C; Br-CH2-benzoxadiazolyl; $Cs_2CO_3$, LiBr | A. NaOH, MeOH, $H_2O$ C. TFA | $(M + H)^+ = 344.0$ $^1H$ NMR (DMSO-$d_6$, 400 MHz): δ 7.95 (d, J = 9.2 Hz, 1H), 7.55 (d, J = 5.6 Hz, 1H), 7.49 (dd, J = 8.8, 6.8 Hz, 1H), 7.20 (d, J = 5.6 Hz, 1H), 7.01 (d, J = 6.8 Hz, 1H), 5.84 (s, 2H). |
| 73 | 4-(4-amino-3-chlorobenzyl)-6-hydroxy-5-oxo-4,5-dihydrothieno[3,2-b]pyridine-7-carboxylic acid | Example 14 | Example 14 Deacylation: NaOH, MeOH, $H_2O$, 100° C. | $(M + H)^+ = 350.9$ $^1H$ NMR (DMSO-$d_6$, 400 MHz): δ 7.33 (d, J = 5.6 Hz, 1H), 7.10 (d, J = 8.0 Hz, 1H), 6.95 (d, J = 5.6 Hz, 1H), 6.54 (d, J = 2.0 Hz, 1H), 6.45 (dd, $J_1$ = 8.4 Hz, $J_2$ = 2.0 Hz, 2H), 5.30 (d, J = 10.8 Hz, 2H) |
| 74 | 4-((1,4-dioxan-2-yl)methyl)-6-hydroxy-5-oxo-4,5-dihydrothieno[3,2-b]pyridine-7-carboxylic acid | Intermediate C; I-CH2-dioxanyl; $Cs_2CO_3$, LiBr | A. NaOH, MeOH, $H_2O$ C. TFA | $(M + H)^+ = 312.0$ $^1H$ NMR (DMSO-$d_6$, 400 MHz): δ 7.62 (d, J = 5.6 Hz, 1 H), 7.31 (d, J = 5.6 Hz, 1H), 4.35-4.20 (m, 2H), 3.93-3.84 (m, 1H), 3.78 (dd, I = 11.6, 2.4 Hz, 1H), 3.68 (d, J = 8.8 Hz, 1H), 3.62-3.56 (m, 1H), 3.46 (d, J = 8.8 Hz, 2H), 3.37 (dd, J = 11.6, 9.6 Hz, 1H). |
| 75 | 4-[(1H-imidazol-5-yl)methyl]-6-hydroxy-5-oxo-4,5-dihydrothieno[3,2-b]pyridine-7-carboxylic acid | Intermediate C; Cl-CH2-imidazolyl-NBoc; $Cs_2CO_3$, LiBr | A. NaOH, MeOH, $H_2O$ C. TFA | $(M + H)^+ = 292.0$ $^1H$ NMR (DMSO-d6, 400 MHz): δ 9.04 (s, 1H), 7.70 (d, J = 5.6 Hz, 1H), 7.57 (s, 1H), 7.46 (d, J = 5.6 Hz, 1H), 5.55 (s, 2H). |

TABLE 1-continued

| Example # | Structure | Intermediate, Reference Methods, Alkylating Agent & Base | Deprotection Methods | Analytics |
|---|---|---|---|---|
| 76 | 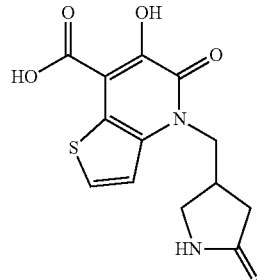<br>6-hydroxy-5-oxo-4-[(5-oxopyrrolidin-3-yl)methyl]-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 309.0<br>$^1$H NMR (DMSO-d$_6$, 400 MHz): δ 7.67 (d, J = 5.6 Hz, 1H), 7.58 (s, 1H), 7.38 (d, J = 5.6 Hz, 1H), 4.35-4.32 (m, 2H), 3.29-3.24 (m, 1H), 3.10-3.06 (m, 1H), 2.94-2.86 (m, 1H), 2.25-2.19 (m, 1H), 2.08-2.02 (m, 1H). |
| 77 | 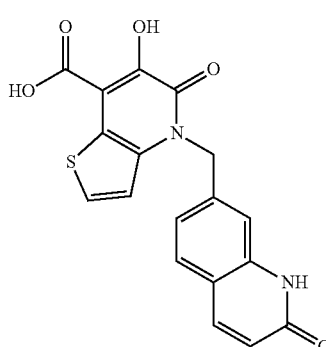<br>6-hydroxy-5-oxo-4-[(2-oxo-1,2-dihydroquinolin-7-yl)methyl]-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 368.9<br>$^1$H NMR (DMSO-d$_6$, 400 MHz): δ 11.59 (s, 1H), 7.85 (d, J = 9.6 Hz, 1H), 7.61 (d, J = 7.6 Hz, 1H), 7.49 (d, J = 4.8 Hz, 1H), 7.09-7.06 (m, 3H), 6.43 (d, J = 11.2 Hz, 1H), 5.56 (s, 2H). |
| 78 | 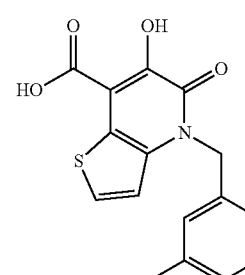<br>6-hydroxy-4-[3-(methylsulfonamido)benzyl]-5-oxo-4,5-dihydrothieno[3,2-b]pyridine-7-carboxylic acid | Intermediate C<br><br>K$_2$CO$_3$, LiBr | A. NaOH, MeOH, H$_2$O<br>C. TFA | (M + H)$^+$ = 394.9<br>$^1$H NMR (DMSO-d$_6$, 400 MHz): δ 9.74 (s, 1H), 7.50 (d, J = 5.6 Hz, 1H), 7.27 (t, J = 8.0 Hz, 1H), 7.11-7.06 (m, 3H), 7.00-7.01 (m, 1H), 5.46 (s, 2H), 2.95 (s, 3H). |

TABLE 1-continued

| Example # | Structure | Intermediate, Reference Methods, Alkylating Agent & Base | Deprotection Methods | Analytics |
|---|---|---|---|---|
| 79 | 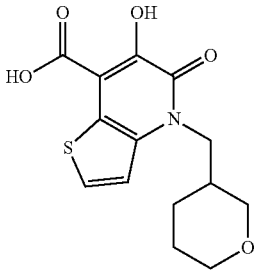 [SMILES: O=C(O)c1c(O)c(=O)n(CC2CCCOC2)c2ccsc12]<br>6-hydroxy-5-oxo-4-[(tetrahydro-2H-pyran-3-yl)methyl]-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 310.0<br>$^1$H NMR (DMSO-d$_6$, 400 MHz): δ 7.68 (d, J = 5.6 Hz, 1H), 7.35 (d, J = 5.6 Hz, 1H), 4.17~4.14 (m, 2H), 3.71-3.64 (m, 2H), 3.24-3.35 (m, 2H), 2.04 (s, 1H), 1.72-1.61 (m, 2H), 1.46-1.31 (m, 2H). |
| 80 | 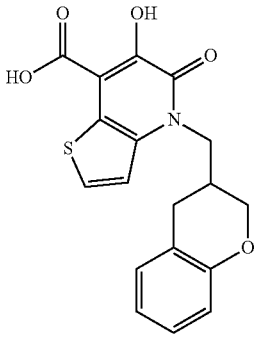 [SMILES: O=C(O)c1c(O)c(=O)n(CC2COc3ccccc3C2)c2ccsc12]<br>4-(chroman-3-ylmethyl)-6-hydroxy-5-oxo-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 358.1<br>$^1$H NMR (DMSO-d$_6$, 400 MHz) δ 7.56 (d, J = 5.6 Hz, 1H), 7.28 (d, J = 5.2 Hz, 1H) 7.02-7.08 (m, 2H), 6.74-6.84 (m, 2H), 4.28 (d, J = 6.8 Hz, 2H), 4.13 (d, J = 10.8 Hz, 1H), 3.92-3.98 (m, 2H), 2.79-2.84 (m, 1H), 2.65-2.69 (m, 1H). |
| 81 | 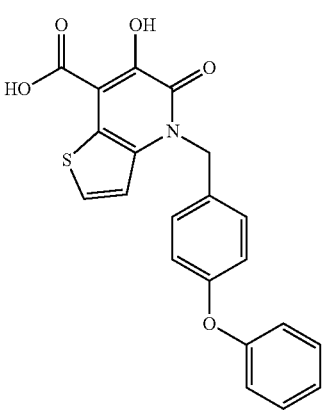 [SMILES: O=C(O)c1c(O)c(=O)n(Cc2ccc(Oc3ccccc3)cc2)c2ccsc12]<br>6-hydroxy-5-oxo-4-(4-phenoxybenzyl)-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 394.0<br>$^1$H NMR (DMSO-d$_6$, 400 MHz): δ 7.62-7.61 (d, J = 5.6 Hz, 1H), 7.39-7.28 (m, 5H), 7.13 (t, J = 2.0 Hz, 1H), 6.99-6.96 (m, 4H), 5.48 (s, 2H). |

TABLE 1-continued

| Example # | Structure | Intermediate, Reference Methods, Alkylating Agent & Base | Deprotection Methods | Analytics |
|---|---|---|---|---|
| 82 | 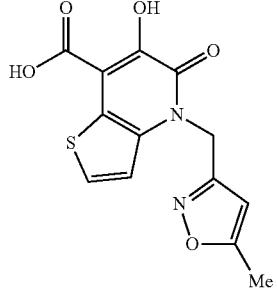 [SMILES: Cc1cc(Cn2c(=O)c(O)c(C(=O)O)c3sccc32)no1]<br>6-hydroxy-4-[(5-methylisoxazol-3-yl)methyl]-5-oxo-4,5-dihydrothieno[3,2-b]pyridine-7-carboxylic acid | Intermediate C<br>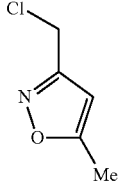<br>Cs$_2$CO$_3$, LiBr | A. NaOH, MeOH, H$_2$O<br>C. TFA | (M + H)$^+$ = 306.9; $^1$H NMR (DMSO-d$_6$, 400 MHz): δ 7.62 (d, J = 5.2, 1H), 7.25 (d, J = 5.2 Hz, 1H), 6.09 (s, 1H), 5.48 (s, 1H), 2.34 (s, 3H). |
| 83 | 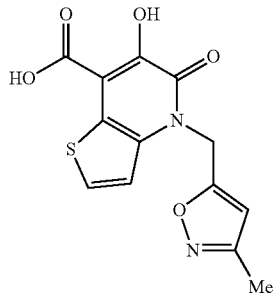 [SMILES: Cc1cc(Cn2c(=O)c(O)c(C(=O)O)c3sccc32)on1]<br>6-hydroxy-4-[(3-methylisoxazol-5-yl)methyl]-5-oxo-4,5-dihydrothieno[3,2-b]pyridine-7-carboxylic acid | Intermediate C<br>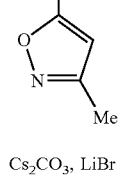<br>Cs$_2$CO$_3$, LiBr | A. NaOH, MeOH, H$_2$O<br>C. TFA | (M + H)$^+$ = 306.9 $^1$H NMR (DMSO-d$_6$, 400 MHz): δ 7.68 (d, J = 5.6 Hz, 1H), 7.35 (d, J = 5.6 Hz, 1H), 6.27 (s, 1H), 5.60 (s, 2H), 2.17 (s, 3H). |
| 84 | 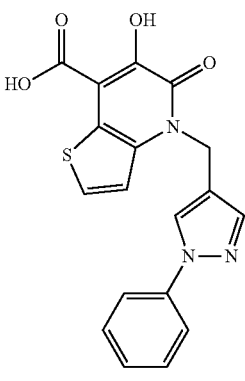 [SMILES: O=C(O)c1c(O)c(=O)n(Cc2cnn(-c3ccccc3)c2)c2ccsc12]<br>6-hydroxy-5-oxo-4-[(1-phenyl-1H-pyrazol-4-yl)methyl]-4,5-dihydrothieno[3,2-b]pyridine-7-carboxylic acid | Intermediate C<br>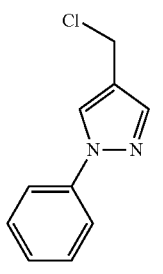 [SMILES: ClCc1cnn(-c2ccccc2)c1]<br>Cs$_2$CO$_3$, LiBr | A. NaOH, MeOH, H$_2$O<br>C. TFA | (M + H)$^+$ = 368.0 $^1$H NMR (DMSO-d$_6$, 400 MHz,) δ 8.02 (s, 1H), 7.77-7.74 (m, 3H), 7.65 (d, J = 5.6 Hz, 1H), 7.50-7.44 (m, 3H), 7.28 (d, J = 7.2 Hz, 1H), 5.37 (s, 2H). |

TABLE 1-continued

| Example # | Structure | Intermediate, Reference Methods, Alkylating Agent & Base | Deprotection Methods | Analytics |
|---|---|---|---|---|
| 85 | 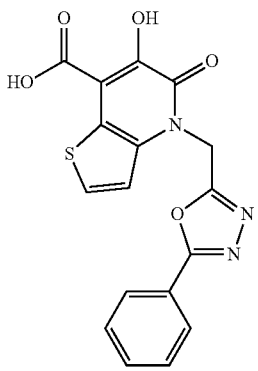<br>6-hydroxy-5-oxo-4-[(5-phenyl-1,3,4-oxadiazol-2-yl)methyl]-4,5-dihydrothieno[3,2-b]pyridine-7-carboxylic acid | Intermediate C<br>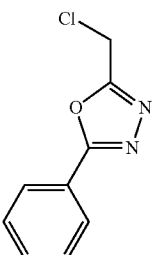<br>Cs$_2$CO$_3$, LiBr | A. NaOH, MeOH, H$_2$O<br>C. TFA | (M + H)$^+$ = 370.0<br>$^1$H NMR (DMSO-d$_6$, 400 MHz): δ 7.94 (d, J = 6.4, 2H), 7.62-7.65 (m, 4H), 7.40 (d, J = 5.6 Hz, 1H), 5.818 (s, 2H). |
| 86 | 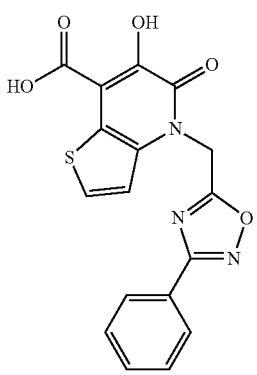 [SMILES: O=C(O)c1c(O)c(=O)n(Cc2nnc(-c3ccccc3)o2)c2ccsc12]<br>6-hydroxy-5-oxo-4-[(3-phenyl-1,2,4-oxadiazol-5-yl)methyl]-4,5-dihydrothieno[3,2-b]pyridine-7-carboxylic acid | Intermediate C<br>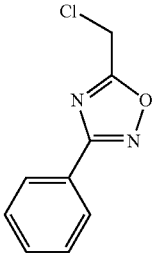 [SMILES: ClCc1nc(-c2ccccc2)no1]<br>Cs$_2$CO$_3$, LiBr | A. NaOH, MeOH, H$_2$O<br>C. TFA | (M + H)$^+$ = 370.0<br>$^1$H NMR (DMSO-d$_6$, 400 MHz): δ 7.67 (d, J = 5.6, 1H), 7.34 (d, J = 5.6, 1H), 7.52-7.61 (m, 3H), 7.40 (d, J = 5.6, 1H), 5.87 (s, 2H). |
| 87 | 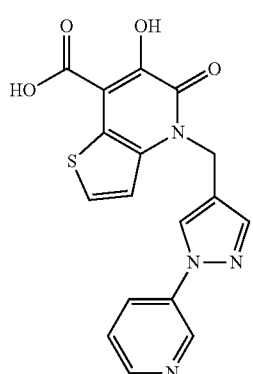<br>6-hydroxy-5-oxo-4-{[1-(pyridin-3-yl)-1H-pyrazol-4-yl]methyl}-4,5-dihydrothieno[3,2-b]pyridine-7-carboxylic acid | Intermediate C<br>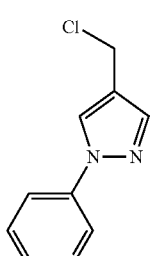<br>Cs$_2$CO$_3$, LiBr | A. NaOH, MeOH, H$_2$O<br>C. TFA | (M + H)$^+$ = 369.0<br>$^1$H NMR (DMSO-d$_6$, 400 MHz): δ 9.05 (d, J = 2.0 Hz, 1 H), 8.61 (s, 1H), 8.51 (d, J = 4.4 Hz, 1H), 8.20 (d, J = 8.4 Hz, 1H), 7.83 (s, 1 H), 7.64 (d, J = 5.6 Hz, 1H), 7.54 (dd, J = 8.4 Hz, 4.8 Hz, 1H), 7.46 (d, J = 5.6 Hz, 1 H), 5.38 (s, 3H). |

TABLE 1-continued

| Example # | Structure | Intermediate, Reference Methods, Alkylating Agent & Base | Deprotection Methods | Analytics |
|---|---|---|---|---|
| 88 | 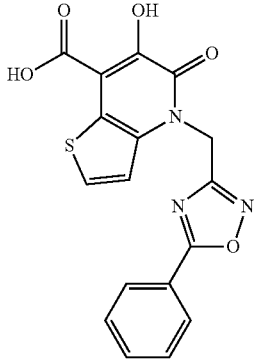 [SMILES: O=C(O)c1c(O)c(=O)n(Cc2noc(-c3ccccc3)n2)c2ccsc12]<br>6-hydroxy-5-oxo-4-[(5-phenyl-1,2,4-oxadiazol-3-yl)methyl]-4,5-dihydrothieno[3,2-b]pyridine-7-carboxylic acid | Intermediate C<br>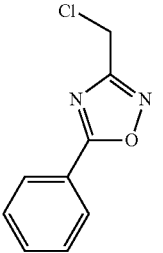<br>Cs$_2$CO$_3$, LiBr | A. NaOH, MeOH, H$_2$O<br>C. TFA | (M + H)$^+$ = 370<br>$^1$H NMR (DMSO-d$_6$, 400 MHz,) δ 8.05 (d, J = 8.0 Hz, 2H), 7.58-7.74 (m, 4H), 7.36 (d, J = 5.6 Hz, 1H), 5.72 (s, 2H) |
| 89 | 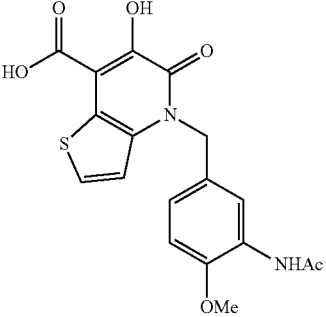 [SMILES: COc1ccc(Cn2c(=O)c(O)c(C(=O)O)c3sccc32)cc1NC(C)=O]<br>4-(3-acetamido-4-methoxybenzyl)-6-hydroxy-5-oxo-4,5-dihydrothieno[3,2-b]pyridine-7-carboxylic acid | Intermediate C<br>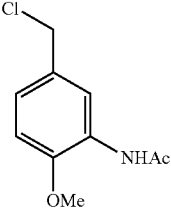<br>Cs$_2$CO$_3$, LiBr | A. NaOH, MeOH, H$_2$O<br>C. TFA | (M + H)$^+$ = 389<br>$^1$H NMR (DMSO-d$_6$, 400 MHz) δ 9.11 (s, 1H), 7.92 (s, 1H), 7.58 (d, J = 5.6 Hz, 1H), 7.20 (d, J = 5.6 Hz, 1H), 6.94-6.99 (m, 1H), 5.41 (s, 2H), 3.78 (s, 3H), 2.04 (s, 3H) |
| 90 | 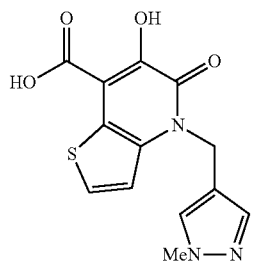 [SMILES: Cn1cc(Cn2c(=O)c(O)c(C(=O)O)c3sccc32)cn1]<br>6-hydroxy-4-[(1-methyl-1H-pyrazol-4-yl)methyl]-5-oxo-4,5-dihydrothieno[3,2-b]pyridine-7-carboxylic acid | Intermediate C<br>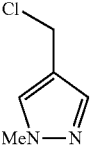<br>Cs$_2$CO$_3$, LiBr | A. NaOH, MeOH, H$_2$O<br>C. TFA | (M + H)$^+$ = 305.9<br>$^1$H NMR (DMSO-d$_6$, 400 MHz): δ 7.69-7.65 (m, 2H), 7.48-7.45 (m, 2H), 5.27 (s, 2H), 3.74 (s, 3H). |

TABLE 1-continued

| Example # | Structure | Intermediate, Reference Methods, Alkylating Agent & Base | Deprotection Methods | Analytics |
|---|---|---|---|---|
| 91 | 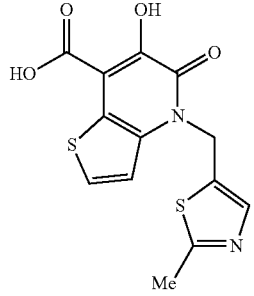 [SMILES: Cc1ncc(Cn2c(=O)c(O)c(C(=O)O)c3sccc32)s1]<br>6-hydroxy-4-[(2-methylthiazol-5-yl)methyl]-5-oxo-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 323.0<br>$^1$H NMR (DMSO-d$_6$, 400 MHz): δ 7.94 (s, 1H), 7.74 (d, J = 5.6 Hz, 1H), 7.61 (d, J = 5.6 Hz, 1H), 5.61 (s, 2H), 2.59 (s, 3H). |
| 92 | 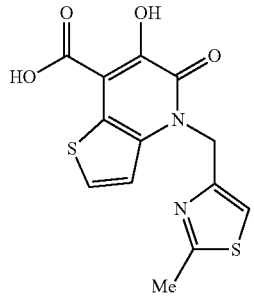 [SMILES: Cc1nc(Cn2c(=O)c(O)c(C(=O)O)c3sccc32)cs1]<br>6-hydroxy-4-[(2-methylthiazol-4-yl)methyl]-5-oxo-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 323.0<br>$^1$H NMR (DMSO-d$_6$, 400 MHz) δ 7.60 (d, J = 5.6 Hz, 1H), 7.22-7.30 (m, 2H), 5.49 (s, 2H), 2.59 (s, 3H) |
| 93 | 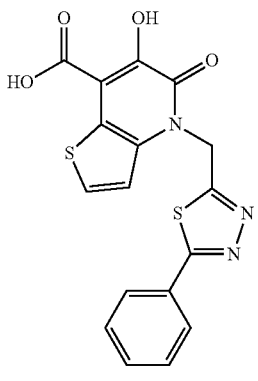 [SMILES: O=C(O)c1c(O)c(=O)n(Cc2nnc(-c3ccccc3)s2)c2ccsc12]<br>6-hydroxy-5-oxo-4-[(5-phenyl-1,3,4-thiadiazol-2-yl)methyl]-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 385.9<br>$^1$H NMR (DMSO-d$_6$, 400 MHz): δ 7.94 (dd, J = 8.0 Hz, 2.0 Hz, 2H), 7.68 (d, J = 5.6 Hz, 1H), 7.52-7.55 (m, 3H), 7.45 (d, J = 5.6 Hz, 1H), 5.93 (s, 2H). |

TABLE 1-continued

| Example # | Structure | Intermediate, Reference Methods, Alkylating Agent & Base | Deprotection Methods | Analytics |
|---|---|---|---|---|
| 94 | 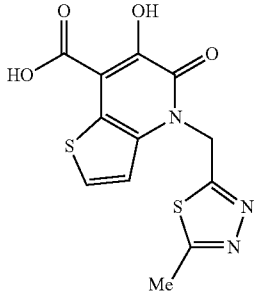 [SMILES: Cc1nnc(Cn2c(=O)c(O)c(C(=O)O)c3sccc32)s1]<br>6-hydroxy-4-[(5-methyl-1,3,4-thiadiazol-2-yl)methyl]-5-oxo-4,5-dihydrothieno[3,2-b]pyridine-7-carboxylic acid | Intermediate C<br><br>[chloromethyl-5-methyl-1,3,4-thiadiazole]<br><br>$Cs_2CO_3$, LiBr | A. NaOH, MeOH, $H_2O$<br>C. TFA | $(M + H)^+$ = 323.9<br>$^1$H NMR (DMSO-$d_6$, 400 MHz): δ 7.63 (d, J = 5.6 Hz, 1H), 7.37 (d, J = 5.6 Hz, 1H), 5.81 (s, 2H), 2.66 (s, 3H). |
| 95 | 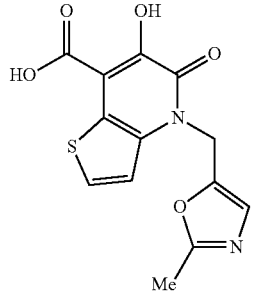 [SMILES: Cc1ncc(Cn2c(=O)c(O)c(C(=O)O)c3sccc32)o1]<br>6-hydroxy-4-[(2-methyloxazol-5-yl)methyl]-5-oxo-4,5-dihydrothieno[3,2-b]pyridine-7-carboxylic acid | Intermediate C<br><br>[chloromethyl-2-methyloxazole]<br><br>$Cs_2CO_3$, LiBr | A. NaOH, MeOH, $H_2O$<br>C. TFA | $(M + H)^+$ = 307.0<br>$^1$H NMR (DMSO-$d_6$, 400 MHz): δ 7.66 (d, J = 5.6 Hz, 1 H), 7.43 (d, J = 5.6 Hz, 1H), 7.10 (s, 1H), 5.50 (s, 2 H), 2.31 (s, 3H). |
| 96 | 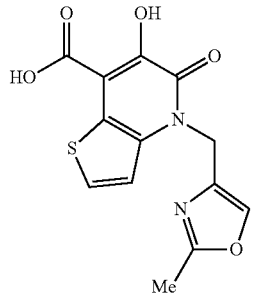 [SMILES: Cc1nc(Cn2c(=O)c(O)c(C(=O)O)c3sccc32)co1]<br>6-hydroxy-4-((2-methyloxazol-4-yl)methyl)-5-oxo-4,5-dihydrothieno[3,2-b]pyridine-7-carboxylic acid | Intermediate C<br><br>[chloromethyl-2-methyloxazole]<br><br>$Cs_2CO_3$, LiBr | A. NaOH, MeOH, $H_2O$<br>C. TFA | $(M + H)^+$ = 307.0<br>$^1$H NMR (DMSO-$d_6$, 400 MHz) δ 8.07 (s, 1H), 7.76 (d, J = 5.6 Hz, 1H), 7.36 (d, J = 5.6 Hz, 1H), 5.28 (s, 2H), 2.42 (s, 3H). |

TABLE 1-continued

| Example # | Structure | Intermediate, Reference Methods, Alkylating Agent & Base | Deprotection Methods | Analytics |
|---|---|---|---|---|
| 97 | 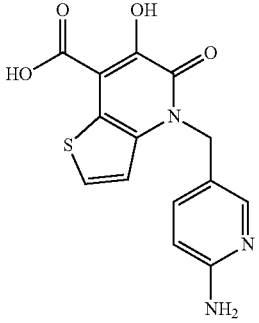 [SMILES: Nc1ccc(Cn2c(=O)c(O)c(C(=O)O)c3sccc32)cn1]<br>4-[(6-aminopyridin-3-yl)methyl]-6-hydroxy-5-oxo-4,5-dihydrothieno[3,2-b]pyridine-7-carboxylic acid | Intermediate C<br>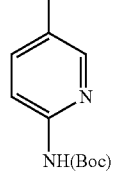<br>$Cs_2CO_3$, LiBr | A. NaOH, MeOH, $H_2O$<br>C. TFA | $(M + H)^+$ = 318.0<br>$^1H$ NMR (DMSO-$d_6$, 400 MHz): δ 7.97 (s, 1H), 7.89-7.84 (m, 3H), 7.44 (d, J = 5.6 Hz, 1H), 7.28 (d, J = 6.0 Hz, 1H), 6.92 (d, J = 9.2 Hz, 1H), 5.31 (s, 2H). |
| 98 | 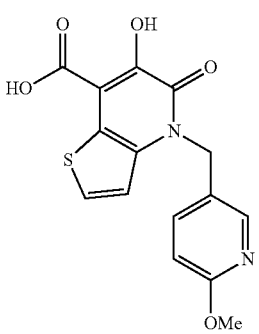 [SMILES: COc1ccc(Cn2c(=O)c(O)c(C(=O)O)c3sccc32)cn1]<br>6-hydroxy-4-[(6-methoxypyridin-3-yl)methyl]-5-oxo-4,5-dihydrothieno[3,2-b]pyridine-7-carboxylic acid | Intermediate C<br>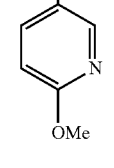<br>$K_2CO_3$, DMF | A. NaOH, MeOH, $H_2O$<br>C. TFA | $(M + H)^+$ = 147.1<br>$^1H$ NMR (DMSO-$d_6$, 400 MHz): δ 8.25 (s, 1H), 7.61-7.65 (m, 2H), 7.35 (d, J = 2.4 Hz, 1H), 6.57 (d, J = 5.2 Hz, 1H), 5.43 (s, 1H), 3.81 (s, 3H). |
| 99 | 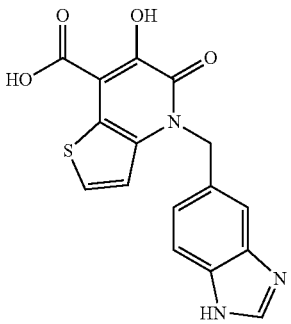 [SMILES: O=C(O)c1c(O)c(=O)n(Cc2ccc3[nH]cnc3c2)c2ccsc12]<br>4-[(1H-benzo[d]imidazol-5-yl)methyl]-6-hydroxy-5-oxo-4,5-dihydrothieno[3,2-b]pyridine-7-carboxylic acid | Intermediate C<br>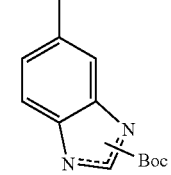<br>(mixture of 2 N-Boc isomers)<br>$Cs_2CO_3$, LiBr | A. NaOH, MeOH, $H_2O$<br>C. TFA | $(M + H)^+$ = 342.0<br>$^1H$ NMR (DMSO-$d_6$, 400 MHz): δ 9.59 (s, 1H), 7.82 (d, J = 8.8 Hz, 1H), 7.77 (s, 1H), 7.66 (d, J = 5.6 Hz, 1H), 7.53 (d, J = 8.0 Hz, 1H), 7.33 (d, J = 5.6 Hz, 1H), 5.69 (s, 2H). |

TABLE 1-continued

| Example # | Structure | Intermediate, Reference Methods, Alkylating Agent & Base | Deprotection Methods | Analytics |
|---|---|---|---|---|
| 100 | 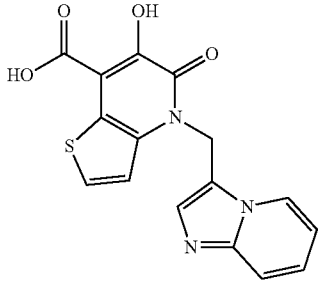 [SMILES: O=C(O)c1c(O)c(=O)n(Cc2cnc3ccccn23)c2ccsc12]<br>6-hydroxy-4-(imidazo[1,2-a]pyridin-3-ylmethyl)-5-oxo-4,5-dihydrothieno[3,2-b]pyridine-7-carboxylic acid | Intermediate C<br><br>$Cs_2CO_3$, LiBr | A. NaOH, MeOH, $H_2O$<br>C. TFA | $(M + H)^+$ = 369.0<br>$^1$H NMR (DMSO-$d_6$, 400 MHz): δ 9.19 (d, J = 6.8 Hz, 1 H), 8.33 (s, 1H), 8.01-7.97 (m, 2H), 7.74 (d, J = 5.6 Hz, 1H), 7.65-7.59 (m, 2H), 5.96 (s, 2H). |
| 101 | 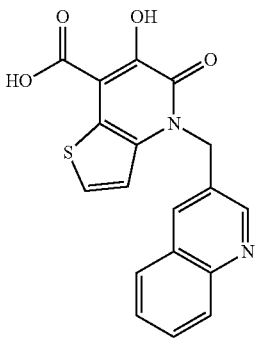 [SMILES: O=C(O)c1c(O)c(=O)n(Cc2cnc3ccccc3c2)c2ccsc12]<br>6-hydroxy-5-oxo-4-(quinolin-3-ylmethyl)-4,5-dihydrothieno[3,2-b]pyridine-7-carboxylic acid | Intermediate C<br>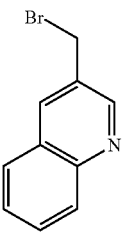<br>$Cs_2CO_3$, LiBr | A. NaOH, MeOH, $H_2O$<br>C. TFA | $(M + H)^+$ = 352.9<br>$^1$H NMR (DMSO-$d_6$, 400 MHz): δ 9.41 (d, J = 1.6 Hz, 1 H), 8.95 (s, 1H), 8.44 (d, J = 8.8 Hz, 1H), 8.28 (d, J = 8.4 Hz, 1H), 8.11 (t, J = 7.2 Hz, 1H), 7.91 (t, J = 8.0 Hz, 1H), 7.68 (t, J = 5.6 Hz, 1H), 7.46 (t, J = 5.6 Hz, 1H), 5.83 (s, 2H). |
| 102 | 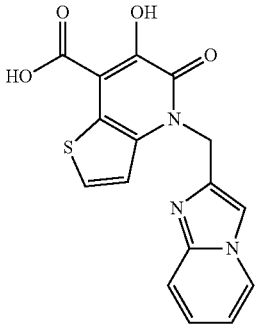 [SMILES: O=C(O)c1c(O)c(=O)n(Cc2cn3ccccc3n2)c2ccsc12]<br>6-hydroxy-4-(imidazo[1,2-a]pyridin-2-ylmethyl)-5-oxo-4,5-dihydrothieno[3,2-b]pyridine-7-carboxylic acid | Intermediate C<br>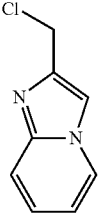 [SMILES: ClCc1cn2ccccc2n1]<br>$K_2CO_3$, DMF | A. NaOH, MeOH, $H_2O$<br>C. TFA | $(M + H)^+$ = 342.0<br>$^1$H NMR (DMSO-$d_6$, 400 MHz) δ 8.84 (d, J = 7.2 Hz, 1H), 8.29 (s, 1H), 7.93 (d, J = 4.0 Hz, 2H), 7.49-7.45 (m, 1H), 5.77 (s, 2H). |

TABLE 1-continued

| Example # | Structure | Intermediate, Reference Methods, Alkylating Agent & Base | Deprotection Methods | Analytics |
|---|---|---|---|---|
| 103 | 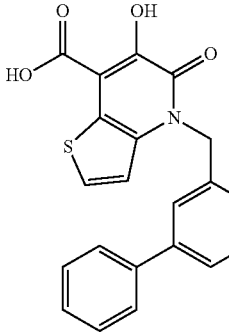<br>6-hydroxy-5-oxo-4-[(5-phenylpyridin-3-yl)methyl]-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 379.0<br>$^1$H NMR (DMSO-d$_6$, 400 MHz): δ 8.85 (s, 1H), 8.57 (s, 1H), 8.16 (s, 1H), 7.68 (d, J = 7.2 Hz, 2H), 7.60 (s, 1H), 7.52 (d, J = 7.2 Hz, 2H), 7.45-7.47 (m, 2 H), 5.6 (s, 2H). |
| 104 | 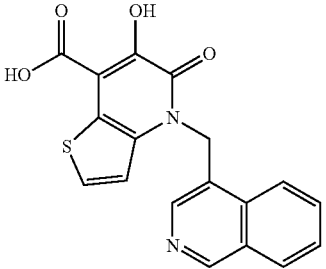 [SMILES: O=C(O)c1c(O)c(=O)n(Cc2cncc3ccccc23)c2ccsc12]<br>6-hydroxy-4-(isoquinolin-4-ylmethyl)-5-oxo-4,5-dihydrothieno[3,2-b]pyridine-7-carboxylic acid | Intermediate C<br><br>K$_2$CO$_3$, DMF | A. NaOH, MeOH, HO<br>C. TFA | (M + H)$^+$ 353.0<br>$^1$H NMR (DMSO-d$_6$, 400 MHz) δ 9.39 (s, 1H), 8.41 (d, J = 8.8 Hz, 1H), 8.32 (d, J = 7.2 Hz, 1H), 8.04 (t, J = 7.2 Hz, 1H), 7.87 (t, J = 7.2 Hz, 1H), 7.82 (s, 1H), 7.48 (d, J = 5.6 Hz, 1H), 7.08 (s, 1H), 6.00 (s, 2H) |
| 105 | 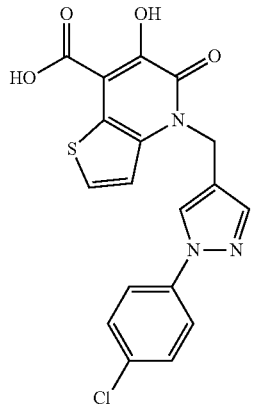 [SMILES: O=C(O)c1c(O)c(=O)n(Cc2cnn(-c3ccc(Cl)cc3)c2)c2ccsc12]<br>4-{[1-(4-chlorophenyl)-1H-pyrazol-4-yl]methyl}-6-hydroxy-5-oxo-4,5-dihydrothieno[3,2-b]pyridine-7-carboxylic acid | Intermediate D<br>Methods: Example 19 | A. NaOH, MeOH, H$_2$O<br>C. TFA | (M + H)$^+$ = 401<br>$^1$H NMR (DMSO-d$_6$, 400 MHz): δ 7.53 (s, 1H), 7.79 (d, J = 11.2 Hz, 3H), 7.52-7.58 (m, 3H), 7.45 (s, 1H), 5.36 (s, 2H) |

TABLE 1-continued

| Example # | Structure | Intermediate, Reference Methods, Alkylating Agent & Base | Deprotection Methods | Analytics |
|---|---|---|---|---|
| 106 | 6-hydroxy-4-{[1-(2-methoxyphenyl)-1H-pyrazol-4-yl]methyl}-5-oxo-4,5-dihydrothieno[3,2-b]pyridine-7-carboxylic acid | Intermediate D Methods: Example 19 — B(OH)$_2$, OMe | A. NaOH, MeOH, H$_2$O C. TFA | (M + H)$^+$ = 398 $^1$H NMR (, DMSO-d$_6$, 400 MHz) δ 8.29 (s, 1H), 7.65-7.70 (m, 2H), 7.54-7.57 (m, 2H), 7.34 (d, J = 7.2 Hz, 1H), 7.23 (d, J = 8 Hz, 1H), 7.05 (d, J = 7.2 Hz, 1H), 5.38 (s, 2H), 3.85 (s, 3H) |
| 107 | 6-hydroxy-4-{[1-(2-nitrophenyl)-1H-pyrazol-4-yl]methyl}-5-oxo-4,5-dihydrothieno[3,2-b]pyridine-7-carboxylic acid | Inermediate D Methods: Example 21 — F, NO$_2$ | A. NaOH, MeOH, H$_2$O C. TFA | (M + H)$^+$ 413.0 $^1$H NMR (DMSO-d$_6$, 400 MHz,) δ 8.35 (s, 1H), 7.99 (d, J = 8.0 Hz, 1H), 7.82-7.73 (m, 3H), 7.67-7.59 (m, 2H), 7.49 (d, J = 5.2 Hz, 1H), 5.37 (s, 2H) |
| 108 | 6-hydroxy-4-{[1-(2-(methylsulfonamido)phenyl]-1H-pyrazol-4-yl}methyl)-5-oxo-4,5-dihydrothieno[3,2-b]pyridine-7-carboxylic acid | Intermediate D — F, NO$_2$ Methods: Example 22 | A. NaOH, MeOH, H$_2$O C. TFA | (M + H)$^+$ 461.1 $^1$H NMR (CD$_3$OD, 400 MHz,) δ 8.25 (s, 1H), 7.91 (s, 1H), 7.65 (dd, J = 8.0, 1.2 Hz, 1H), 7.60 (d, J = 5.6 Hz, 1H), 7.52-7.46 (m, 2H), 7.42 (td, J = 7.6, 1.2 Hz, 1H), 7.33 (td, J = 7.8, 1.6 Hz, 1H), 5.54 (s, 2H), 2.72 (s, 3H). |

TABLE 1-continued

| Example # | Structure | Intermediate, Reference Methods, Alkylating Agent & Base | Deprotection Methods | Analytics |
|---|---|---|---|---|
| 109 | 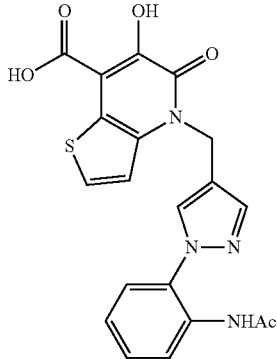<br>4-{[1-(2-acetamidophenyl)-1H-pyrazol-4-yl]methyl}-6-hydroxy-5-oxo-4,5-dihydrothieno[3,2-b]pyridine-7-carboxylic acid | Intermediate D<br>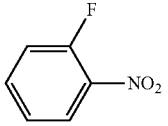<br>Methods: Example 22 | A. NaOH, MeOH, H$_2$O<br>C. TFA | (M + H)$^+$ 425.0<br>$^1$H NMR (DMSO-d$_6$, 400 MHz,) δ 9.81 (s, 1H), 8.19 (s, 1H), 7.84 (s, 1H), 7.78 (d, J = 8.0 Hz, 1H), 7.50 (dd, J = 16.8, 8.2 Hz, 3H), 7.35 (t, J = 7.0 Hz, 1H), 7.30-7.24 (m, 1H), 5.35 (br s, 2H), 1.90 (s, 3H). |
| 110 | 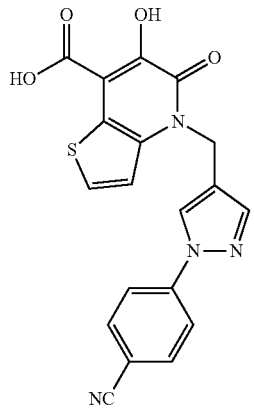 [SMILES: N#Cc1ccc(-n2cc(Cn3c(=O)c(O)c(C(=O)O)c4sccc43)cn2)cc1]<br>4-{[1-(4-cyanophenyl)-1H-pyrazol-4-yl]methyl}-6-hydroxy-5-oxo-4,5-dihydrothieno[3,2-b]pyridine-7-carboxylic acid | Intermediate D<br>Methods: Example 21<br>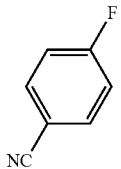<br>K$_2$CO$_3$, DMF, 80° C. | A. NaOH, MeOH, H$_2$O<br>C. TFA | (M + H)$^+$ = 392.9<br>$^1$H NMR (DMSO-d$_6$, 400 MHz) δ 8.67 (s, 1H), 7.99 (q, J = 8.4 Hz, 4H), 7.86 (s, 1H), 7.60 (d, J = 5.6 Hz, 1H), 7.44 (d, J = 5.2 Hz, 1H), 5.37 (s, 2H) |
| 111 | 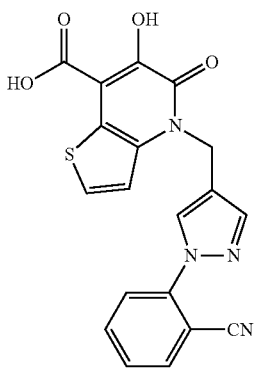 [SMILES: N#Cc1ccccc1-n1cc(Cn2c(=O)c(O)c(C(=O)O)c3sccc32)cn1]<br>4-{[1-(2-cyanophenyl)-1H-pyrazol-4-yl]methyl}-6-hydroxy-5-oxo-4,5-dihydrothieno[3,2-b]pyridine-7-carboxylic acid | Inermediate D<br>Methods: Example 21<br>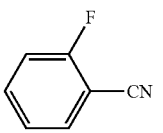<br>K$_2$CO$_3$, DMF, 80° C. | A. NaOH, MeOH, H$_2$O<br>C. TFA | (M + H)$^+$ = 393.1<br>$^1$H NMR (DMSO-d$_6$, 400 MHz) δ 8.45 (s, 1H), 7.98 (dd, J = 8.0, 1.2 Hz, 1H), 7.88 (s, 1H), 7.85-7.79 (m, 1H), 7.78-7.73 (m, 1H), 7.62 (d, J = 5.6 Hz, 1H), 7.58-7.53 (m, 1H), 7.50 (d, J = 6.0 Hz, 1H), 5.39 (s, 2H) |

TABLE 1-continued

| Example # | Structure | Intermediate, Reference Methods, Alkylating Agent & Base | Deprotection Methods | Analytics |
|---|---|---|---|---|
| 112 | 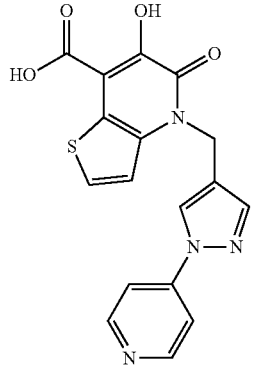 [SMILES: O=C(O)c1c(O)c(=O)n(Cc2cnn(-c3ccncc3)c2)c2ccsc12]

6-hydroxy-5-oxo-4-{[1-(pyridin-4-yl)-1H-pyrazol-4-yl]methyl}-4,5-dihydrothieno[3,2-b]pyridine-7-carboxylic acid | Intermediate D Methods: Example 21

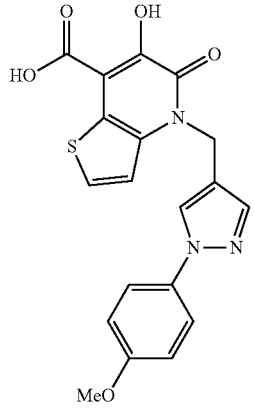 [SMILES: COc1ccc(-n2cc(Cn3c(=O)c(O)c(C(=O)O)c4sccc43)cn2)cc1]

Acetonitrile, 90° C. | A. NaOH, MeOH, H$_2$O C. TFA | (M + H)$^+$ = 369.0 $^1$H NMR (DMSO-d$_6$, 400 MHz): δ 8.95-8.90 (m, 3H), 8.37 (d, J = 7.2 Hz, 2H), 8.10 (s, 1H), 7.70 (d, J = 6.4 Hz, 2H), 7.45 (d, J = 7.2 Hz, 2H), 5.43 (s, 3H). |
| 113 | 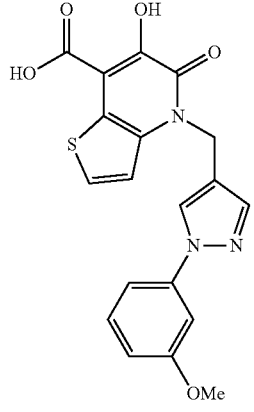 [SMILES: COc1cccc(-n2cc(Cn3c(=O)c(O)c(C(=O)O)c4sccc43)cn2)c1]

6-hydroxy-4-{[1-(4-methoxyphenyl)-1H-pyrazol-4-yl]methyl}-5-oxo-4,5-dihydrothieno[3,2-b]pyridine-7-carboxylic acid | Intermediate D Methods: Example 19

B(OH)$_2$–C$_6$H$_4$–OMe | A. NaOH, MeOH, H$_2$O C. TFA | (M + H)$^+$ = 398 $^1$H NMR (DMSO-d$_6$, 400 MHz) δ 8.40 (s, 1H), 7.65-7.70 (m, 4H), 7.50 (d, J = 5.6 Hz, 1H), 7.02 (d, J = 8.8 Hz, 1H), 5.36 (s, 2H), 3.78 (s, 3H). |
| 114 | 6-hydroxy-4-{[1-(3-methoxyphenyl)-1H-pyrazol-4-yl]methyl}-5-oxo-4,5-dihydrothieno[3,2-b]pyridine-7-carboxylic acid | Intermediate D Methods: Example 19

B(OH)$_2$–C$_6$H$_4$–OMe (3-) | A. NaOH, MeOH, H$_2$O C. TFA | (M + H)$^+$ = 396 $^1$H NMR (DMSO-d$_6$, 400 MHz) δ 8.54 (s, 1H), 7.74 (s, 1H), 7.64 (d, J = 5.6 Hz, 1H), 7.47 (d, J = 5.6 Hz, 1H), 7.33-7.39 (m, 3H), 6.86 (d, J = 7.6 Hz, 1H), 5.37 (s, 2H), 3.81 (s, 3H) |

TABLE 1-continued

| Example # | Structure | Intermediate, Reference Methods, Alkylating Agent & Base | Deprotection Methods | Analytics |
|---|---|---|---|---|
| 115 | 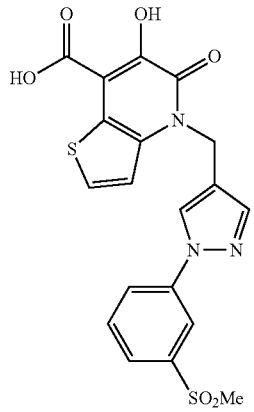 [SMILES: CS(=O)(=O)c1cccc(-n2cc(Cn3c(=O)c(O)c(C(=O)O)c4sccc43)cn2)c1]<br>6-hydroxy-4-({1-[3-(methylsulfonyl)phenyl]-1H-pyrazol-4-yl}methyl)-5-oxo-4,5-dihydrothieno[3,2-b]pyridine-7-carboxylic acid | Intermediate D Methods: Example 19 | A. NaOH, MeOH, H$_2$O C. TFA | (M + H)$^+$ = 446 $^1$H NMR (DMSO-d$_6$, 400 MHz) δ 8.66 (s, 1H), 8.27 (s, 1H), 8.14 (d, J = 7.6 Hz, 1H), 7.84 (d, J = 10.0 Hz, 2H), 7.76 (d, J = 8.0 Hz, 1H), 7.59 (d, J = 5.6 Hz, 1H), 7.46 (s, 1H), 5.38 (s, 2H), 3.28 (s, 3H) |
| 116 | 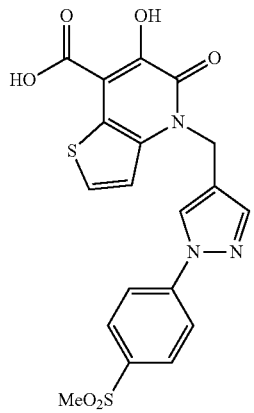 [SMILES: CS(=O)(=O)c1ccc(-n2cc(Cn3c(=O)c(O)c(C(=O)O)c4sccc43)cn2)cc1]<br>6-hydroxy-4-({1-[4-(methylsulfonyl)phenyl]-1H-pyrazol-4-yl}methyl)-5-oxo-4,5-dihydrothieno[3,2-b]pyridine-7-carboxylic acid | Intermediate D Methods: Example 19 | A. NaOH, MeOH, H$_2$O C. TFA | (M + H)$^+$ = 446 $^1$H NMR (DMSO-d$_6$, 400 MHz) δ 8.67 (s, 1H), 8.00-8.07 (m, 4H), 7.86 (s, 1H), 7.63 (d, J = 6.0 Hz, 1H), 7.46 (d, J = 5.6 Hz, 1H), 5.39 (s, 2H), 3.24 (s, 3H) |

| Example # | Structure | Intermediate, Reference Methods, Alkylating Agent & Base | Deprotection Methods | Analytics |
|---|---|---|---|---|
| 117 | 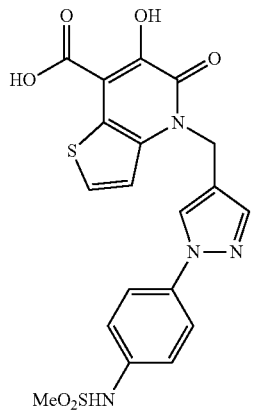<br>6-hydroxy-4-({1-[4-(methylsulfonamido)phenyl]-1H-pyrazol-4-yl}methyl)-5-oxo-4,5-dihydrothieno[3,2-b]pyridine-7-carboxylic acid | Intermediate D<br>Methods: Example 22 | A. NaOH, MeOH, $H_2O$<br>C. TFA | $(M + H)^+$ = 460.1<br>$^1H$ NMR (DMSO-$d_6$, 400 MHz): δ 9.85 (s, 1H), 8.44 (s, 1H), 7.74-7.70 (m, 3H), 7.64 (d, J = 5.6 Hz, 1H), 7.49 (d, J = 5.6 Hz, 1H), 7.28 (d, J = 8.8 Hz, 2H), 5.38 (s, 2H), 2.99 (s, 3H). |
| 118 | 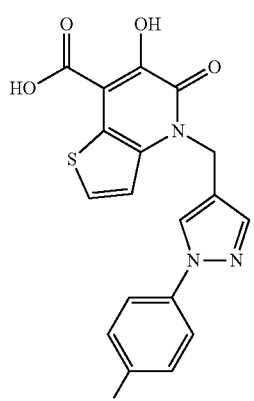<br>4-{[1-(4-aminophenyl)-1H-pyrazol-4-yl]methyl}-6-hydroxy-5-oxo-4,5-dihydrothieno[3,2-b]pyridine-7-carboxylic acid | Intermediate D<br><br>Methods: Example 22 | A. NaOH, MeOH, $H_2O$<br>C. Pd/C, $H_2$<br>Boc deprotection: TFA | $(M + H)^+$ = 383<br>$^1H$ NMR (DMSO-$d_6$, 400 MHz): δ 8.53 (s, 1 H), 7.85 (d, J = 8.0 Hz, 2H), 7.76 (s, 1H), 7.68 (d, J = 3.6 Hz, 1H), 7.51-7.49 (m, 3H), 5.37 (s, 2H). |
| 119 | 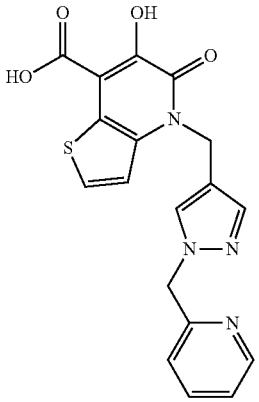 [SMILES: O=C(O)c1c(O)c(=O)n(Cc2cnn(Cc3ccccn3)c2)c2ccsc12]<br>6-hydroxy-5-oxo-4-{[1-(pyridin-2-ylmethyl)-1H-pyrazol-4-yl]methyl}-4,5-dihydrothieno[3,2-b]pyridine-7-carboxylic acid | Intermediate D<br><br>$K_2CO_3$, DMF, 80° C. | A. NaOH, MeOH, $H_2O$<br>C. TFA | $(M + H)^+$ = 383.0<br>$^1H$ NMR (DMSO-$d_6$, 400 MHz) δ 8.51 (s, 1H), 7.84 (s, 1H), 7.74 (t, J = 7.2 Hz, 1H), 7.51 (s, 1H), 7.39 (d, J = 4.8 Hz, 1H), 7.31 (d, J = 4.0 Hz, 2H), 6.99 (d, J = 7.6 Hz, 1H), 5.34 (s, 2H), 5.22 (s, 2H). |

US 11,584,755 B2

171                                    172

TABLE 1-continued

| Example # | Structure | Intermediate, Reference Methods, Alkylating Agent & Base | Deprotection Methods | Analytics |
|---|---|---|---|---|
| 120 | 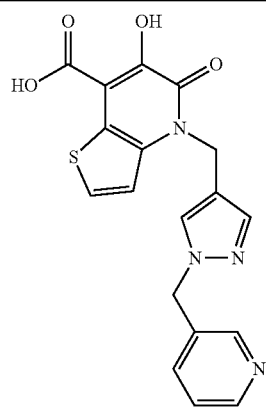<br>6-hydroxy-5-oxo-4-{[1-(pyridin-3-ylmethyl)-1H-pyrazol-4-yl]methyl}-4,5-dihydrothieno[3,2-b]pyridine-7-carboxylic acid | Intermediate D<br>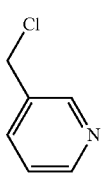<br>K₂CO₃, DMF, 80° C. | A. NaOH, MeOH, H₂O<br>C. TFA | (M + H)⁺ = 383.0<br>¹H NMR (DMSO-d₆, 400 MHz) δ 8.61-8.53 (m, 2H), 7.90 (s, 1H), 7.81 (d, J = 7.6 Hz, 1H), 7.63 (d, J = 5.2 Hz, 1H), 7.57-7.49 (m, 2H), 7.45 (d, J = 5.60 Hz, 1H), 5.36 (s, 2H), 5.28 (s, 2H). |
| 121 | 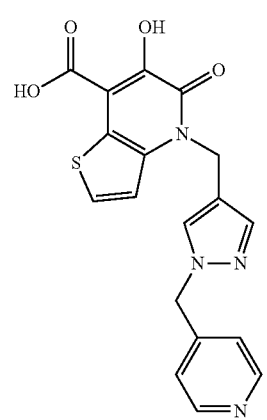 [SMILES: O=C(O)c1c(O)c(=O)n(Cc2cnn(Cc3ccncc3)c2)c2ccsc12]<br>6-hydroxy-5-oxo-4-{[1-(pyridin-4-ylmethyl)-1H-pyrazol-4-yl]methyl}-4,5-dihydrothieno[3,2-b]pyridine-7-carboxylic acid | Intermediate D<br>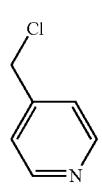<br>K₂CO₃, DMF, 80° C. | A. NaOH, MeOH, H₂O<br>C. TFA | (M + H)⁺ = 383.0<br>¹H NMR (DMSO-d₆, 400 MHz): δ 8.85 (d, J = 5.6 Hz, 2H), 7.99 (s, 1H), 7.71 (d, J = 5.6 Hz, 1H), 7.66-7.63 (m, 3H), 7.50 (d, J = 5.2 Hz, 1H), 5.67 (s, 2H), 5.34 (s, 2H). |
| 122 | 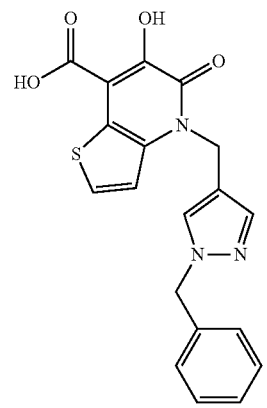 [SMILES: O=C(O)c1c(O)c(=O)n(Cc2cnn(Cc3ccccc3)c2)c2ccsc12]<br>4-[(1-benzyl-1H-pyrazol-4-yl)methyl]-6-hydroxy-5-oxo-4,5-dihydrothieno[3,2-b]pyridine-7-carboxylic acid | Intermediate D<br>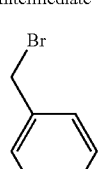<br>K₂CO₃, DMF, 80° C. | A. NaOH, MeOH, H₂O<br>C. TFA | (M + H)⁺ = 382.0<br>¹H NMR (DMSO-d₆, 400 MHz) δ 7.82 (s, 1H), 7.60 (d, J = 3.6 Hz, 1H), 7.51 (s, 1H), 7.44 (s, 1H), 7.23-7.36 (m, 3H), 7.19 (d, J = 6.8 Hz, 2H), 5.27 (s, 2H), 5.24 (s, 2H). |

TABLE 1-continued

| Example # | Structure | Intermediate, Reference Methods, Alkylating Agent & Base | Deprotection Methods | Analytics |
|---|---|---|---|---|
| 123 | 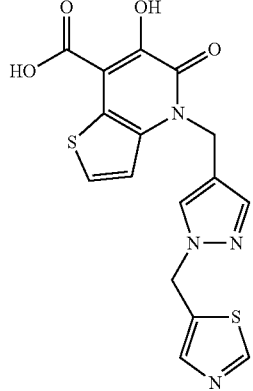 [SMILES: O=C(O)c1c(O)c(=O)n(Cc2cnn(Cc3cncs3)c2)c2ccsc12]<br>6-hydroxy-5-oxo-4-{[1-(thiazol-5-ylmethyl)-1H-pyrazol-4-yl]methyl}-4,5-dihydrothieno[3,2-b]pyridine-7-carboxylic acid | Intermediate D<br><br>ClCH₂-thiazole<br><br>Cs₂CO₃, DMF | A. NaOH, MeOH, H₂O<br>C. TFA | (M + H)⁺ = 389.0<br>¹H NMR (DMSO-d₆, 400 MHz): δ 9.00 (s, 1H), 7.84 (d, J = 6.4 Hz, 2H), 7.61 (d, J = 5.6 Hz, 1H), 7.53 (s, 1H), 7.44 (d, J = 5.6 Hz, 1H), 5.53 (s, 2H), 5.26 (s, 2H). |
| 124 | 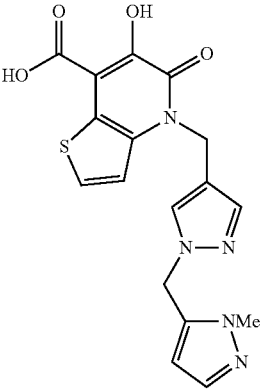 [SMILES: Cn1nccc1Cn1cc(Cn2c(=O)c(O)c(C(=O)O)c3sccc32)cn1]<br>6-hydroxy-4-({1-[(1-methyl-1H-pyrazol-5-yl)methyl]-1H-pyrazol-4-yl}methyl)-5-oxo-4,5-dihydrothieno[3,2-b]pyridine-7-carboxylic acid | Intermediate D<br><br>ClCH₂-(1-methyl-pyrazole)<br><br>K₂CO₃, DMF | A. NaOH, MeOH, H₂O<br>C. TFA | (M + H)⁺ = 386.1<br>¹H NMR (DMSO-d₆, 400 MHz) δ 7.80 (s, 1H), 7.67 (d, J = 5.6 Hz, 1H), 7.52 (s, 1H), 7.47 (d, J = 5.6 Hz, 1H), 7.31 (d, J = 2.0 Hz, 1H), 6.16 (d, J = 1.6 Hz, 1H), 5.37 (s, 2H), 5.28 (s, 2H), 3.76 (s, 3H). |

TABLE 1-continued

| Example # | Structure | Intermediate, Reference Methods, Alkylating Agent & Base | Deprotection Methods | Analytics |
|---|---|---|---|---|
| 125 | 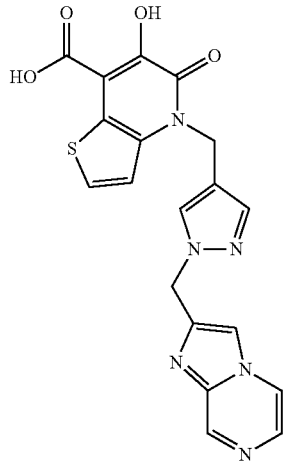 [SMILES: O=C(O)c1c(O)c(=O)n(Cc2cnn(Cc3cn4ccncc4n3)c2)c2ccsc12]<br>6-hydroxy-4-{[1-(imidazo[1,2-a]pyrazin-2-ylmethyl)-1H-pyrazol-4-yl]methyl}-5-oxo-4,5-dihydrothieno[3,2-b]pyridine-7-carboxylic acid | Intermediate D<br>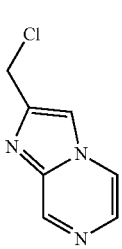<br>$K_2CO_3$, DMF | A. NaOH, MeOH, $H_2O$<br>C. TFA | $(M + H)^+$ = 423.1<br>$^1H$ NMR (DMSO-$d_6$, 400 MHz) δ 9.02 (s, 1H), 8.57 (d, J = 5.6 Hz, 1H), 7.98 (s, 1H), 7.91-7.85 (m, 2H), 7.66 (d, J = 6.0 Hz, 1H), 7.53 (s, 1H), 7.48 (d, J = 5.6 Hz, 1H), 5.45 (s, 2H), 5.28 (s, 2H). |
| 126 | 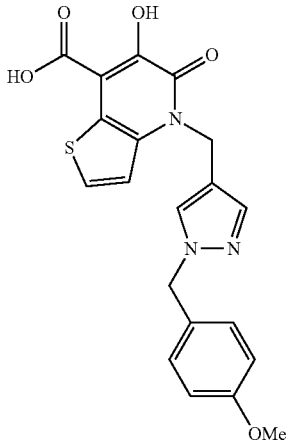 [SMILES: COc1ccc(Cn2cc(Cn3c(=O)c(O)c(C(=O)O)c4sccc43)cn2)cc1]<br>6-hydroxy-4-{[1-(4-methoxybenzyl)-1H-pyrazol-4-yl]methyl}-5-oxo-4,5-dihydrothieno[3,2-b]pyridine-7-carboxylic acid | Intermediate D<br>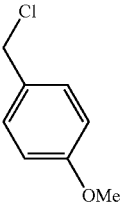<br>$Cs_2CO_3$, DMF, 80° C. | A. NaOH, MeOH, $H_2O$<br>C. TFA | $(M + H)^+$ = 413<br>$^1H$ NMR (DMSO-$d_6$, 400 MHz) δ 8.10 (d, J = 2.0 Hz, 1H), 7.84 (s, 1H), 7.67 (d, J = 5.2 Hz, 1H), 7.57 (d, J = 6.4 Hz, H), 7.51 (s, 1H), 7.47 (d, J = 6.0 Hz, 2H), 6.77 (d, J = 8.8 Hz, 2H), 5.27 (s, 2H), 5.19 (s, 2H), 3.82 (s, 3H) |

TABLE 1-continued

| Example # | Structure | Intermediate, Reference Methods, Alkylating Agent & Base | Deprotection Methods | Analytics |
|---|---|---|---|---|
| 127 | 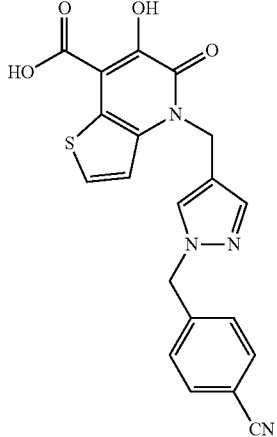 [SMILES: N#Cc1ccc(Cn2cc(Cn3c(=O)c(O)c(C(=O)O)c4sccc43)cn2)cc1]<br>4-{[1-(4-cyanobenzyl)-1H-pyrazol-4-yl]methyl}-6-hydroxy-5-oxo-4,5-dihydrothieno[3,2-b]pyridine-7-carboxylic acid | Intermediate D<br><br>Cl-CH2-C6H4-CN<br><br>K2CO3, DMF | A. LiOH, MeOH, H2O<br>C. TFA | (M + H)+ = 407.1<br>1H NMR (DMSO-d6, 400 MHz) δ 7.88 (s, 1H), 7.81-7.75 (m, 2H), 7.64 (d, J = 5.6 Hz, 1H), 7.54 (s, 1H), 7.44 (d, J = 5.6 Hz, 1H), 7.30 (d, J = 8.0 Hz, 2H), 5.35 (s, 2H), 5.28 (s, 2H). |
| 128 | 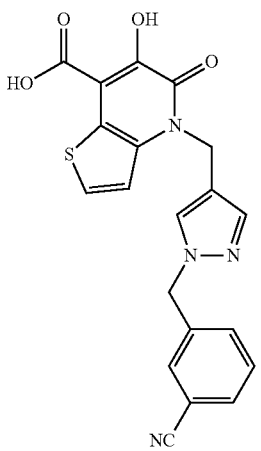<br>4-{[1-(3-cyanobenzyl)-1H-pyrazol-4-yl]methyl}-6-hydroxy-5-oxo-4,5-dihydrothieno[3,2-b]pyridine-7-carboxylic acid | Intermediate D<br><br>Cl-CH2-C6H4-CN<br><br>K2CO3, DMF | A. LiOH, MeOH, H2O<br>C. TFA | (M + H)+ = 407.0<br>1H NMR (DMSO-d6, 400 MHz) δ 7.89 (s, 1H), 7.77 (d, J = 8.0, 1H), 7.63-7.65 (m, 2H), 7.51-7.54 (m, 3H), 7.45 (d, J = 5.2 Hz, 1H), 5.32 (s, 2H), 5.28 (s, 2H). |

TABLE 1-continued

| Example # | Structure | Intermediate, Reference Methods, Alkylating Agent & Base | Deprotection Methods | Analytics |
|---|---|---|---|---|
| 129 | 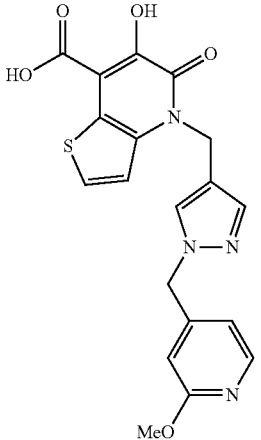 [SMILES: COc1cc(Cn2cc(Cn3c(=O)c(O)c(C(=O)O)c4sccc43)cn2)ccn1]<br>6-hydroxy-4-({1-[(2-methoxypyridin-4-yl)methyl]-1H-pyrazol-4-yl}methyl)-5-oxo-4,5-dihydrothieno[3,2-b]pyridine-7-carboxylic acid | Intermediate D<br><br>Br—CH₂—(2-methoxypyridin-4-yl), OMe<br><br>K₂CO₃, DMF | A. NaOH, MeOH, H₂O<br>C. TFA | $(M + H)^+ = 413.0$<br>$^1$H NMR (DMSO-$d_6$, 400 MHz): δ 7.84 (s, 1H), 7.60-7.59 (m, 2H), 7.55 (s, 1H), 7.43 (d, J = 5.6 Hz, 1H), 5.97 (s, 1H), 5.93 (dd, $J_1$ = 7.2 Hz, $J_2$ = 5.2 Hz, 1H), 5.29 (s, 2H), 5.11 (s, 2H), 3.35 (s, 3H). |
| 130 | 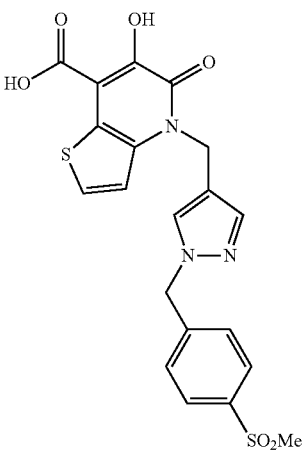 [SMILES: CS(=O)(=O)c1ccc(Cn2cc(Cn3c(=O)c(O)c(C(=O)O)c4sccc43)cn2)cc1]<br>6-hydroxy-4-({1-[4-(methylsulfonyl)benzyl]-1H-pyrazol-4-yl}methyl)-5-oxo-4,5-dihydrothieno[3,2-b]pyridine-7-carboxylic acid | Intermediate D<br><br>Br—CH₂—C₆H₄—SO₂Me<br><br>K₂CO₃, DMF | A. NaOH, MeOH, H₂O<br>C. TFA | $(M + H)^+ = 459.9$<br>$^1$H NMR (DMSO-$d_6$, 400 MHz) δ 7.86-7.88 (m, 3H), 7.59 (s, 1H), 7.40-7.46 (m, 5H), 5.38 (s, 2H), 5.27 (s, 2H), 3.18 (s, 3H). |

TABLE 1-continued

| Example # | Structure | Intermediate, Reference Methods, Alkylating Agent & Base | Deprotection Methods | Analytics |
|---|---|---|---|---|
| 131 | 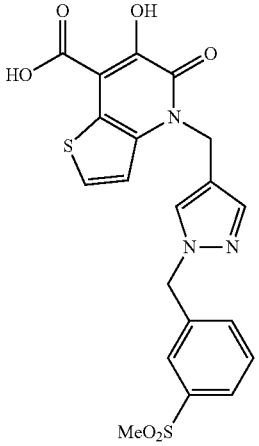 [SMILES: CS(=O)(=O)c1cccc(Cn2cc(Cn3c(=O)c(O)c(C(=O)O)c4sccc43)cn2)c1]<br>6-hydroxy-4-({1-[3-(methylsulfonyl)benzyl]-1H-pyrazol-4-yl}methyl)-5-oxo-4,5-dihydrothieno[3,2-b]pyridine-7-carboxylic acid | Intermediate D<br>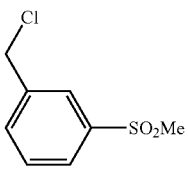 [SMILES: CS(=O)(=O)c1cccc(CCl)c1]<br>$Cs_2CO_3$, DMF | A. NaOH, MeOH, $H_2O$<br>C. TFA | $(M + H)^+ = 460.0$<br>$^1H$ NMR (DMSO-$d_6$, 400 MHz): δ 7.91 (s, 1H), 7.84 (d, J = 7.6 Hz, 1H), 7.80 (s, 1H), 7.66 (d, J = 5.6 Hz, 1H), 7.60 (t, J = 7.6 Hz, 1H), 7.54 (s, 1H), 7.50 (d, J = 7.6 Hz, 1H), 7.46 (d, J = 5.6 Hz, 1H), 5.38 (s, 2H), 5.29 (s, 2H), 3.18 (s, 3H). |
| 132 | <br>6-hydroxy-5-oxo-4-{[1-(pyridazin-4-ylmethyl)-1H-pyrazol-4-yl]methyl}-4,5-dihydrothieno[3,2-b]pyridine-7-carboxylic acid | Intermediate D<br>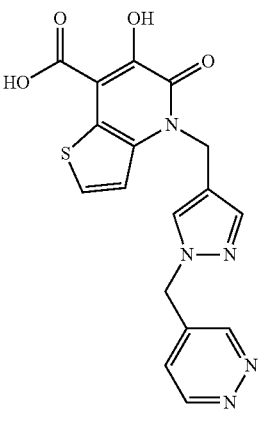 [SMILES: O=C(O)c1c(O)c(=O)n(Cc2cnn(Cc3ccnnc3)c2)c2ccsc12]<br>$K_2CO_3$, TBAB, DCM | A. NaOH, MeOH, $H_2O$<br>C. TFA | $(M + H)^+ = 384$<br>$^1H$ NMR (DMSO-$d_6$, 400 MHz) δ 9.16 (dd, J = 5.2, 1.2 Hz, 1H), 9.02 (s, 1H), 7.94 (s, 1H), 7.65 (d, J = 5.6 Hz, 1H), 7.60 (s, 1H), 7.46 (d, J = 5.6 Hz, 1H), 7.32 (t, J = 2.4 Hz, 1H), 5.41 (s, 2H), 5.40 (s, 2H), 5.31 (s, 2H). |

TABLE 1-continued

| Example # | Structure | Intermediate, Reference Methods, Alkylating Agent & Base | Deprotection Methods | Analytics |
|---|---|---|---|---|
| 133 | 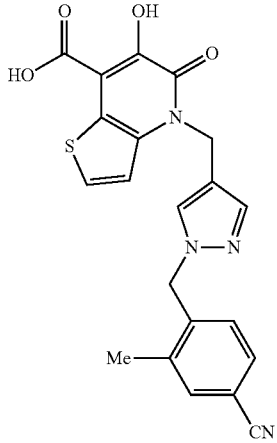 [SMILES: Cc1cc(C#N)ccc1Cn1cc(Cn2c(=O)c(O)c(C(=O)O)c3sccc32)cn1]<br>4-{1-(4-cyano-2-methylbenzyl)-1H-pyrazol-4-yl]methyl}-6-hydroxy-5-oxo-4,5-dihydrothieno[3,2-b]pyridine-7-carboxylic acid | Coupling: Intermediate D<br>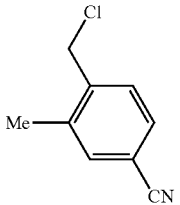<br>$K_2CO_3$, TBAB, DCM | A. NaOH, MeOH, $H_2O$<br>C. TFA | $(M + H)^+ = 421.0$<br>$^1H$ NMR (DMSO-$d_6$, 400 MHz): δ 7.83 (s, 1H), 7.67-7.66 (m, 2H), 7.59 (d, J = 8.0 Hz, 1H), 7.56 (s, 1H), 7.46 (d, J = 5.6 Hz, 1H), 6.89 (d, J = 8.0 Hz, 1H), 5.37 (s, 2H), 5.31 (s, 2H), 2.30 (s, 3H). |
| 134 | 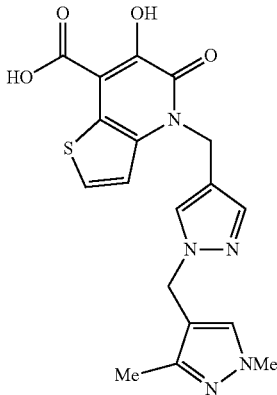 [SMILES: Cc1nn(C)cc1Cn1cc(Cn2c(=O)c(O)c(C(=O)O)c3sccc32)cn1]<br>4-({1-[(1,3-dimethyl-1H-pyrazol-4-yl)methyl]-1H-pyrazol-4-yl}methyl)-6-hydroxy-5-oxo-4,5-dihydrothieno[3,2-b]pyridine-7-carboxylic acid | Intermediate D<br>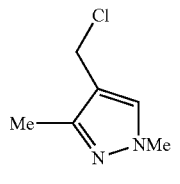<br>$K_2CO_3$, TBAB, DCM | A. NaOH, MeOH, $H_2O$<br>C. TFA | $(M - H)^- = 400.0$<br>$^1H$ NMR (DMSO-$d_6$, 400 MHz) δ 7.67 (s, 1H), 7.63 (d, J = 5.6 Hz, 1H), 7.56 (s, 1H), 7.47-7.43 (m, 2H), 5.24 (s, 2H), 5.01 (s, 2H), 3.69 (s, 3H), 2.04 (s, 3H). |
| 135 | 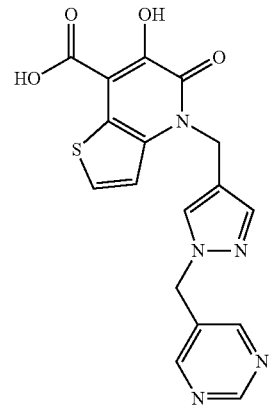 [SMILES: O=C(O)c1c(O)c(=O)n(Cc2cnn(Cc3cncnc3)c2)c2ccsc12]<br>6-hydroxy-5-oxo-4-{[1-(pyrimidin-5-ylmethyl)-1H-pyrazol-4-yl]methyl}-4,5-dihydrothieno[3,2-b]pyridine-7-carboxylic acid | Intermediate D<br>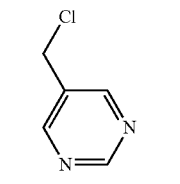<br>$K_2CO_3$, TBAB, DCM | A. LiOH, MeOH, $H_2O$<br>C. TFA | $(M + H)^+ = 384.0$<br>$^1H$ NMR (DMSO-$d_6$, 400 MHz) δ 9.11 (s, 1H), 8.68 (s, 2H), 7.93 (s, 1H), 7.66 (d, J = 5.6 Hz, 1H), 7.55 (s, 1H), 7.46 (d, J = 5.6 Hz, 1H), 5.35 (s, 2H), 5.29 (s, 2H). |

TABLE 1-continued

| Example # | Structure | Intermediate, Reference Methods, Alkylating Agent & Base | Deprotection Methods | Analytics |
|---|---|---|---|---|
| 136 | 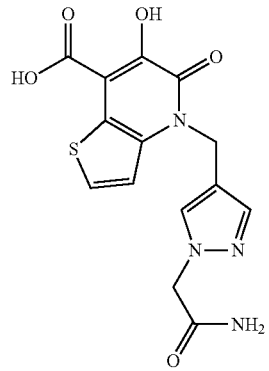 [SMILES: NC(=O)Cn1cc(Cn2c(=O)c(O)c(C(=O)O)c3sccc32)cn1]<br>4-{[1-(2-amino-2-oxoethyl)-1H-pyrazol-4-yl]methyl}-6-hydroxy-5-oxo-4,5-dihydrothieno[3,2-b]pyridine-7-carboxylic acid | Intermediate D<br><br>Br—CH$_2$—CN<br><br>K$_2$CO$_3$, DMF | A. NaOH, MeOH, H$_2$O<br>C. TFA | (M + H)$^+$ = 349.1<br>$^1$H NMR (DMSO-d$_6$, 400 MHz) δ 7.71 (s, 1H), 7.63 (d, J = 5.6 Hz, 1H), 7.48 (s, 1H), 7.41 (d, J = 5.6 Hz, 1H), 5.32 (s, 2H), 4.67 (s, 2H) |
| 137 | 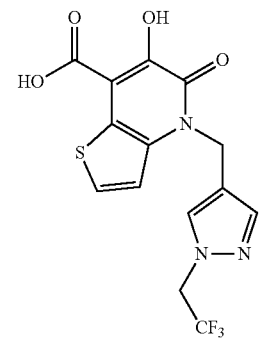 [SMILES: O=C(O)c1c(O)c(=O)n(Cc2cnn(CC(F)(F)F)c2)c2ccsc12]<br>6-hydroxy-5-oxo-4-{[1-(2,2,2-trifluoroethyl)-1H-pyrazol-4-yl]methyl}-4,5-dihydrothieno[3,2-b]pyridine-7-carboxylic acid | Intermediate D<br><br>TfO—CH$_2$—CF$_3$<br><br>Cs$_2$CO$_3$, DMF | A. NaOH, MeOH, H$_2$O<br>C. TFA | (M + H)$^+$ 374<br>$^1$H NMR (DMSO-d$_6$, 400 MHz) δ 7.86 (s, 1H), 7.63 (d, J = 4.8 Hz, 2H), 7.46 (d, J = 5.6 Hz, 1H), 5.30 (s, 2H), 5.06 (q, J = 9.2 Hz, 2H). |
| 138 | 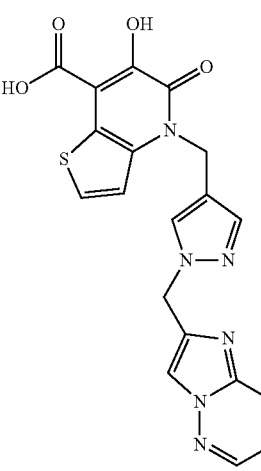<br>6-hydroxy-4-{1-(imidazo[1,2-b]pyridazin-2-ylmethyl)-1H-pyrazol-4-yl]methyl}-5-oxo-4,5-dihydrothieno[3,2-b]pyridine-7-carboxylic acid | Intermediate D<br><br>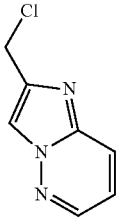 [SMILES: ClCc1cn2ncccc2n1]<br><br>Cs$_2$CO$_3$, DMF | A. NaOH, MeOH, H$_2$O<br>C. TFA | (M + H)$^+$ = 423.0<br>$^1$H NMR (DMSO-d$_6$, 400 MHz): δ 8.50 (dd, J = 1.6, 4.4 Hz, 1H), 8.18 (s, 1H), 8.07 (d, J = 10.4 Hz, 1H), 7.86 (s, 1H), 7.65 (d, J = 5.6 Hz, 1H), 7.49 (s, 1H), 7.48 (d, J = 5.6 Hz, 1H), 7.23 (dd, J = 4.4, 9.2 Hz, 1H), 5.39 (s, 2H), 5.27 (s, 2H). |

TABLE 1-continued

| Example # | Structure | Intermediate, Reference Methods, Alkylating Agent & Base | Deprotection Methods | Analytics |
|---|---|---|---|---|
| 139 | 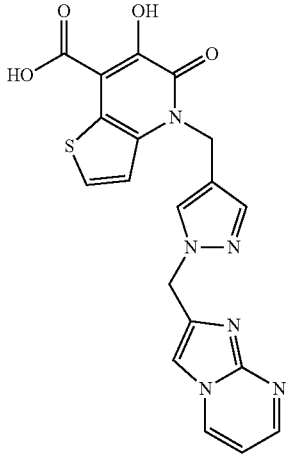 [SMILES: O=C(O)c1c(O)c(=O)n(Cc2cnn(Cc3cn4cccnc4n3)c2)c2ccsc12]<br>6-hydroxy-4-{[1-(imidazo[1,2-a]pyrimidin-2-ylmethyl)-1H-pyrazol-4-yl]methyl}-5-oxo-4,5-dihydrothieno[3,2-b]pyridine-7-carboxylic acid | Intermediate D<br><br>K$_2$CO$_3$, DMF | A. NaOH, MeOH, H$_2$O<br>C. TFA | (M + H)$^+$ = 423.2<br>$^1$H NMR (DMSO-d$_6$, 400 MHz) δ 8.91 (dd, J = 6.8, 2.0 Hz, 1H), 8.51 (dd, J = 4.4, 2.0 Hz, 1H), 7.84 (s, 1H), 7.69 (s, 1H), 7.50 (s, 1H), 7.40 (d, J = 5.6 Hz, 1H), 7.33 (d, J = 5.2 Hz, 1H), 7.03 (dd, J = 6.8, 4.4 Hz, 1H), 5.38 (s, 2H), 5.21 (s, 2H) |
| 140 | 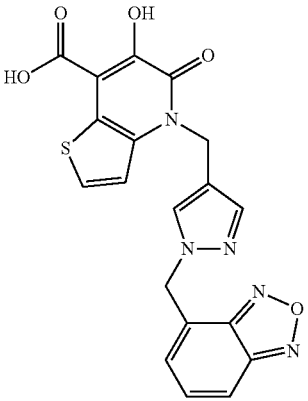 [SMILES: O=C(O)c1c(O)c(=O)n(Cc2cnn(Cc3cccc4nonc34)c2)c2ccsc12]<br>4-{[1-(benzo[c][1,2,5]oxadiazol-4-ylmethyl)-1H-pyrazol-4-yl]methyl}-6-hydroxy-5-oxo-4,5-dihydrothieno[3,2-b]pyridine-7-carboxylic acid | Intermediate D<br><br>K$_2$CO$_3$, TBAB, DMF | A. NaOH, MeOH, H$_2$O<br>C. TFA | (M + H)$^+$ = 424<br>$^1$H NMR (DMSO-d$_6$, 400 MHz) δ 8.01-7.96 (m, 2H), 7.71-7.65 (m, 1H), 7.59-7.54 (m, 2H), 7.49-7.47 (m, 1H), 7.20 (d, J = 6.4 Hz, 1H), 5.67 (s, 2H), 5.31 (s, 2H). |

TABLE 1-continued

| Example # | Structure | Intermediate, Reference Methods, Alkylating Agent & Base | Deprotection Methods | Analytics |
|---|---|---|---|---|
| 141 | 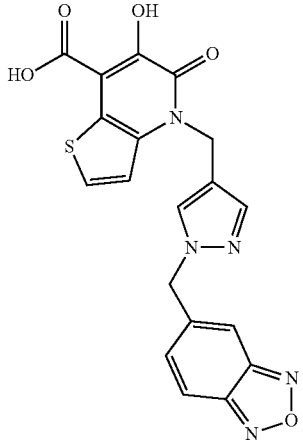 [SMILES: O=C(O)c1c(O)c(=O)n(Cc2cnn(Cc3ccc4nonc4c3)c2)c2ccsc12]<br>4-{[1-(benzo[c][1,2,5]oxadiazol-5-ylmethyl)-1H-pyrazol-4-yl]methyl}-6-hydroxy-5-oxo-4,5-dihydrothieno[3,2-b]pyridine-7-carboxylic acid | Intermediate D<br><br>Br—[benzo[c][1,2,5]oxadiazol-5-ylmethyl bromide]<br><br>$K_2CO_3$, TBAB, DCM | A. NaOH, MeOH, $H_2O$<br>C. TFA | $(M + H)^+$ = 424.0<br>$^1$H NMR (DMSO-$d_6$, 400 MHz): δ 8.02 (d, J = 9.2 Hz, 1H), 7.95 (s, 1H), 7.71 (s, 1H), 7.67 (d, J = 6.0 Hz, 1H), 7.59 (s, 1H), 7.48 (d, J = 5.6 Hz, 1H), 7.39 (d, J = 9.2 Hz, 1H), 5.43 (s, 2H), 5.31 (s, 2H). |
| 142 | 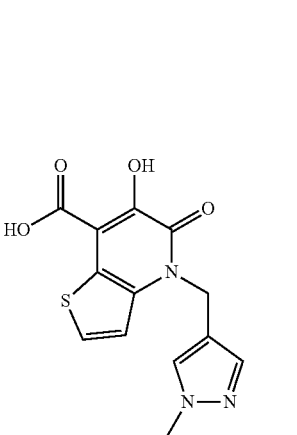<br>4-{[1-(benzo[c][1,2,5]oxadiazol-5-ylmethyl)-1H-pyrazol-4-yl]methyl}-6-hydroxy-5-oxo-4,5-dihydrothieno[3,2-b]pyridine-7-carboxylic acid | Intermediate D<br><br>Br—[imidazo[1,2-a]pyridin-3-ylmethyl bromide]<br><br>$K_2CO_3$, TBAB, DCM | A. NaOH, MeOH, $H_2O$<br>C. TFA | $(M + H)^+$ = 422.0<br>$^1$H NMR (DMSO-$d_6$, 400 MHz): δ 8.38 (d, J = 7.2 Hz, 1H), 7.89 (s, 1H), 7.63-7.60 (m, 2H), 7.51-7.49 (m, 2H), 7.43 (d, J = 5.6 Hz, 1H), 6.92-6.88 (m, 1H), 6.82 (t, J = 7.2 Hz, 1H), 5.78 (s, 2H), 5.24 (s, 2H). |

TABLE 1-continued

| Example # | Structure | Intermediate, Reference Methods, Alkylating Agent & Base | Deprotection Methods | Analytics |
|---|---|---|---|---|
| 143 | 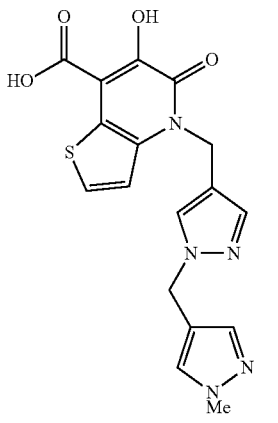 [SMILES: Cn1cc(Cn2cc(Cn3c(=O)c(O)c(C(=O)O)c4sccc43)cn2)cn1]<br>6-hydroxy-4-({1-[(1-methyl-1H-pyrazol-4-yl)methyl]-1H-pyrazol-4-yl}methyl)-5-oxo-4,5-dihydrothieno[3,2-b]pyridine-7-carboxylic acid | Intermediate D<br><br>$K_2CO_3$, DMF (alkylating agent: 4-(chloromethyl)-1-methyl-1H-pyrazole) | A. NaOH, MeOH, $H_2O$<br>C. TFA | $(M + H)^+ = 386.0$<br>$^1H$ NMR (DMSO-$d_6$, 400 MHz) δ 7.71 (s, 1H), 7.67 (d, J = 5.6 Hz, 1H), 7.65 (s, 1H), 7.49-7.45 (m, 2H), 7.36 (s, 1H), 5.25 (s, 2H), 5.07 (s, 2H), 3.77 (s, 3H). |
| 144 | 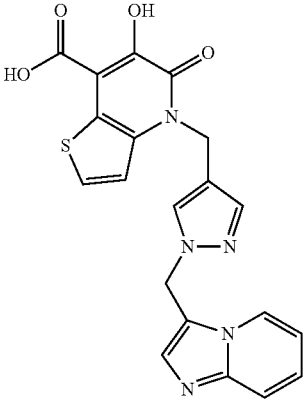 [SMILES: O=C(O)c1c(O)c(=O)n(Cc2cnn(Cc3cnc4ccccn34)c2)c2ccsc12]<br>6-hydroxy-4-{[1-(imidazo[1,2-a]pyridin-3-ylmethyl)-1H-pyrazol-4-yl]methyl}-5-oxo-4,5-dihydrothieno[3,2-b]pyridine-7-carboxylic acid | Intermediate D<br><br>$Cs_2CO_3$, DMF (alkylating agent: 3-(chloromethyl)imidazo[1,2-a]pyridine) | A. NaOH, MeOH, $H_2O$<br>C. TFA | $(M + H)^+ = 422.0$<br>$^1H$ NMR (DMSO-$d_6$, 400 MHz) 8.87 (d, J = 6.8 Hz, 1H), 8.17 (s, 1H), 7.93-7.84 (m, 3H), 7.54 (s, 1H), 7.49 (s, 1H), 7.46 (d, J = 5.6 Hz, 1H), 7.32 (d, J = 5.6 Hz, 1H), 5.80 (s, 2H), 5.20 (s, 2H). |

TABLE 1-continued

| Example # | Structure | Intermediate, Reference Methods, Alkylating Agent & Base | Deprotection Methods | Analytics |
|---|---|---|---|---|
| 145 | 4-({1-(1,1-dioxidotetrahydro-2H-thiopyran-4-yl)methyl]-1H-pyrazol-4-yl}methyl)-6-hydroxy-5-oxo-4,5-dihydrothieno[3,2-b]pyridine-7-carboxylic acid | Intermediate D; OTs-CH2-(tetrahydrothiopyranyl-SO2); K2CO3, DMF | A. NaOH, MeOH, H2O C. TFA | $(M + H)^+$ = 438 $^1$H NMR (DMSO-$d_6$, 400 MHz) δ 7.76 (s, 1H), 7.69 (d, J = 5.2 Hz, 2H), 7.46-7.50 (m, 2H), 5.28 (s, 2H), 7.98 (d, J = 7.2 Hz, 2H), 2.96-3.09 (m, 4H), 2.08 (s, 1H), 1.77 (d, J = 13.6 Hz, 2H), 1.56-1.61 (m, 2H). |
| 146 | 4-({1-[4-cyano-2-(trifluoromethyl)benzyl]-1H-pyrazol-4-yl}methyl)-6-hydroxy-5-oxo-4,5-dihydrothieno[3,2-b]pyridine-7-carboxylic acid | Intermediate D; 4-bromo-2-(trifluoromethyl)benzyl bromide; Methods: Example 26 | A. LiOH, MeOH, H2O C. TFA | $(M + H)^+$ = 475.1 $^1$H NMR (DMSO-$d_6$, 400 MHz): δ 8.31 (s, 1H), 8.08 (d, J = 8.4 Hz, 1H), 7.94 (s, 1H), 7.65-7.62 (m, 2H), 7.45 (d, J = 5.6 Hz, 1H), 6.92 (d, J = 8.0 Hz, 1H), 5.56 (s, 2H), 5.32 (s, 2H). |

TABLE 1-continued

| Example # | Structure | Intermediate, Reference Methods, Alkylating Agent & Base | Deprotection Methods | Analytics |
|---|---|---|---|---|
| 147 | 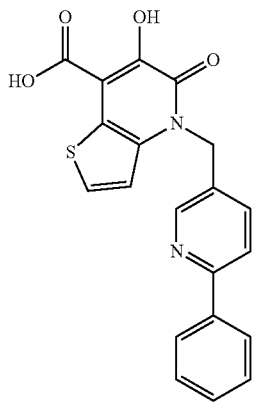 [SMILES: O=C(O)c1c(O)c(=O)n(Cc2ccc(-c3ccccc3)nc2)c2ccsc12]<br>6-hydroxy-5-oxo-4-[(6-phenylpyridin-3-yl)methyl]-4,5-dihydrothieno[3,2-b]pyridine-7-carboxylic acid | Intermediate C<br>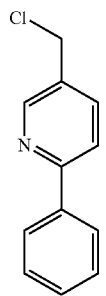 [SMILES: ClCc1ccc(-c2ccccc2)nc1]<br>Cs$_2$CO$_3$, LiBr | A. NaOH, MeOH, H$_2$O<br>C. TFA | (M + H)$^+$ = 379<br>$^1$H NMR (CD$_3$OD, 400 MHz): δ 8.75 (s, 1H), 8.17 (s, 1H), 8.06 (s, 1H), 7.92 (s, 2H), 7.63 (d, J = 6.0 Hz, 1H), 7.57 (s, 3H), 7.37 (d, J = 4.8 Hz, 1H), 5.76 (s, 2H) |
| 148 | 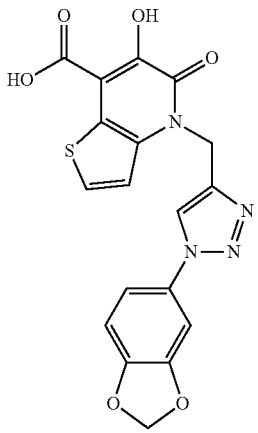 [SMILES: O=C(O)c1c(O)c(=O)n(Cc2cn(-c3ccc4c(c3)OCO4)nn2)c2ccsc12]<br>4-{[1-(benzo[d][1,3]dioxol-5-yl)-1H-1,2,3-triazol-4-yl]methyl}-6-hydroxy-5-oxo-4,5-dihydrothieno[3,2-b]pyridine-7-carboxylic acid | Methods: Example 25<br>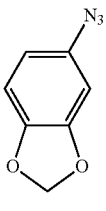 | A. NaOH, MeOH, H2O | (M − H)$^−$ = 410.8<br>$^1$H NMR (DMSO-d$_6$, 400 MHz) δ 8.60 (s, 1H), 7.60 (d, J = 5.6 Hz, 1H), 7.48 (s, 1H), 7.42-7.29 (m, 2H), 7.12-7.01 (m, 1H), 6.19-6.06 (m, 2H), 5.57 (s, 2H). |
| 149 | 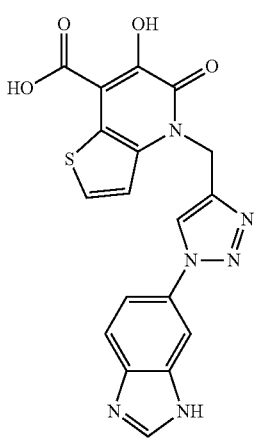 [SMILES: O=C(O)c1c(O)c(=O)n(Cc2cn(-c3ccc4nc[nH]c4c3)nn2)c2ccsc12]<br>4-{[1-(1H-benzo[d]imidazol-6-yl)-1H-1,2,3-triazol-4-yl]methyl}-6-hydroxy-5-oxo-4,5-dihydrothieno[3,2-b]pyridine-7-carboxylic acid | Methods: Example 25<br>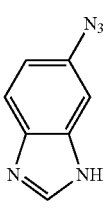 [SMILES: [N-]=[N+]=Nc1ccc2nc[nH]c2c1] | A. NaOH, MeOH, H$_2$O | (M + H)$^+$ = 409.0<br>$^1$H NMR (DMSO-d$_6$, 400 MHz) δ 9.64 (br s, 1H), 8.88 (s, 1H), 8.33 (s, 1H), 8.06 (t, J = 8.4 Hz, 2H), 7.68 (d, J = 6.0 Hz, 1H), 7.44 (d, J = 5.6 Hz, 1H), 5.64 (s, 2H). |

TABLE 1-continued

| Example # | Structure | Intermediate, Reference Methods, Alkylating Agent & Base | Deprotection Methods | Analytics |
|---|---|---|---|---|
| 150 | 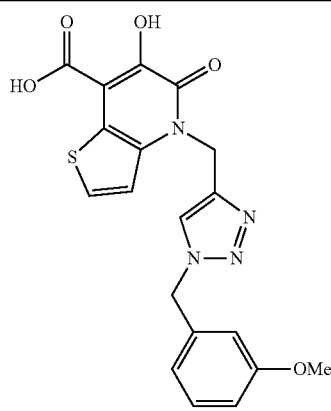<br>6-hydroxy-4-{[1-(3-methoxybenzyl)-1H-1,2,3-triazol-4-yl]methyl}-5-oxo-4,5-dihydrothieno[3,2-b]pyridine-7-carboxylic acid | Methods: Example 25<br>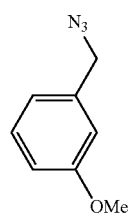 [SMILES: COc1cccc(CN=[N+]=[N-])c1] | A. NaOH, MeOH, H$_2$O | (M + H)$^+$ 413.1<br>$^1$H NMR (DMSO-d$_6$, 400 MHz): δ 8.09 (s, 1H), 7.62 (d, J = 5.6 Hz, 1H), 7.35 (d, J = 5.6 Hz, 1H), 7.26 (t, J = 8.0 Hz, 1H), 6.89-6.81 (m, 3H), 5.50 (s, 2H), 3.71 (s, 3H). |
| 151 | 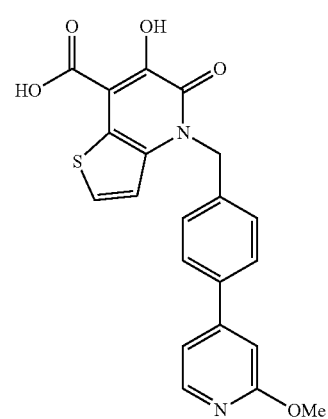 [SMILES: COc1cc(-c2ccc(Cn3c(=O)c(O)c(C(=O)O)c4sccc43)cc2)ccn1]<br>6-hydroxy-4-(4-(2-methoxypyridin-4-yl)benzyl)-5-oxo-4,5-dihydrothieno[3,2-b]pyridine-7-carboxylic acid | Intermediate C<br>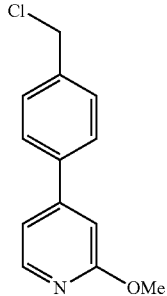 [SMILES: COc1cc(-c2ccc(CCl)cc2)ccn1]<br>Cs$_2$CO$_3$, LiBr | A. NaOH, MeOH, H$_2$O<br>C. TFA | (M + H)$^+$ = 409<br>$^1$H NMR (DMSO-d$_6$, 400 MHz) δ 8.21 (d, J = 5.6 Hz, 1H), 7.72 (d, J = 7.6 Hz, 2H), 7.59 (d, J = 5.6 Hz, 1H), 7.39 (d, J = 8.4 Hz, 2H), 7.26 (t, J = 6.4 Hz, 2H), 7.06 (s, 1H), 5.56 (s, 2H), 3.88 (s, 3H). |
| 152 | 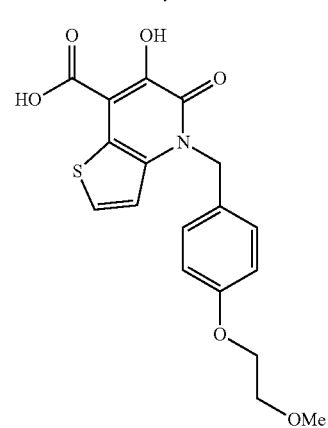<br>6-hydroxy-4-[4-(2-methoxyethoxy)benzyl]-5-oxo-4,5-dihydrothieno[3,2-b]pyridine-7-carboxylic acid | Intermediate C<br>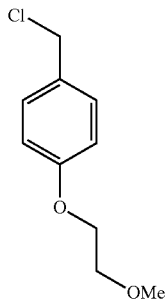 [SMILES: COCCOc1ccc(CCl)cc1]<br>Cs$_2$CO$_3$, LiBr | A. NaOH, MeOH, H$_2$O<br>C. TFA | (M + H)$^+$ = 376.1.<br>$^1$H NMR (DMSO-d$_6$, 400 MHz) δ 7.33 (d, J = 5.6 Hz, 1H), 7.21 (d, J = 8.8 Hz, 2H), 7.09 (d, J = 5.6 Hz, 1H), 6.86 (d, J = 8.8 Hz, 2H), 5.35 (s, 2H), 4.02 (t, J = 4.8 Hz, 2H), 3.61 (t, J = 4.8 Hz, 2H), 3.28 (s, 3H) |

| Example # | Structure | Intermediate, Reference Methods, Alkylating Agent & Base | Deprotection Methods | Analytics |
|---|---|---|---|---|
| 153 | 6-hydroxy-4-{4-[(methylsulfonyl)methoxy]benzyl}-5-oxo-4,5-dihydrothieno[3,2-b]pyridine-7-carboxylic acid | Intermediate C<br><br>Cs$_2$CO$_3$, LiBr | A. NaOH, MeOH, H$_2$O<br>C. TFA | (M + H)$^+$ = 410.1<br>$^1$H NMR (DMSO-d$_6$, 400 MHz) δ 7.61 (d, J = 6.0 Hz, 1H), 7.26-7.28 (m, 3H), 7.09 (d, J = 8.8 Hz, 2H), 5.45 (s, 2H), 5.27 (s, 2H), 3.02 (s, 3H) |
| 154 | (S)-6-hydroxy-4-({1-[2-(3-hydroxypyrrolidin-1-yl)-2-oxoethyl]-1H-pyrazol-4-yl}methyl)-5-oxo-4,5-dihydrothieno[3,2-b]pyridine-7-carboxylic acid | Methods: Example 27 | | (M − H)$^−$ = 419.1<br>$^1$H NMR (DMSO-d$_6$, 400 MHz) δ 7.68 (s, 1H), 7.61 (d, J = 5.6 Hz, 1H), 7.45-7.48 (m, 2H), 5.28 (s, 2H), 4.93 (dd, J = 3.2, 20.0 Hz, 2H), 4.22-4.35 (m, 2H), 3.44-3.58 (m, 3H), 3.22-3.43 (m, 2H), 1.69-1.96 (m, 2H). |
| 155 | 6-(benzyloxy)-4-[(1-{2-[methyl(phenyl)amino]-2-oxoethyl}-1H-pyrazol-4-yl)methyl]-5-oxo-4,5-dihydrothieno[3,2-b]pyridine-7-carboxylic acid | Intermediate D<br><br>K$_2$CO$_3$, DMF | A. NaOH, MeOH, H$_2$O<br>C. TFA | (M + H)$^+$ = 439.0<br>$^1$H NMR (DMSO-d$_6$, 400 MHz) δ 7.60-7.63 (m, 2H), 7.31-7.46 (m, 7H), 5.25 (s, 2H), 4.64 (s, 2H), 3.16 (s, 3H) |

TABLE 1-continued

| Example # | Structure | Intermediate, Reference Methods, Alkylating Agent & Base | Deprotection Methods | Analytics |
|---|---|---|---|---|
| 156 | 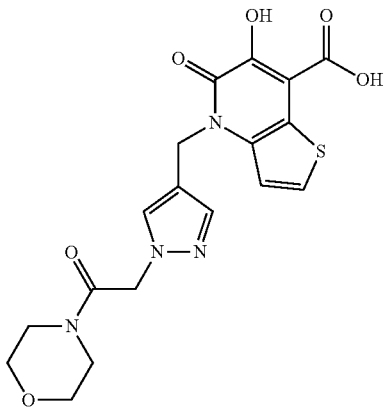 [SMILES: O=C(O)c1c(O)c(=O)n(Cc2cnn(CC(=O)N3CCOCC3)c2)c2ccsc12]<br>6-(benzyloxy)-4-{[1-(2-morpholino-2-oxoethyl)-1H-pyrazol-4-yl]methyl}-5-oxo-4,5-dihydrothieno[3,2-b]pyridine-7-carboxylic acid | Intermediate D<br>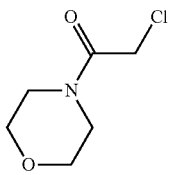<br>K$_2$CO$_3$, DMF | A. NaOH, MeOH, H$_2$O<br>C. TFA | (M + H)$^+$ = 419.0<br>$^1$H NMR (DMSO-d$_6$, 300 MHz) δ 7.62 (s, 1H), 7.45 (s, 1H), 7.38 (d, J = 5.4 Hz, 1H), 7.29 (d, J = 5.4 Hz, 1H), 5.20 (s, 2H), 5.04 (s, 2H), 3.54 (s, 4H), 3.40-3.42 (m, 4H) |
| 157 | 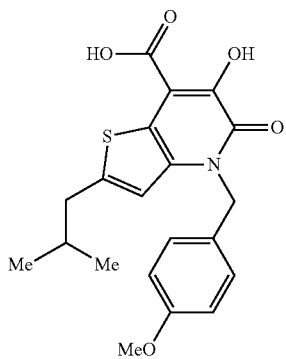 [SMILES: COc1ccc(Cn2c(=O)c(O)c(C(=O)O)c3sc(CC(C)C)cc32)cc1]<br>6-hydroxy-2-isobutyl-4-(4-methoxybenzyl)-5-oxo-4,5-dihydrothieno[3,2-b]pyridine-7-carboxylic acid | Intermediate G<br>Methods: Example 30<br>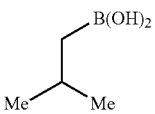 | A. NaOH, MeOH, H$_2$O<br>C. TFA | (M − H)$^-$ = 386<br>1H NMR (CD$_3$OD, 400 MHz) δ 7.10 (d, J = 8.4 Hz, 2H), 6.81-6.70 (m, 3H), 5.36 (s, 2H), 3.63 (s, 3H), 2.63-2.50 (m, 2H), 1.85-1.67 (m, 1H), 0.80 (d, J = 6.6 Hz, 6H). |
| 158 | 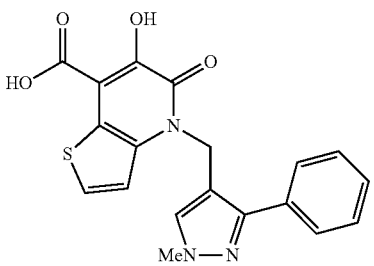 [SMILES: Cn1cc(Cn2c(=O)c(O)c(C(=O)O)c3sccc32)c(-c2ccccc2)n1]<br>6-hydroxy-4-[(1-methyl-3-phenyl-1H-pyrazol-4-yl)methyl]-5-oxo-4,5-dihydrothieno[3,2-b]pyridine-7-carboxylic acid | Intermediate C<br>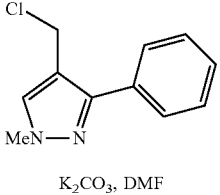<br>K$_2$CO$_3$, DMF | A. NaOH, MeOH, H$_2$O<br>C. TFA | (M − H)$^-$ = 380<br>1H NMR (400 MHz, CD$_3$OD) δ 7.52-7.45 (d, J = 5.4 Hz, 2H), 7.42-7.30 (m, 4H), 7.27 (d, J = 5.7 Hz, 1H), 6.50 (d, J = 5.6 Hz, 1H), 5.41 (s, 2H), 3.71 (s, 3H). |

TABLE 1-continued

| Example # | Structure | Intermediate, Reference Methods, Alkylating Agent & Base | Deprotection Methods | Analytics |
|---|---|---|---|---|
| 159 | 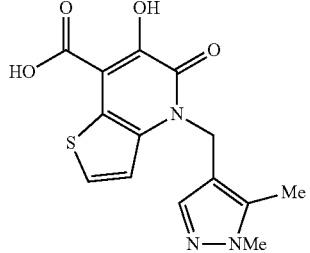 [SMILES: Cc1c(Cn2c(=O)c(O)c(C(=O)O)c3sccc32)cnn1C]<br>4-[(1,5-dimethyl-1H-pyrazol-4-yl)methyl]-6-hydroxy-5-oxo-4,5-dihydrothieno[3,2-b]pyridine-7-carboxylic acid | Intermediate C<br>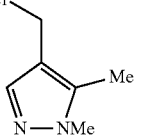<br>$K_2CO_3$, DMF | A. NaOH, MeOH, $H_2O$<br>C. TFA | $(M - H)^- = 319$<br>$^1H$ NMR ($CD_3OD$, 400 MHz) δ 7.47 (d, J = 5.6 Hz, 1H), 7.26-7.19 (m, 2H), 5.27 (s, 2H), 3.62 (s, 3H), 2.28 (s, 3H). |
| 160 | 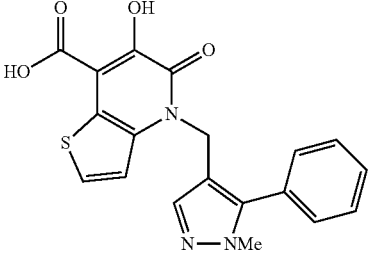 [SMILES: Cn1ncc(Cn2c(=O)c(O)c(C(=O)O)c3sccc32)c1-c1ccccc1]<br>6-hydroxy-4-[(1-methyl-5-phenyl-1H-pyrazol-4-yl)methyl]-5-oxo-4,5-dihydrothieno[3,2-b]pyridine-7-carboxylic acid | Intermediate C<br>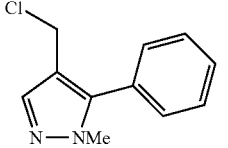 [SMILES: Cn1ncc(CCl)c1-c1ccccc1]<br>$K_2CO_3$, DMF | A. NaOH, MeOH, $H_2O$<br>C. TFA | $(M - H)^- = 380$<br>$^1H$ NMR ($CD_3OD$, 400 MHz) δ 7.41 (s, 1H), 7.39-7.33 (m, 3H), 7.26 (d, J = 5.6 Hz, 1H), 7.16-7.11 (m, 2H), 6.49 (d, J = 5.7 Hz, 1H), 5.27 (s, 2H), 3.53 (s, 3H). |
| 161 | 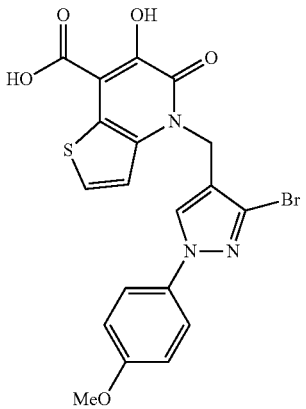 [SMILES: COc1ccc(-n2cc(Cn3c(=O)c(O)c(C(=O)O)c4sccc43)c(Br)n2)cc1]<br>4-{[3-bromo-1-(4-methoxyphenyl)-1H-pyrazol-4-yl]methyl}-6-hydroxy-5-oxo-4,5-dihydrothieno[3,2-b]pyridine-7-carboxylic acid | Intermediate C<br>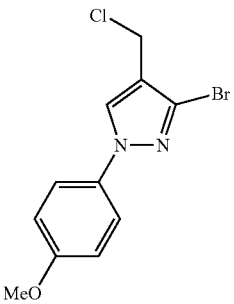 [SMILES: COc1ccc(-n2cc(CCl)c(Br)n2)cc1]<br>$K_2CO_3$, DMF | A. NaOH, MeOH, $H_2O$<br>C. TFA | $(M - H)^- = 475$<br>$^1H$ NMR ($CD_3OD$, 400 MHz) δ 7.88 (d, J = 8.1 Hz, 1H), 7.47 (d, J = 5.6 Hz, 1H), 7.43 (d, J = 8.8 Hz, 2H), 7.23 (d, J = 5.6 Hz, 1H), 6.87 (d, J = 9.0 Hz, 2H), 5.31 (s, 2H), 3.70 (s, 3H). |

TABLE 1-continued

| Example # | Structure | Intermediate, Reference Methods, Alkylating Agent & Base | Deprotection Methods | Analytics |
|---|---|---|---|---|
| 162 | 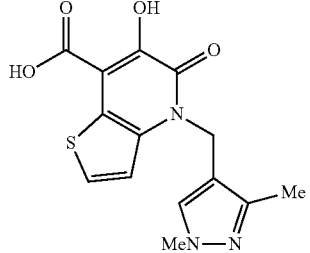 [SMILES: Cc1nn(C)cc1Cn1c(=O)c(O)c(C(=O)O)c2sccc21]

4-[(1,3-dimethyl-1H-pyrazol-4-yl)methyl]-6-hydroxy-5-oxo-4,5-dihydrothieno[3,2-b]pyridine-7-carboxylic acid | Intermediate C

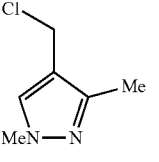

K₂CO₃, DMF | A. NaOH, MeOH, H₂O
C. TFA | (M − H)⁻ = 319
¹H NMR (CD₃OD, 400 MHz) δ 7.58 (d, J = 5.6 Hz, 1H), 7.40 (s, 1H), 7.34 (d, J = 5.7 Hz, 1H), 5.39 (s, 2H), 3.63 (s, 3H), 2.20 (s, 3H). |
| 163 | 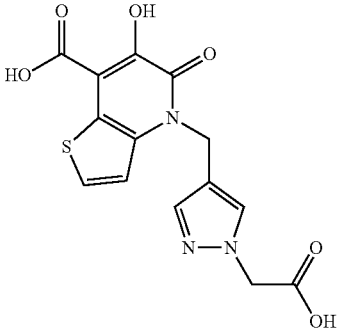 [SMILES: O=C(O)Cn1cc(Cn2c(=O)c(O)c(C(=O)O)c3sccc32)cn1]

4-{[1-(carboxymethyl)-1H-pyrazol-4-yl]methyl}-6-hydroxy-5-oxo-4,5-dihydrothieno[3,2-b]pyridine-7-carboxylic acid | Intermediate C

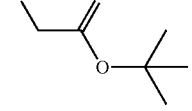

K₂CO₃, DMF | A. NaOH, MeOH, H₂O
C. TFA | (M − H)⁻ = 348
¹H NMR (CD₃OD, 400 MHz) δ 7.74 (s, 1H), 7.60 (s, 1H), 7.52 (d, J = 5.6 Hz, 1H), 7.35 (d, J = 5.7 Hz, 1H), 5.42 (s, 2H). |
| 164 | 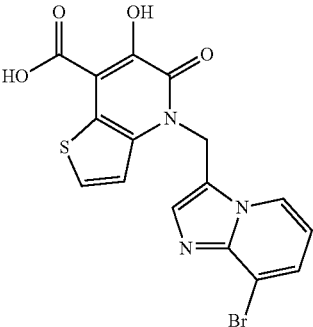 [SMILES: O=C(O)c1c(O)c(=O)n(Cc2cnc3c(Br)cccn23)c2ccsc12]

4-[(8-bromoimidazo[1,2-a]pyridin-3-yl)methyl]-6-hydroxy-5-oxo-4,5-dihydrothieno[3,2-b]pyridine-7-carboxylic acid | Intermediate C

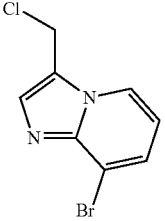 [SMILES: ClCc1cnc2c(Br)cccn12]

K₂CO₃, DMF | A. NaOH, MeOH, H₂O
C. TFA | (M + H)⁺ = 420, 422
¹H NMR (CD₃OD, 400 MHz) δ 8.98 (s, 1H), 7.86 (t, J = 4.3 Hz, 2H), 7.44 (d, J = 31.9 Hz, 2H), 7.02 (s, 1H), 5.87 (s, 2H). |

TABLE 1-continued

| Example # | Structure | Intermediate, Reference Methods, Alkylating Agent & Base | Deprotection Methods | Analytics |
|---|---|---|---|---|
| 165 | 6-hydroxy-4-{[8-(2-methoxypyridin-4-yl)imidazo[1,2-a]pyridin-3-yl]methyl}-5-oxo-4,5-dihydrothieno[3,2-b]pyridine-7-carboxylic acid | Intermediate C<br><br>(chloromethyl-bromo-imidazopyridine)<br><br>K$_2$CO$_3$, DMF<br>Methods: Example 31<br><br>(2-methoxypyridin-4-yl)boronic acid | A. NaOH, MeOH, H$_2$O<br>C. TFA | (M − H)$^-$ = 447<br>$^1$H NMR (CD$_3$OD, 400 MHz) δ 8.96 (d, J = 6.9 Hz, 1H), 8.17-8.08 (m, 1H), 7.77 (s, 1H), 7.53 (d, J = 7.3 Hz, 1H), 7.49-7.36 (m, 2H), 7.27 (d, J = 5.3 Hz, 1H), 7.20 (s, 1H), 7.17-7.06 (m, 1H), 5.91 (s, 2H), 3.86 (s, 3H). |
| 166 | 6-hydroxy-4-({2-[4-(methylsulfonyl)phenyl]thiazol-5-yl}methyl)-5-oxo-4,5-dihydrothieno[3,2-b]pyridine-7-carboxylic acid | Example 32 | A. NaOH, MeOH, H$_2$O<br>C. TFA | (M + H)$^+$ = 463<br>$^1$H NMR (CD$_3$OD, 400 MHz) δ 7.94 (s, 1H), 7.81 (d, J = 8.4 Hz, 2H), 7.62 (d, J = 5.7 Hz, 1H), 7.46 (d, J = 5.7 Hz, 1H), 7.28 (d, J = 8.5 Hz, 2H), 5.72 (s, 2H), 3.01 (s, 3H). |

TABLE 1-continued

| Example # | Structure | Intermediate, Reference Methods, Alkylating Agent & Base | Deprotection Methods | Analytics |
|---|---|---|---|---|
| 167 | 6-hydroxy-4-({2-[4-(methylsulfonamido)phenyl]thiazol-5-yl}methyl)-5-oxo-4,5-dihydrothieno[3,2-b]pyridine-7-carboxylic acid | Example 32 | A. NaOH, MeOH, $H_2O$<br>C. TFA | $(M + H)^+ = 478$<br>$^1$H NMR (CD$_3$OD, 400 MHz) δ 7.94 (s, 1H), 7.82 (d, J = 8.3 Hz, 2H), 7.56 (d, J = 5.6 Hz, 1H), 7.42 (d, J = 5.7 Hz, 1H), 7.29 (d, J = 8.5 Hz, 2H), 5.73 (s, 2H), 3.01 (s, 3H). |
| 168 | 6-hydroxy-4-{[2-(isoquinolin-5-yl)thiazol-5-yl]methyl}-5-oxo-4,5-dihydrothieno[3,2-b]pyridine-7-carboxylic acid | Example 32 | A. NaOH, MeOH, $H_2O$<br>C. TFA | $(M + H)^+ = 436$<br>$^1$H NMR (CD$_3$OD, 400 MHz) δ 9.31 (s, 1H), 8.68 (d, J = 6.2 Hz, 1H), 8.50 (d, J = 6.3 Hz, 1H), 8.23 (d, J = 8.2 Hz, 1H), 8.18 (s, 1H), 8.13 (d, J = 7.2 Hz, 1H), 7.76 (t, J = 7.8 Hz, 1H), 7.57 (d, J = 5.6 Hz, 1H), 7.47 (d, J = 5.6 Hz, 1H), 5.82 (s, 2H). |
| 169 | 6-hydroxy-5-oxo-4-{[2-(quinolin-5-yl)thiazol-5-yl]methyl}-4,5-dihydrothieno[3,2-b]pyridine-7-carboxylic acid | Example 32 | A. NaOH, MeOH, $H_2O$<br>C. TFA | $(M + H)^+ = 436$<br>$^1$H NMR (CD$_3$OD, 400 MHz) δ 9.23 (d, J = 8.7 Hz, 1H), 8.91 (d, J = 4.3 Hz, 1H), 8.21-8.10 (m, 2H), 7.94 (d, J = 7.4 Hz, 1H), 7.85 (d, J = 8.1 Hz, 1H), 7.60 (t, J = 5.3 Hz, 2H), 7.48 (d, J = 5.7 Hz, 1H), 5.82 (s, 2H). |

TABLE 1-continued

| Example # | Structure | Intermediate, Reference Methods, Alkylating Agent & Base | Deprotection Methods | Analytics |
|---|---|---|---|---|
| 170 | 6-hydroxy-5-oxo-4-{[2-(quinolin-4-yl)thiazol-5-yl]methyl}-4,5-dihydrothieno[3,2-b]pyridine-7-carboxylic acid | Example 32 | A. NaOH, MeOH, H$_2$O C. TFA | (M + H)$^+$ = 436 $^1$H NMR (CD$_3$OD, 400 MHz) δ 8.90 (d, J = 4.6 Hz, 1H), 8.81 (d, J = 8.6 Hz, 1H), 8.25 (s, 1H), 8.10 (d, J = 8.6 Hz, 1H), 7.88-7.73 (m, 2H), 7.68 (t, J = 7.8 Hz, 1H), 7.58 (d, J = 5.7 Hz, 1H), 7.47 (d, J = 5.7 Hz, 1H), 5.84 (s, 2H). |

Enzymatic IC$_{50}$ Assays

FEN1, EXO1 or XPG enzyme was incubated with compound or vehicle (DMSO) and the FAM-labeled DNA oligomer substrate in a microtiter plate. The stop buffer contains EDTA to stop the enzymatic reaction. The plate is read for fluorescence intensity. The high control (DMSO) with high fluorescence intensity represents no inhibition of enzymatic reaction while the low control (10 µM) with low fluorescence intensity represents full inhibition of enzymatic reaction.

Materials:
Enzymes:
  FEN1
    hFEN1: 70 pM
    Substrate: 100 nM
    Reaction time: 20 minutes
  EXO1
    hEXO1: 6 nM, Isoform1
    Substrate: 30 nM
    Reaction time: 60 minutes
  XPG
    hXPG: 100 nM
    Substrate: 100 nM
    Reaction time: 120 minutes

```
(SEQ ID NO: 1):
5'GGTGGACGGGTGGATTGAAATTTAGGCTGGCACGGTCG3'

(SEQ ID NO: 2):
5'CGACCGTGCCAGCCTAAATTTCAATC3'

(SEQ ID NO: 3):
5'FAM-CCAAGGCCACCCGTCCAC-3'IABkFQ
```

Annealing Buffer: 50 mM Tris-HCl, 50 mM NaCl, 1 mM DTT
Assay buffer: 50 mM Tris-HCl pH 8.0, 10 mM MgCl$_2$, 0.01% BSA, 1 mM DTT
Stop buffer: 50 mM EDTA in assay buffer
Temperature: 23° C.
Total volume: 40 µl Controls:
  0% inhibition control: DMSO
  100% inhibition control: 10 µM (final) 5-chloro-3-hydroxy-1,3-dihydroquinazoline-2,4-dione Enzyme Reaction and Detection:
1. Prepare 25 µM intermediate stock of the substrate by diluting SEQ ID NO:1, SEQ ID NO:2, and SEQ ID NO:3 in annealing buffer, in a PCR tube.
2. Place the PCR tube on a heat block, heat at 95° C. for 3 minutes, then drop in 0.2° C. increments over 2 minutes, stopping at 25° C.
3. Remove the tube and let the tube cool at room temperature.
4. Transfer 10 µL of 3× final concentration test compounds or DMSO to the appropriate wells of a microtiter plate.
5. Transfer 10 µL of 3× final concentration enzyme in assay buffer or assay buffer alone to the appropriate wells.
6. Incubate the plate at room temperature for 15 minutes.
7. Transfer 10 µL of 3× substrate in assay buffer to all the test wells.
8. Incubate the plate at room temperature for prescribed reaction time.
9. Centrifuge the plate at 1000 rpm for 1 minute.
10. Transfer 10 µL of stop buffer to all the test wells.
11. Centrifuge the plate at 1000 rpm for 1 minute.
12. Read the plate on a plate reader.

TABLE 2

Data in the following table was generated using the enzymatic assays described above. Activity is reported as follows:
** IC$_{50}$ < 0.2 uM, * 0.25 < IC$_{50}$ < 0.75 uM,
** 0.75 < IC$_{50}$ < 2.25 uM,
* IC$_{50}$ 2.25 < IC$_{50}$ < 10 uM, -IC$_{50}$ > 10 uM

| Example # | FEN1 IC$_{50}$ (uM) | EXO1 IC$_{50}$ (uM) | XPG IC$_{50}$ (UM) |
|---|---|---|---|
| 1 | *** | * | * |
| 2 | *** | * | * |
| 3 | ** | * | * |
| 4 | * | | |

TABLE 2-continued

Data in the following table was generated using the enzymatic assays described above. Activity is reported as follows:
** $IC_{50} < 0.2$ uM, * $0.25 < IC_{50} < 0.75$ uM,
** $0.75 < IC_{50} < 2.25$ uM,
* $2.25 < IC_{50} < 10$ uM, — $IC_{50} > 10$ uM

| Example # | FEN1 IC$_{50}$ (uM) | EXO1 IC$_{50}$ (uM) | XPG IC$_{50}$ (uM) |
|---|---|---|---|
| 5 | *** | * | * |
| 6 | *** | * |  |
| 7 | **** | ** | * |
| 8 | ** |  |  |
| 9 | * | * |  |
| 10 | * |  |  |
| 11 | *** |  |  |
| 12 | **** | * | * |
| 13 | **** |  |  |
| 14 | ** |  |  |
| 15 | **** |  |  |
| 16 | **** | *** | * |
| 17 | ** |  |  |
| 18 | *** | *** | ** |
| 19 | **** |  |  |
| 20 | *** |  |  |
| 21 | **** |  |  |
| 22 | **** | *** | *** |
| 24 | **** | ** | **** |
| 25 | **** |  |  |
| 26 | **** |  |  |
| 27 | **** |  |  |
| 28 | **** | * | * |
| 29 | * | * | * |
| 30 | ** | *** | * |
| 31 | * | * |  |
| 32 | *** | ** |  |
| 33 | * |  |  |
| 34 | **** | * | * |
| 35 | * |  |  |
| 37 | *** | * |  |
| 38 | * |  |  |
| 39 | * |  |  |
| 40 | **** | * | * |
| 41 | *** | * |  |
| 42 | * | * | * |
| 43 | *** |  |  |
| 44 | * |  |  |
| 45 | * | * |  |
| 47 | * |  |  |
| 48 | * | * |  |
| 49 | * | * |  |
| 50 | *** | ** | * |
| 51 | * |  |  |
| 52 | *** |  |  |
| 53 | **** | * | * |
| 54 | * |  |  |
| 55 | ** |  |  |
| 56 | * |  |  |
| 57 | **** |  |  |
| 58 | * |  |  |
| 59 | *** |  |  |
| 60 | ** |  |  |
| 61 | * |  |  |
| 62 | * | * |  |
| 63 | ** | * | * |
| 64 | * |  |  |
| 65 | *** |  |  |
| 66 | * | * |  |
| 67 | *** |  |  |
| 68 | * |  |  |
| 69 | * |  |  |
| 70 | **** | ** |  |
| 71 | *** |  |  |
| 72 | * | * |  |
| 73 | *** |  |  |
| 74 | * |  |  |
| 75 | ** | * | — |
| 76 | *** |  |  |
| 77 | *** |  |  |
| 78 | *** | ** | * |
| 79 | * |  |  |
| 80 | * |  |  |
| 81 | *** | * | * |
| 82 | ** |  |  |
| 83 | *** | — | — |
| 84 | **** | *** | *** |
| 85 | *** | * | ** |
| 86 | *** | ** | ** |
| 87 | **** | *** | ** |
| 88 | ** | *** | * |
| 89 | *** |  |  |
| 90 | **** | * | * |
| 91 | **** | * | * |
| 92 | * | — |  |
| 93 | **** |  |  |
| 94 | *** |  |  |
| 95 | *** |  |  |
| 96 | — | — |  |
| 97 | **** | * |  |
| 98 | **** | * | * |
| 99 | **** | ** | * |
| 100 | **** | ** | * |
| 101 | *** | *** | * |
| 102 | ** |  |  |
| 103 | *** |  |  |
| 104 | * |  |  |
| 105 | *** |  |  |
| 106 | **** |  |  |
| 107 | **** |  |  |
| 108 | *** |  |  |
| 109 | ** |  |  |
| 110 | **** |  |  |
| 111 | *** | *** | ** |
| 112 | *** |  |  |
| 113 | **** | *** | ** |
| 114 | **** |  |  |
| 115 | **** | **** | ** |
| 116 | **** | *** | ** |
| 117 | **** | *** | *** |
| 118 | **** |  |  |
| 119 | **** | * | — |
| 120 | **** | * | * |
| 121 | **** | * | * |
| 122 | **** | * | ** |
| 123 | **** |  |  |
| 124 | **** |  |  |
| 125 | **** | ** | * |
| 126 | **** | * | * |
| 127 | **** | ** | * |
| 128 | **** | * | * |
| 129 | **** |  |  |
| 130 | **** | * | * |
| 131 | **** | * | * |
| 132 | **** | * | * |
| 133 | **** | * | ** |
| 134 | **** |  |  |
| 135 | **** |  |  |
| 136 | **** | * | — |
| 137 | **** |  |  |
| 138 | **** | * | * |
| 139 | **** |  |  |
| 140 | **** | * | * |
| 141 | **** | ** | * |
| 142 | **** |  |  |
| 143 | **** | * | * |
| 144 | **** | * | — |
| 145 | *** |  |  |
| 146 | **** | * | ** |
| 147 | *** |  |  |
| 148 | **** | *** | *** |
| 149 | **** | * | ** |

TABLE 2-continued

Data in the following table was generated using the enzymatic assays described above. Activity is reported as follows:
** $IC_{50} < 0.2$ uM, * $0.25 < IC_{50} < 0.75$ uM,
** $0.75 < IC_{50} < 2.25$ uM,
* $IC_{50}\ 2.25 < IC_{50} < 10$ uM, – $IC_{50} > 10$ uM

| Example # | FEN1 IC$_{50}$ (uM) | EXO1 IC$_{50}$ (uM) | XPG IC$_{50}$ (UM) |
|---|---|---|---|
| 150 | **** | | |
| 151 | *** | | |
| 152 | **** | | |
| 153 | *** | | |
| 154 | *** | — | — |
| 155 | **** | * | * |
| 156 | **** | * | * |
| 157 | * | | |
| 158 | * | ** | |
| 159 | **** | * | |
| 160 | — | — | |
| 161 | *** | ** | |
| 162 | ** | * | |
| 163 | **** | * | |
| 164 | *** | *** | |
| 165 | ** | ** | |
| 166 | *** | *** | |
| 167 | **** | ** | |
| 168 | * | * | |
| 169 | * | ** | |
| 170 | ** | ** | |

The invention claimed is:
1. A compound having Formula (I):

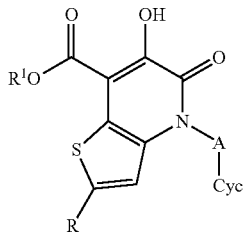

(I)

or a pharmaceutically acceptable salt, hydrate, or solvate thereof, wherein,
R is a member selected from the group consisting of H, halogen, $C_{1-6}$ alkyl, $C_{1-6}$ haloalkyl, $C_{3-6}$ cycloalkyl and benzyl;
$R^1$ is a member selected from the group consisting of H and $C_{1-8}$ alkyl, wherein the $C_{1-8}$ alkyl is optionally substituted with 1 to 4 $R^{1a}$;
A is $C_{1-3}$ alkylene, wherein one or two H atoms are optionally and independently replaced with F or Cl;
Cyc is selected from:
(i) 5- or 6-membered heteroaryl;
(ii) phenyl;
(iii) 9- or 10-membered fused bicyclic heteroaryl;
(iv) 5- or 6-membered heterocyclic ring, optionally substituted with oxo, and optionally fused to a phenyl; and
(v) $C_{5-10}$ cycloalkyl;
and each of (i), (ii), (iii), (iv) and (v) is optionally further substituted with
(i') 1 to 4 members independently selected from $R^2$, $C_{1-3}$alkylene-$R^2$ and —O—$C_{1-3}$alkylene-$R^2$;
(ii') phenyl, phenoxy, pyridyl, or pyridyloxy each of which is optionally substituted with from 1 to 4 $R^{2a}$;
(iii') a $C_{1-3}$alkylene-Y, wherein Y is selected from the group consisting of phenyl, 4- to 7-membered heterocycloalkyl, 5- or 6-membered heteroaryl, and 9-or 10-membered fused bicyclic heteroaryl, each of which is optionally substituted with from 1 to 4 $R^{2a}$ and wherein the $C_{1-3}$alkylene portion is optionally substituted with oxo;
(iv') a 9- or 10-membered fused bicyclic heteroaryl, which is optionally substituted with from 1 to 4 $R^{2a}$; or
(v') a $C_{3-10}$ cycloalkyl, which is optionally substituted with from 1 to 4 $R^{2a}$;
each $R^{1a}$ is a member selected from the group consisting of halogen, —CN, —$CO_2R^a$, —$CONR^aR^b$, —$C(O)R^a$, —$OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$ and —$NR^aS(O)_2R^b$;
each $R^2$ and $R^{2a}$ is a member independently selected from the group consisting of halogen, —CN, —$NO_2$, —$CO_2R^a$, —$CONR^aR^b$, —$C(O)R^a$, —$OC(O)NR^aR^b$, —$NR^aC(O)R^b$, —$NR^aC(O)_2R^c$, —$NR^aC(O)NR^aR^b$, —$NR^aR^b$, —$OR^a$, —$S(O)_2NR^aR^b$, —$NR^aS(O)_2R^b$, —$S(O)_2R^b$, —$S(O)(NR^c)R^b$ and $R^c$;
wherein each $R^a$ and $R^b$ is independently selected from hydrogen, $C_{1-4}$ alkyl, $C_{1-4}$ hydroxyalkyl, $C_{1-4}$ haloalkyl and phenyl; or $R^a$ and $R^b$ when attached to a nitrogen atom are combined to form a 5- or 6-membered ring having from 0 or 1 additional O, S or N atoms as a ring member, wherein the ring is optionally further substituted with —OH, —$NH_2$, oxo, or —$CO_2H$, and each $R^c$ is selected from $C_{1-4}$ alkyl, $C_{1-4}$ hydroxyalkyl and $C_{1-4}$ haloalkyl.

2. A compound of claim 1, wherein Cyc is a 5- or 6-membered heteroaryl, and is optionally substituted as provided in groups (i'), (ii'), (iii'), (iv') and (v').

3. A compound of claim 1, wherein Cyc is phenyl, and is optionally substituted as provided in groups (i'), (ii'), (iii'), (iv') and (v').

4. A compound of claim 1, wherein Cyc is a 9- or 10-membered fused bicyclic heteroaryl, and is optionally substituted as provided in groups (i'), (ii'), (iii'), (iv') and (v').

5. A compound of claim 1, wherein Cyc is a 5- or 6-membered heterocyclic ring, optionally fused to a phenyl, and is optionally substituted as provided in groups (i'), (ii'), (iii'), (iv') and (v').

6. A compound of claim 1, wherein $R^1$ is H.

7. A compound of claim 1, wherein $R^1$ is $C_{1-4}$ alkyl.

8. A compound of claim 1, wherein A is methylene.

9. A compound of claim 2, wherein Cyc is a 5-membered heteroaryl, selected from the group consisting of imidazolyl, isoxazolyl, pyrazolyl, 1,2,3-triazolyl, 1,2,4-triazolyl, thiazolyl, 1,2,4-oxadiazolyl, 1,3,4-oxadiazolyl, and 1,3,4-thiadiazolyl, each of which is optionally substituted with 1-2 $R^2$.

10. A compound of claim 3, wherein Cyc is phenyl, optionally substituted with 1 to 4 $R^2$.

11. A compound of claim 4, wherein Cyc is a 9-10-membered fused bicyclic heteroaryl, selected from the group consisting of

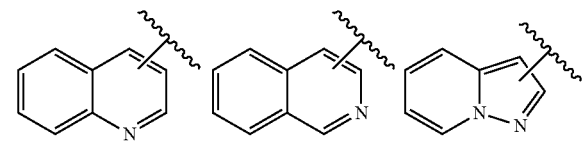

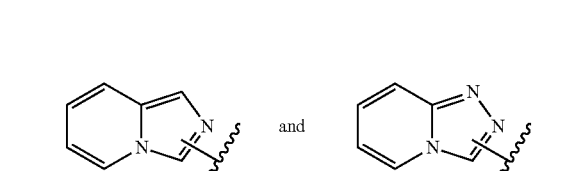

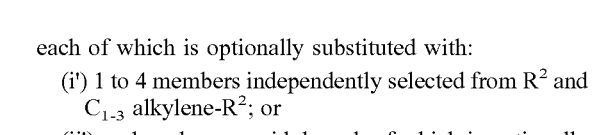

each of which is optionally substituted with:
(i') 1 to 4 members independently selected from $R^2$ and $C_{1-3}$ alkylene-$R^2$; or
(ii') a phenyl or a pyridyl, each of which is optionally substituted with from 1 to 4 $R^{2a}$.

12. A compound of claim 2, wherein Cyc is a 6-membered heteroaryl selected from the group consisting of pyridyl, pyrazinyl, pyridazinyl, and pyrimidinyl, each of which is optionally substituted with 1-3 $R^2$.

13. A compound of claim 1, having the formula:

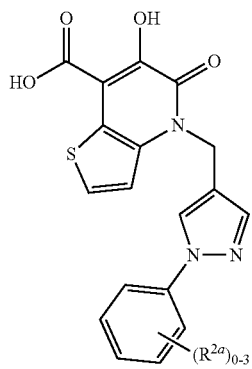

wherein each $R^{2a}$ is independently selected from the group consisting of halogen, —CN, —NO$_2$, —CO$_2$R$^a$, —CONR$^a$R$^b$, —NR$^a$C(O)R$^b$, —NR$^a$R$^b$, —OR$^a$, —NR$^a$S(O)$_2$R$^b$, —S(O)$_2$R$^b$, and R$^c$, wherein each R$^a$ and R$^b$ is independently selected from hydrogen, C$_{1-4}$ alkyl, C$_{1-4}$ haloalkyl and phenyl; or R$^a$ and R$^b$ when attached to a nitrogen atom are combined to form a 5- or 6-membered ring having from 0 or 1 additional O, S or N atoms as a ring member, wherein the ring is optionally further substituted with —OH, and each R$^c$ is selected from C$_{1-4}$ alkyl, and C$_{1-4}$ haloalkyl.

14. A compound of claim 1, having the formula:

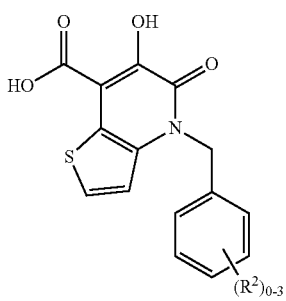

wherein each $R^2$ is independently selected from the group consisting of halogen, —CN, —NO$_2$, —CO$_2$R$^a$, —CONR$^a$R$^b$, —NR$^a$C(O)R$^b$, —NR$^a$R$^b$, —OR$^a$, —NR$^a$S(O)$_2$R$^b$, —S(O)$_2$R$^b$, and R$^c$, wherein each R$^a$ and R$^b$ is independently selected from hydrogen, C$_{1-4}$ alkyl, C$_{1-4}$ haloalkyl and phenyl; or R$^a$ and R$^b$ when attached to a nitrogen atom are combined to form a 5- or 6-membered ring having from 0 or 1 additional O, S or N atoms as a ring member, wherein the ring is optionally further substituted with —OH, and each R$^c$ is selected from C$_{1-4}$ alkyl, and C$_{1-4}$ haloalkyl.

15. A compound of claim 1, having the formula:

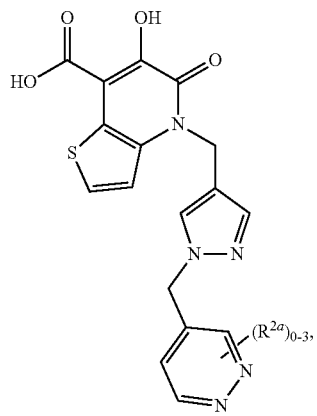

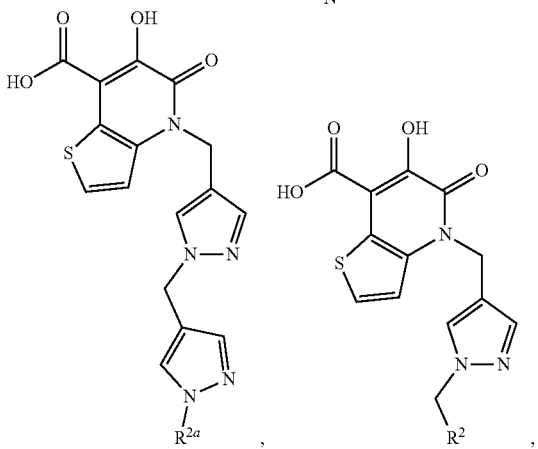

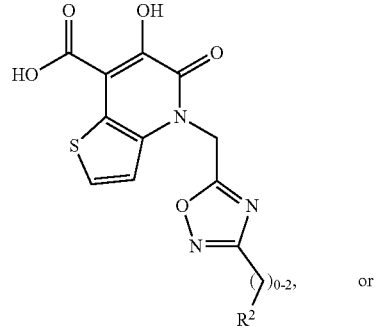

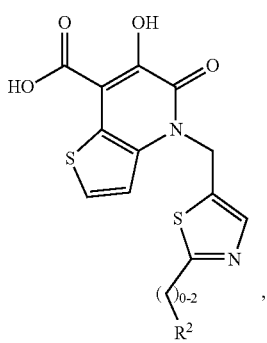

or a pharmaceutically acceptable salt thereof.

16. A compound selected from the group consisting of
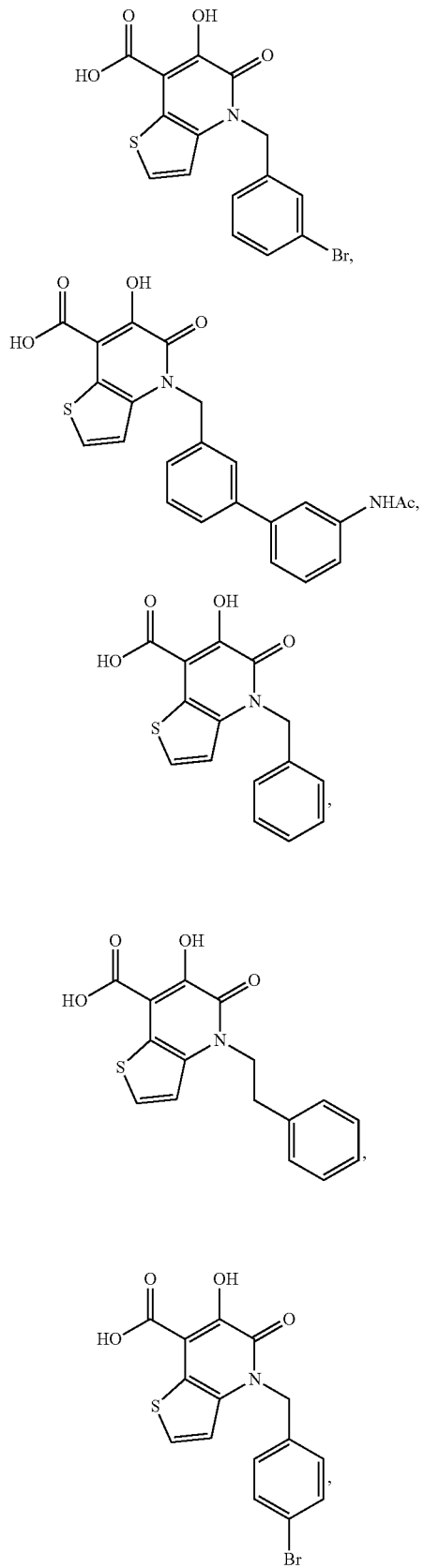
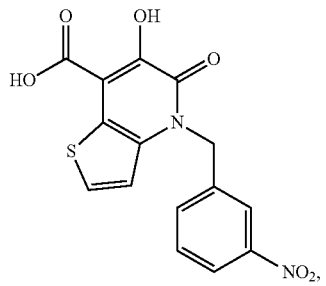
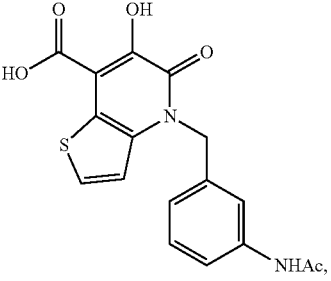
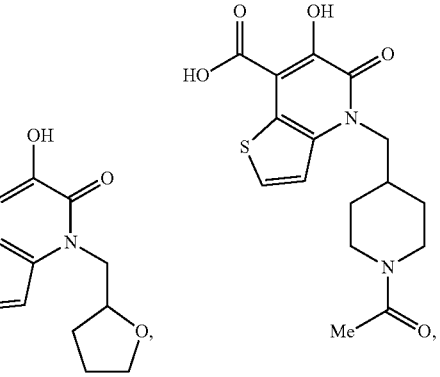
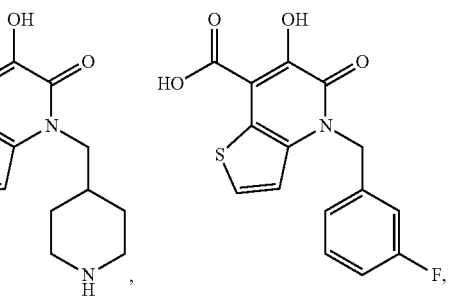
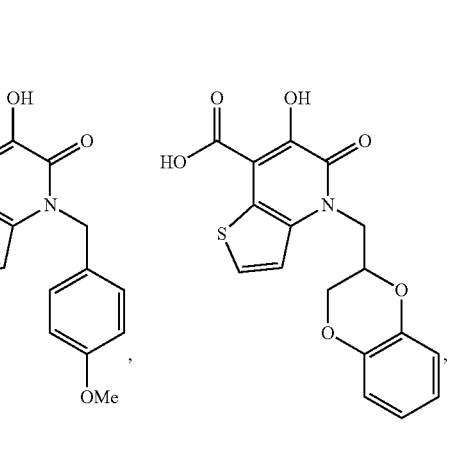

223
-continued
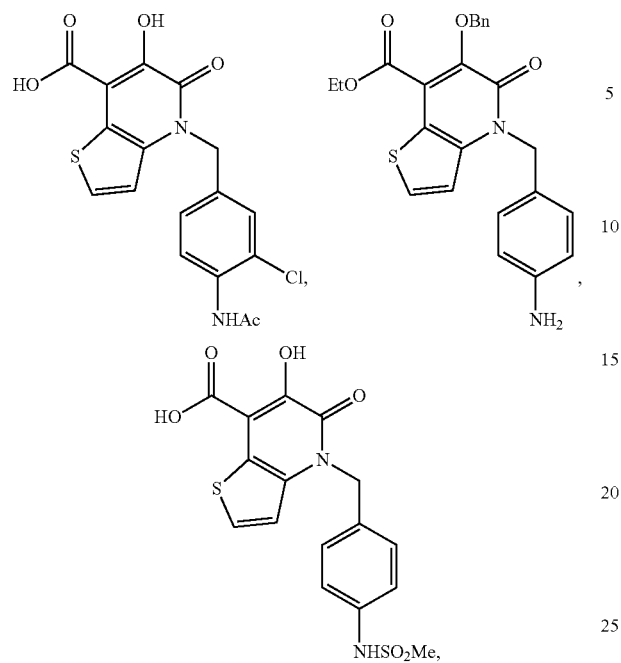
224
-continued
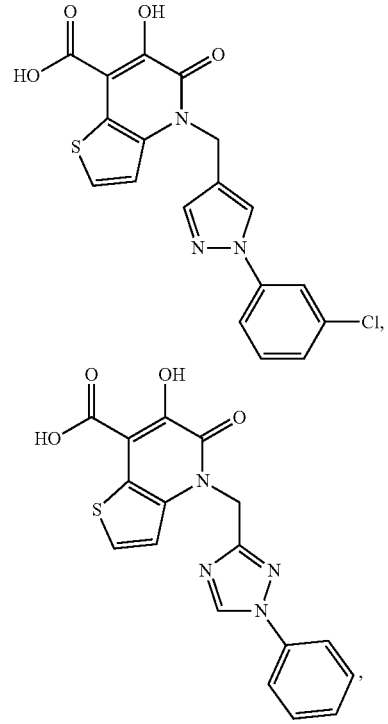
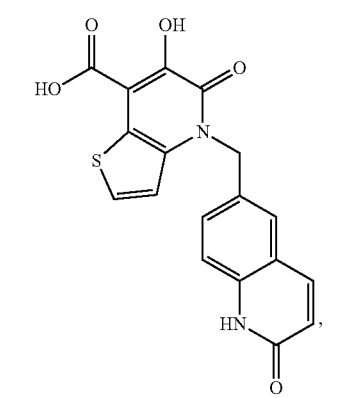
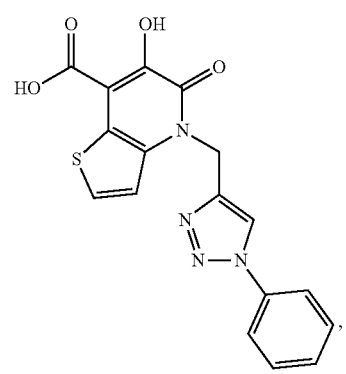
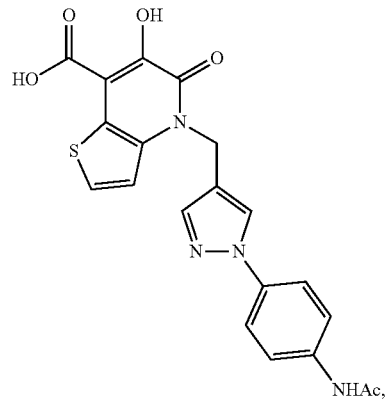

225
-continued
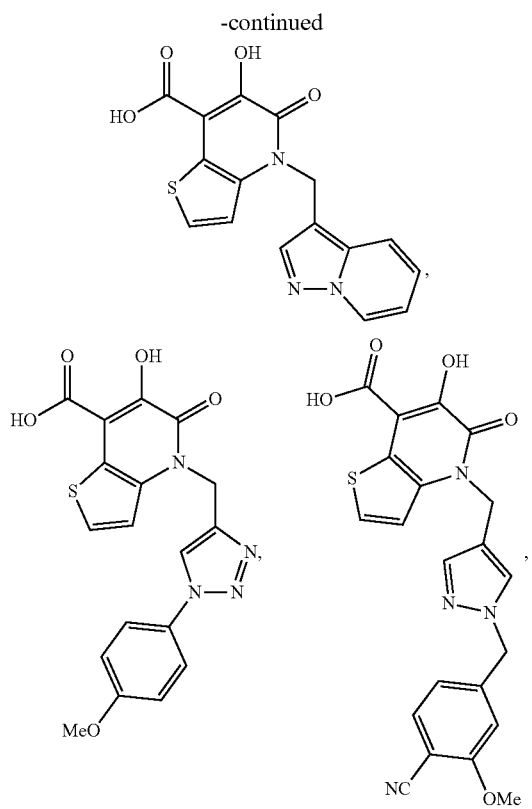
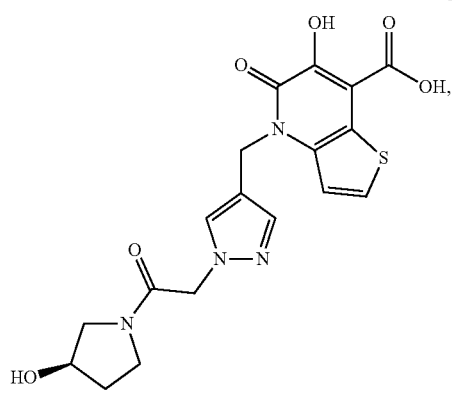
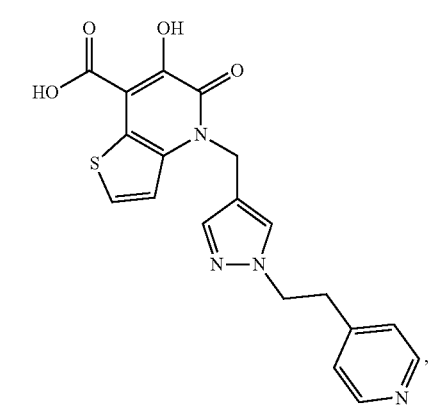
226
-continued
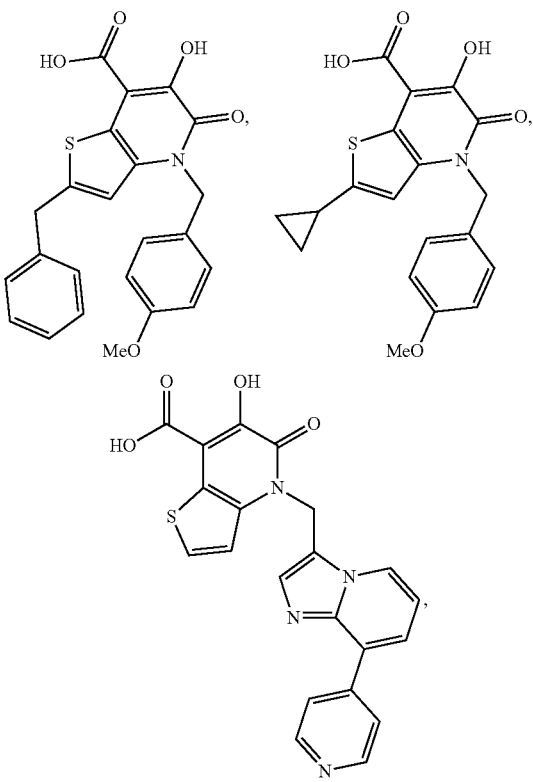
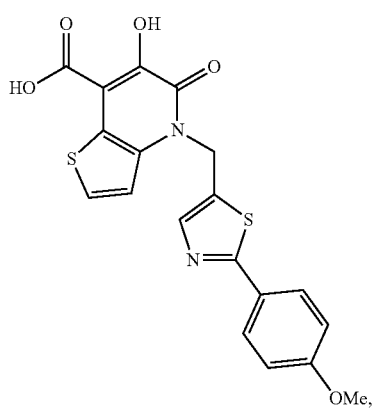
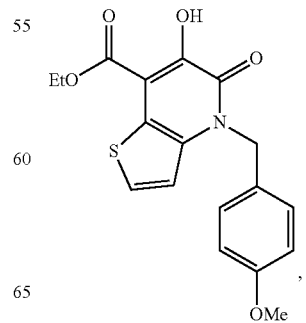
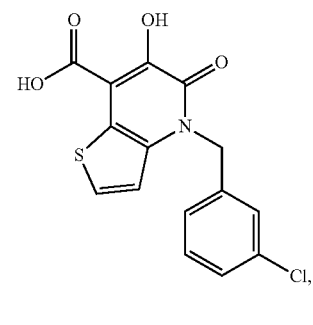

227
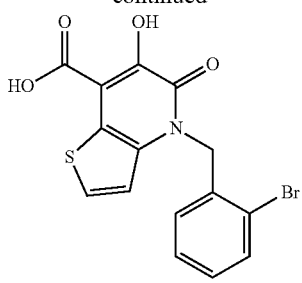
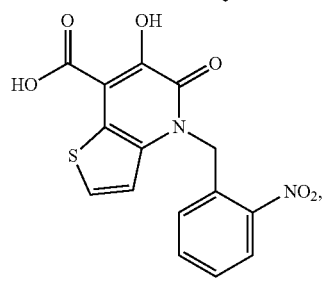
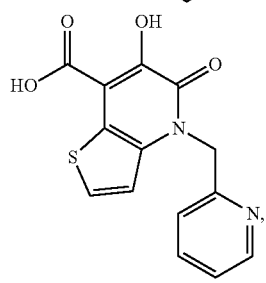
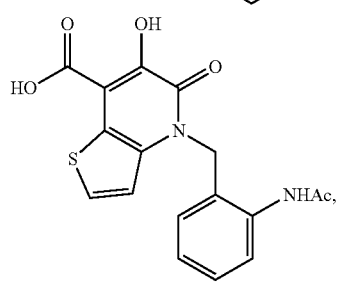
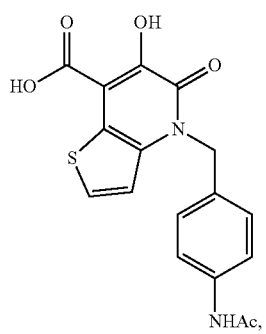
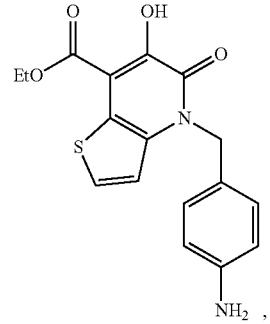
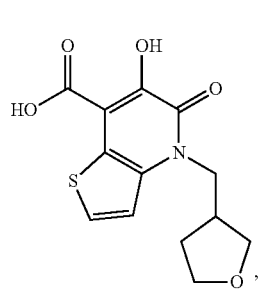
228
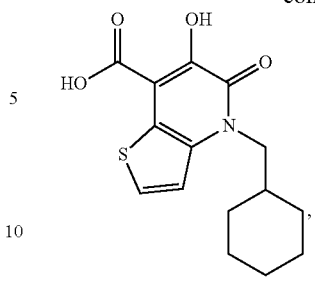
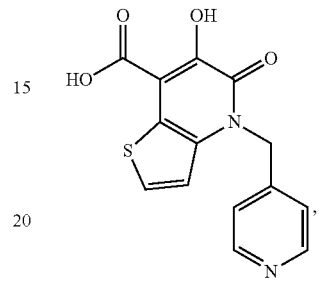
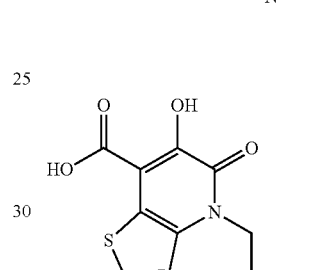
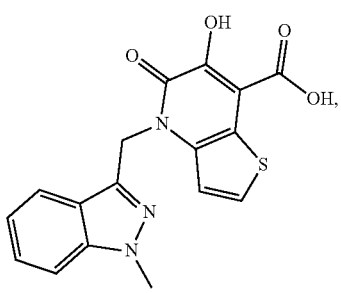
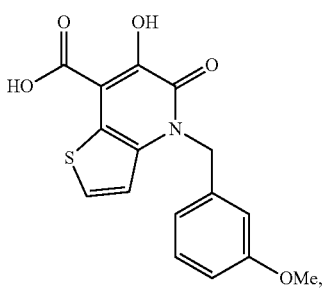

229
-continued
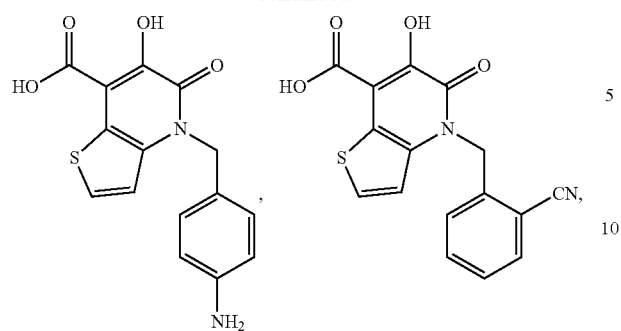
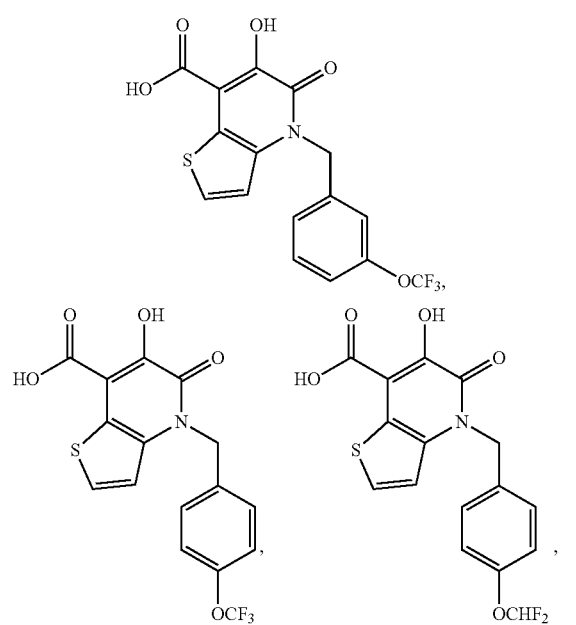
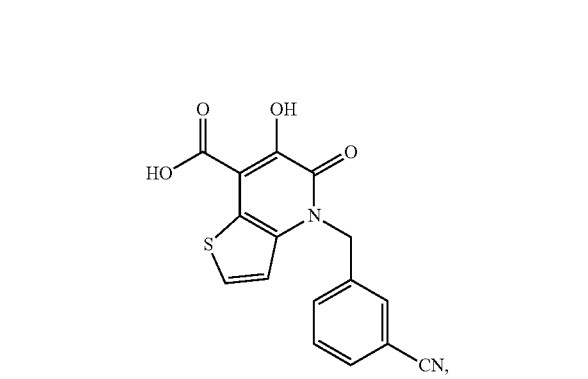
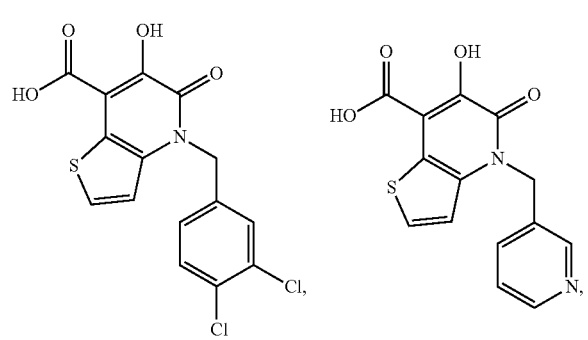
230
-continued
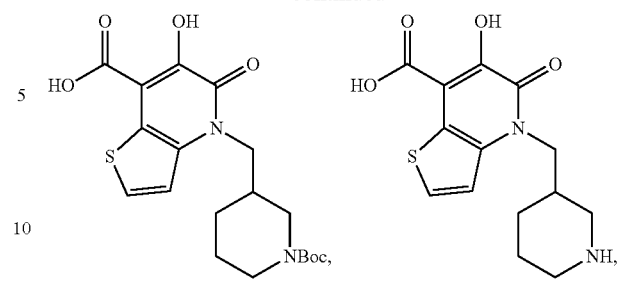
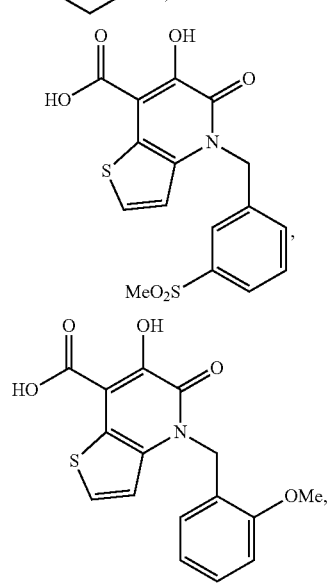
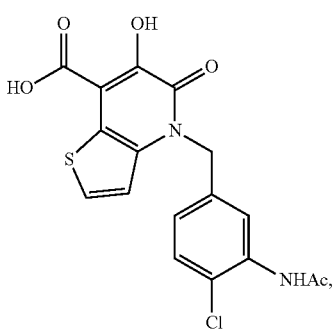
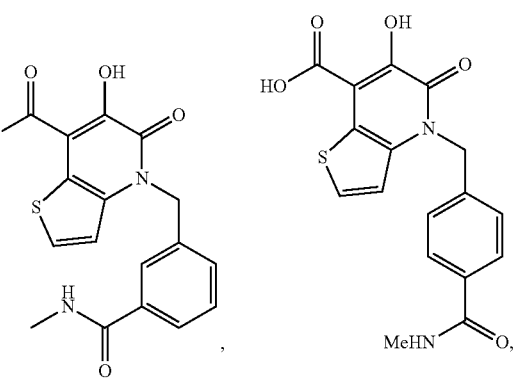

231
-continued
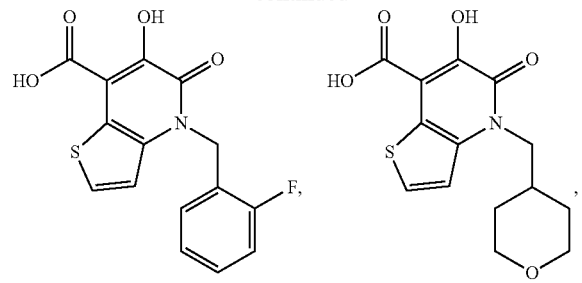
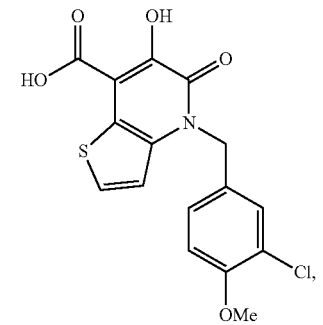
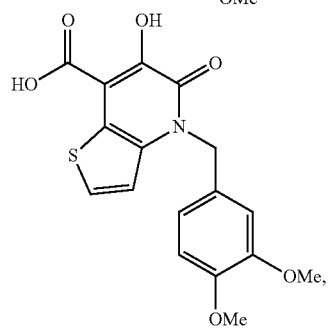
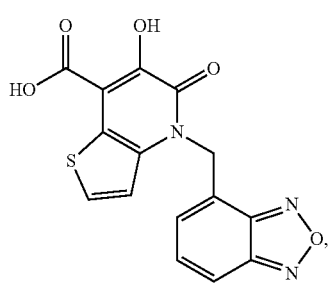
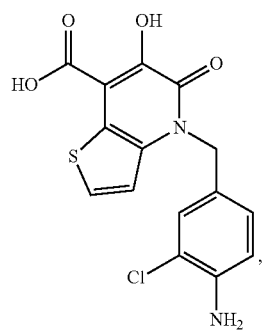
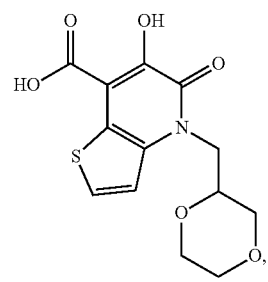
232
-continued
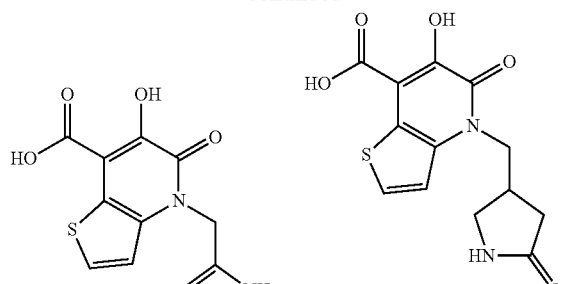
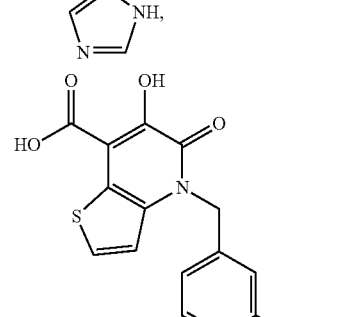
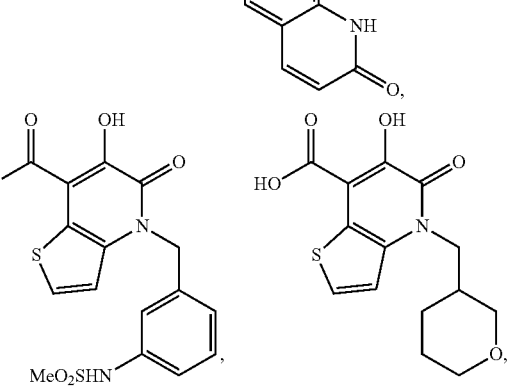
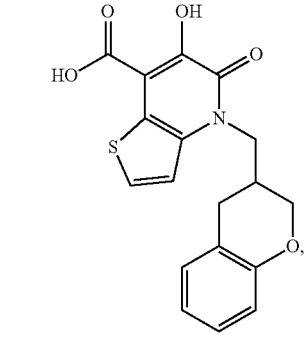
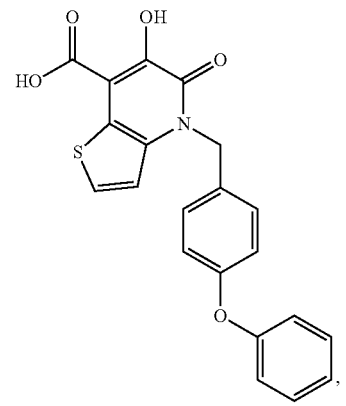

233
-continued
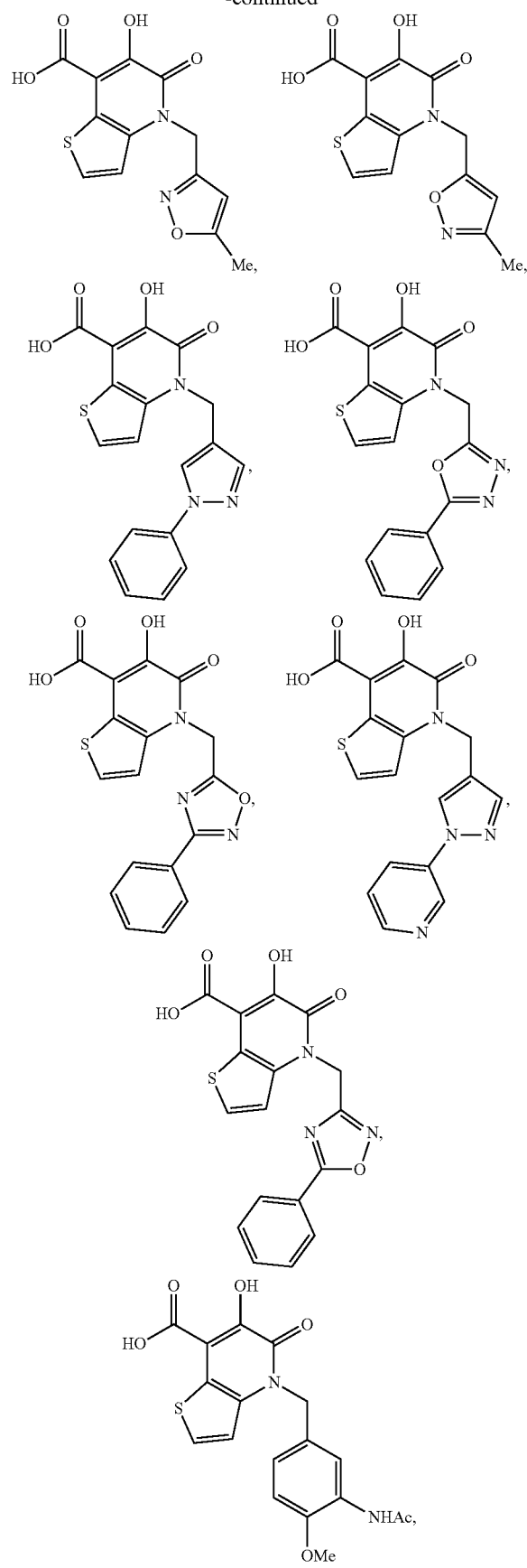
234
-continued
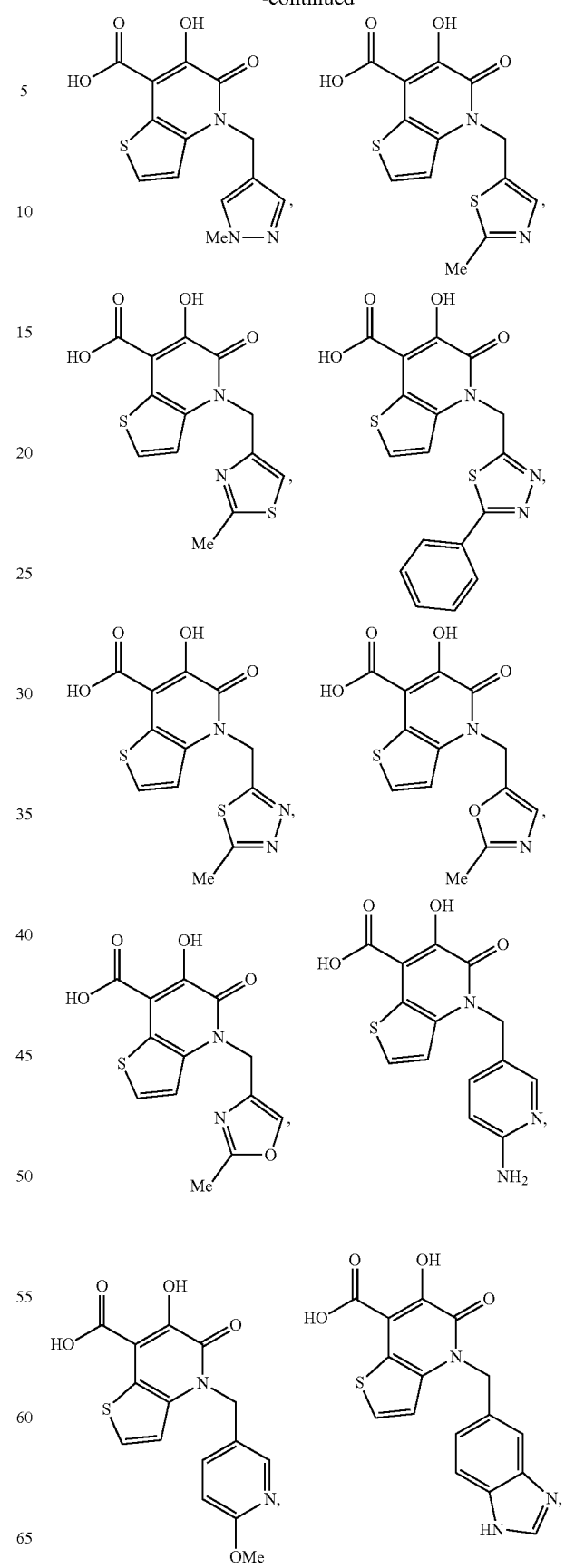

235
-continued
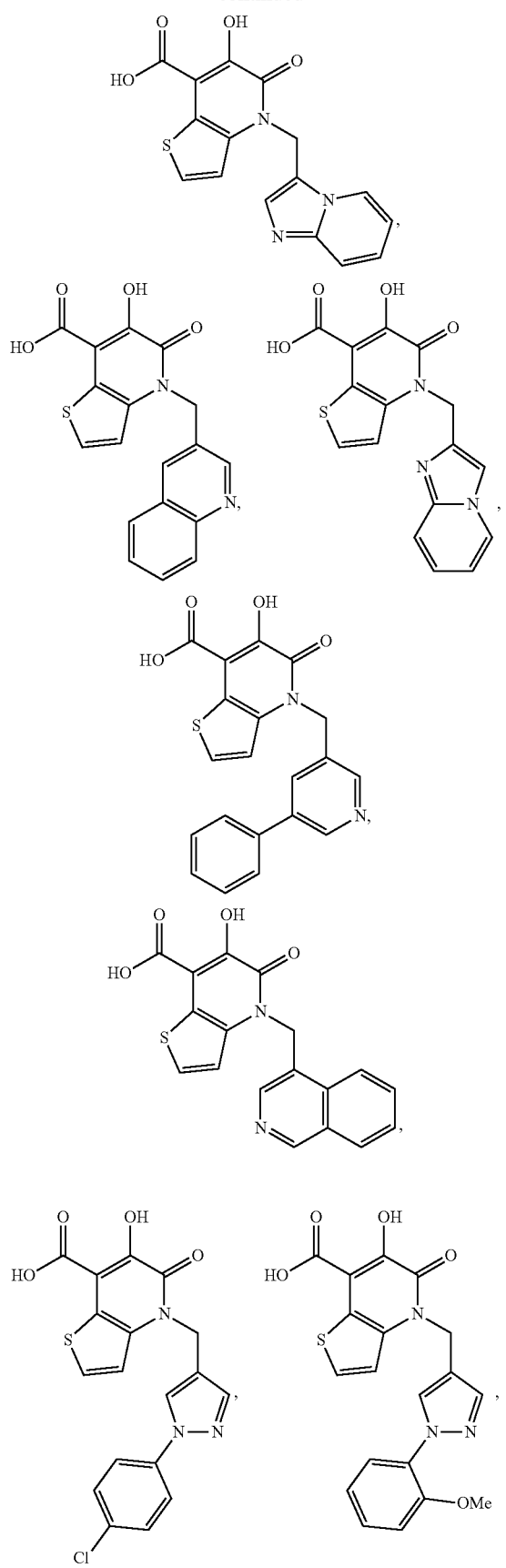
236
-continued
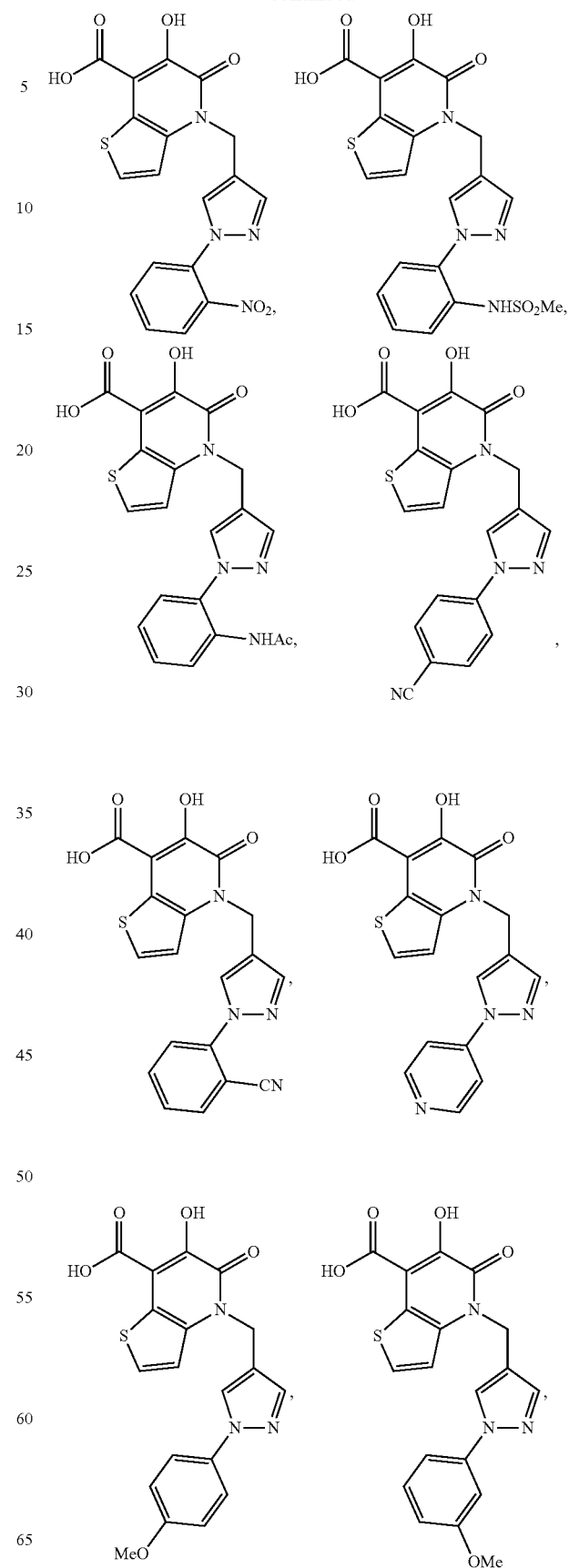

237
-continued
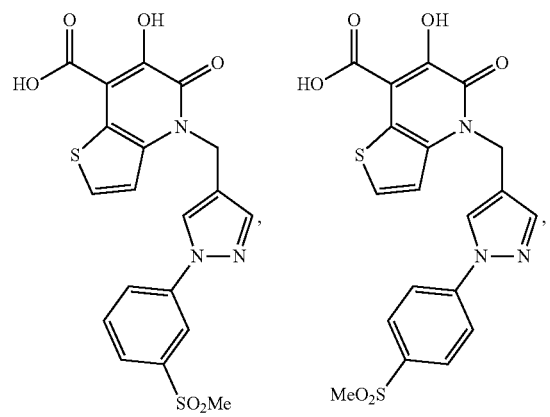
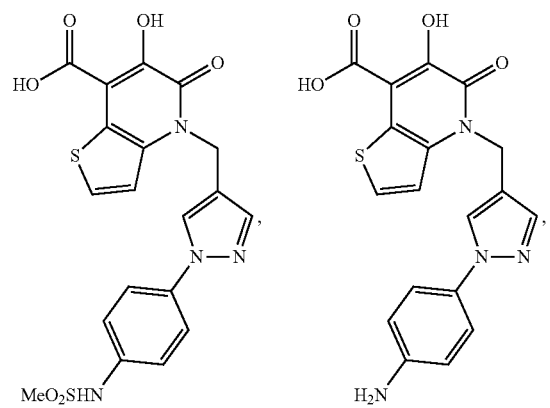
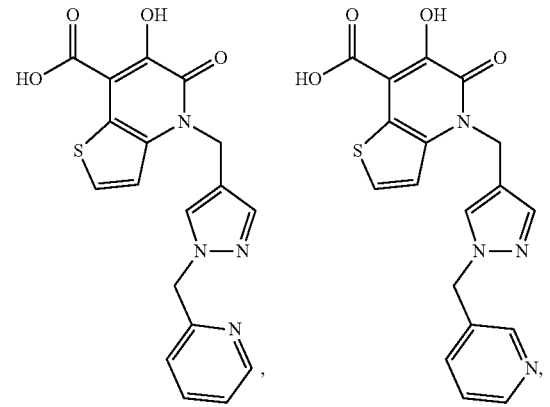
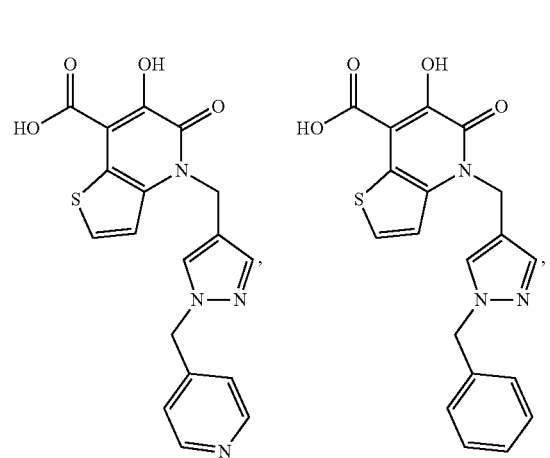
238
-continued
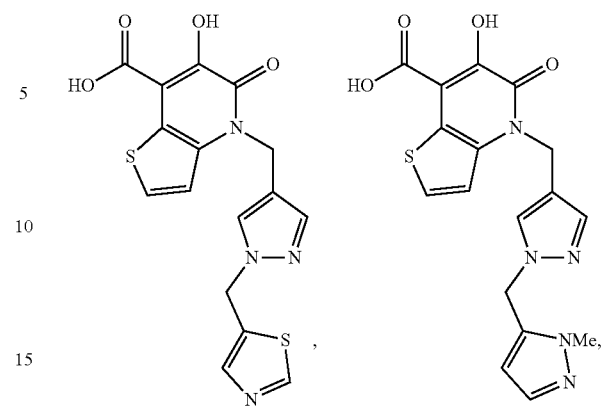
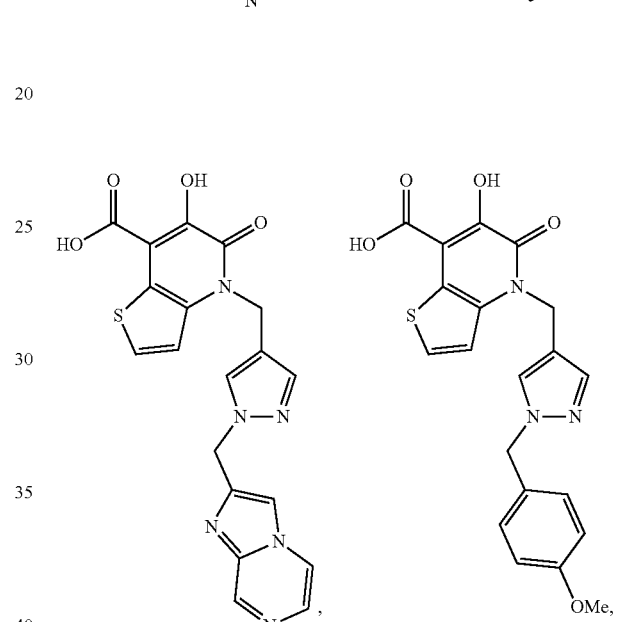
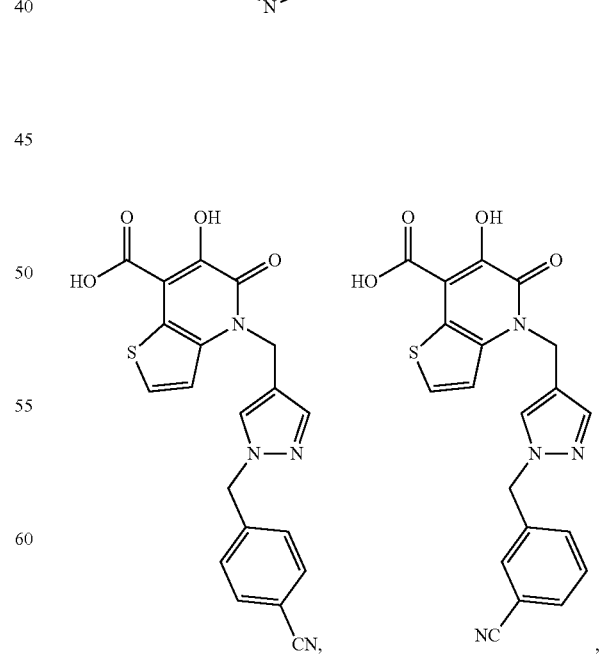

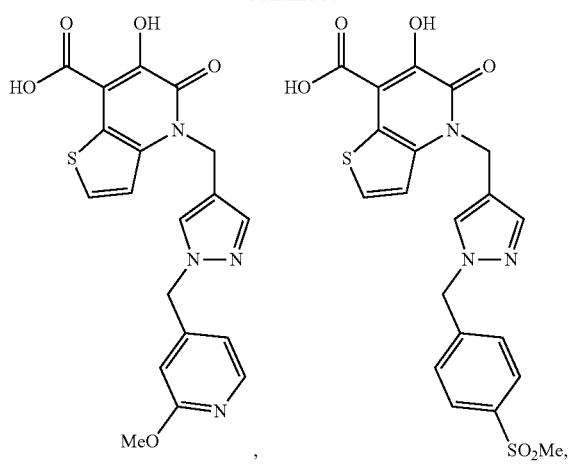
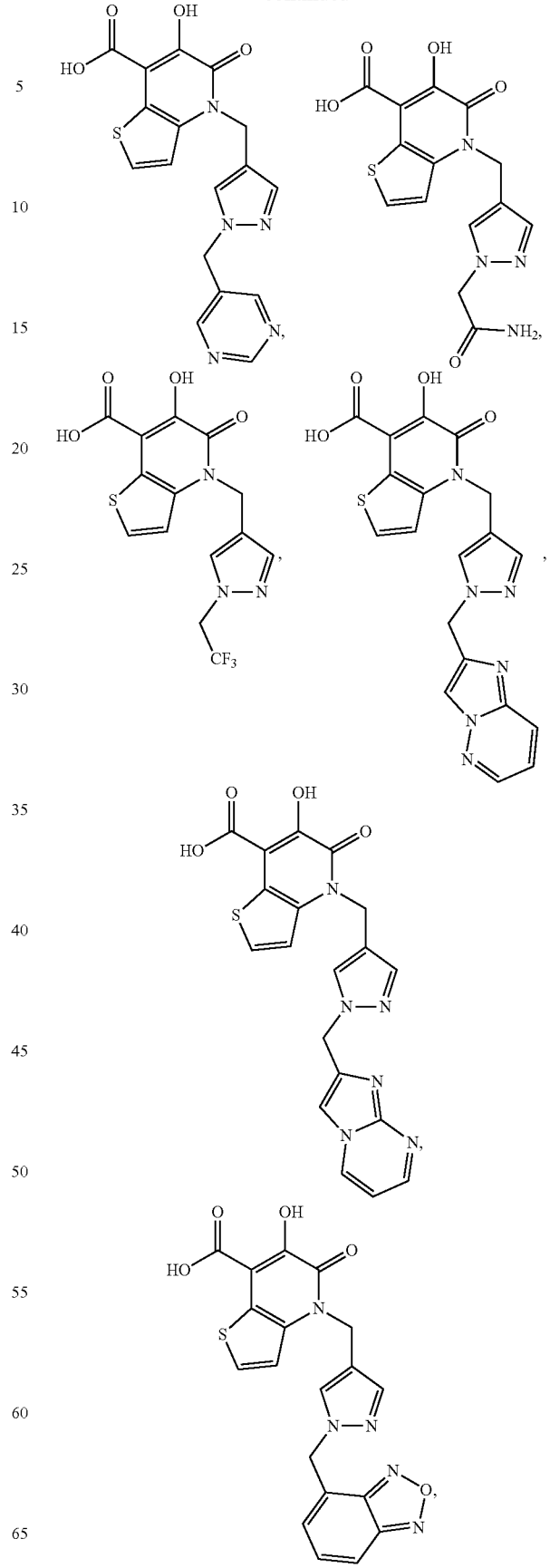

241
-continued
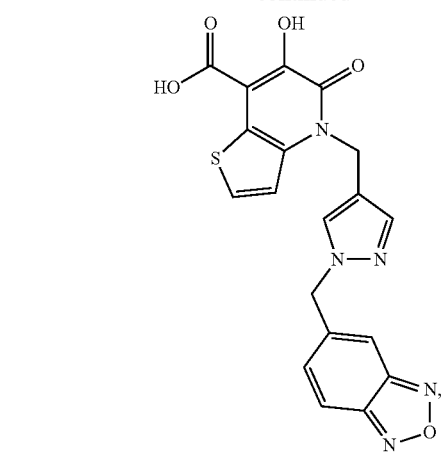
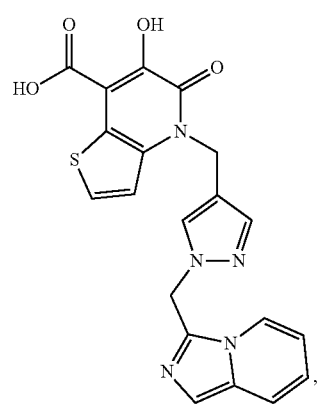
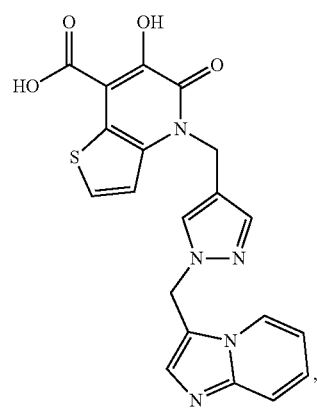
242
-continued
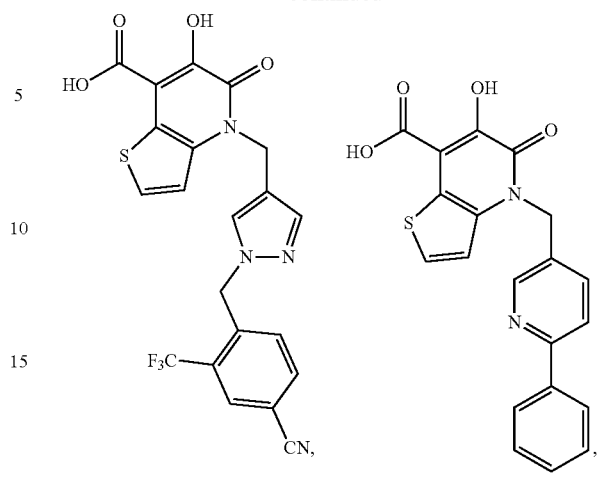
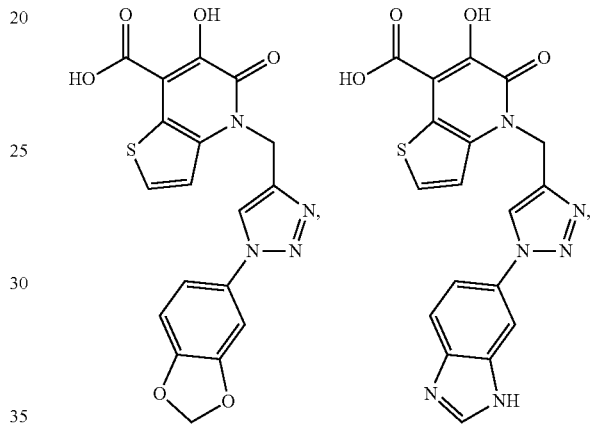
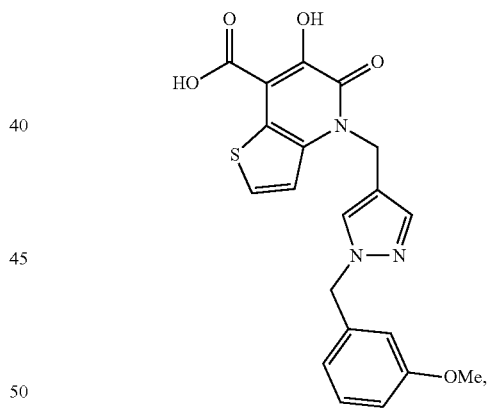
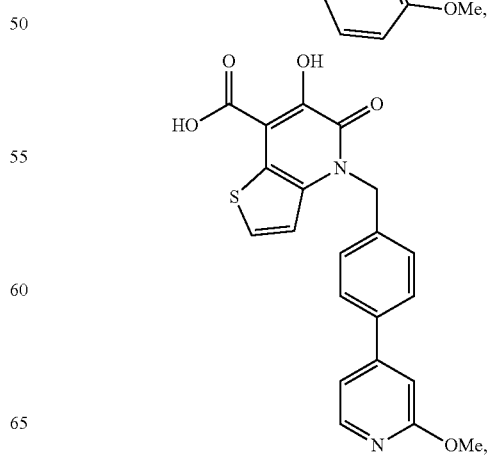

243
-continued
244
-continued
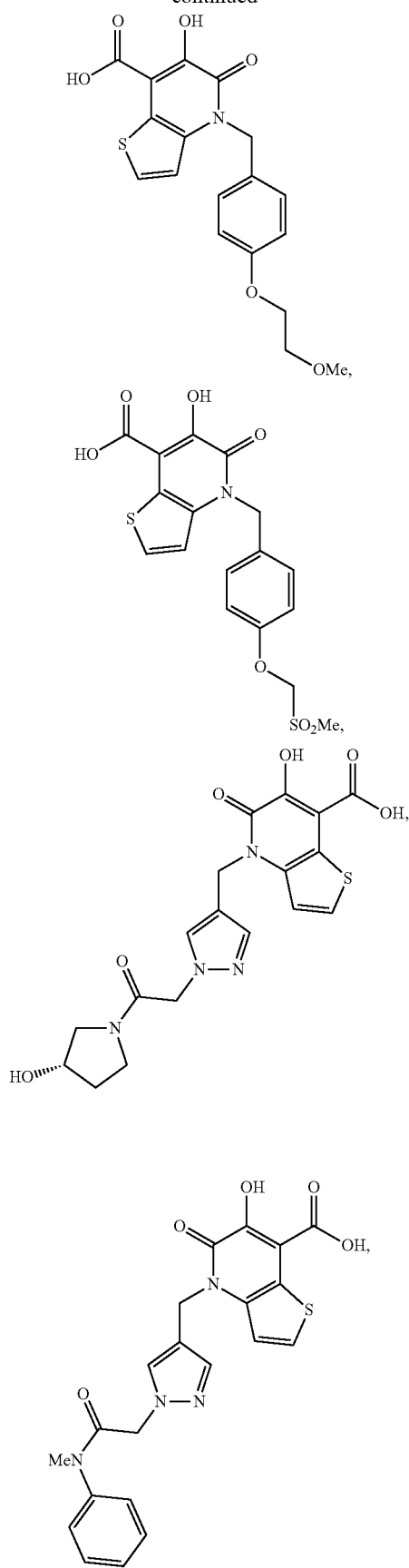
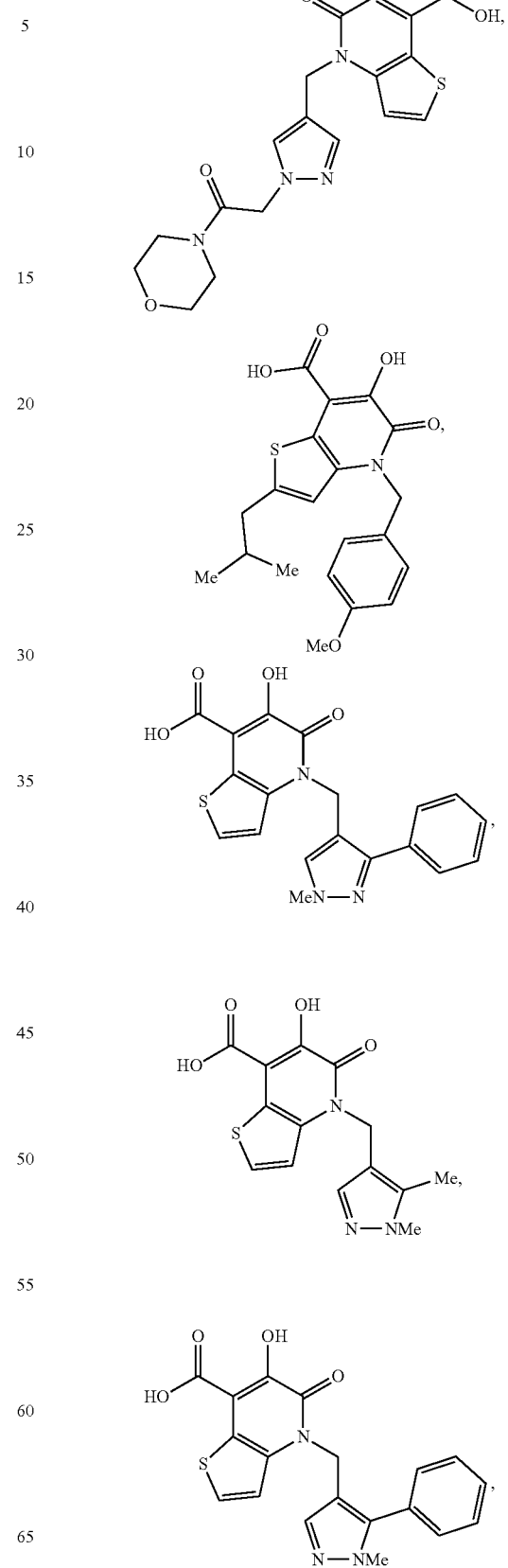

245
-continued
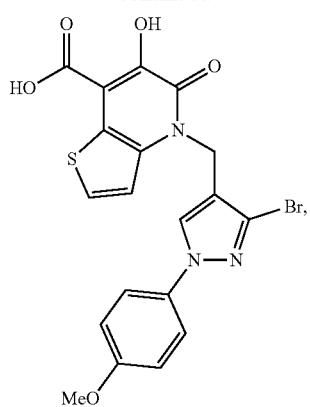
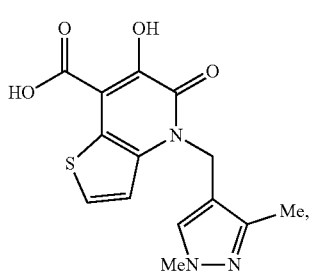
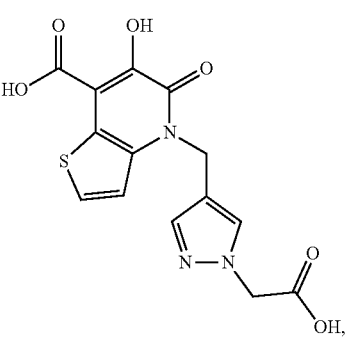
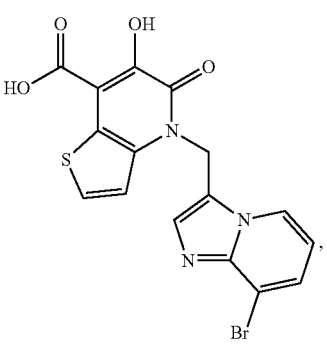
246
-continued
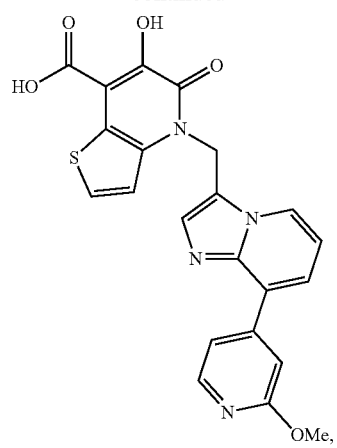
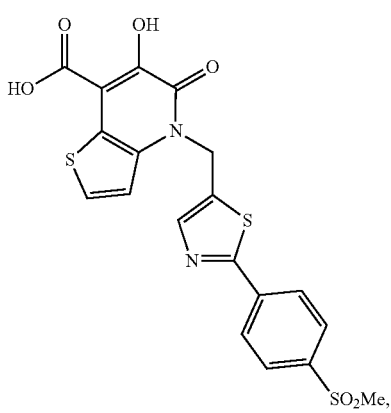
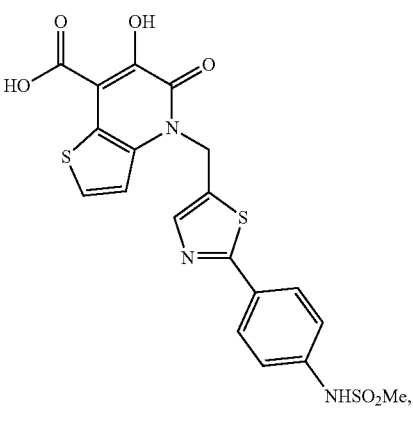

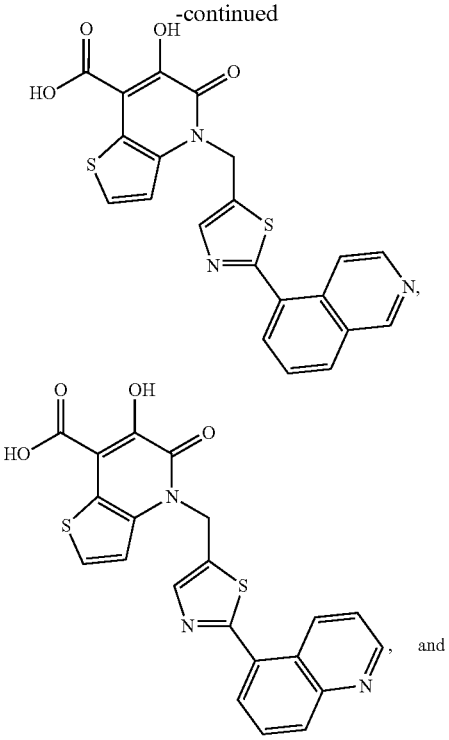

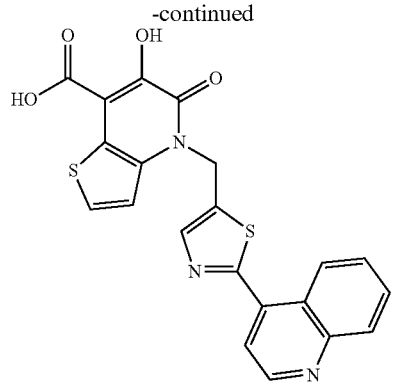

or a pharmaceutically acceptable salt thereof.

17. A pharmaceutical composition comprising a compound of claim 1 and a pharmaceutically acceptable excipient.

18. A method of treating cancer in a subject in need thereof, said method comprising administering to said subject an effective amount of a compound of claim 1, wherein the cancer is selected from the group consisting of colon cancer, ovarian cancer, breast cancer, melanoma, lung cancer, glioblastoma, and leukemia.

* * * * *

SEQUENCE LISTING

<160> NUMBER OF SEQ ID NOS: 3

<210> SEQ ID NO 1
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 1
ggtggacggg tggattgaaa tttaggctgg cacggtcg         38

<210> SEQ ID NO 2
<211> LENGTH: 26
<212> TYPE: DNA
<213> ORGANISM: Artificial sequence
<220> FEATURE:
<223> OTHER INFORMATION: Synthetic polynucleotide

<400> SEQUENCE: 2
cgaccgtgcc agcctaaatt tcaatc         26

<210> SEQ ID NO 3
<211> LENGTH: 18
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' FAM
<220> FEATURE:
<221> NAME/KEY: misc_feature
<222> LOCATION: (18)..(18)
<223> OTHER INFORMATION: 3' Iowa Black Forward Quencher

<400> SEQUENCE: 3
ccaaggccac ccgtccac         18